(12) United States Patent
Wallace et al.

(10) Patent No.: US 8,394,054 B2
(45) Date of Patent: Mar. 12, 2013

(54) ROBOTIC CATHETER SYSTEM

(75) Inventors: Daniel T. Wallace, Santa Cruz, CA (US); Frederic H. Moll, San Francisco, CA (US); Robert G. Younge, Portola Valley, CA (US); Kenneth M. Martin, Los Gatos, CA (US); Gregory J. Stahler, San Jose, CA (US); David F. Moore, San Carlos, CA (US); Daniel T. Adams, Palo Alto, CA (US); Michael R. Zinn, Pleasanton, CA (US); Gunter D. Niemeyer, Mountain View, CA (US)

(73) Assignee: Hansen Medical, Inc., Mountain View, CA (US)

( * ) Notice: Subject to any disclaimer, the term of this patent is extended or adjusted under 35 U.S.C. 154(b) by 0 days.

(21) Appl. No.: 13/118,309

(22) Filed: May 27, 2011

(65) Prior Publication Data
US 2011/0230896 A1    Sep. 22, 2011

Related U.S. Application Data

(63) Continuation of application No. 11/073,363, filed on Mar. 4, 2005, now Pat. No. 7,972,298.

(60) Provisional application No. 60/550,961, filed on Mar. 5, 2004, provisional application No. 60/553,029, filed on Mar. 12, 2004, provisional application No. 60/600,869, filed on Aug. 12, 2004, provisional application No. 60/644,505, filed on Jan. 13, 2005.

(51) Int. Cl.
*A61M 31/00* (2006.01)
(52) U.S. Cl. .................. 604/95.04; 600/114; 600/146
(58) Field of Classification Search .............. 604/95.04, 604/164.12, 164.09; 600/407–427, 101–114, 600/146
See application file for complete search history.

(56) References Cited

U.S. PATENT DOCUMENTS

| | | | |
|---|---|---|---|
| 4,945,305 A | 7/1990 | Blood | |
| 5,078,714 A | 1/1992 | Katims | |
| 5,339,799 A | 8/1994 | Kami | |
| 5,341,807 A | 8/1994 | Nardella | |
| 5,368,015 A | 11/1994 | Wilk | |
| 5,394,875 A | 3/1995 | Lewis | |
| 5,397,443 A | 3/1995 | Michaels | |
| 5,398,691 A | 3/1995 | Martin | |

(Continued)

FOREIGN PATENT DOCUMENTS

| | | |
|---|---|---|
| CA | 2285342 | 10/1998 |
| JP | 10-295822 | 11/1998 |

(Continued)

OTHER PUBLICATIONS

PCT International Search Report for PCT/US2005/007108, Applicant: Hansen Medical, Inc., Forms PCT/ISA/210 and 220, dated Jun. 26, 2005 (9 pages).

(Continued)

*Primary Examiner* — Sanjay Cattungal
(74) *Attorney, Agent, or Firm* — Visa IP Law Group LLP

(57) ABSTRACT

A robotic catheter system includes a controller with a master input device. An instrument driver is in communication with the controller and has a guide instrument interface including a plurality of guide instrument drive elements responsive to control signals generated, at least in part, by the master input device. An elongate guide instrument has a base, distal end, and a working lumen, wherein the guide instrument base is operatively coupled to the guide instrument interface. The guide instrument includes a plurality of guide instrument control elements operatively coupled to respective guide drive elements and secured to the distal end of the guide instrument. The guide instrument control elements are axially moveable relative to the guide instrument such that movement of the guide instrument distal end may be controlled by the master input device.

10 Claims, 167 Drawing Sheets

U.S. PATENT DOCUMENTS

| | | |
|---|---|---|
| 5,408,409 A | 4/1995 | Glassman |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,600,330 A | 2/1997 | Blood |
| 5,631,973 A | 5/1997 | Green |
| 5,662,108 A | 9/1997 | Budd et al. |
| 5,673,704 A | 10/1997 | Marchlinski et al. |
| 5,697,377 A | 12/1997 | Wittkampf |
| 5,713,946 A | 2/1998 | Ben-Haim |
| 5,738,096 A | 4/1998 | Ben-Haim |
| 5,749,362 A | 5/1998 | Funda |
| 5,754,741 A | 5/1998 | Wang |
| 5,762,458 A | 6/1998 | Wang |
| 5,784,542 A | 7/1998 | Ohm |
| 5,799,055 A | 8/1998 | Peshkin |
| 5,815,640 A | 9/1998 | Wang |
| 5,825,982 A | 10/1998 | Wright |
| 5,833,608 A | 11/1998 | Acker |
| 5,836,869 A | 11/1998 | Kudo |
| 5,836,874 A | 11/1998 | Swanson et al. |
| 5,836,990 A | 11/1998 | Li |
| 5,843,076 A | 12/1998 | Webster |
| 5,876,325 A | 3/1999 | Mizuno |
| 5,878,193 A | 3/1999 | Wang |
| 5,891,095 A | 4/1999 | Eggers et al. |
| 5,935,079 A | 8/1999 | Swanson et al. |
| 5,950,629 A | 9/1999 | Taylor |
| 5,953,683 A | 9/1999 | Hansen |
| 5,983,126 A | 11/1999 | Wittkampf |
| 6,004,271 A | 12/1999 | Moore |
| 6,063,022 A | 5/2000 | Ben-Haim |
| 6,063,095 A | 5/2000 | Wang |
| 6,080,181 A | 6/2000 | Jensen |
| 6,083,170 A | 7/2000 | Ben-Haim |
| 6,096,004 A | 8/2000 | Meglan |
| 6,106,511 A | 8/2000 | Jensen |
| 6,132,368 A | 10/2000 | Cooper |
| 6,161,032 A | 12/2000 | Acker |
| 6,172,499 B1 | 1/2001 | Ashe |
| 6,226,543 B1 | 5/2001 | Gilboa |
| 6,228,028 B1 | 5/2001 | Klein |
| 6,233,476 B1 | 5/2001 | Strommer |
| 6,233,504 B1 | 5/2001 | Das |
| 6,246,200 B1 | 6/2001 | Blumenkranz |
| 6,266,551 B1 | 7/2001 | Osadchy |
| 6,272,371 B1 | 8/2001 | Shlomo |
| 6,301,496 B1 | 10/2001 | Reisfeld |
| 6,309,397 B1 | 10/2001 | Julian |
| 6,310,828 B1 | 10/2001 | Mumm |
| 6,312,435 B1 | 11/2001 | Wallace |
| 6,331,181 B1 | 12/2001 | Tierney |
| 6,370,411 B1 | 4/2002 | Osadchy |
| 6,371,952 B1 | 4/2002 | Madhani |
| 6,375,471 B1 | 4/2002 | Wendlandt |
| 6,380,732 B1 | 4/2002 | Gilboa |
| 6,393,340 B2 | 5/2002 | Funda |
| 6,398,731 B1 | 6/2002 | Mumm |
| 6,400,979 B1 | 6/2002 | Stoianovici |
| 6,415,171 B1 | 7/2002 | Gueziec |
| 6,424,885 B1 | 7/2002 | Niemeyer |
| 6,490,468 B2 | 12/2002 | Panescu et al. |
| 6,491,701 B2 | 12/2002 | Tierney |
| 6,493,573 B1 | 12/2002 | Martinelli |
| 6,493,608 B1 | 12/2002 | Niemeyer |
| 6,530,913 B1 | 3/2003 | Giba et al. |
| 6,544,230 B1 | 4/2003 | Flaherty et al. |
| 6,565,554 B1 | 5/2003 | Niemeyer |
| 6,574,355 B2 | 6/2003 | Green |
| 6,580,938 B1 | 6/2003 | Acker |
| 6,587,750 B2 | 7/2003 | Gerbi |
| 6,594,552 B1 | 7/2003 | Nowlin |
| 6,610,007 B2 | 8/2003 | Belson |
| 6,615,155 B2 | 9/2003 | Gilboa |
| 6,618,612 B1 | 9/2003 | Acker |
| 6,620,173 B2 | 9/2003 | Gerbi |
| 6,626,899 B2 | 9/2003 | Houser |
| 6,659,939 B2 | 12/2003 | Moll |
| 6,669,709 B1 | 12/2003 | Cohn et al. |
| 6,685,698 B2 | 2/2004 | Morley |
| 6,699,235 B2 | 3/2004 | Wallace |
| 6,716,166 B2 | 4/2004 | Govari |
| 6,726,675 B1 | 4/2004 | Beyar |
| 6,774,624 B2 | 8/2004 | Anderson |
| 6,783,524 B2 | 8/2004 | Anderson |
| 6,799,065 B1 | 9/2004 | Niemeyer |
| 6,817,973 B2 | 11/2004 | Merril |
| 6,817,974 B2 | 11/2004 | Cooper |
| 6,852,107 B2 | 2/2005 | Wang |
| 6,858,003 B2 | 2/2005 | Evans |
| 6,905,460 B2 | 6/2005 | Wang |
| 6,963,792 B1 | 11/2005 | Green |
| 7,021,173 B2 | 4/2006 | Stoianovici |
| 7,074,179 B2 | 7/2006 | Wang |
| 7,087,049 B2 | 8/2006 | Nowlin |
| 7,169,141 B2 | 1/2007 | Brock |
| 7,214,230 B2 | 5/2007 | Brock et al. |
| 7,225,012 B1 | 5/2007 | Susil |
| 7,276,044 B2 | 10/2007 | Ferry et al. |
| 7,297,142 B2 | 11/2007 | Brock |
| 7,320,700 B2 | 1/2008 | Cooper |
| 7,331,967 B2 | 2/2008 | Lee |
| 7,343,195 B2 | 3/2008 | Strommer |
| 7,371,210 B2 | 5/2008 | Brock |
| 7,413,568 B2 | 8/2008 | Swanson et al. |
| 7,494,494 B2 | 2/2009 | Stoianovici |
| 7,607,440 B2 | 10/2009 | Coste-Maniere et al. |
| 7,637,924 B2 | 12/2009 | Gifford, III |
| 7,699,835 B2 | 4/2010 | Lee et al. |
| 7,766,894 B2 | 8/2010 | Weitzner et al. |
| 7,781,724 B2 | 8/2010 | Childers |
| 7,901,348 B2 | 3/2011 | Soper et al. |
| 2003/0074011 A1 | 4/2003 | Gilboa |
| 2003/0135204 A1 | 7/2003 | Lee |
| 2004/0034282 A1* | 2/2004 | Quaid, III .................... 600/300 |
| 2004/0034365 A1 | 2/2004 | Lentz |
| 2004/0176751 A1 | 9/2004 | Weitzner |
| 2005/0027397 A1* | 2/2005 | Niemeyer .................... 700/245 |
| 2005/0059960 A1 | 3/2005 | Simaan |
| 2005/0165276 A1 | 7/2005 | Belson |
| 2005/0200324 A1 | 9/2005 | Guthart |
| 2005/0203382 A1 | 9/2005 | Govari |
| 2006/0013523 A1 | 1/2006 | Childers |
| 2006/0178556 A1 | 8/2006 | Hasser et al. |
| 2006/0200049 A1 | 9/2006 | Leo |
| 2007/0060847 A1 | 3/2007 | Leo |
| 2007/0123851 A1 | 5/2007 | Alejandro |
| 2007/0287999 A1 | 12/2007 | Malecki |
| 2007/0293724 A1 | 12/2007 | Saadat |
| 2007/0299434 A1 | 12/2007 | Malecki |
| 2008/0009750 A1 | 1/2008 | Aeby |
| 2008/0015445 A1 | 1/2008 | Saadat |
| 2008/0300592 A1 | 12/2008 | Weitzner |
| 2009/0054884 A1 | 2/2009 | Farley et al. |

FOREIGN PATENT DOCUMENTS

| | | |
|---|---|---|
| JP | 2000-514320 | 10/2000 |
| WO | WO 97/44089 | 11/1997 |
| WO | WO 00/11495 | 2/2000 |
| WO | WO 00/45193 | 3/2000 |
| WO | WO 03/091839 | 6/2003 |
| WO | WO 03/077769 | 9/2003 |

OTHER PUBLICATIONS

PCT Written Opinion of the International Search Authority for PCT/US2005/007108, Applicant: Hansen Medical, Inc., Form PCT/ISA/237, dated Jun. 26, 2005 (6 pages).

Response to Office Action for EP Patent Application No. 05724618.3 mailed on Mar. 3, 2011, submitted on May 17, 2011 (15 pages).

Response to Office Action for EP Patent Application No. 05724618.3 mailed on Jun. 4, 2009, submitted on Dec. 1, 2009 (25 pages).

Notice of Rejection for JP Patent Application No. 2007-502015 with English Translation, dated Aug. 17, 2010 (4 pages).

Office Action for EP Patent Application No. 05 724 618.3-2310, dated Mar. 3, 2011 (4 pages).
Office Action for EP Patent Application No. 05 724 618.3-2310, dated Jun. 4, 2009 (3 pages).

Notice of Rejection for JP Application No. 2007-502015 with English Translation, dated Jan. 11, 2011 (5 pages).

* cited by examiner

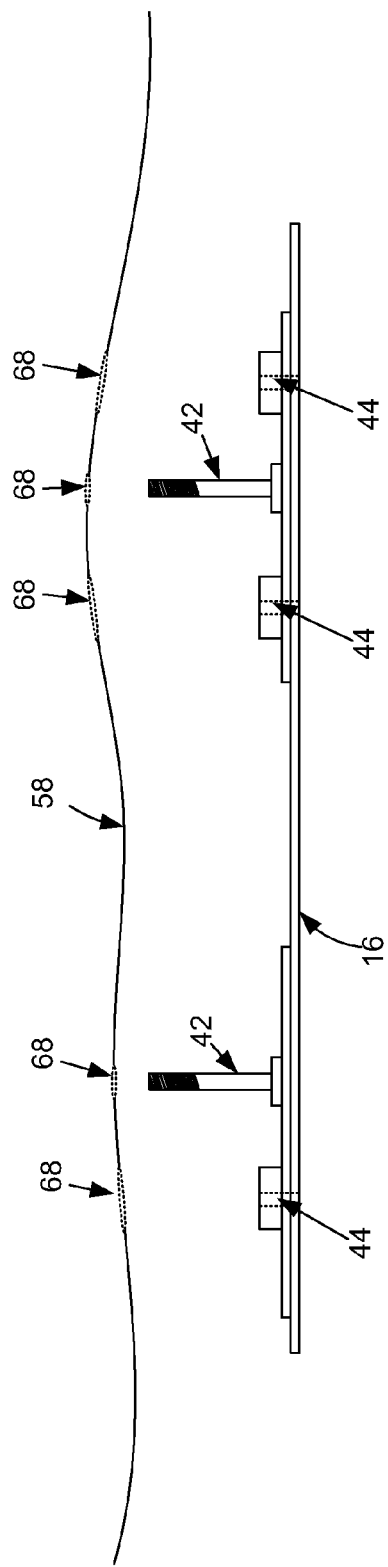
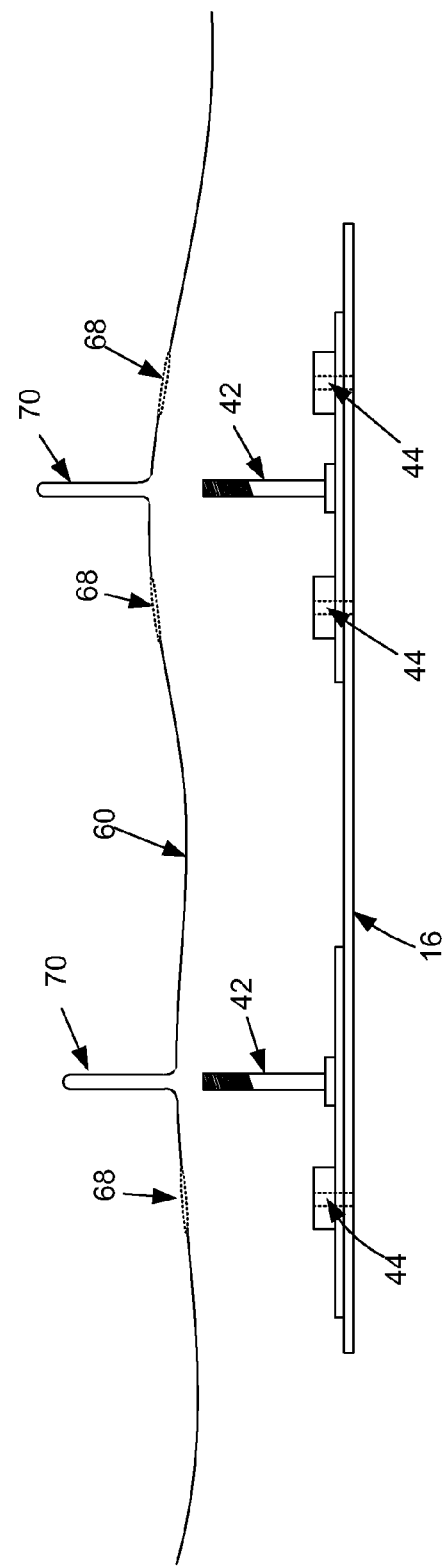

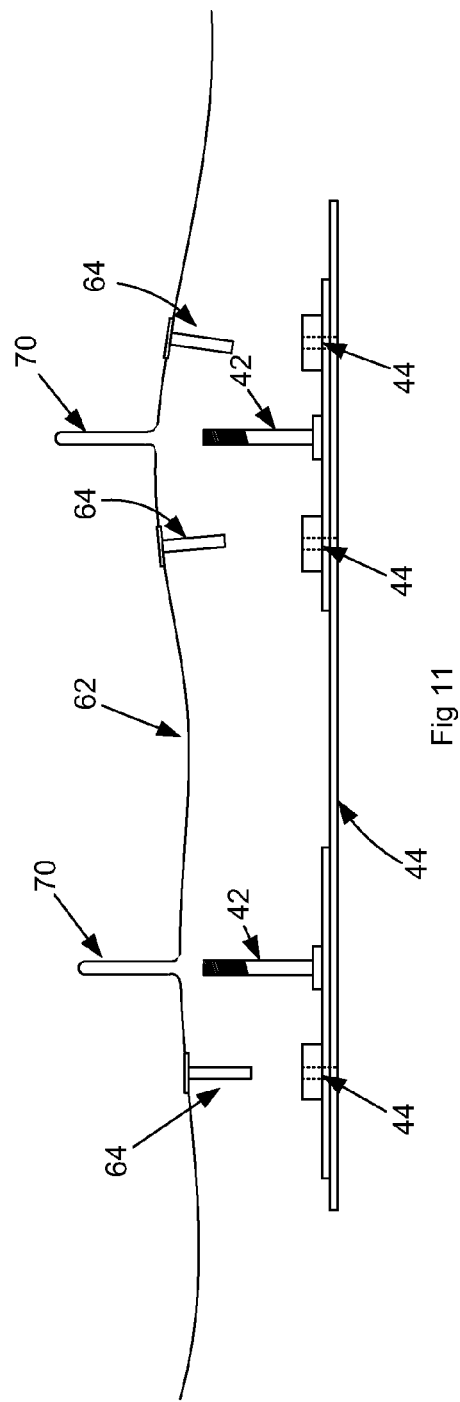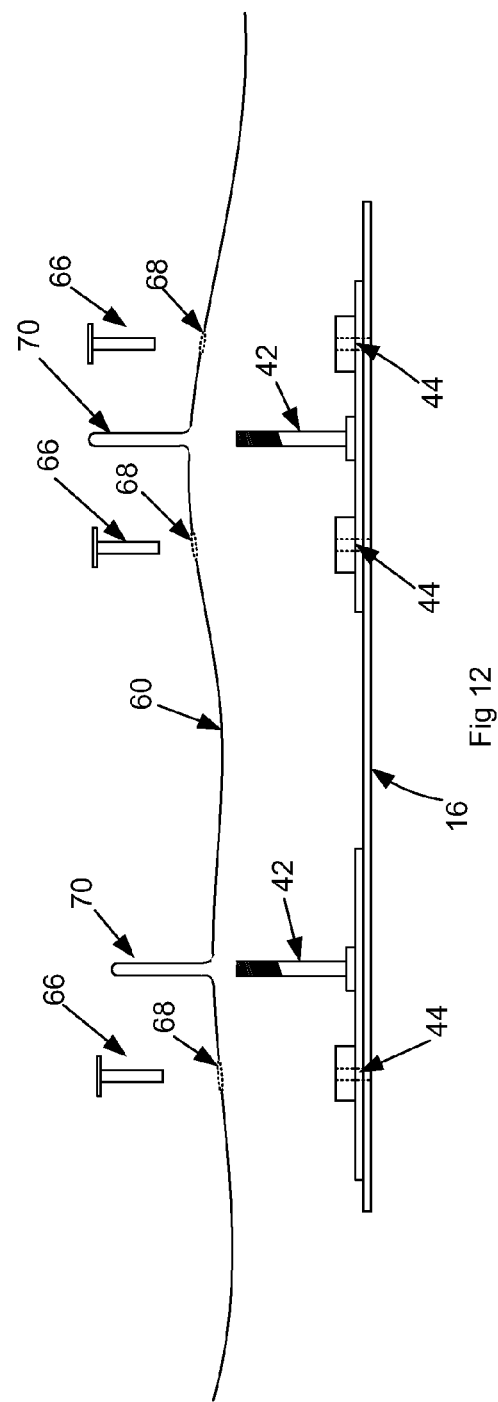

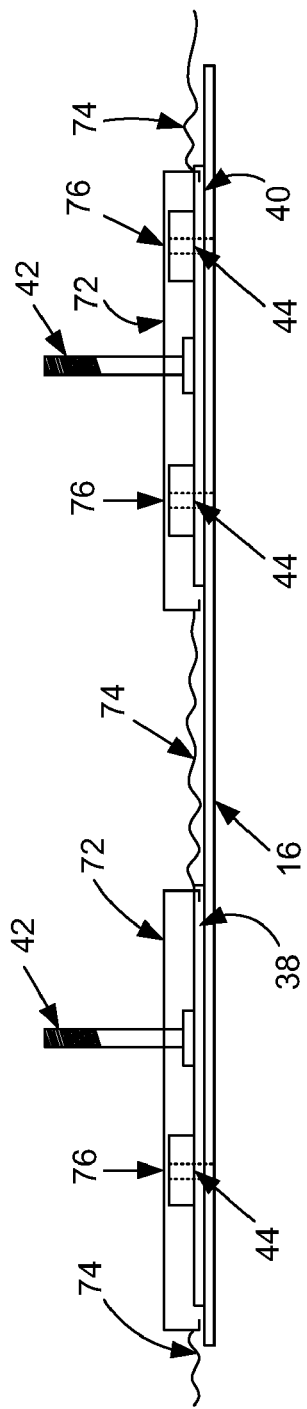
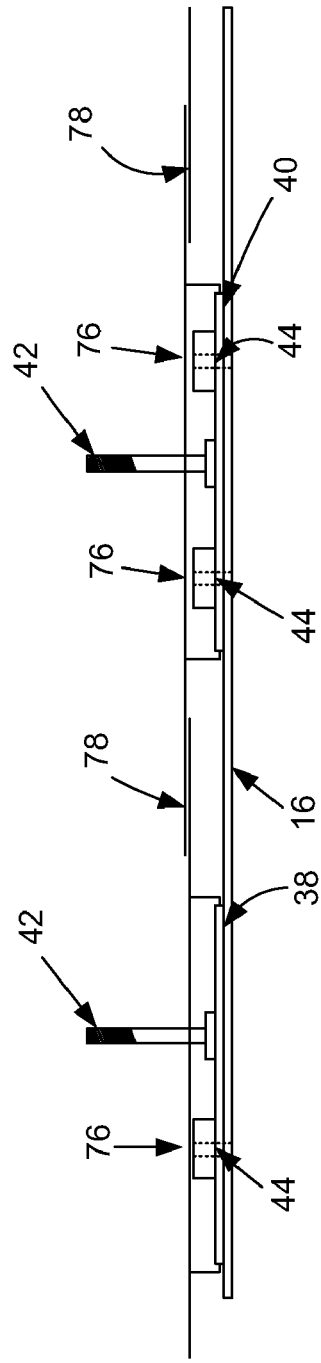

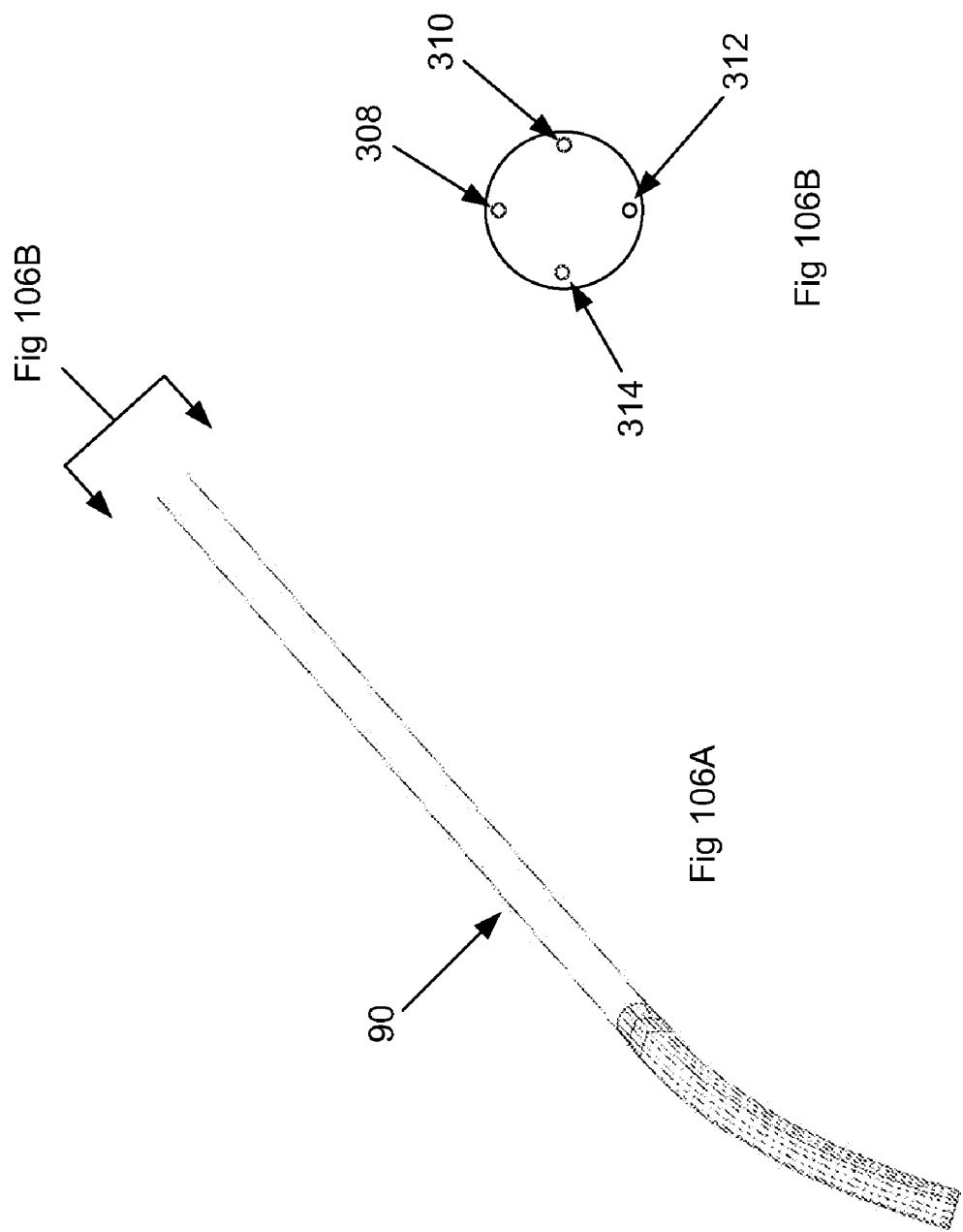

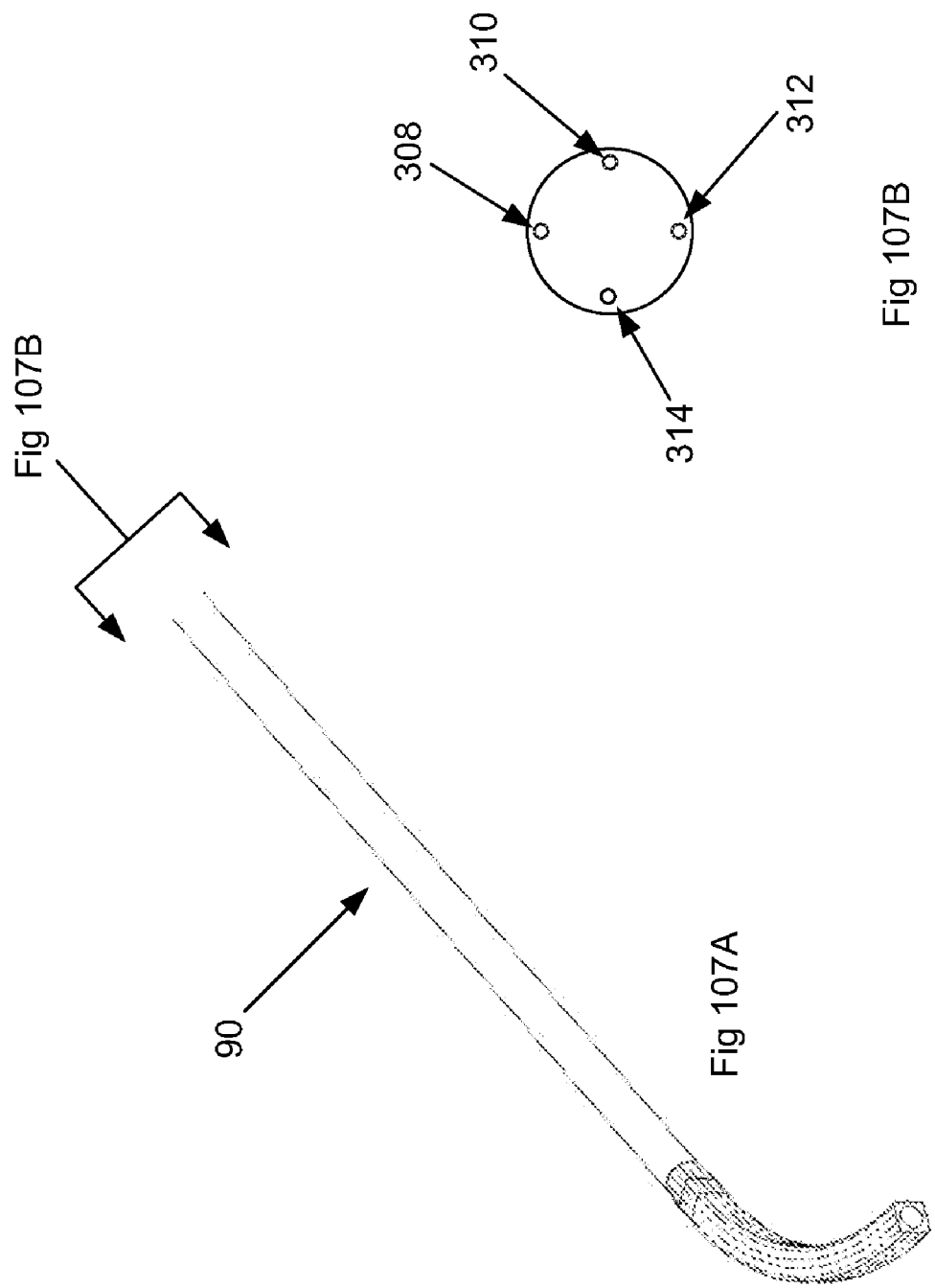

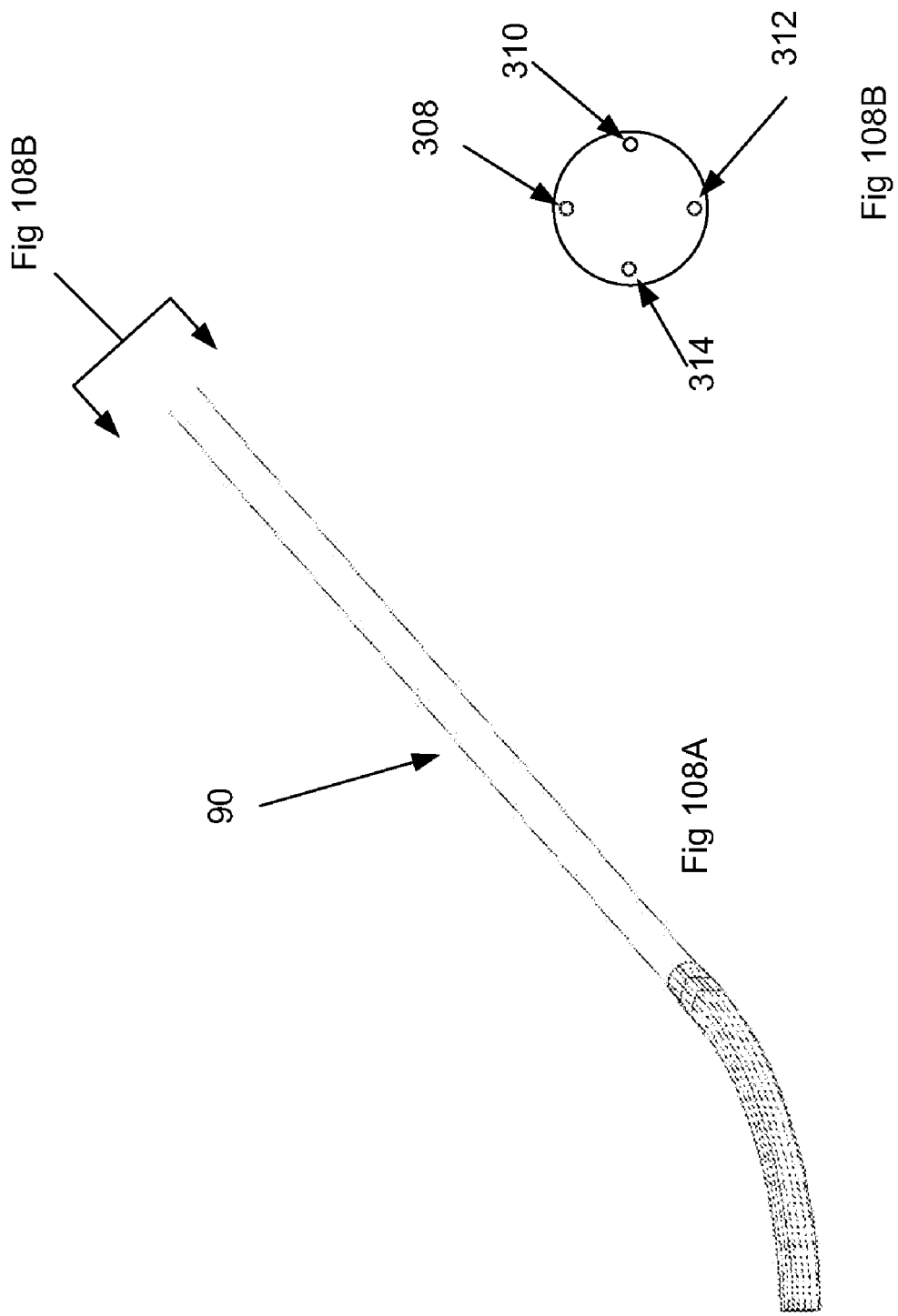

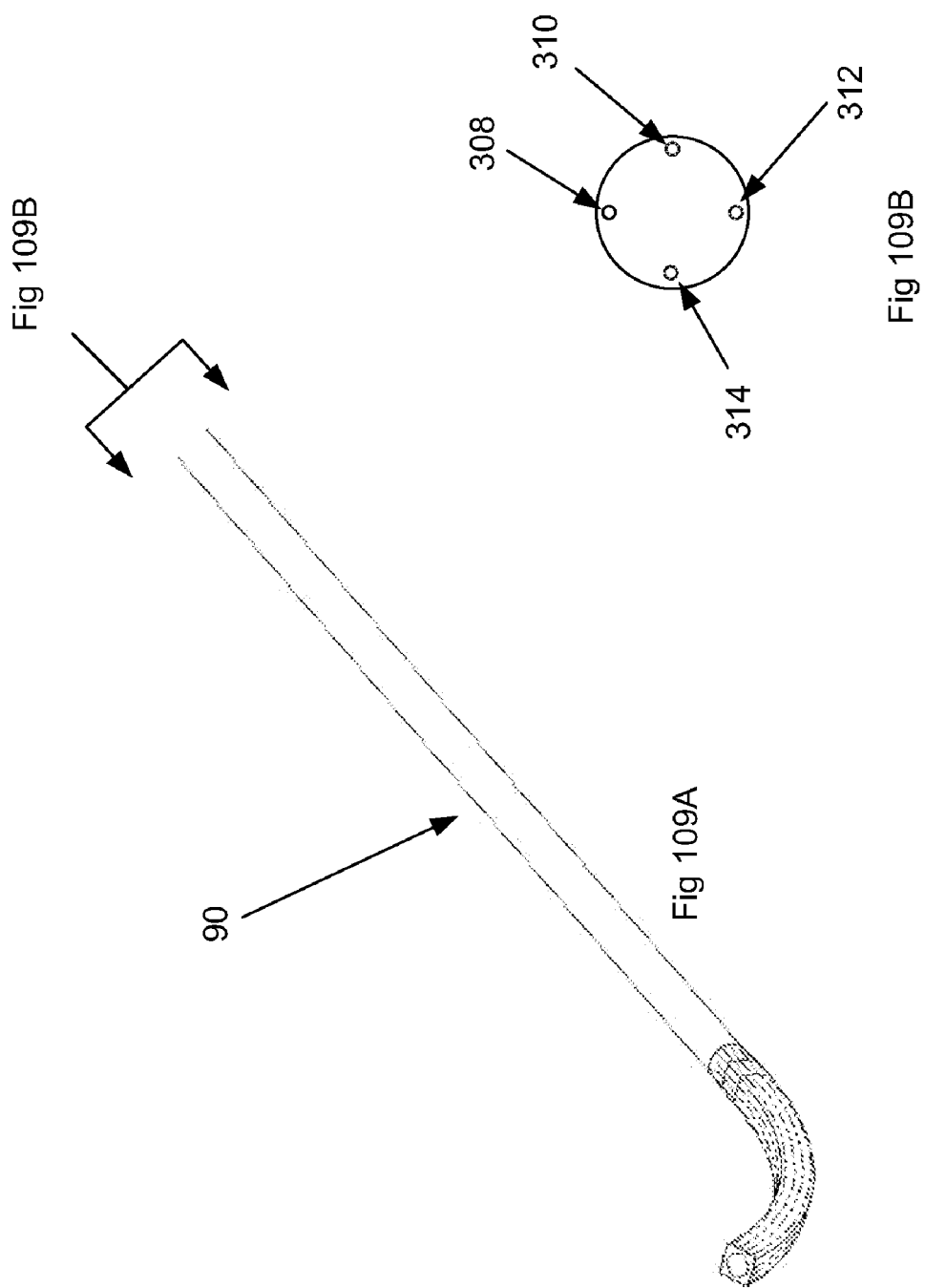

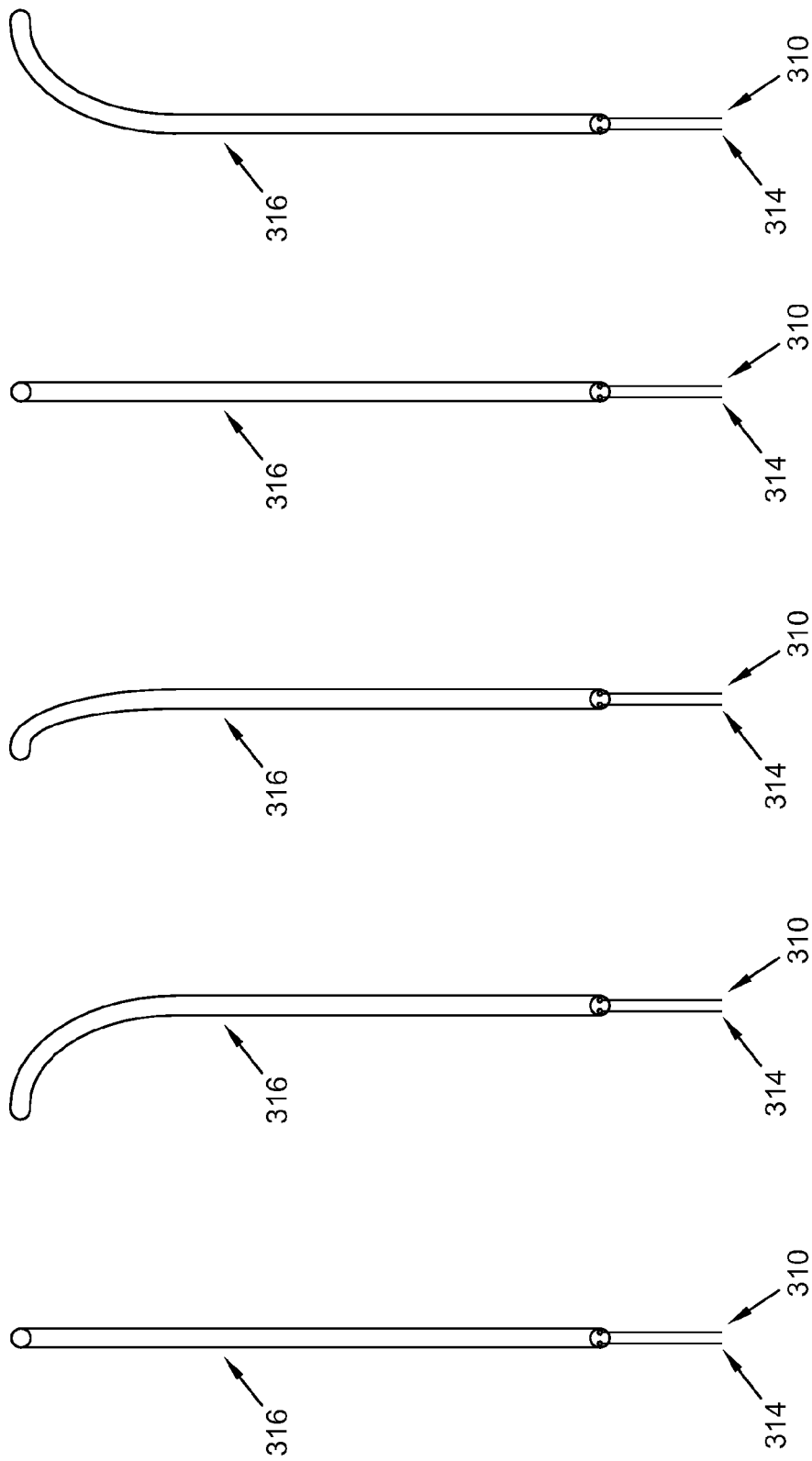

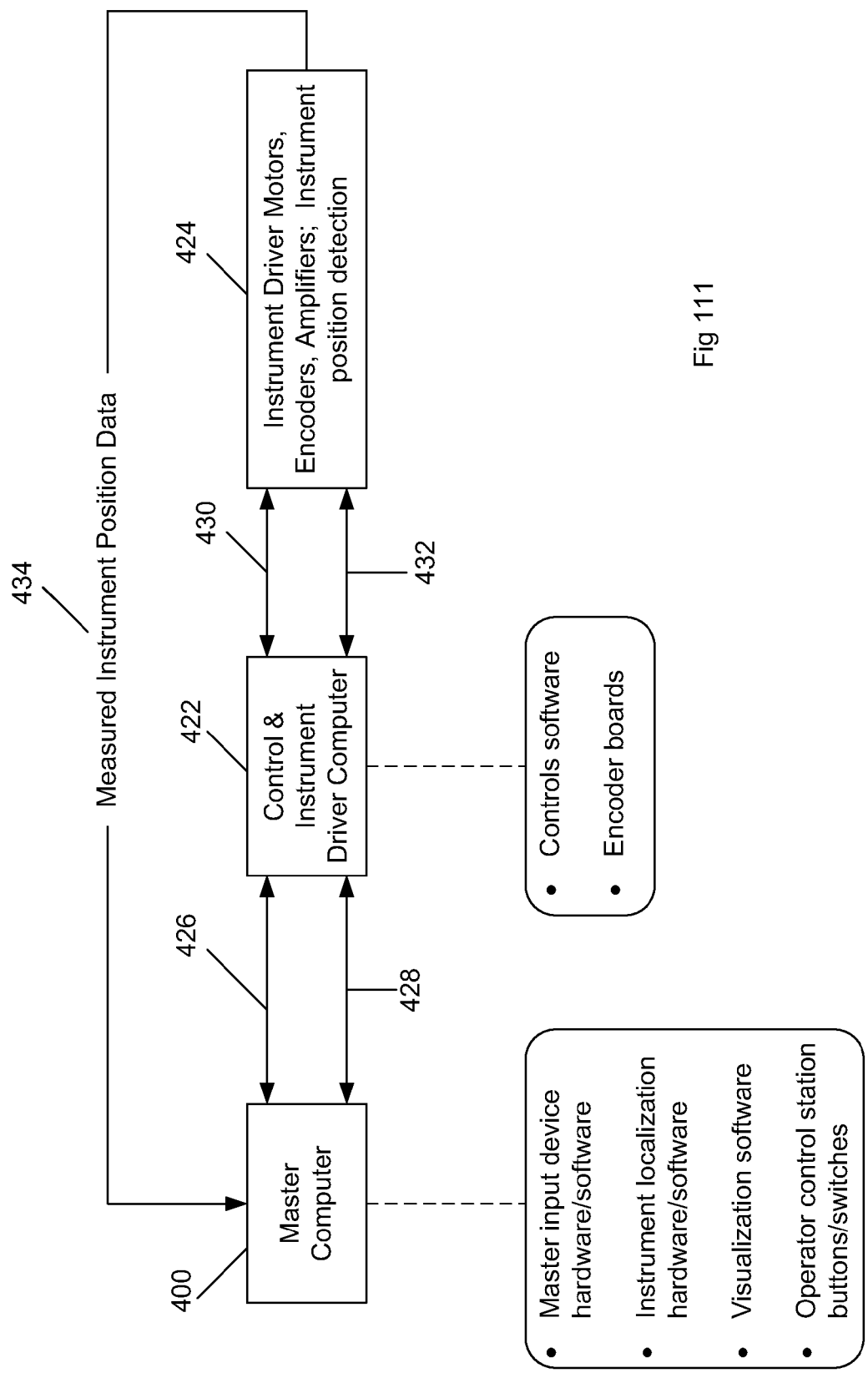

Forward Kinematics:
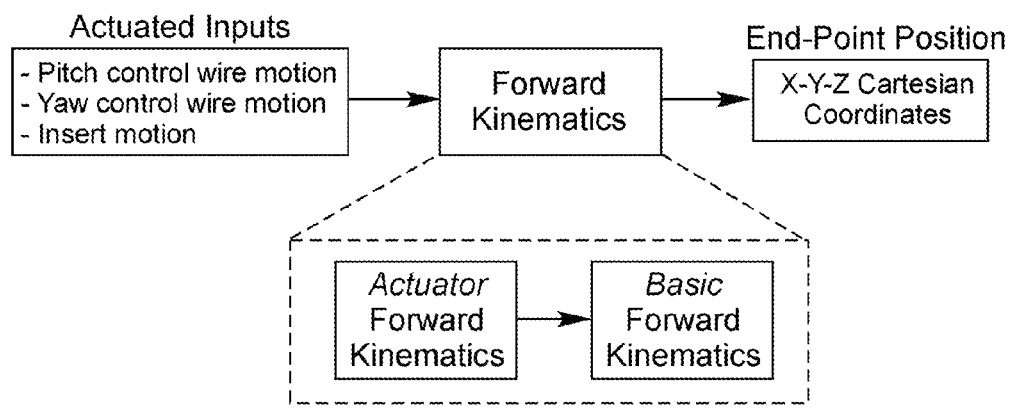
Inverse Kinematics:
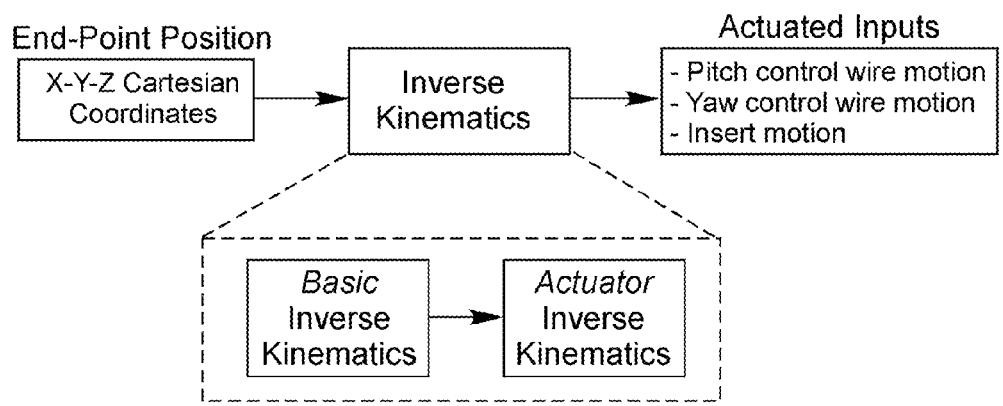
Fig 125

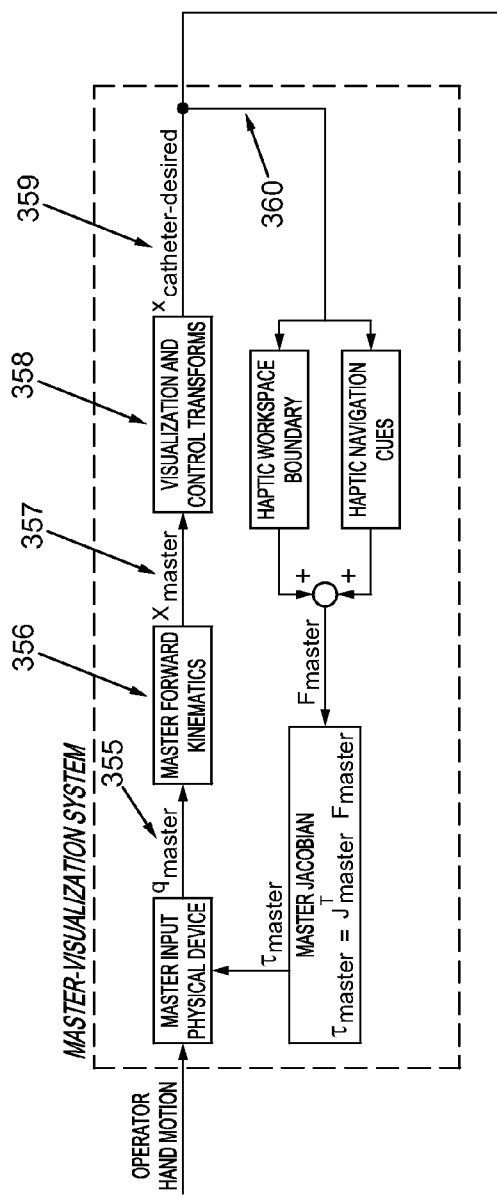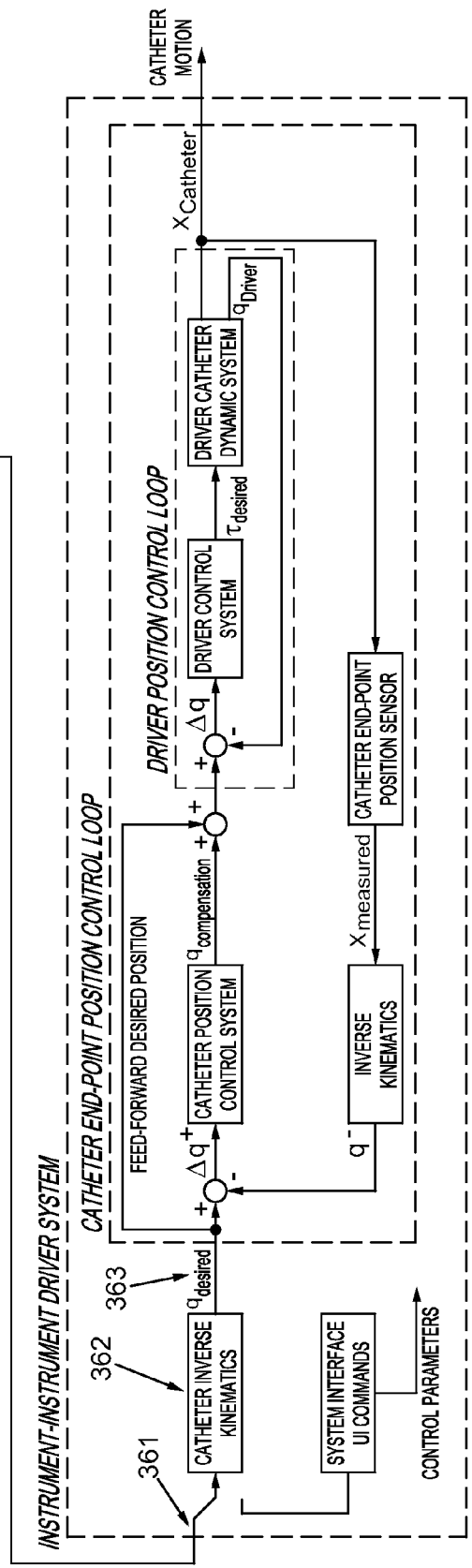
Fig 130

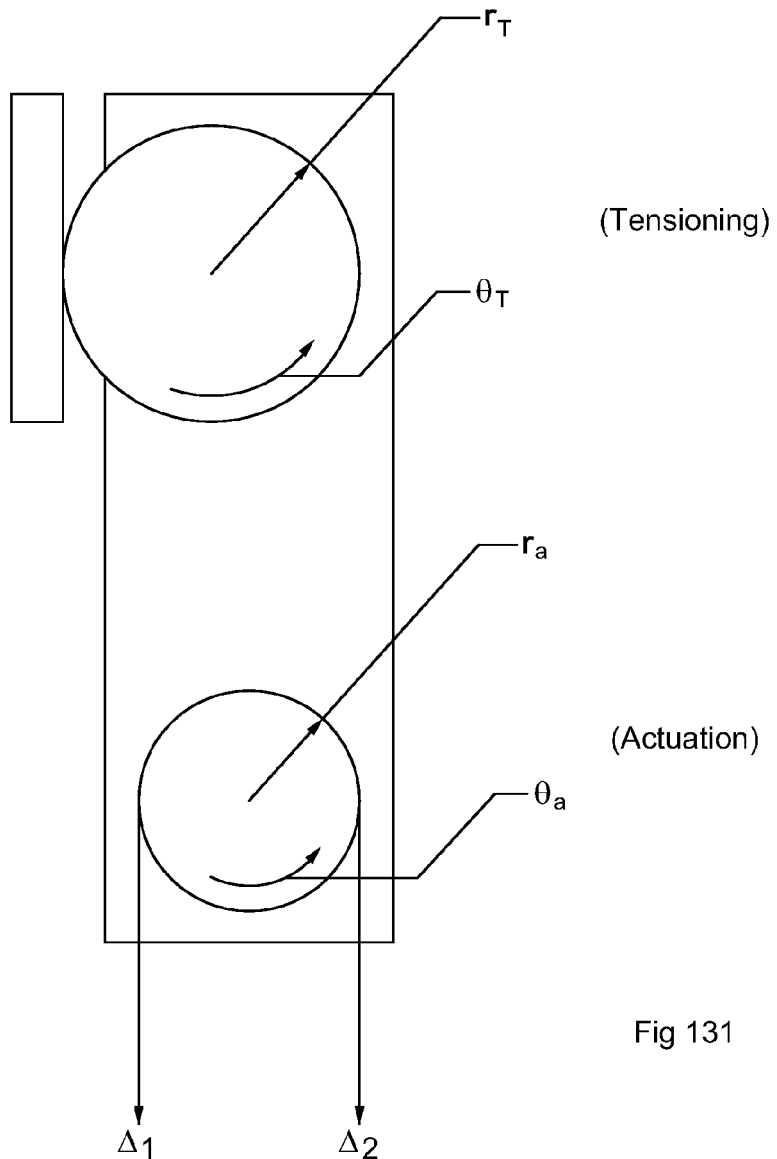

Actuation $\quad \varnothing_a = \dfrac{(\Delta_1 - \Delta_2)}{\Delta_c} \quad$ [Radians] $\quad$ 366

Tension $\quad \delta_T = \Delta_1 - \Delta_2 \quad$ [mm]

$$\varnothing_a = \left(\dfrac{2 \cdot r_a}{\Delta_c}\right) \theta_a \qquad \text{Desired Actuation} \quad 368$$

$$\delta_T = (-2\ r_T)\ \theta_T \qquad \text{Desired Tensioning}$$

Desired Tension - 1 DOF:

$$\delta_T = K_T \|\varnothing_a\|$$

Desired Tension - 2 DOF (i.e., pitch & yaw):

$$\begin{pmatrix} \delta_{T_{Pitch}} \\ \delta_{T_{Yaw}} \end{pmatrix} = \begin{bmatrix} K_T & K_{TC} \\ K_{TC} & K_T \end{bmatrix} \cdot \begin{pmatrix} \varnothing_{a_{Pitch}} \\ \varnothing_{a_{Yaw}} \end{pmatrix}$$

Tension coupling ← 370     Tension slope

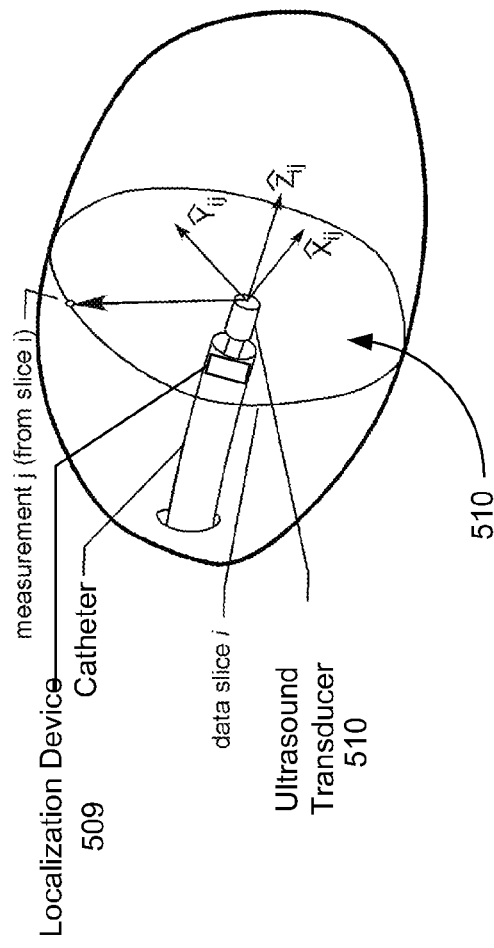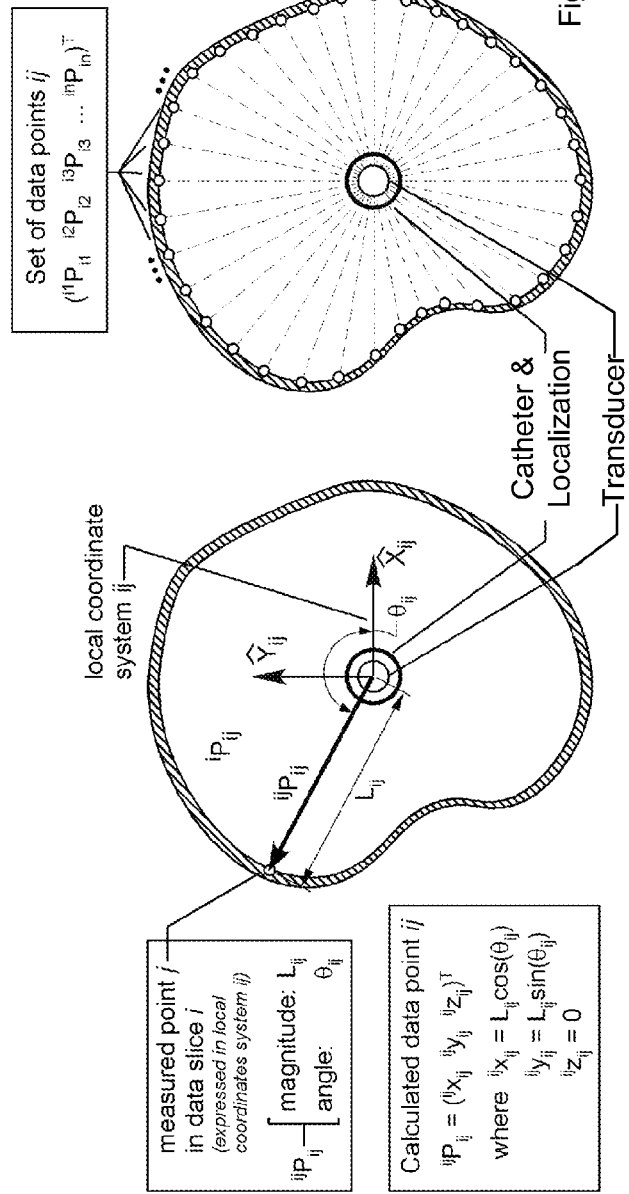

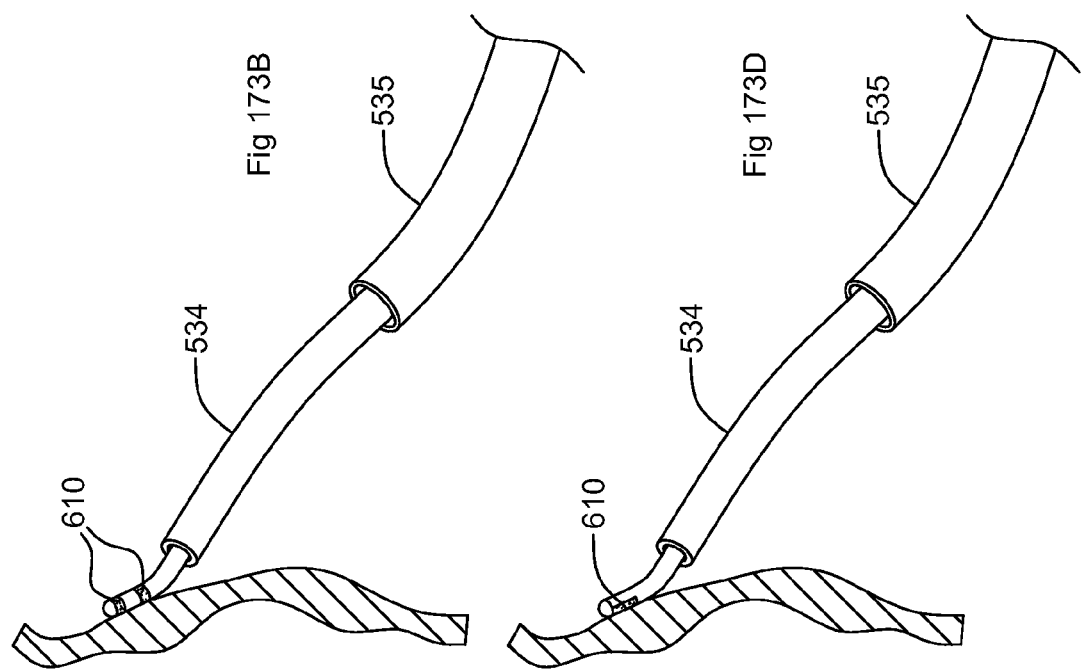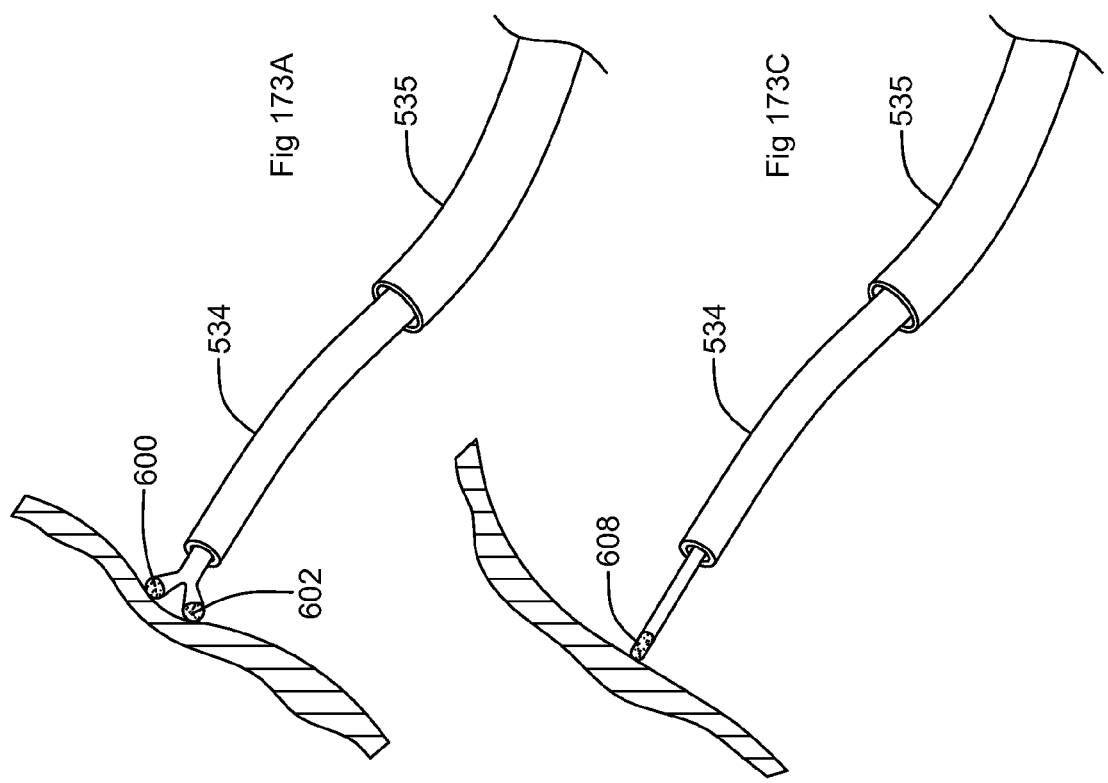

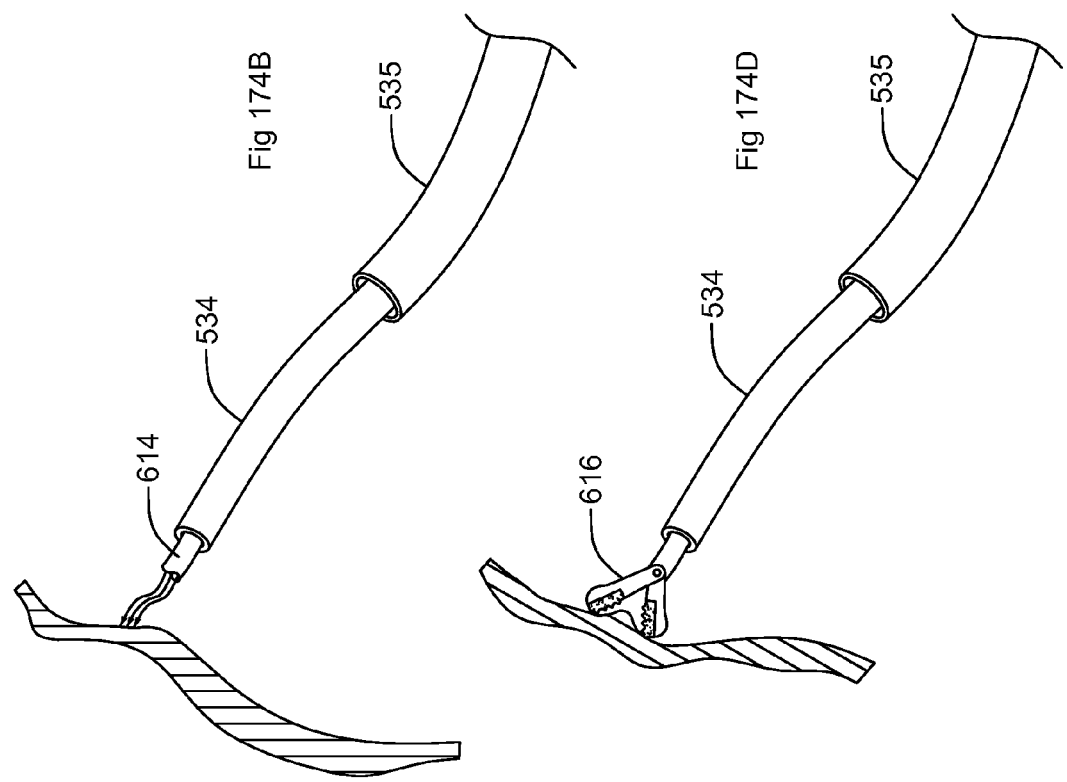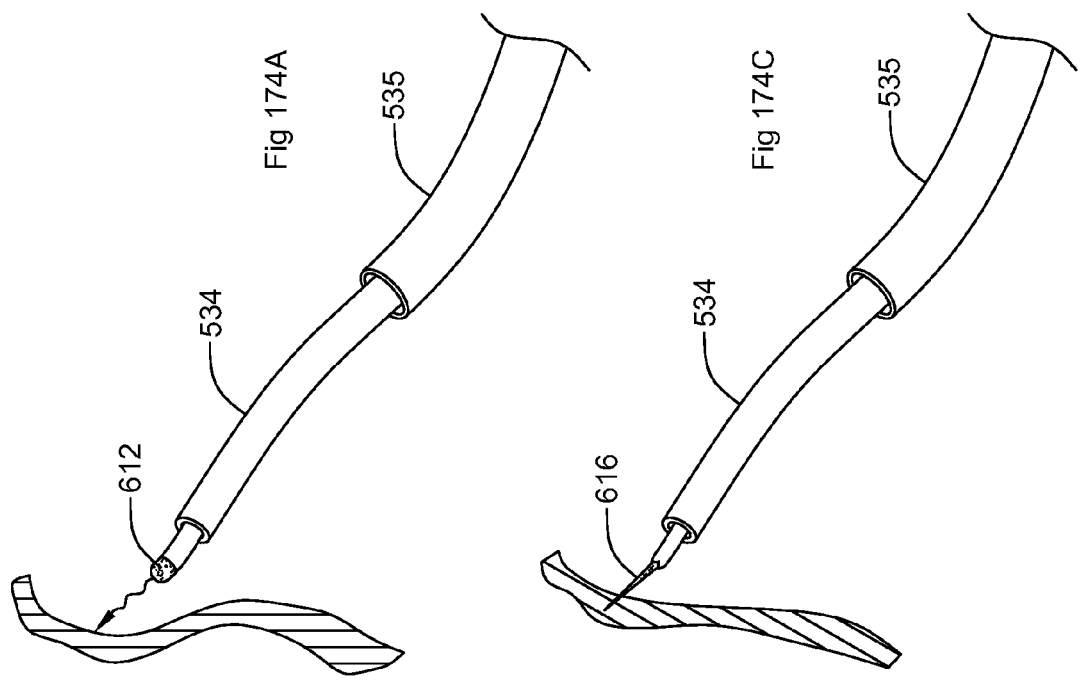

ROBOTIC CATHETER SYSTEM

RELATED APPLICATION DATA

The present application is a continuation of pending U.S. patent application Ser. No. 11/073,363, filed Mar. 4, 2005, which claims the benefit under 35 U.S.C. §119 to U.S. provisional patent application Ser. Nos. 60/550,961, filed Mar. 5, 2004, 60/553,029, filed Mar. 12, 2004, 60/600,869, filed Aug. 12, 2004, and 60/644,505, filed Jan. 13, 2005. The foregoing applications are hereby incorporated by reference into the present application in their entirety.

FIELD OF INVENTION

The invention relates generally to robotically controlled systems, such as telerobotic surgical systems, and more particularly to a robotic catheter system for performing minimally invasive diagnostic and therapeutic procedures.

BACKGROUND

Robotic surgical systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be preferably accessed only via naturally-occurring pathways such as blood vessels or the gastrointestinal tract.

SUMMARY OF THE INVENTION

In accordance with a general aspect of the invention, a robotic catheter system is provided. The system includes a controller having a master input device. An instrument driver is in communication with the controller, the instrument driver having a guide instrument interface including a plurality of guide instrument drive elements responsive to control signals generated, at least in part, by the master input device. The system further includes an elongate guide instrument having a base, distal end, and a working lumen, the guide instrument base being operatively coupled to the guide instrument interface. The guide instrument comprises a plurality of guide instrument control elements operatively coupled to respective guide drive elements and secured to the distal end of the guide instrument. The guide instrument control elements are axially moveable relative to the guide instrument such that movement of the guide instrument distal end may be controlled by movement of the master input device. In some embodiments, an operative contact sensing element is carried on the distal end of the guide instrument.

In some embodiments, the system comprises an elongate sheath instrument having a base, distal end, and a lumen through which the guide instrument is coaxially disposed. In such embodiments, the instrument driver preferably includes a sheath instrument interface operatively coupled to the sheath instrument base, wherein the instrument driver may be configured such that the guide instrument interface is moveable relative to the sheath instrument interface, whereby the guide instrument is moveable axially relative to the sheath instrument. The sheath instrument interface may further include a sheath instrument drive element responsive to control signals generated, at least in part, by the master input device, the sheath instrument comprising a sheath instrument control element operatively coupled to the sheath instrument drive element and secured to the distal end of the sheath instrument, the sheath instrument control element axially moveable relative to the sheath instrument such that movement of the sheath instrument distal end may be controlled by movement of the master input device. An outer surface of the guide instrument and a surface defining the sheath instrument lumen may be jointly configured to limit rotational movement of the guide instrument relative to the sheath instrument.

The controller and instrument driver are preferably configured to independently control the guide instrument drive elements and corresponding guide instrument control elements in order to achieve a desired bending of the guide instrument distal end. In particular, the controller can determine a tensioning to be applied to a respective guide instrument control element based on a kinematic relationship between the desired bending and a linear movement of the guide instrument control element relative to the guide instrument.

In accordance with another aspect of the invention, a working instrument may be disposed through the working lumen of, and be axially movable relative to, the guide instrument. By way of non-limiting examples, the working instrument may be an ablation catheter, a guidewire, or an instrument comprising one or both of a dialator and a needle.

The robotic catheter system may further comprises an imaging system and a display, each operatively coupled to the controller. By way of non-limiting examples, the imaging system may be an ultrasound imaging system, an optical imaging system, a fluoroscopic imaging system, a computer tomography imaging system, or an MR imaging system. In one embodiment, the imaging system includes an elongate imaging instrument with an operative imaging element on a distal portion thereof. The imaging instrument is configured for placement in a body passage or cavity, the operative imaging element being configured for acquiring images of the body passage or cavity, the imaging system being configured for presenting the acquired images on the display. In certain embodiments of the invention, the controller determines a tensioning to be applied to a respective guide instrument control element based on data from the acquired images.

The robotic catheter system may further comprise a localization system, e.g., an ultrasound localization system or an electromagnetic localization system, that is operatively coupled to the controller and configured to obtain position information of the guide instrument. In certain embodiments of the invention, the controller determines a tensioning to be applied to a respective guide instrument control element based on data from the localization system.

Other and further embodiments and aspects of the invention will become apparent upon review of the following detailed description in view of the illustrated embodiments.

BRIEF DESCRIPTION OF THE DRAWINGS

The drawings illustrate the design and utility of illustrated embodiments of the invention, in which similar elements are referred to by common reference numerals, and in which:

FIGS. 9-12 illustrate different drapes in accordance with some embodiments;

FIG. 15 illustrates a drape for use with an instrument driver in accordance with other embodiments;

FIG. 16 illustrates a covering assembly for use with an instrument driver in accordance with some embodiments;

FIGS. 106-109 illustrate kinematics of a catheter in accordance with various embodiments;

FIGS. 110A-110E illustrates different bending configurations of a catheter in accordance with various embodiments;

FIG. 111 illustrates a control system in accordance with some embodiments;

FIG. 125 illustrates forward kinematics and inverse kinematics in accordance with some embodiments;

FIG. 130 illustrates a method for converting an operator hand motion to a catheter motion in accordance with some embodiments;

FIG. 131 illustrates a diagram representing an operation of the device of FIG. 102 in accordance with some embodiments;

FIG. 132 illustrates a set of equations associated with the diagram of FIG. 131;

FIGS. 133-136 illustrate equations associated with an operation of a guide instrument interface socket in accordance with some embodiments;

FIG. 142 illustrates a circumferentially-firing ultrasound catheter device in accordance with some embodiments;

FIG. 143 illustrates two views taken along a longitudinal axis of the catheter device of FIG. 142 in accordance with some embodiments;

FIG. 144 illustrates mathematics for transforming position and orientation data from a local reference to a desired frame of reference;

FIGS. 145A-145B illustrate two views of a catheter being used to acquire data slices in a tissue cavity in accordance with some embodiments;

FIGS. 146A-146D illustrate different configurations of a catheter being used to acquire slice data within a tissue cavity;

FIG. 147 illustrates different bending configurations of a catheter in accordance with some embodiments;

FIGS. 148A-148C illustrate different embodiments of a method for generating a three dimensional model of a tissue cavity;

FIG. 149 illustrates a method for acquiring a three-dimensional tissue structure model in accordance with some embodiments;

FIG. 150 illustrates a method for acquiring a three-dimensional tissue structure model in accordance with other embodiments FIG. 151 illustrates an instrument having localization capability in accordance with some embodiments;

FIG. 152 illustrates an instrument having two vibratory devices in accordance with some embodiments;

FIG. 153 illustrates an instrument having tissue sensing capability in accordance with some embodiments;

FIG. 154 illustrates the instrument of FIG. 153 being used on a patient in accordance with some embodiments;

FIG. 155 illustrates a circuit diagram associated with the instrument of FIG. 153 in accordance with some embodiments;

Figure 156:
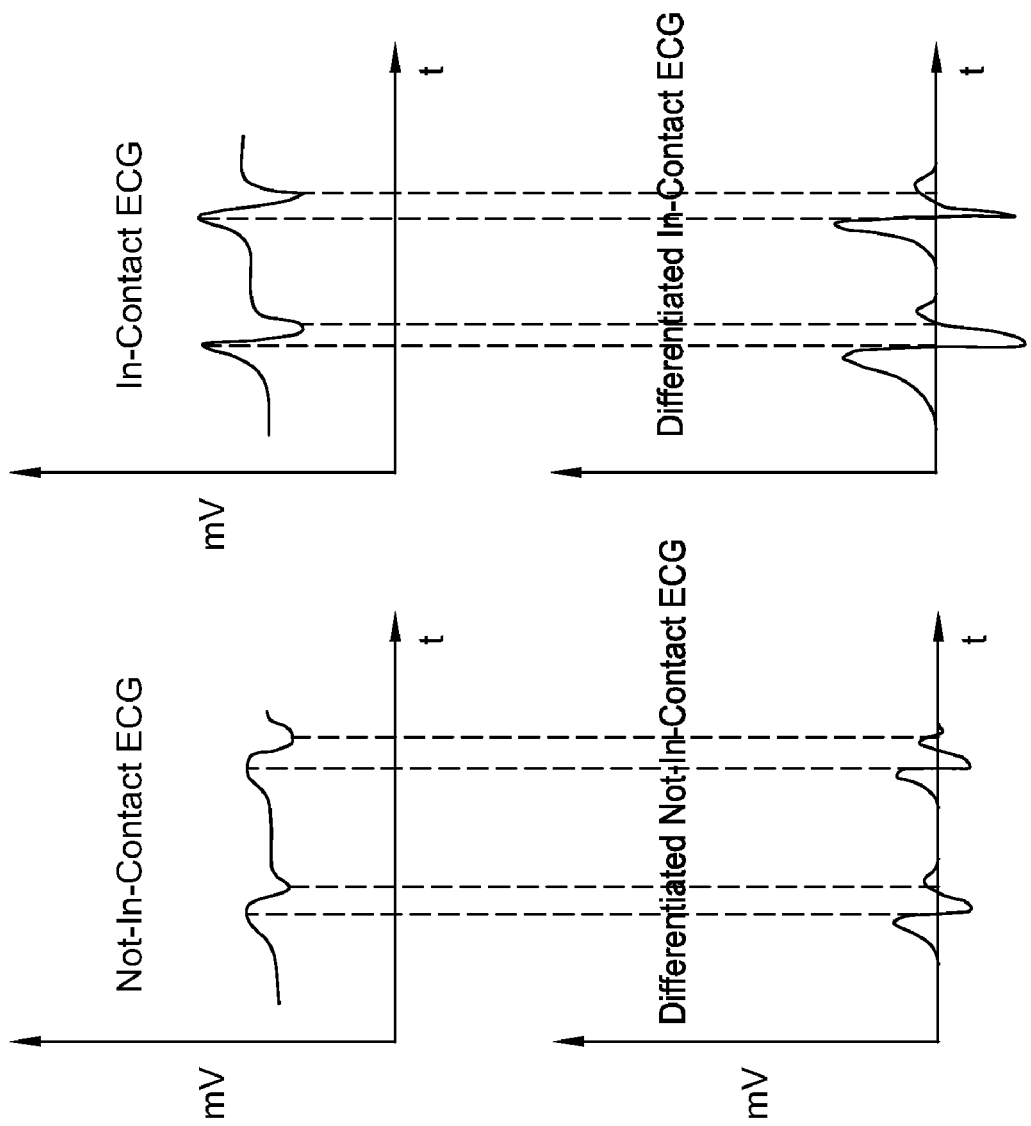
Figure 157:
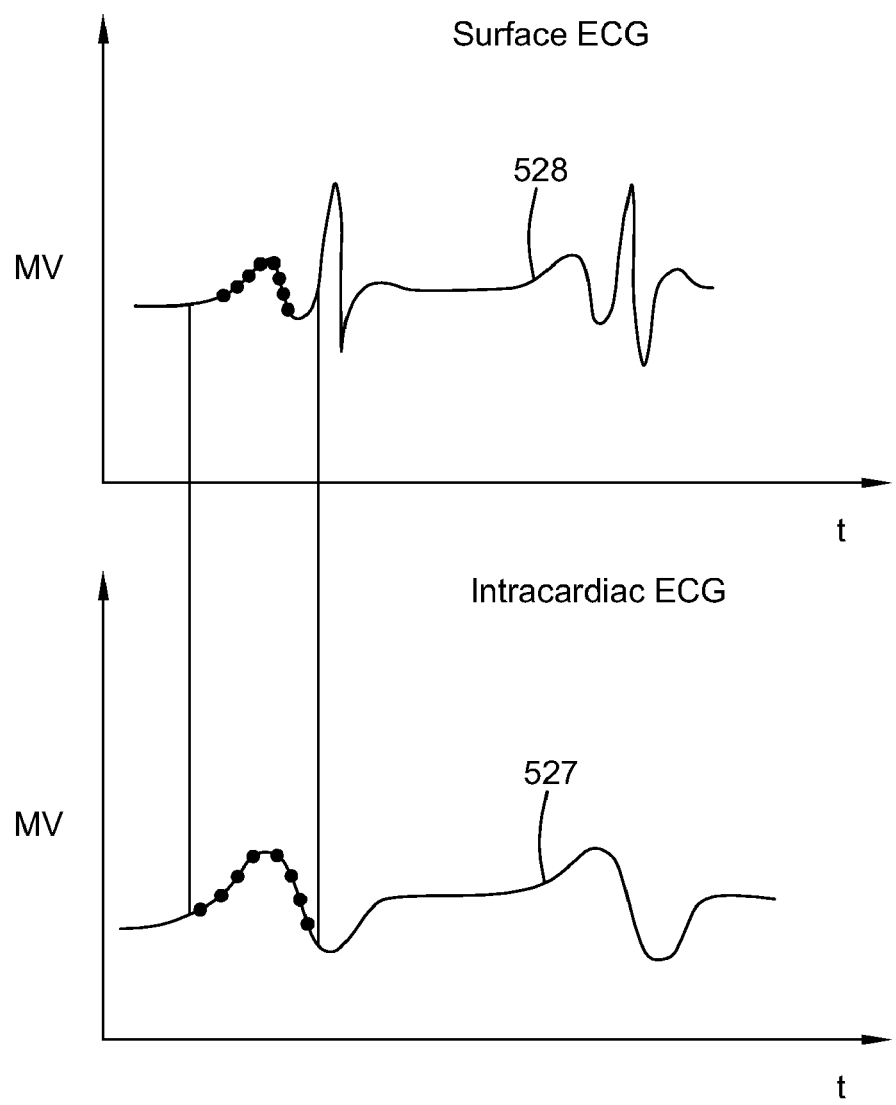
Figure 158A:
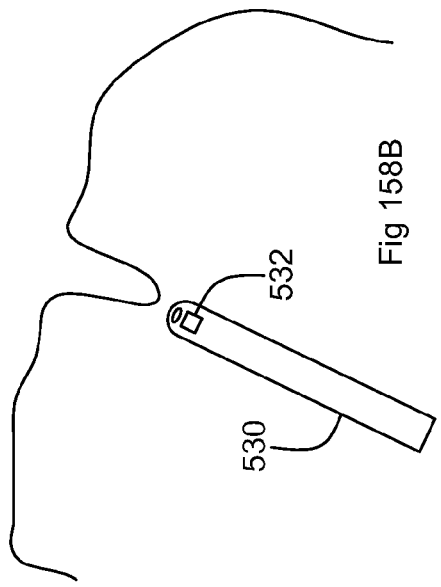
Figure 158B:
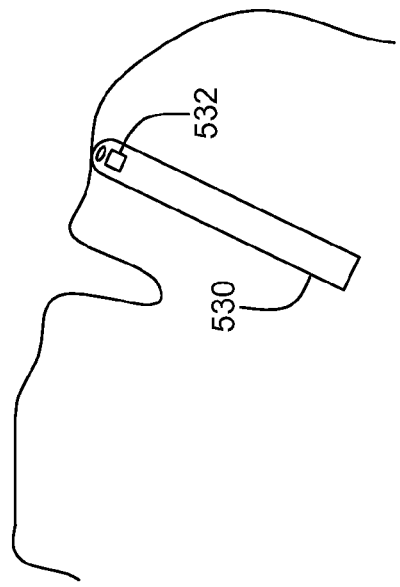
Figure 158C:
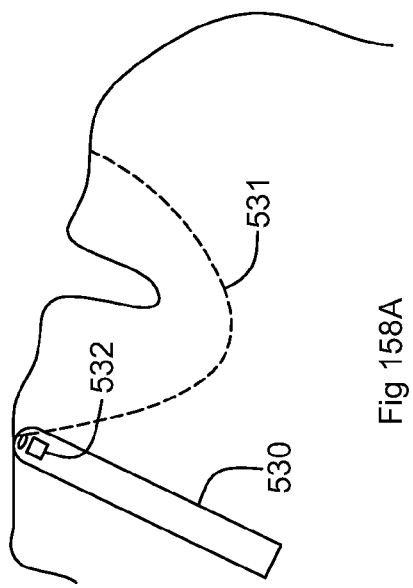
Figure 158D:
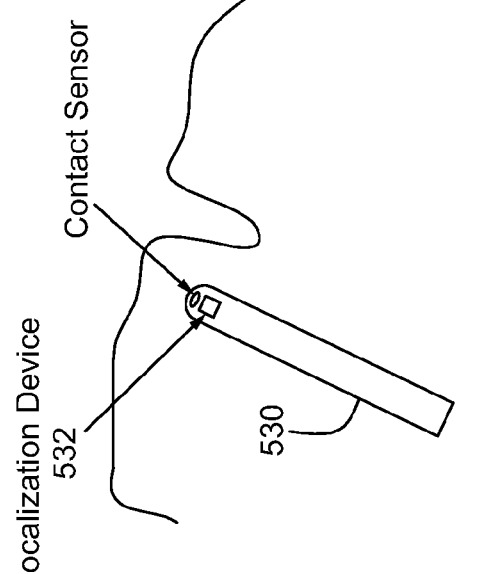
Figure 159B:
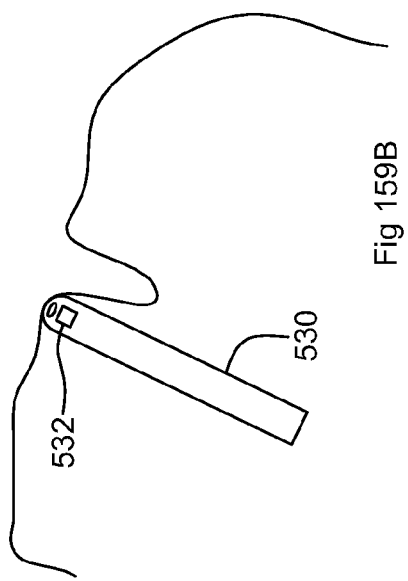
Figure 159D:
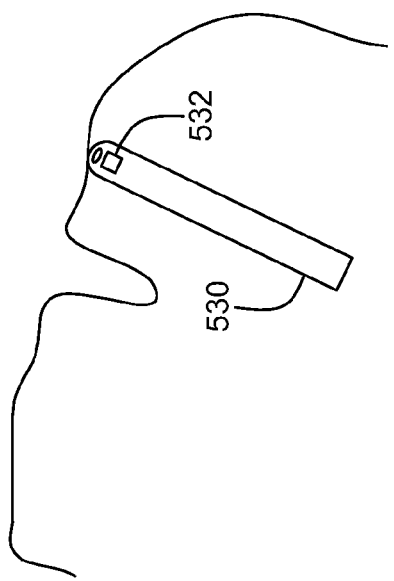
Figure 159A:
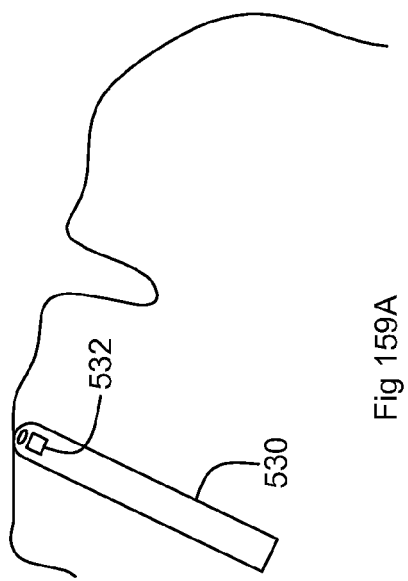
Figure 159C:
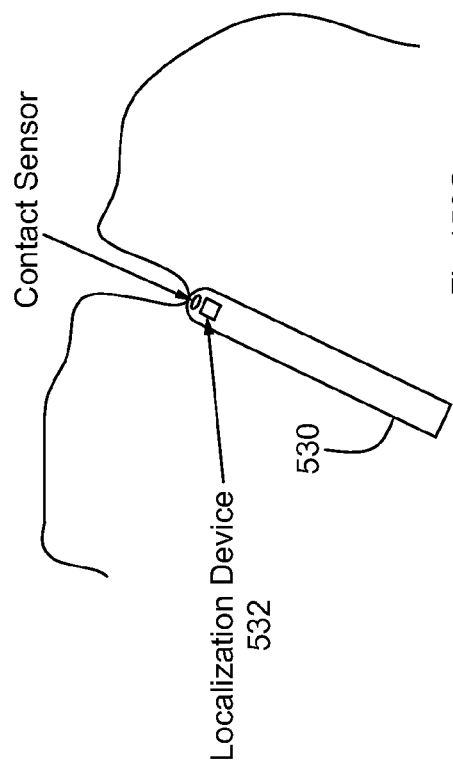
Figure 160B:
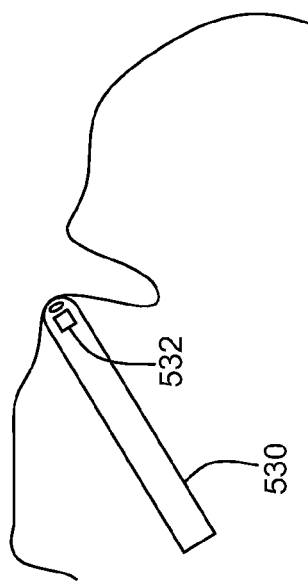
Figure 160D:
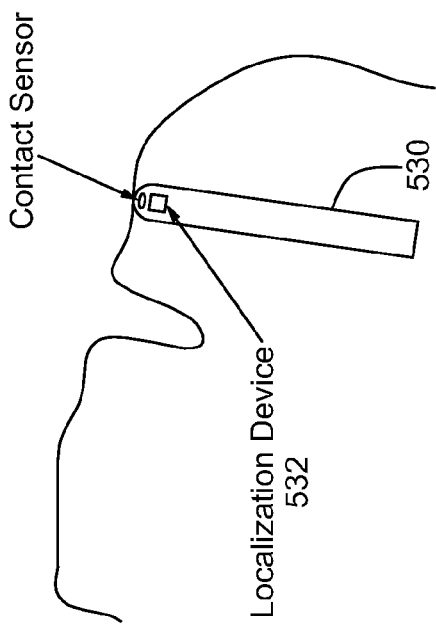
Figure 160A:
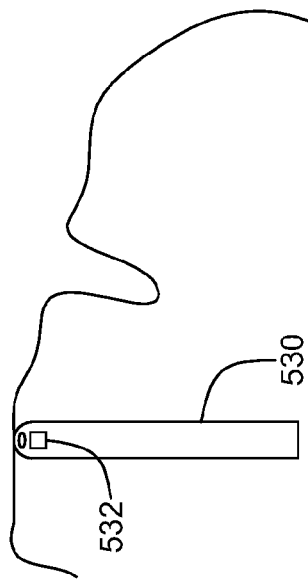
Figure 160C:
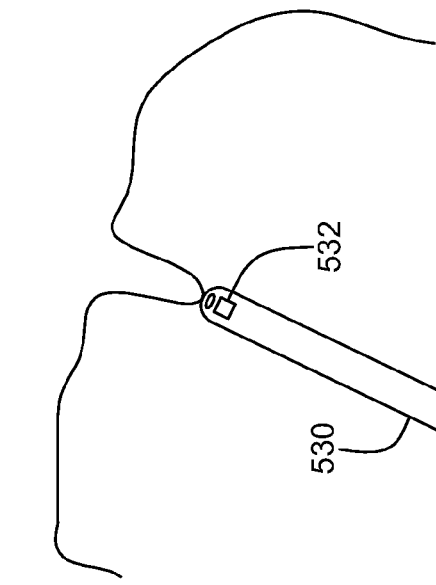
Figure 170:
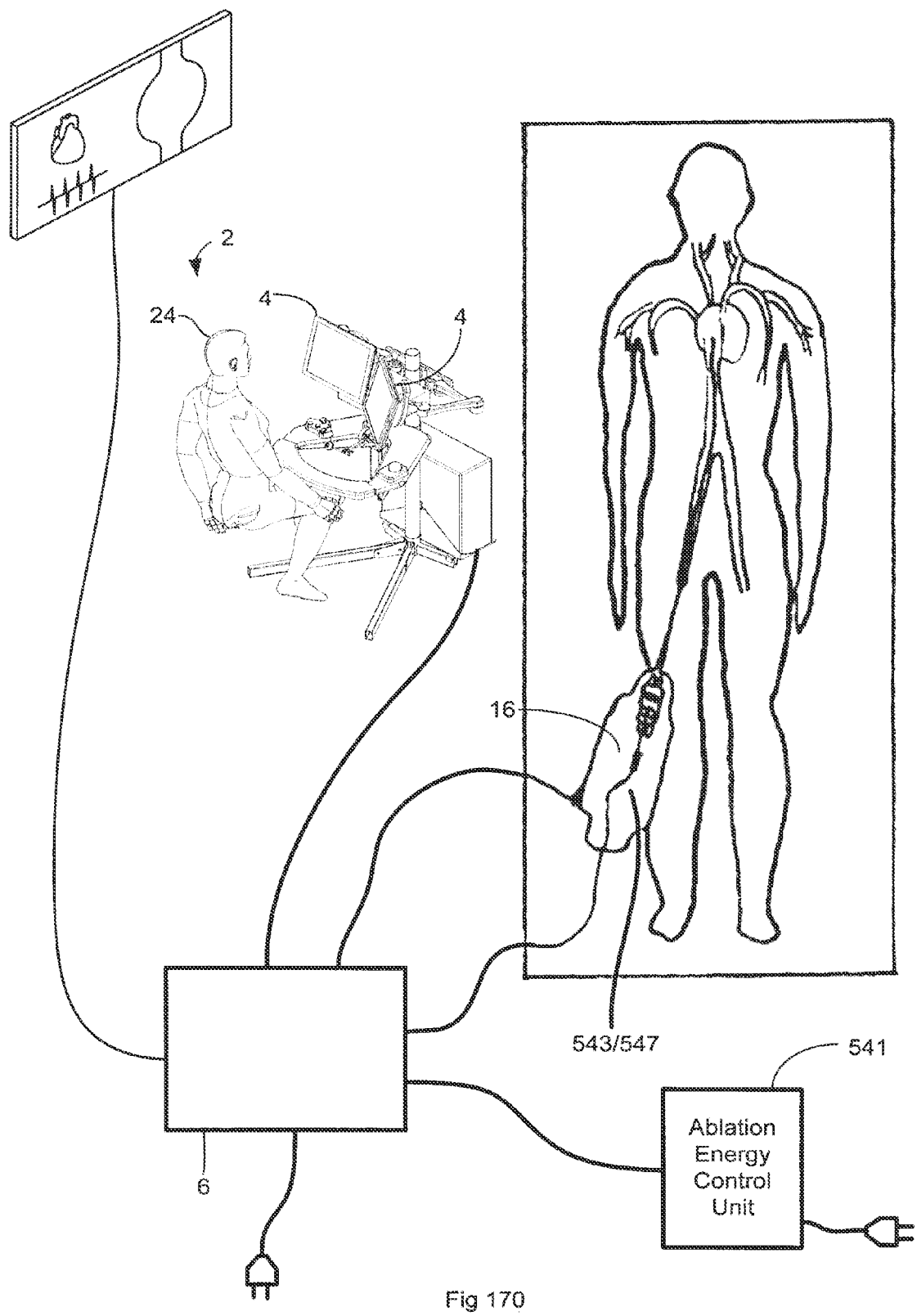
Figure 171:
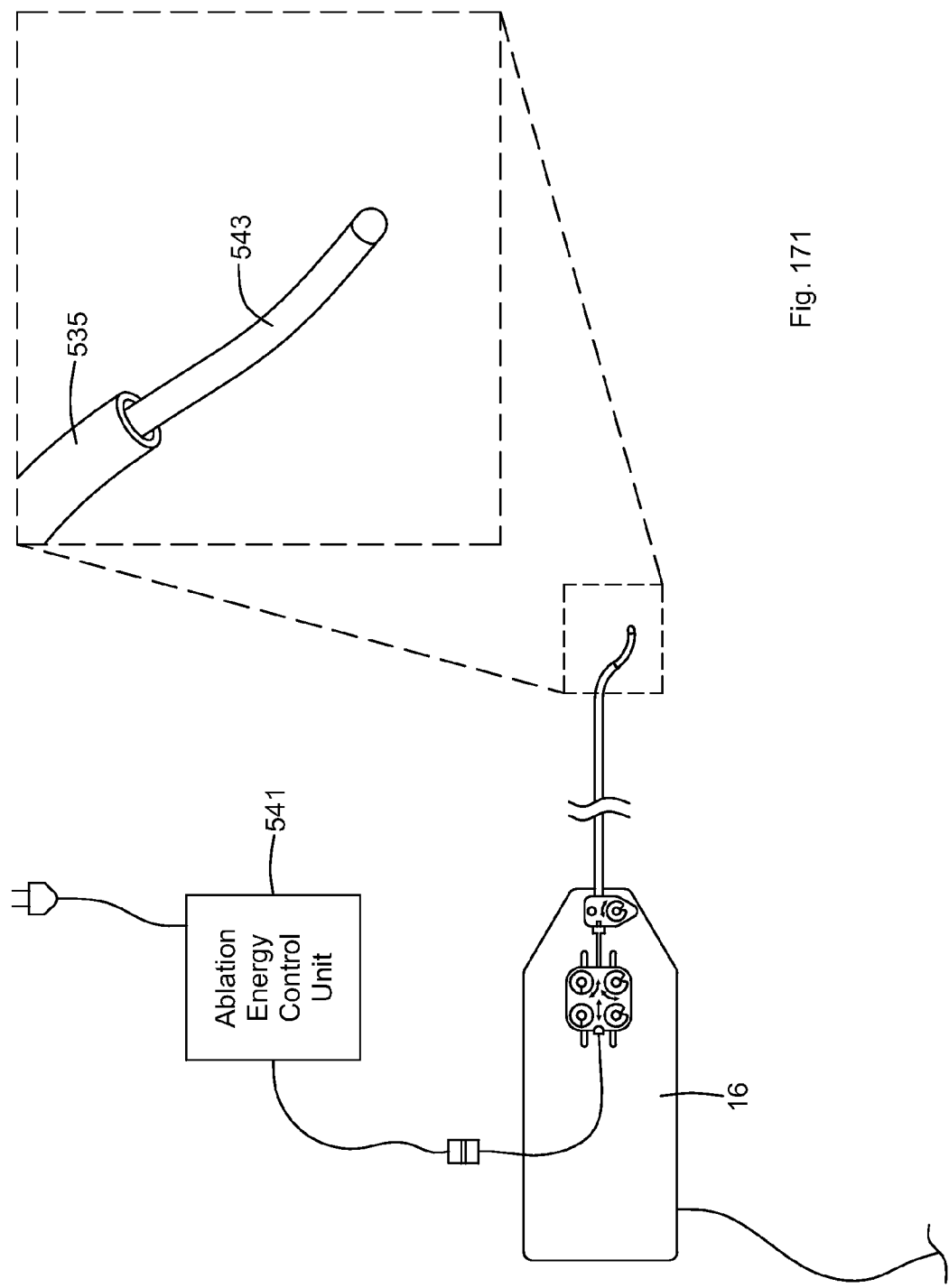
Figure 172:
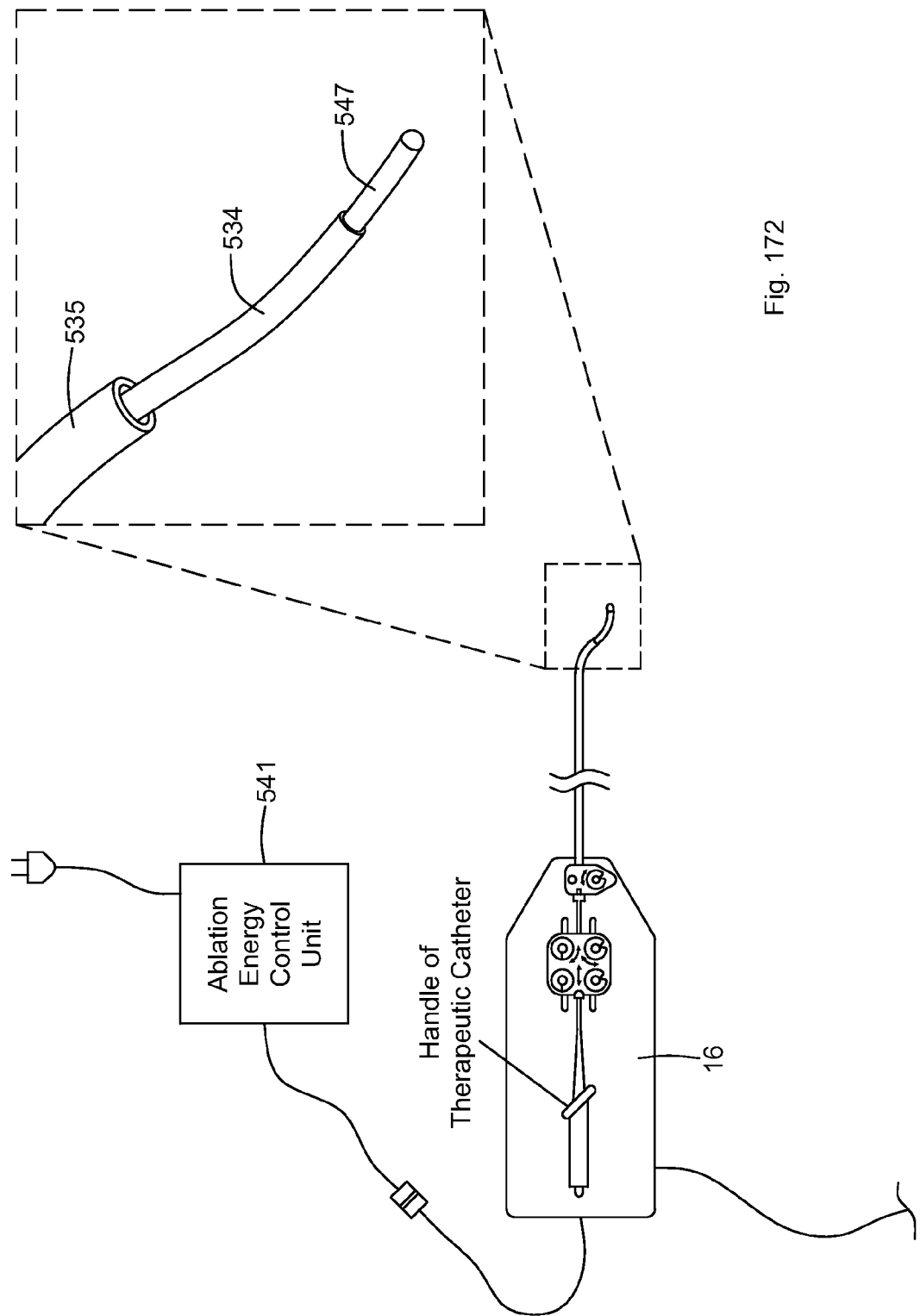

FIG. 156 illustrates examples of various ECG signals;

FIG. 157 illustrates a signal processing technique for comparing an intracardiac ECG signal with a body surface ECG signal in accordance with some embodiments;

FIGS. 158A-158D illustrate a method of moving a distal end of an instrument from a first position to a second position in accordance with some embodiments;

FIGS. 159A-159D illustrate a method of moving a distal end of an instrument from a first position to a second position in accordance with other embodiments;

FIGS. 160A-160D illustrate a method of moving a distal end of an instrument from a first position to a second position in accordance with other embodiments;

FIGS. 161-169 illustrate a method of using a robotically controlled guide catheter instrument and sheath instrument in an atrial septal approach in accordance with some embodiments;

FIG. 170 illustrates a system having an instrument driver and an ablation energy control unit in accordance with some embodiments;

FIG. 171 illustrates the instrument driver of FIG. 170, showing a therapeutic catheter inserted through a sheath catheter in accordance with some embodiments;

FIG. 172 illustrates the instrument driver of FIG. 170, showing a guide catheter inserted through a sheath catheter, and a therapeutic catheter inserted through the guide catheter in accordance with some embodiments;

FIG. 173A illustrates a device inserted through a guide catheter in accordance with some embodiments, showing the device having two bipolar electrodes;

FIG. 173B illustrates a device inserted through a guide catheter in accordance with some embodiments, showing the device having two bipolar electrodes spaced axially;

FIG. 173C illustrates a device inserted through a guide catheter in accordance with some embodiments, showing the device having a monopolar electrode;

FIG. 173D illustrates a device inserted through a guide catheter in accordance with some embodiments, showing the device having a side monopolar electrode;

FIG. 174A illustrates a device inserted through a guide catheter in accordance with some embodiments, showing the device having an energy transmitter;

FIG. 174B illustrates a device inserted through a guide catheter in accordance with some embodiments, showing the device having a laser generator;

FIG. 174C illustrates a device inserted through a guide catheter in accordance with some embodiments, showing the device having a needle; and FIG. 174D illustrates a device inserted through a guide catheter in accordance with some embodiments, showing the device having a tissue disruption mechanism.

DETAILED DESCRIPTION OF THE ILLUSTRATED EMBODIMENTS

Figure 1:
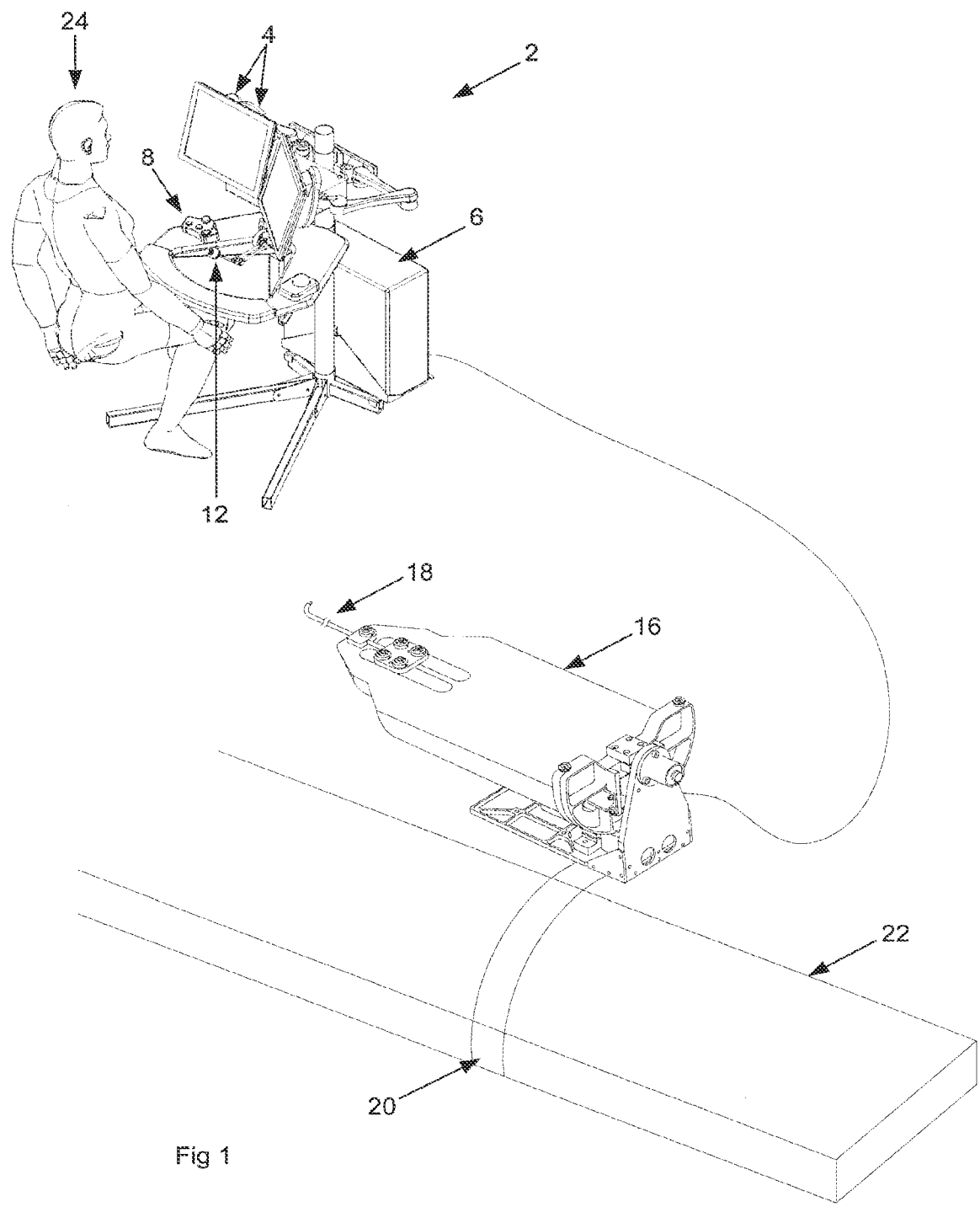
FIG. 1 illustrates a robotic surgical system in accordance with some embodiments.

Referring to FIG. 1, one embodiment of a robotic surgical system (32), includes an operator control station (2) located remotely from an operating table (22), to which a instrument driver (16) and instrument (18) are coupled by a instrument driver mounting brace (20). A communication link (14) transfers signals between the operator control station (2) and instrument driver (16). The instrument driver mounting brace (20) of the depicted embodiment is a relatively simple, arcuate-shaped structural member configured to position the instrument driver (16) above a patient (not shown) lying on the table (22).

Figure 2:
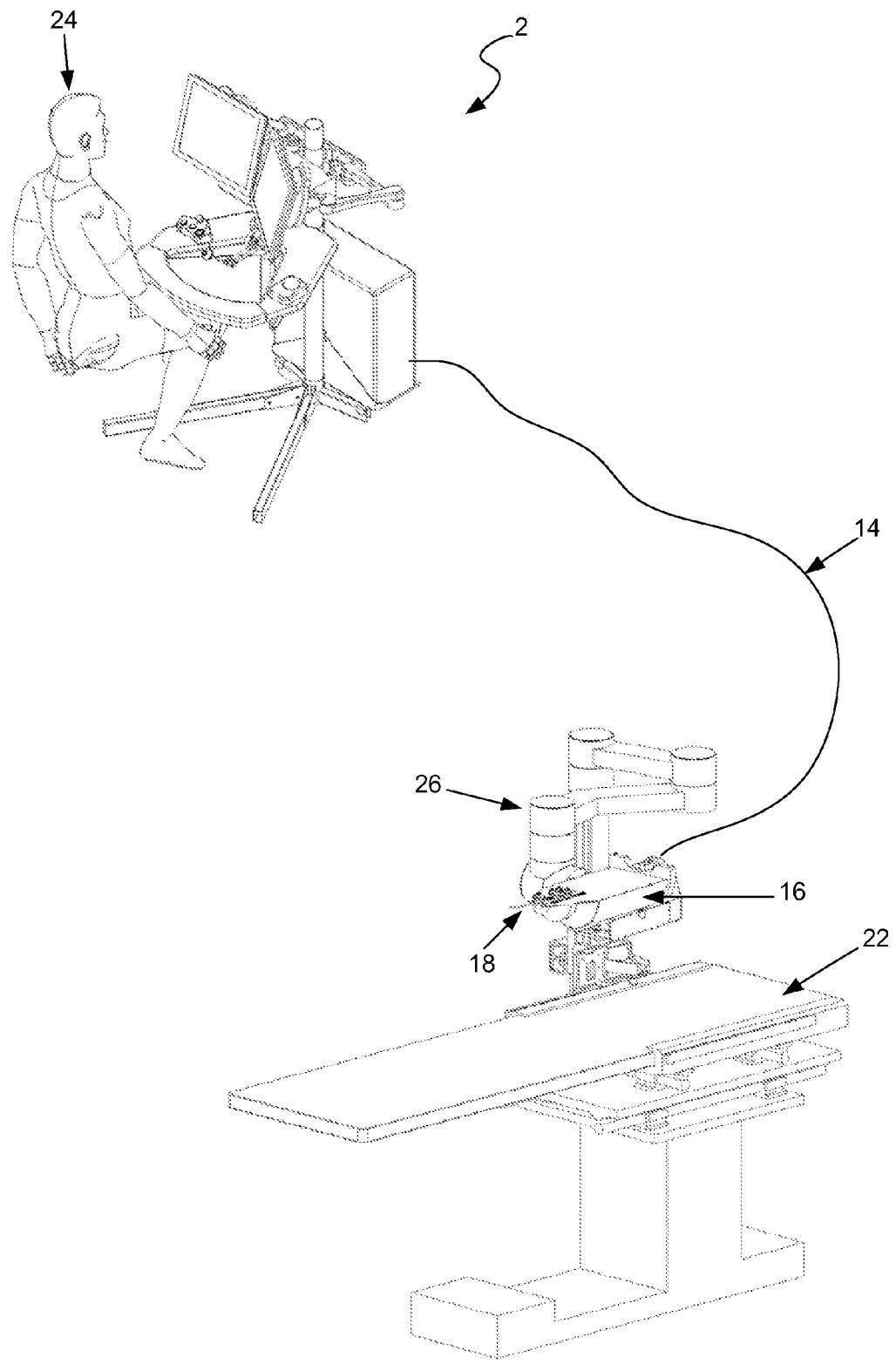
FIG. 2 illustrates a robotic surgical system in accordance with other embodiments.
Figure 3:
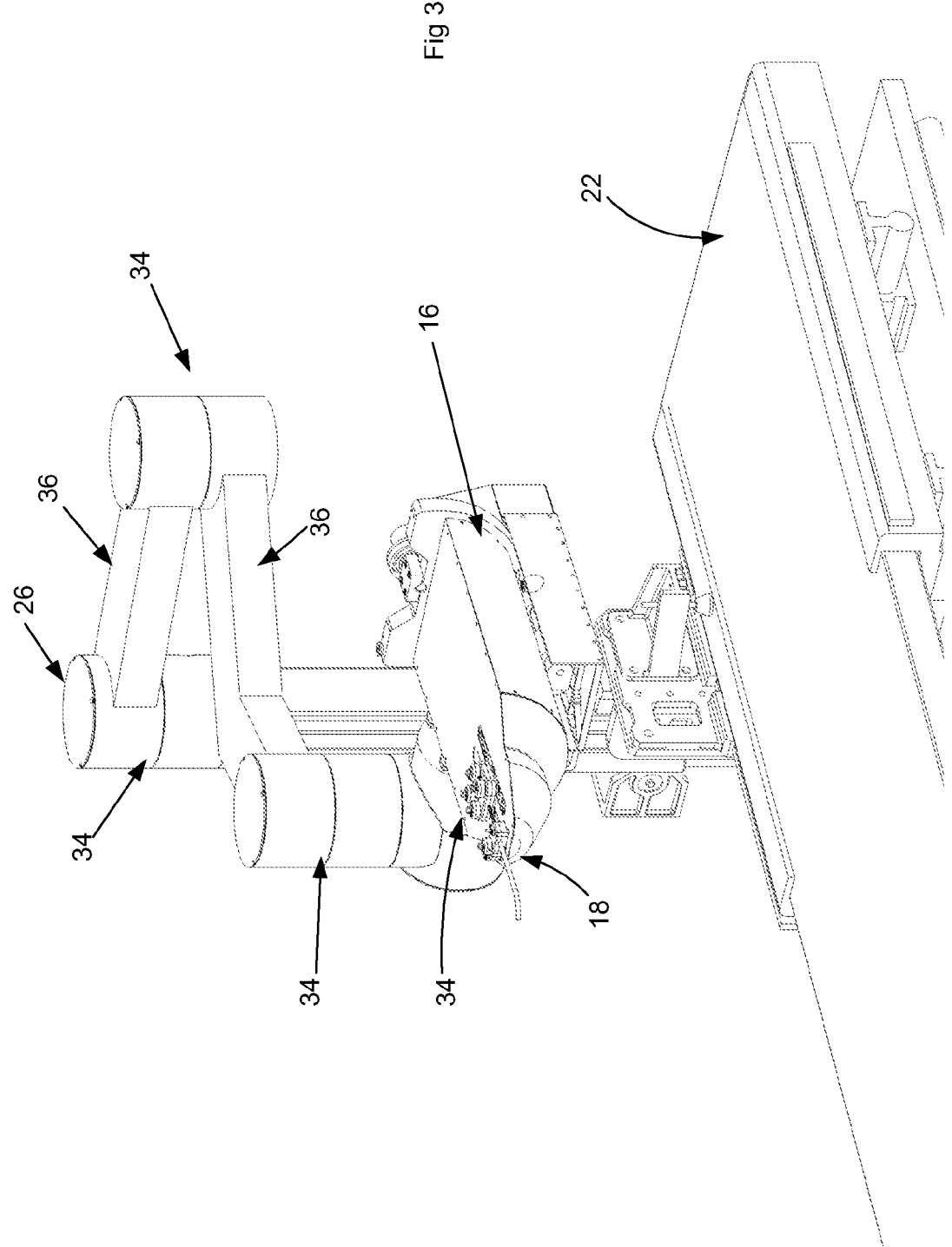
FIG. 3 illustrates a closer view of the robotic surgical system of FIG. 2.

Referring to FIG. 2, another embodiment is depicted wherein a movable setup mount (26) is configured to movably support the instrument driver (16) above the table (22) to provide convenient access to the desired portions of the patient (not shown) and provide a means to lock the instrument driver (16) into position subsequent to preferred placement. FIG. 3 provides a closer view of the embodiment depicted in FIG. 2, showing the movable setup mount (26) in further detail. In one embodiment, the movable setup mount comprises a series of rigid links coupled by electronically braked joints (34) which prevent joint motion when unpowered, and allow joint motion when energized by a control system, such as a switch or computer interface. In another embodiment, the rigid links may be coupled by more conventional mechanically lockable joints, which may be locked and unlocked manually using, for example, locking pins, screws, or clamps. The rigid links (36) preferably comprise a light but strong material, such as high-gage aluminum, shaped to withstand the stresses and strains associated with precisely maintaining three-dimensional position of the approximately ten pound weight of a typical embodiment of the instrument driver (16) sized or intravenous use subsequent to application of the brakes.

Figure 4:
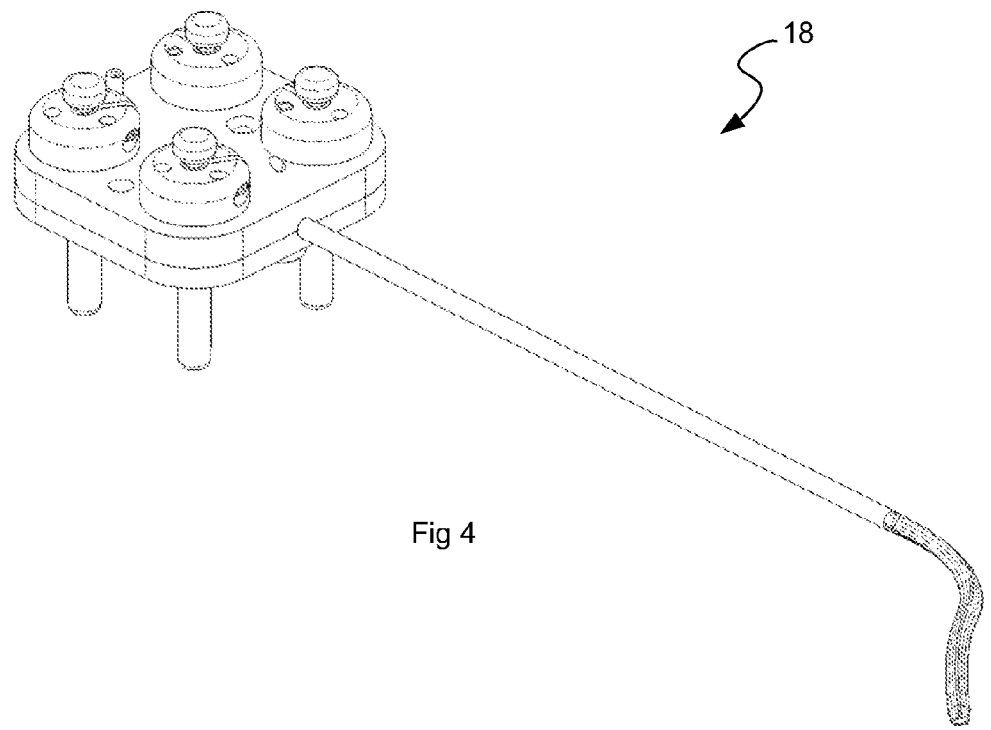
FIG. 4 illustrates an isometric view of an instrument having a guide catheter in accordance with some embodiments.
Figure 5:
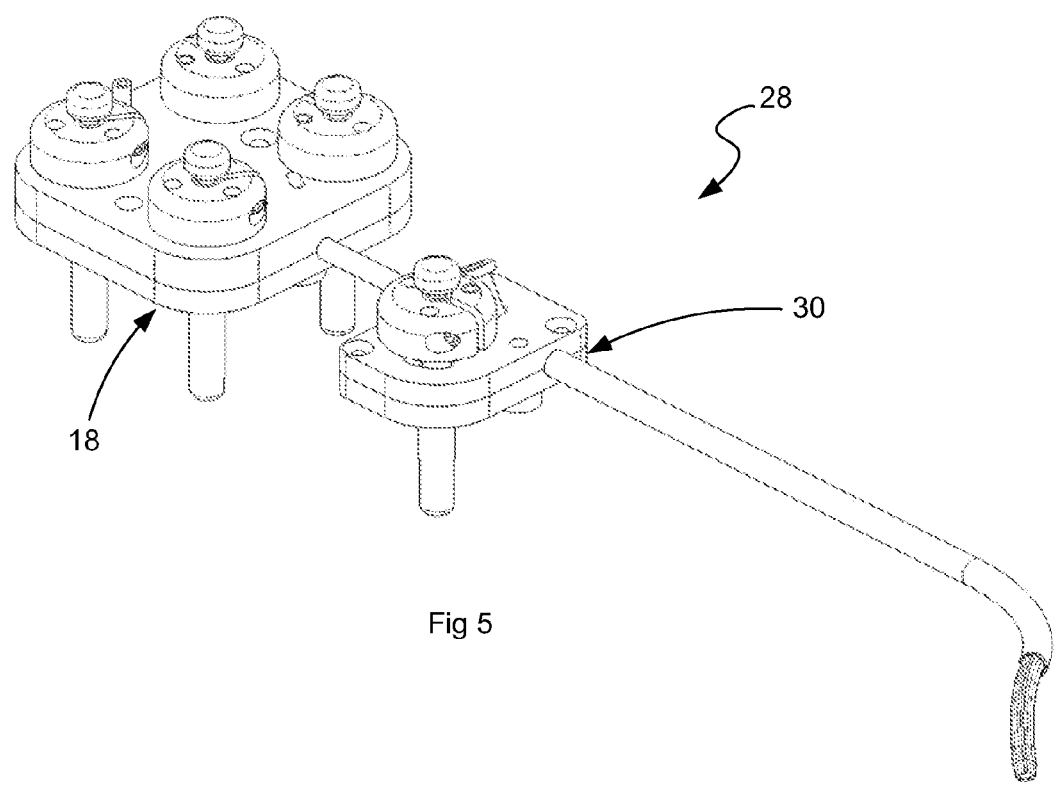
FIG. 5 illustrates an isometric view of the instrument of FIG. 4, showing the instrument coupled to a sheath instrument in accordance with some embodiments.

FIGS. 4 and 5 depict isometric views of respective embodiments of instruments configured for use with an embodiment of the instrument driver (16), such as that depicted in FIGS. 1-3. FIG. 4 depicts an instrument (18) embodiment without an associated coaxial sheath coupled at its midsection. FIG. 5 depicts a set of two instruments (28), combining an embodiment like that of FIG. 4 with a coaxially coupled and independently controllable sheath instrument (30). To distinguish the non-sheath instrument (18) from the sheath instrument (30) in the context of this disclosure, the "non-sheath" instrument may also be termed the "guide" instrument (18).

Figure 6:
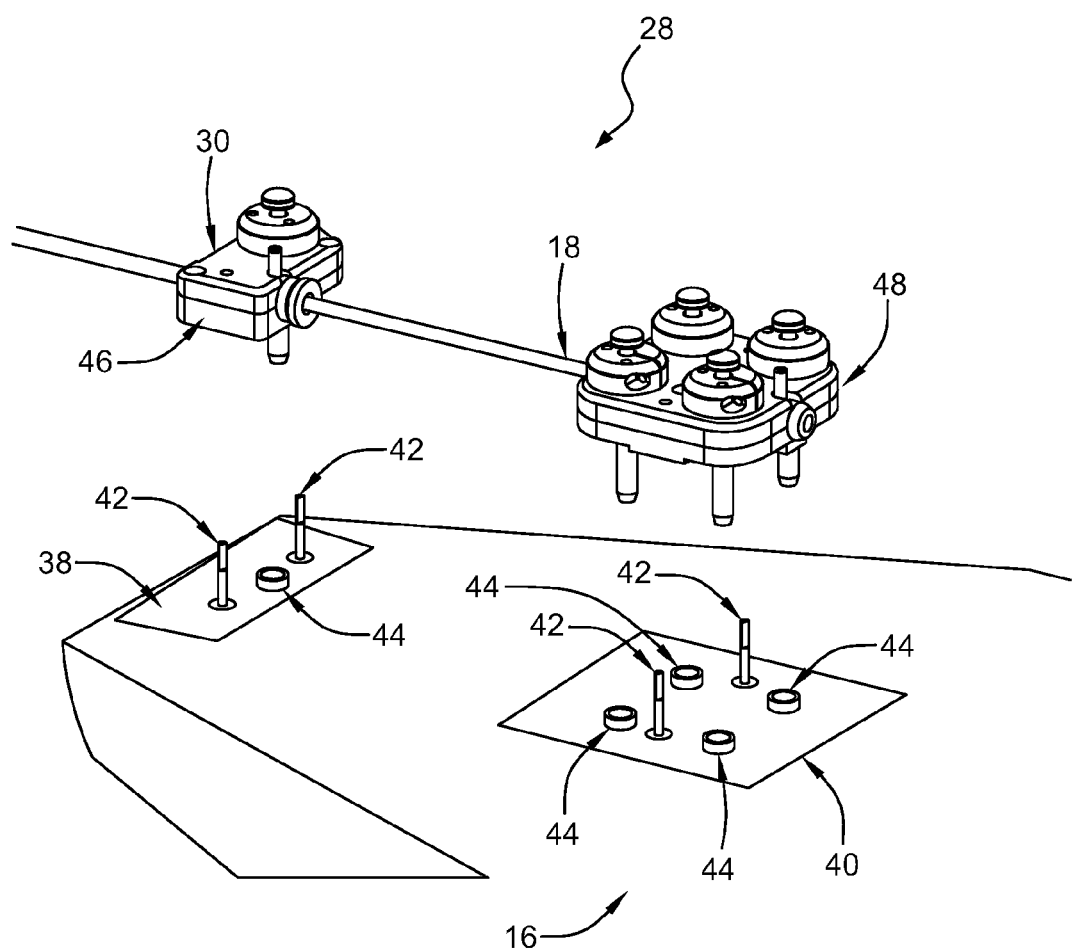
FIG. 6 illustrates an isometric view of a set of instruments for use with an instrument driver in accordance with some embodiments.

Referring to FIG. 6, a set of instruments (28), such as those in FIG. 5, is depicted adjacent an instrument driver (16) to illustrate an exemplary mounting scheme. The sheath instrument (30) may be coupled to the depicted instrument driver (16) at a sheath instrument interface surface (38) having two mounting pins (42) and one interface socket (44) by sliding the sheath instrument base (46) over the pins (42). Similarly, and preferably simultaneously, the guide instrument (18) base (48) may be positioned upon the guide instrument interface surface (40) by aligning the two mounting pins (42) with alignment holes in the guide instrument base (48). As will be appreciated, further steps may be required to lock the instruments (18, 30) into place upon the instrument driver (16).

Figure 7A:
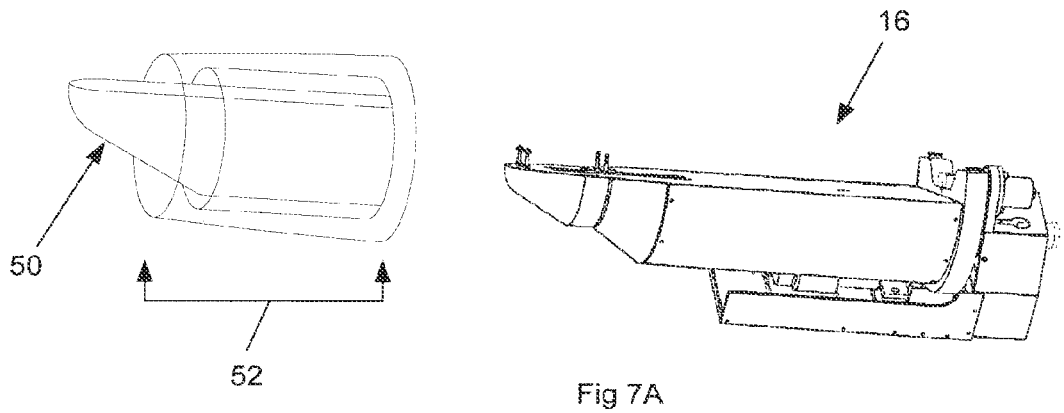
FIGS. 7A-7C illustrate a method of using a drape with an instrument driver in accordance with some embodiments.
Figure 7B:
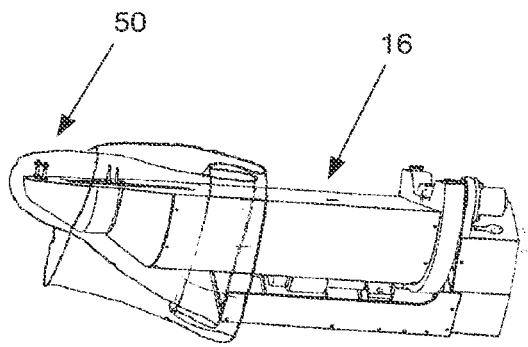
Figure 7C:
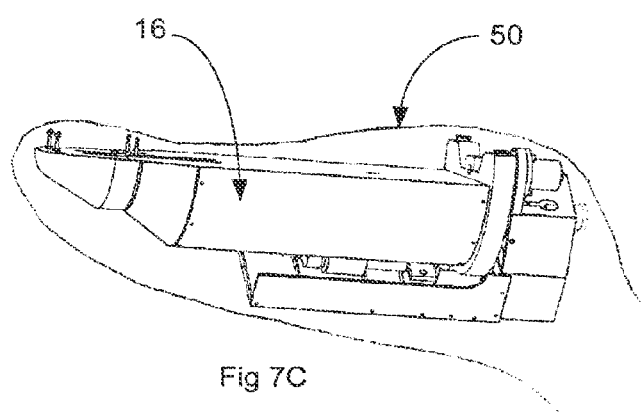

In one embodiment, the instruments (18, 30) are provided for a medical procedure in sterile packaging, while the instrument driver (16) is not necessarily sterile. In accordance with conventional sterile medical procedure, the nonsterile instrument driver (16) must be isolated from the patient by a sterile barrier of some type. Referring to FIGS. 7A-7C, a drape (50)

comprising conventional surgical draping material may be folded into a configuration (52) to enable gloved hands of a person (not shown) to slide the drape (50) over the instrument driver (16), from one end to the other without contamination of the sterile side of the drape (50). The drape (50) is then unrolled around the instrument driver (16), as shown in FIGS. 7B and 7C.

Figure 8A:
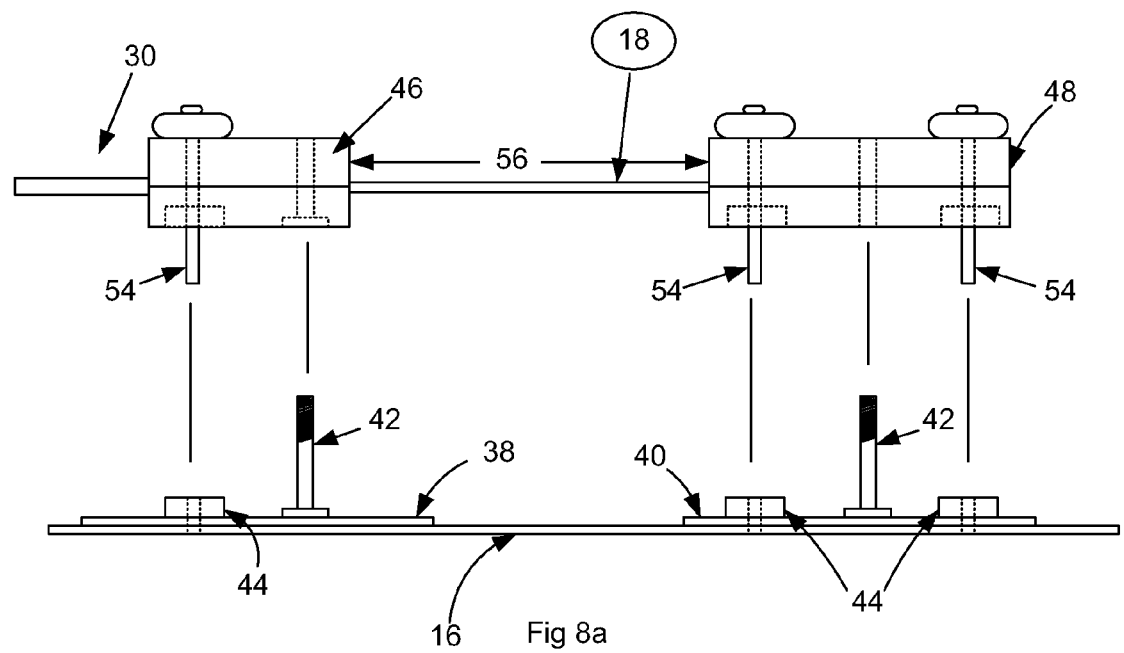
FIG. 8A illustrates an instrument driver and a set of instruments before they are coupled to each other.
Figure 8B:
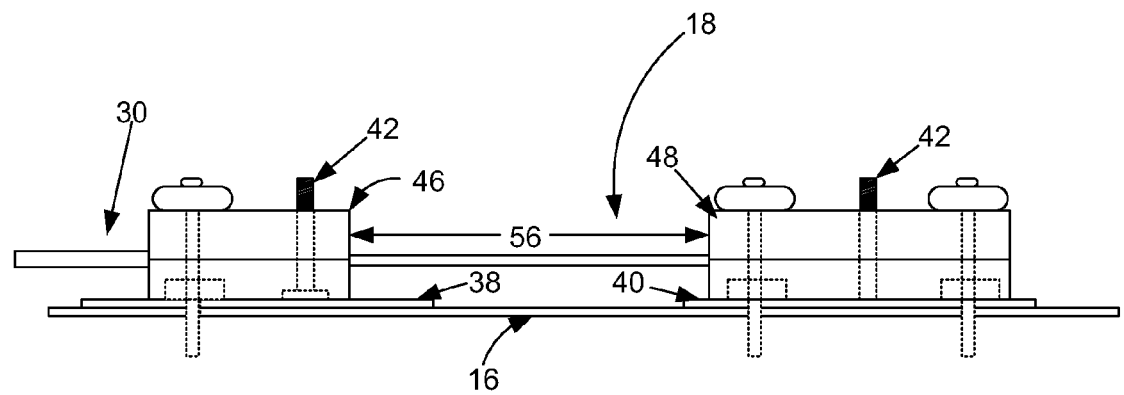
FIG. 8B illustrates the instrument driver and the set of instruments of FIG. 8A after they are coupled to each other.

Referring to FIGS. 8A and 8B, the interfacing between instrument driver (16) and instrument bases (46, 48) utilizing alignment pins (42) is depicted to further illustrate the issues associated with providing a sterile barrier between the instruments and driver. In the illustrated embodiment(s), wherein the instrument is a set of two instruments comprising both a sheath instrument (30) and a guide instrument (18), the draping is preferably configured to accommodate relative motion (56) between the two instrument bases (46, 48). Further, the fit between the instrument bases (46, 48) and pertinent alignment pins (42) preferably is not loose and does not allow for relative motion. Similarly, the interface between axels (54) extending from the instruments and sockets (44) comprising the instrument driver (16) preferably is a precision interface.

Referring to FIGS. 9-16, various embodiments of suitable draping schemas are depicted. As shown in FIG. 9, a perforated drape (58) may be utilized, wherein perforations (68) are sized to fit the alignment pins (42) and interface sockets (44). The perforated drape (58), preferably made from conventional draping materials, is simply aligned appropriately and pulled down upon the instrument driver (16).

Referring to FIG. 10, a perforated drape with socks (60) may also be utilized. The depicted drape (60) has perforations (68) for the underlying interface sockets (44), but has socks (70), also formed from conventional draping material, which are sized to encapsulate the mounting pins (42) of the instrument driver (16).

Referring to FIG. 11, the depicted drape (62) may comprise "socks" (70) to engage the mounting pins (42), as with the drape in FIG. 10, but also have integrated plastic sleeves (64) rotatably coupled to the surrounding conventional drape material. The integrated plastic sleeves (64) are preferably precisely sized to engage both the interface sockets (44) of the instrument driver (16) and the axels (not shown) of an instrument. The sleeves (64) are preferably constructed of a sterilizable, semi-rigid plastic material, such as polypropylene or polyethylene, which has a relatively low coefficient of friction as compared with conventional drape material. To decrease rotational friction between the integrated plastic sleeves (64) and the surrounding drape material, perforations in the drape material through which the sleeves (64) are to be placed may be circumferentially lined with plastic collars (not shown), comprising a material having a low coefficient of friction relative to that of the integrated plastic sleeves (64).

Figure 13:
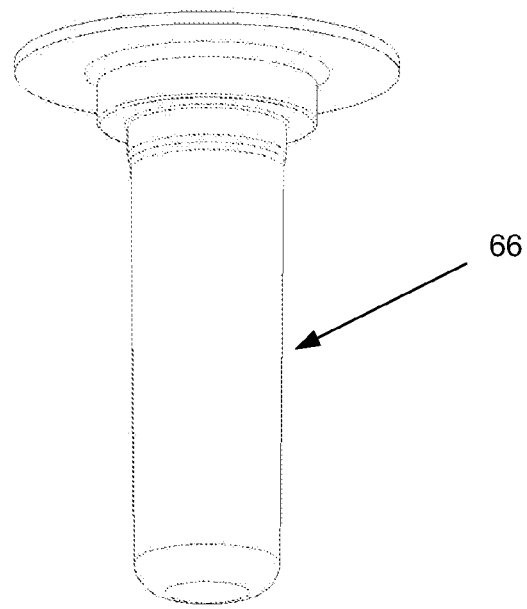
FIG. 13 illustrates a sleeve in accordance with some embodiments.
Figure 14:
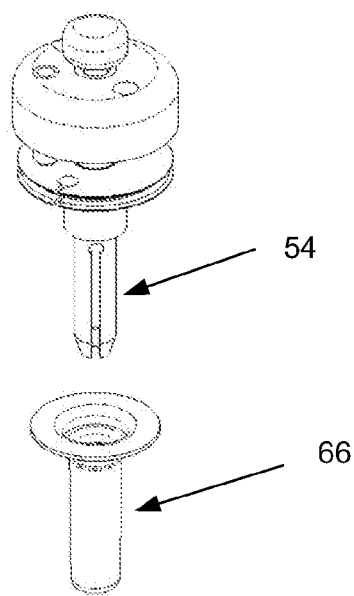
FIG. 14 illustrates an axel mating with the sleeve of FIG. 13 in accordance with some embodiments.

Referring to FIG. 12, an embodiment similar to that of FIG. 11 is depicted, with the exception that removable plastic sleeves (66) are not integrated into the drape, as delivered and unwrapped. Instead, the drape (60) may be delivered with perforations (68), circumferentially lined in one embodiment with plastic collars (not shown), positioned for convenient drop-in positioning of the sleeves (66). FIG. 13 is a close up view of a plastic sleeve (66) suitable, for example, in the embodiment of FIG. 12. The sleeve (66) may also be integrated into the embodiment depicted in FIG. 11. FIG. 14 illustrates that the inside of the sleeve (66) may be fitted to engage an axel (54) extending down from an instrument body.

Referring to FIG. 15, another draping embodiment is depicted, wherein two semi-rigid covers or plates (72) are incorporated into a larger piece of conventional draping material. The covers (72) are configured to snap into position upon the sheath instrument interface surface (38) and guide instrument interface surface (40), fit over the mounting pins (42), and provide relatively high-tolerance access to the underlying interface sockets (44), with pre-drilled holes (76) fitted for the pertinent drive axel structures (not shown). Due to the anticipated relative motion between the two instrument interfaces, as previously described with reference to FIGS. 8A and 8B, it may be preferable to have elastic draping material or extra draping material bunched or bellowed in between the two interfaces, as shown in FIG. 15, and similarly applicable to the embodiments of FIGS. 9-14.

Referring to FIG. 16, another semi-rigid covering embodiment comprises a semi-rigid covering for the entire local surface of the instrument driver (16), without conventional draping in between semi-rigid sub-pieces. To accommodate relative motion, high tolerance overlap sections (78) are provided with sufficient overlap to allow relative motion without friction binding, as well as gapping of sufficient tightness that the sterility of the barrier remains intact. The semi-rigid covers of the embodiments of FIGS. 15 and 16 may be molded or machined from polymeric materials, such as polycarbonate, which are inexpensive, sterilizable, somewhat flexible for manual snap-on installation, and fairly translucent to facilitate installation and troubleshooting.

Figure 17:
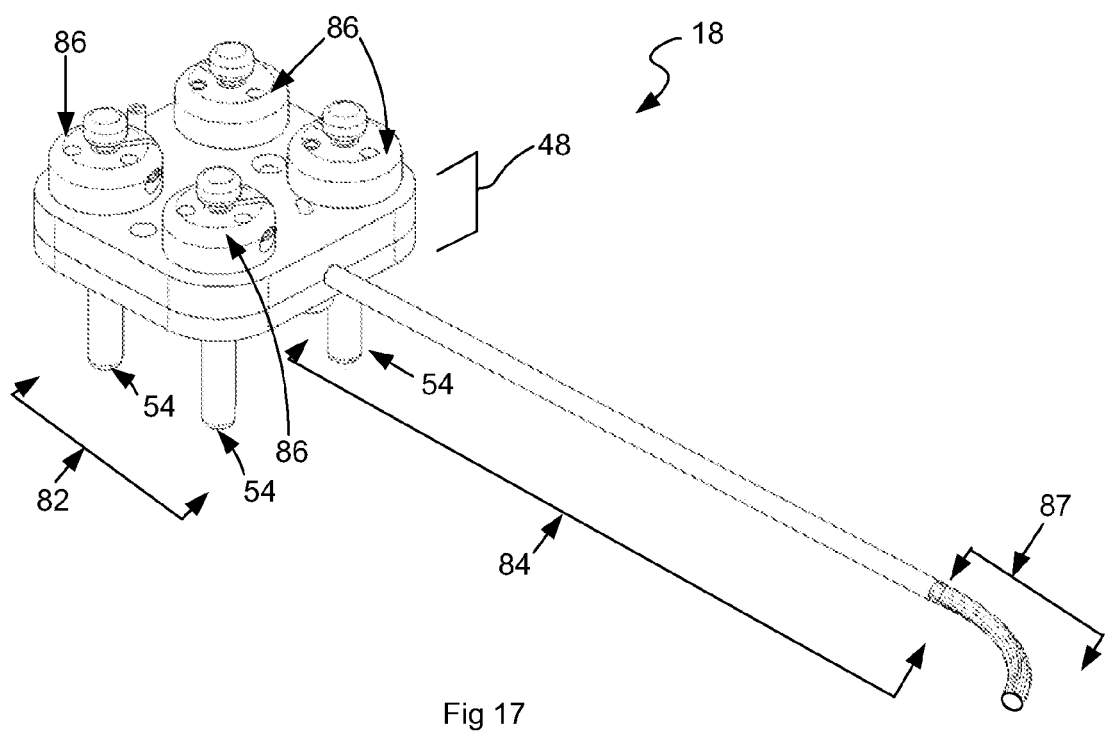
FIG. 17 illustrates an isometric view of an instrument in accordance with other embodiments.

FIG. 17 is an isometric view of one embodiment of an instrument (18) configured for instrument steering via independent control of four catheter control elements, or four tension elements, such as cables comprising materials, e.g., stainless steel. The proximal portion (82) comprises a guide instrument base (48) and four axels (54) with associated manual adjustment knobs (86). The middle (84) and distal portions (87) comprise a catheter member which extends into the guide instrument base (48) forming part of the proximal portion (82).

Figure 18:
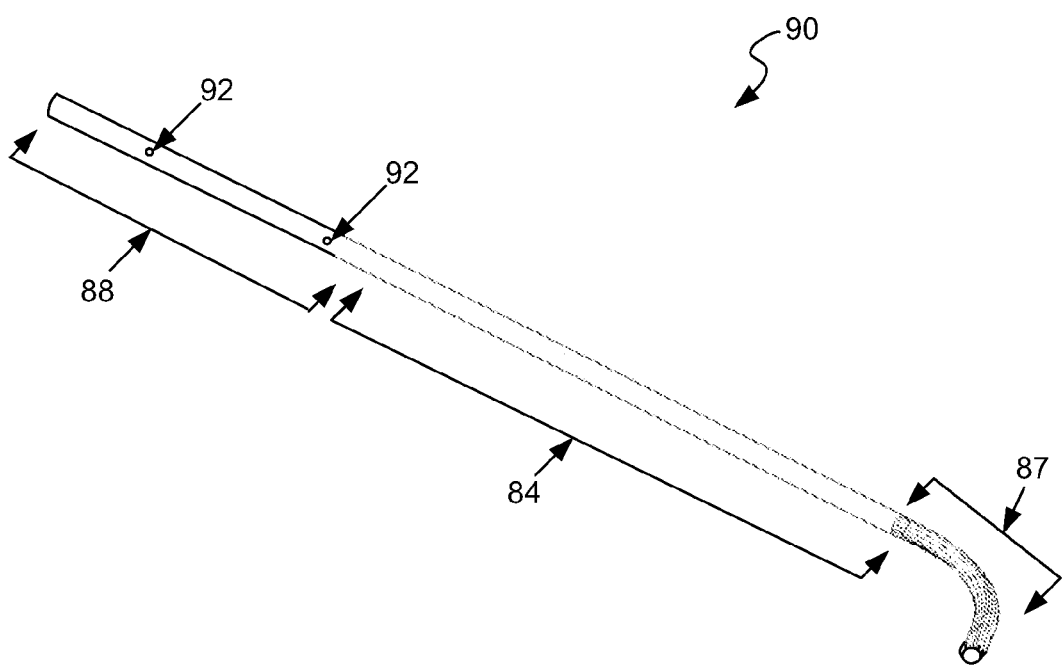
FIG. 18 illustrates a catheter member of the instrument of FIG. 17 in accordance with some embodiments.

Referring to FIG. 18, a catheter member (90) is depicted having control element apertures (92) through the proximal portion (88) of the catheter member to accommodate control elements (not shown), such as tension cables. The control elements may be disposed along the length of the catheter member (90), and positioned to exit the catheter through the apertures (92) and into association with other structures comprising the proximal portion (82) of the instrument. The proximal (88) and middle (84) portions of the catheter member (90) are shown in a substantially straight configuration, which is preferred for controllability of the more flexible distal portion (87). Indeed, the proximal (88) and middle (84) portions are structurally reinforced and made from stiffer materials to enhance torque transmission and insertability to the distal portion, while also providing enough cantilever bendability to facilitate access to remote tissue locations, such as the chambers of the heart.

Figure 19:
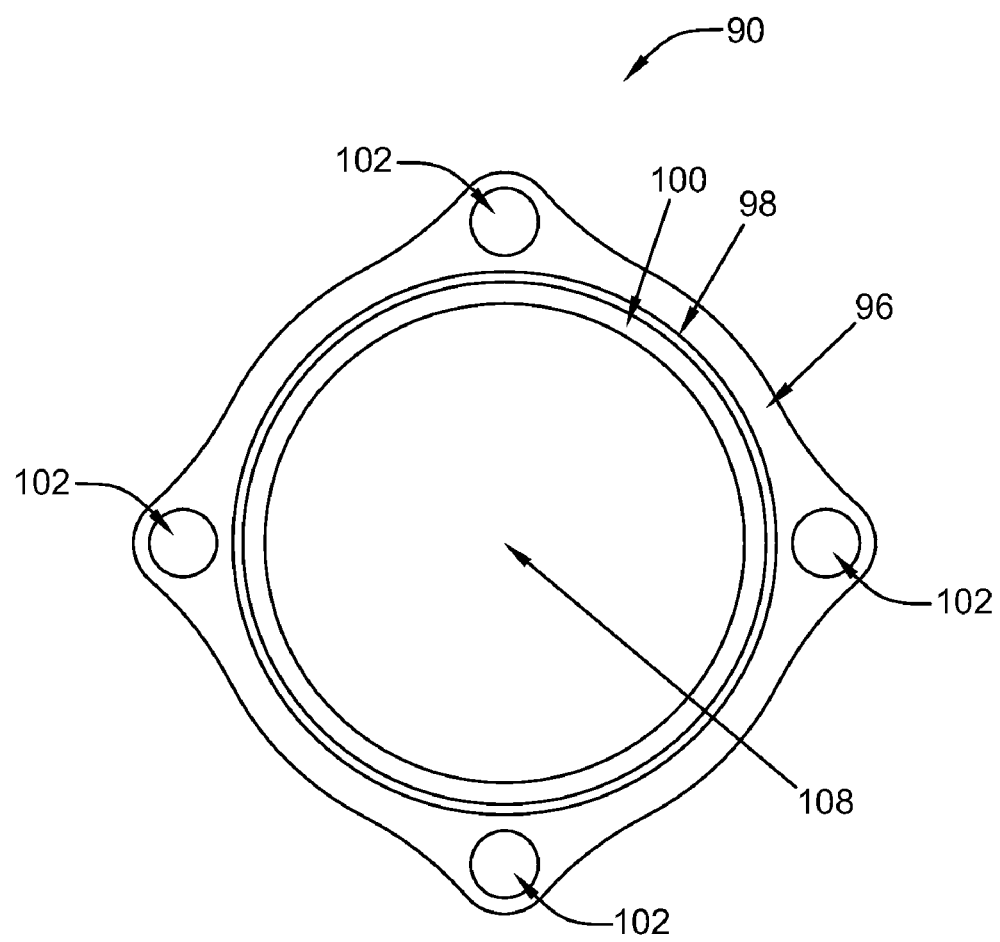
FIG. 19 illustrates a cross sectional view of the catheter member of FIG. 18 in accordance with some embodiments.

FIG. 19 is a cross sectional view of the catheter member (90) at either the proximal (88) or middle (84) portion. At the center of the cross sectional construct is a central (or "working") lumen (108), the geometry of which is selected in accordance with the requisite medical application. For example, in one embodiment it is desired to pass a commercially available ablation catheter having an outer diameter of about 7 French through the working lumen (108), in which case it is preferable to have a working lumen in the range of 7 French in diameter. The catheter member (90), and the entire system (32), for that matter, can be sized up or down in accordance with the desired procedure and tools. The proximal portion of the catheter member (90) may be reinforced with a stiffening member such as a braiding layer (98) which is preferably encapsulated on the outside by an outer layer (96) having at least one lumen (102) to accommodate a control element, such as a tension cable (not shown), and a low-friction inner layer (100) selected to provide a low-friction surface over the inside of the braiding layer (98). Four extruded lumens (102) are provided in the illustrated embodiment to accommodate four respective control elements (not shown).

Figure 20:
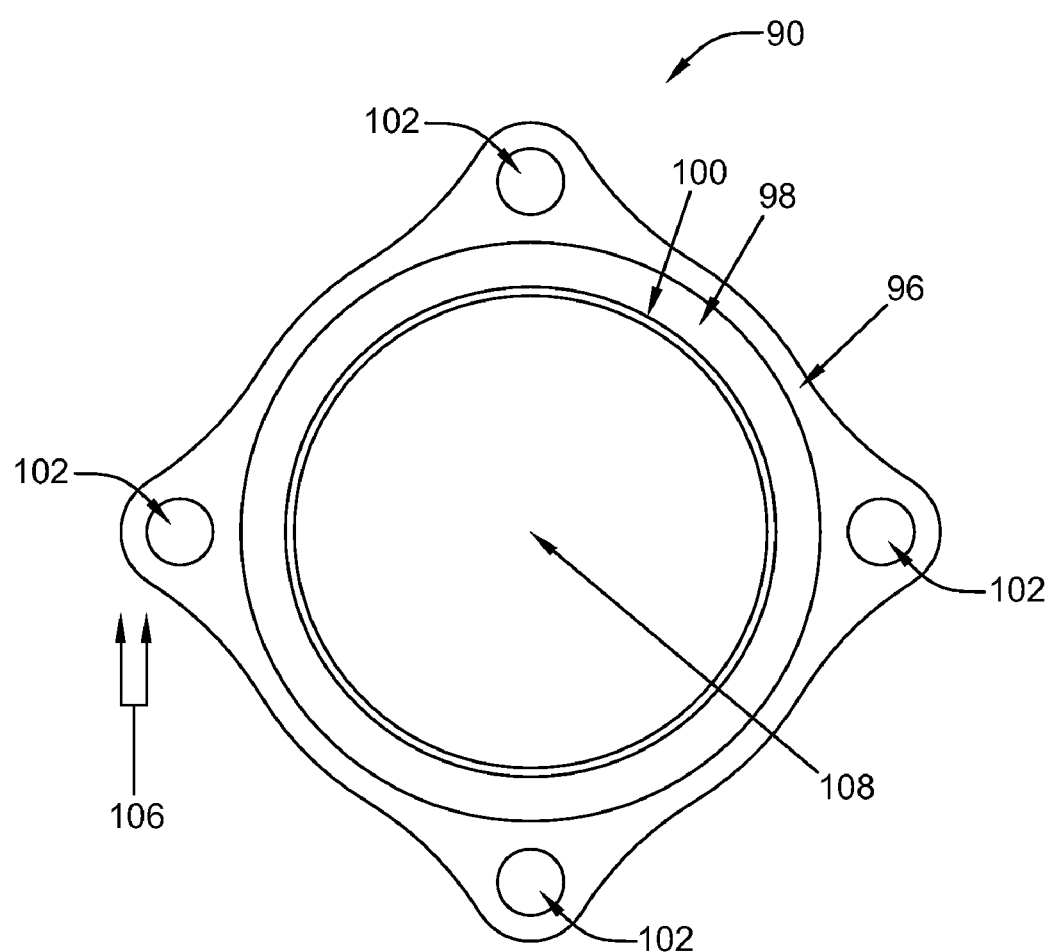
FIGS. 20-24 illustrate cross sectional views of catheter members in accordance with other embodiments.

To prevent relative rotational motion between the catheter member (90) and other structures which may surround it, the profile of the outer layer adjacent the control element lumens (102) may be increased. The cross section of the embodiment of FIG. 19 has a relatively low surface profile (104) adjacent the control element lumens (102), as compared with the cross section of the embodiment of FIG. 20, which is otherwise similar to that of FIG. 19. Indeed, within the same catheter member, it is preferable to have a more pronounced surface profile distally to interface with surrounding structures and prevent "wind up", or torsional rotation, of the distal and middle portions of the catheter member. With the braiding layer (98) in the middle (84) and proximal (82) portions of the instrument, "wind up" is not as significant an issue, and therefore it is less important to have a pronounced surface profile to interface or "key" with other adjacent structures.

Figure 21:
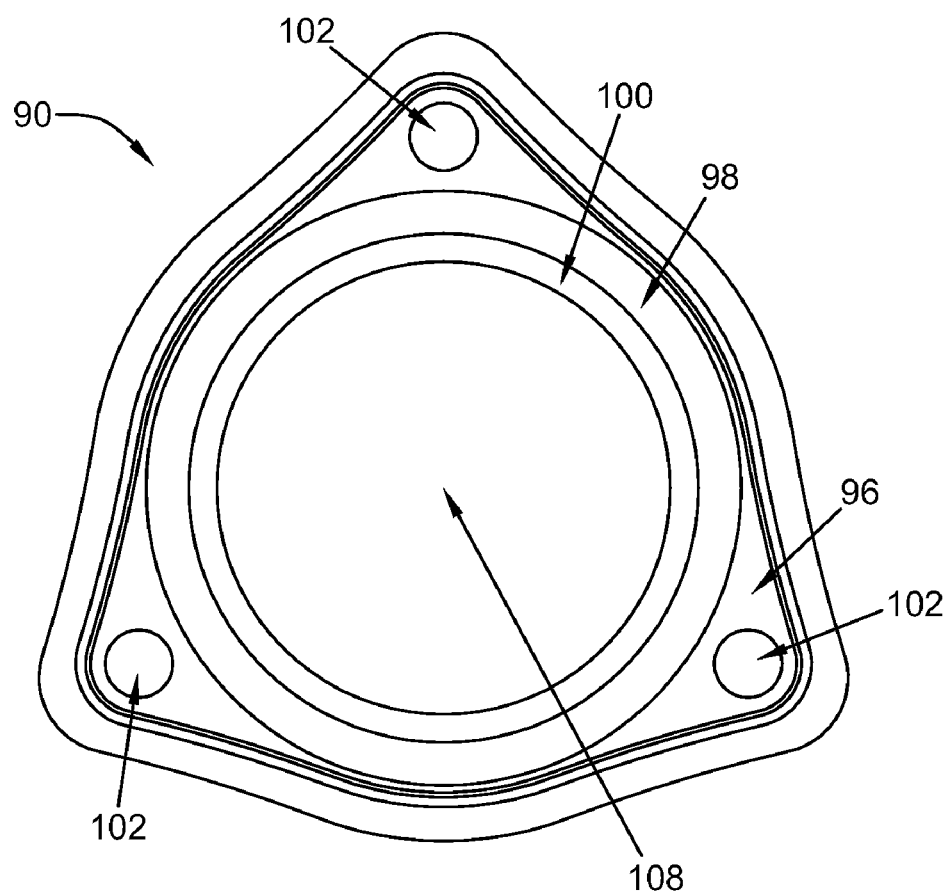
Figure 22:
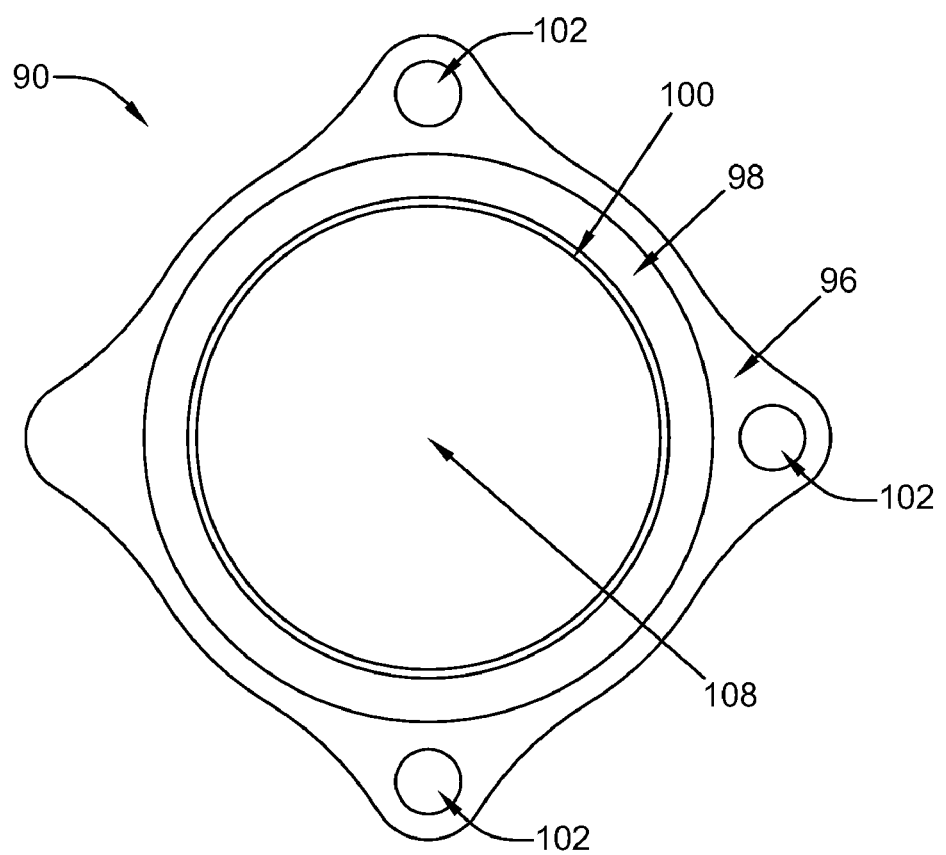
Figure 23:
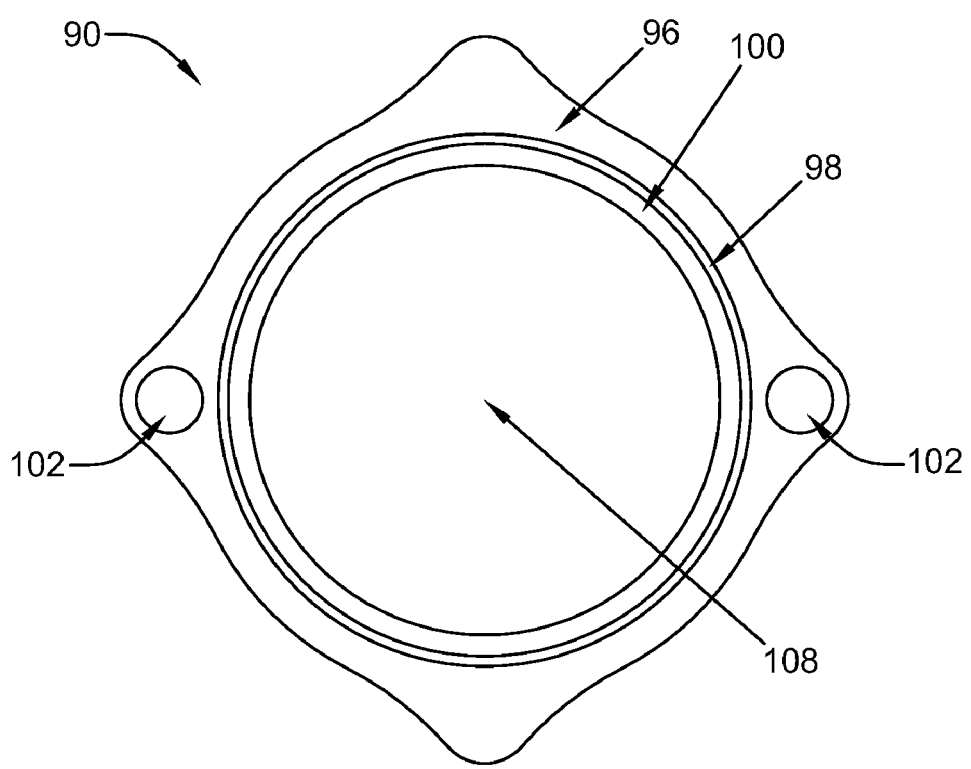
Figure 24:
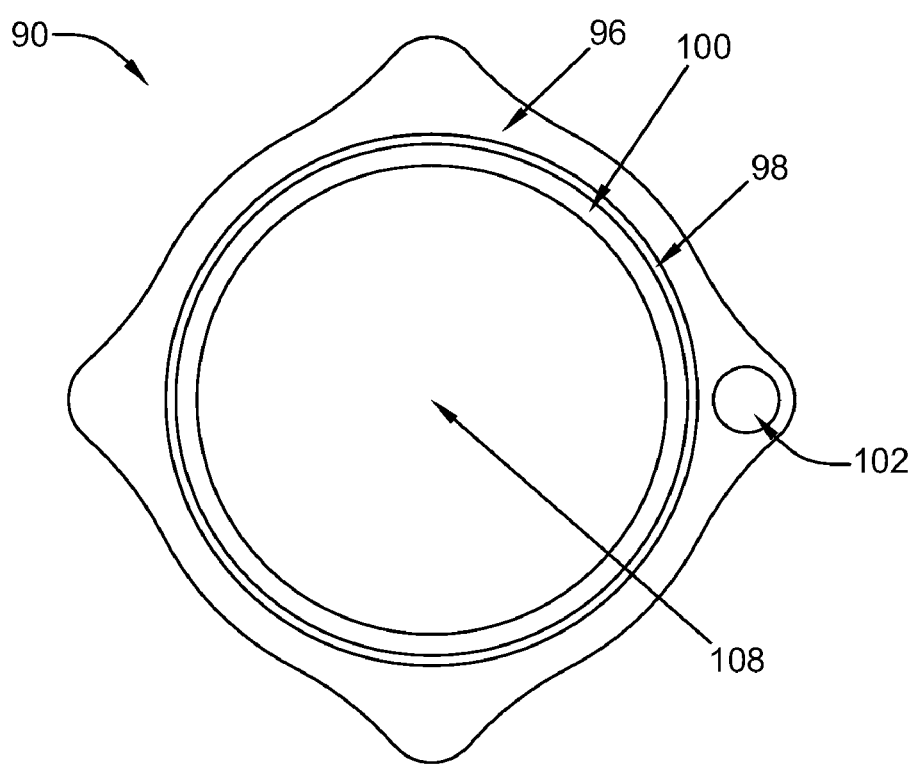

FIG. 21 depicts an embodiment having three control element lumens (102) disposed approximately equidistantly from each other about the perimeter of the catheter member (90) cross section. This embodiment illustrates by way of non-limiting example that the catheter member (90) need not be limited to configurations comprising four control element lumens or four control elements. By way of another example, FIG. 22 illustrates a non-equidistant, three-lumen (102) configuration, with two-lumen (102) and single lumen (102) variations shown in FIGS. 23 and 24, respectively.

Figure 25:
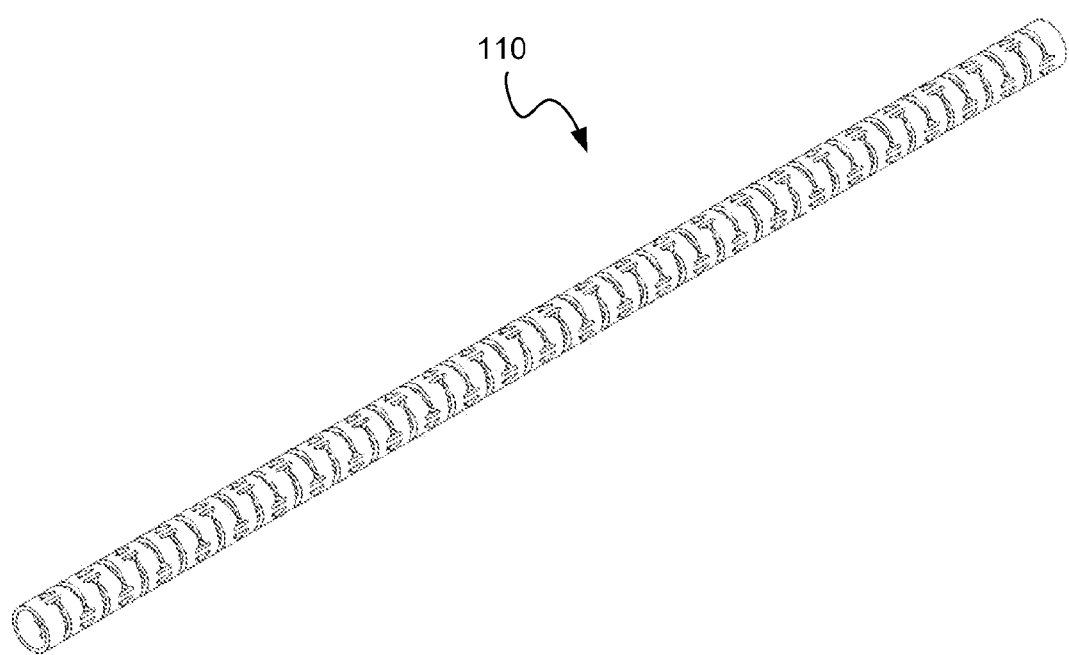
FIG. 25 illustrates an isometric view of a spine in accordance with some embodiments.
Figure 26:
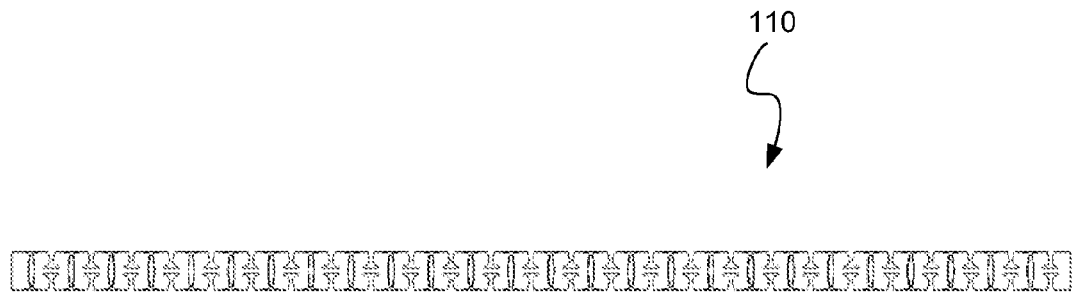
FIG. 26 illustrates a side view of the spine of FIG. 25.
Figure 27:
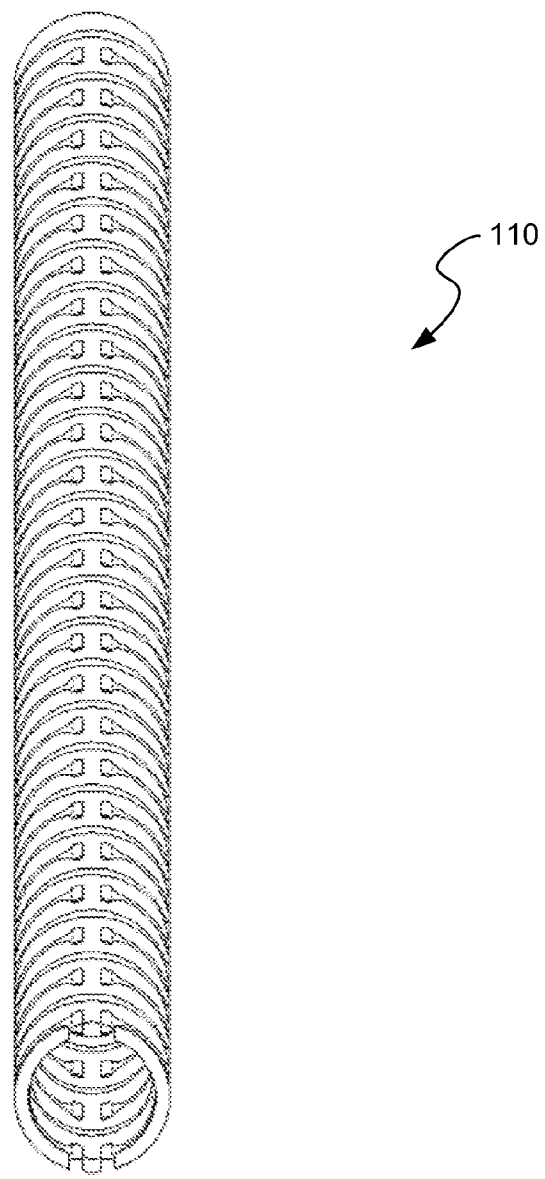
FIG. 27 illustrates another spine in accordance with other embodiments.
Figure 28:
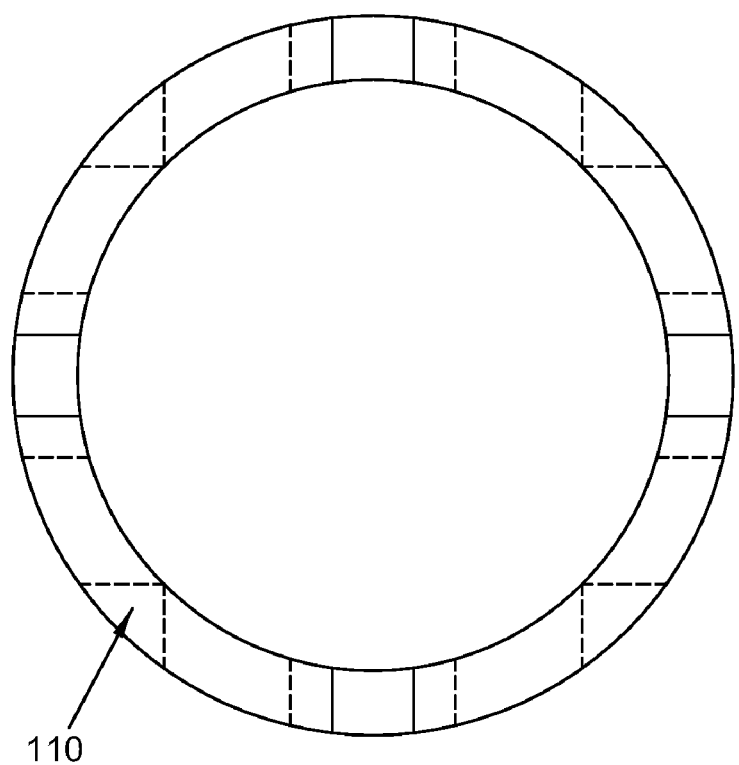
FIG. 28 illustrates a cross sectional view of the spine of FIG. 25.

To facilitate more dramatic bendability at the distal portion (87) of the catheter member (90), a reinforcing structure other than a braiding layer may be preferred. By way of non-limiting example, FIGS. 25-27 depict a metal spine (110) having a unique stress relief geometry cut into its walls. FIG. 28 depicts a cross section of an embodiment of a metal spine (110) to illustrate that the working lumen may be continued from the proximal (88) and middle (84) portions of the catheter member into the distal portion (87) through the center of the metal spine (110). Indeed, the metal spine preferably has similar inner and outer diameter sizes as the braiding layer (98) in the more proximal portions of the catheter member (90). Depending upon the metal utilized for the metal spine (110), very tight bend radius operation of the distal portion (87) of the catheter member (90) is possible, due in significant part to such a highly bendable reinforcing structure and its associated repeated stress relief pattern. To further enhance the flexibility of the distal portion (87) of the catheter member (90), softer polymeric materials may be utilized in the construct, such as Pebax™. For example, in one embodiment, the outer layer (96) in the proximal (88) and middle (84) portions of the catheter member (90) preferably comprise 70 durometer Pebax™, while in the distal portion (84) and outer layer (96) preferably comprise 35 or 40 durometer Pebax™.

Figure 29:
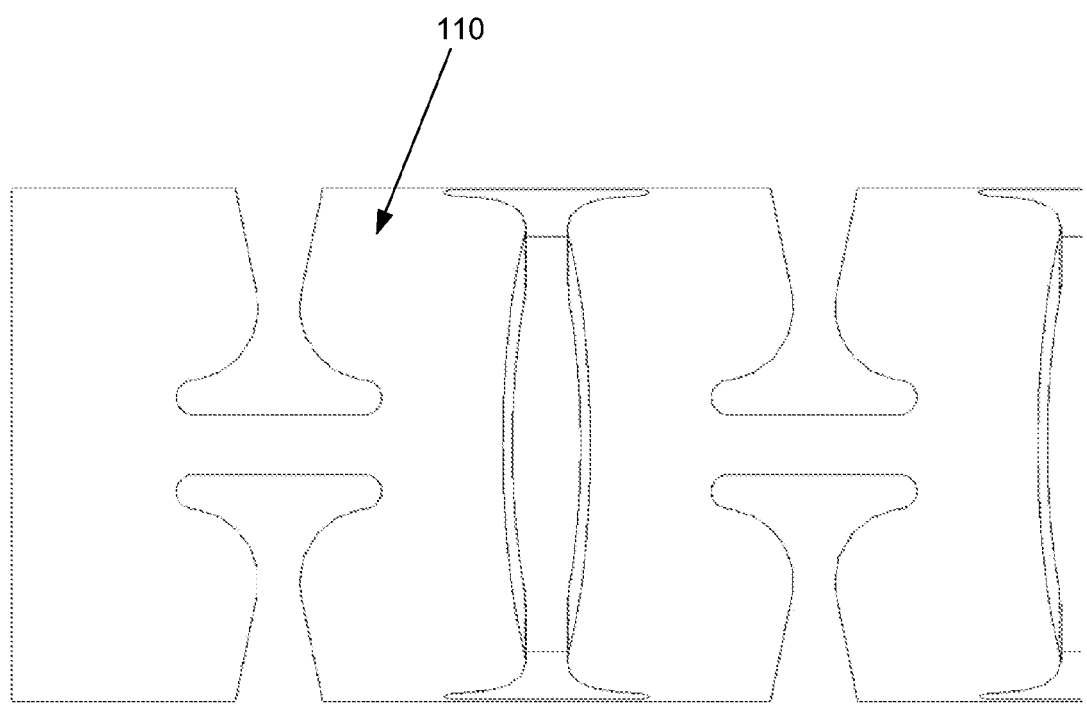
FIG. 29 illustrates a close up view of the spine of FIG. 25 in accordance with some embodiments.
Figure 30:
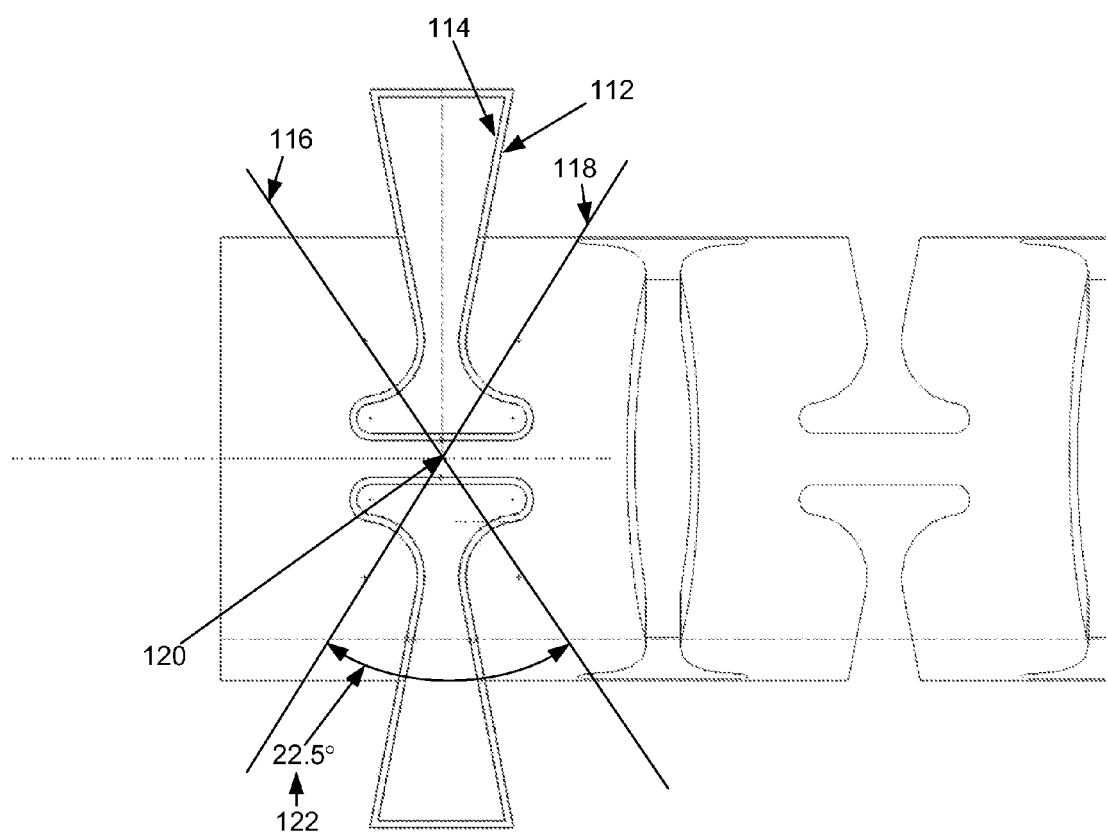
FIG. 30 illustrates a close up view of the spine of FIG. 25 in accordance with other embodiments, showing stress relief angles.

Referring to FIGS. 29 and 30, one embodiment of a stress relief pattern is depicted in close-up view to illustrate that the pattern may be shifted by about ninety degrees with each longitudinal step along the spine (110) to maximize the homogeneity of stress concentration and bending behavior of the overall construct. To further enhance the flexibility of the metal spine, and clean up undesirable geometric discrepancies left behind after laser cutting, the metal spine may be chemically etched and electropolished before incorporation into the catheter member (90). As shown in FIG. 30, chemical etching takes the pattern from the original lasercut positioning (114) to a revised positioning (112) with larger windows in the pattern. In this embodiment, subsequent to chemical etching, the pattern forms a relief angle with sides (116a-116b, 118a-118b) with an intersection (120) and included angle (122). Preferred metal spine materials include, but are not limited to, stainless steel and nitinol.

Figure 31:
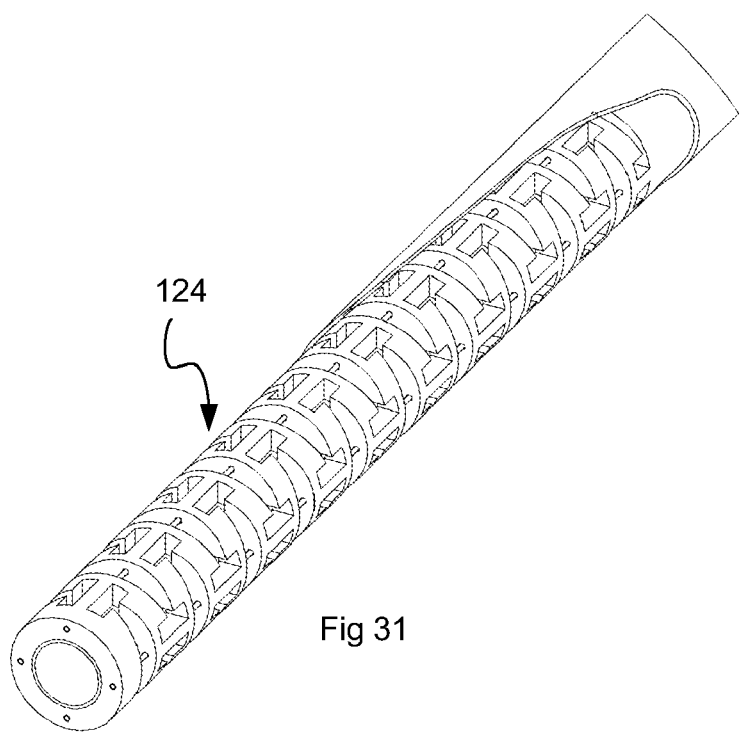
FIGS. 31-32 illustrate another spine in accordance with other embodiments.
Figure 32:
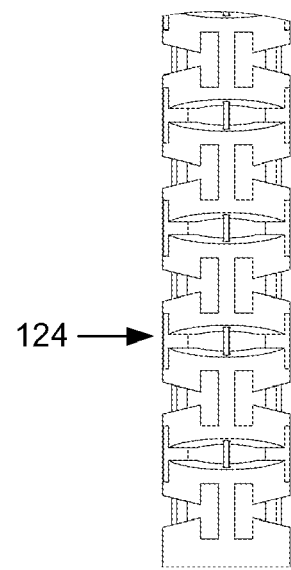

Referring to FIGS. 31 and 32, the distal reinforcing structure may also comprise a polymeric spine (124) similarly configured to homogeneously bend due to a stress relief pattern comprising the tubular wall of the spine (124). In particular, due to the greater fracture toughnesses of many available polymeric materials, a more squared stress concentrating pattern may be repeated with polymer structures. Further, high-precision structures such as the depicted polymeric spine (124), may be formed using injection molding and/or other techniques less inexpensive than laser cutting and etching. As will be apparent to those skilled in the art, many other distal spine structures for concentrating and relieving stress may also be utilized to provide the requisite tight bend radius functionality distally within the catheter member (90) construct, including but not limited to coils and braids.

Figure 33:
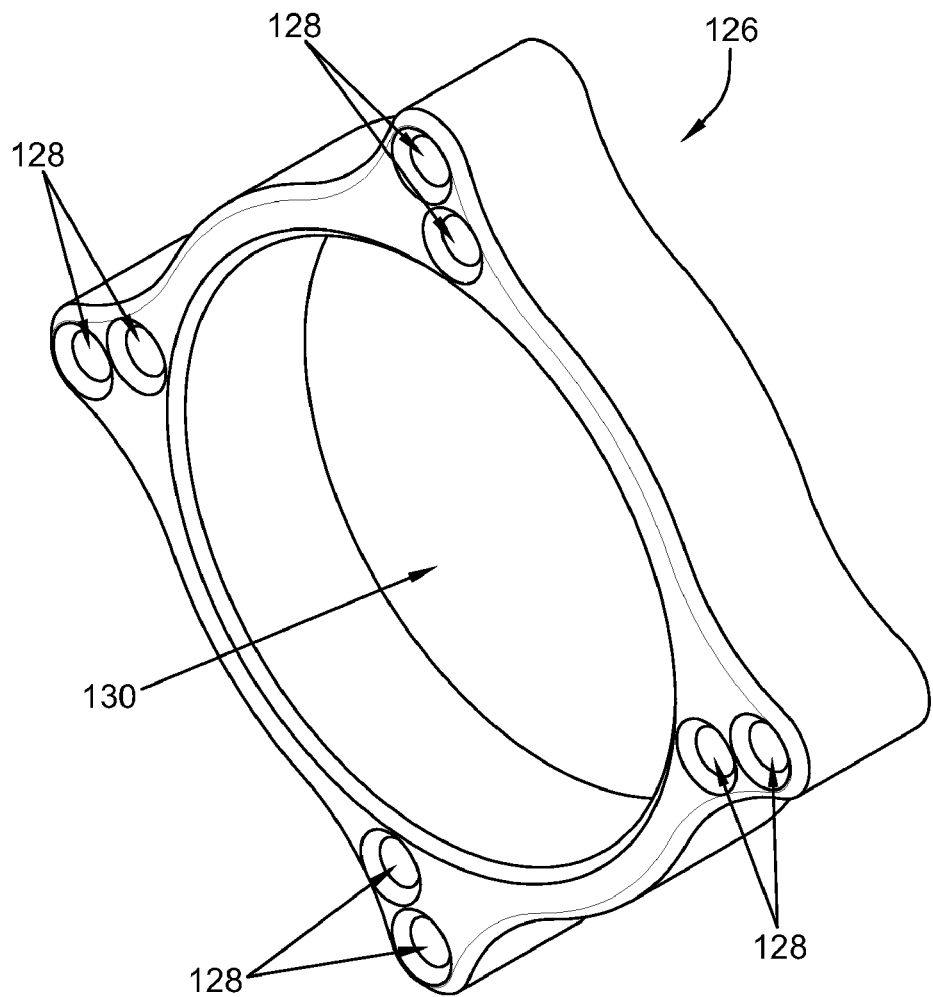
FIG. 33 illustrates an isometric view of an anchoring ring for use at a distal tip of a catheter member in accordance with some embodiments.
Figure 34:
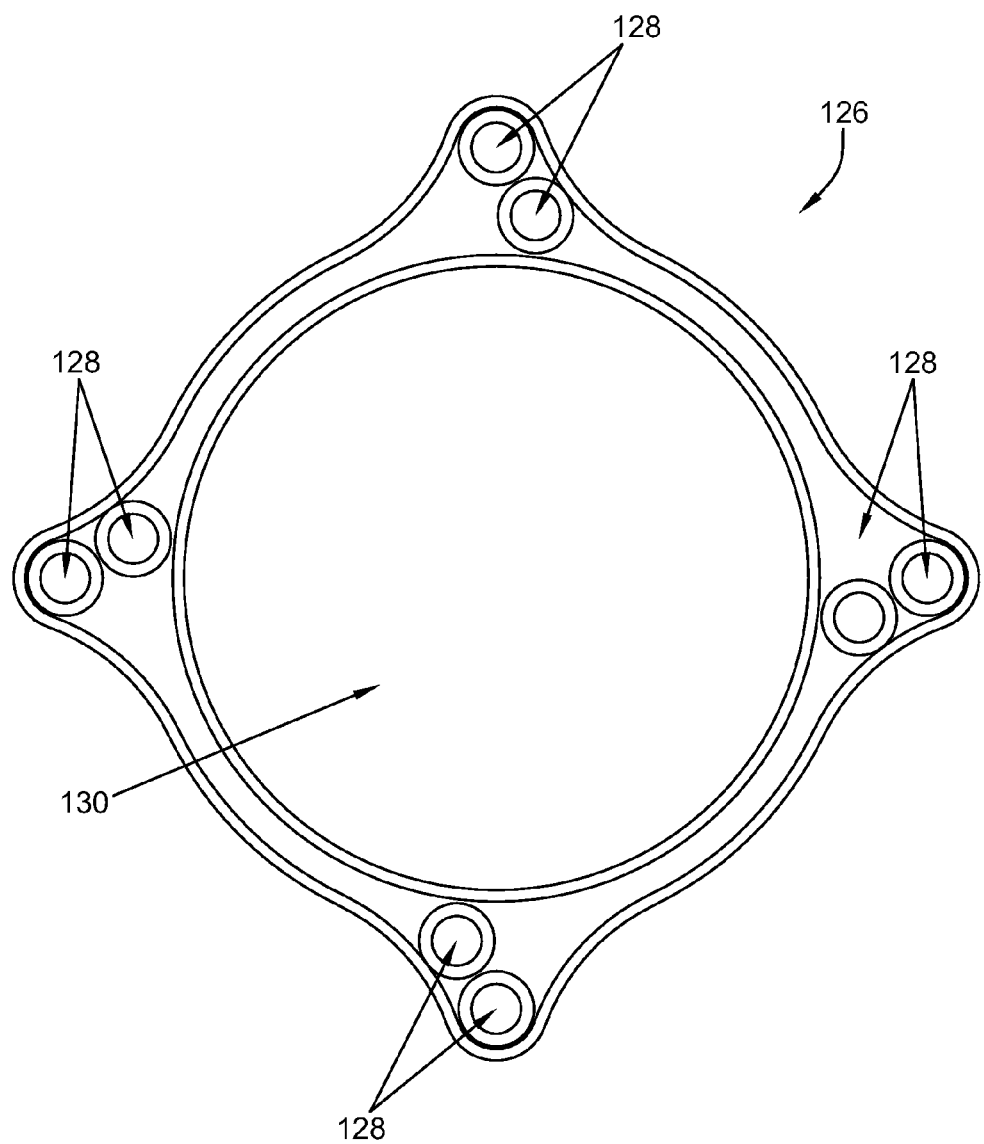
FIG. 34 illustrates a cross sectional view of the anchoring ring of FIG. 32.

Referring to FIG. 33, a control element anchoring ring (126) is depicted having two anchoring lumens (128) for each incoming control element to be anchored at the distal tip of the catheter member (90). The anchoring ring (126) comprises the last rigid construct at the distal tip of the catheter member (90), beyond which only a low durometer polymeric atraumatic distal tip (not shown) extends, as the low friction liner (100) meets the outer layer (96) subsequent to these two layers encapsulating the anchoring ring (126). The anchoring ring (126) is the "anchor" into which the relatively high-tension control elements are fixedly inserted—and is therefore a key to the steerability and controllability of the catheter member (90) regardless of the number of control elements pulling upon it. In one embodiment, tension wire control elements (not shown) insert into the outermost of the anchoring lumens, then bend directly back into the innermost of the anchoring lumens, where they are soldered to the anchoring ring, which comprise machined or gold plated stainless steel for solderability.

Figure 35:
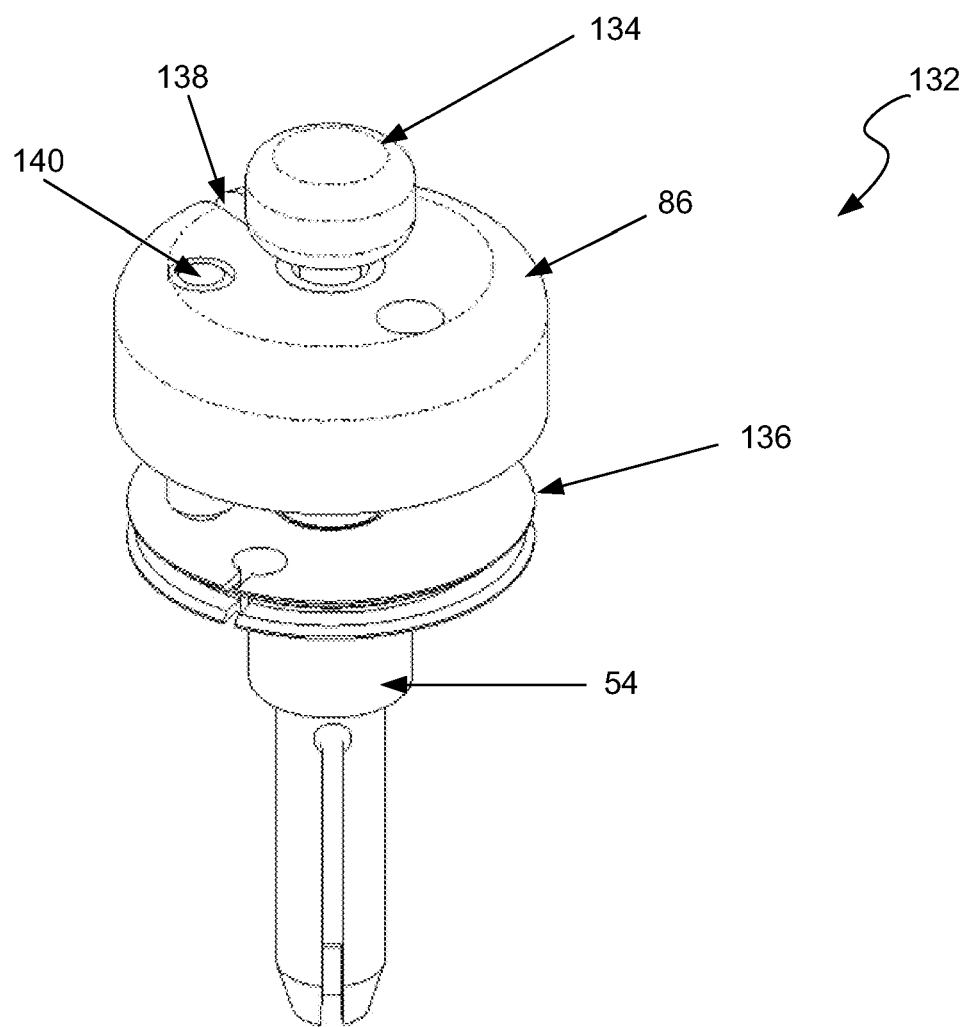
FIG. 35 illustrates a control element interface assembly in accordance with some embodiments.
Figure 35A:
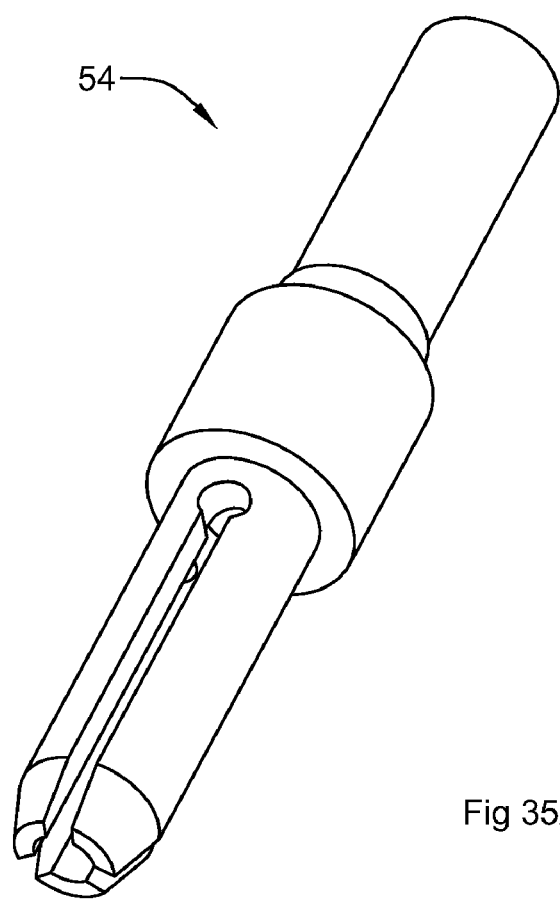
FIG. 35A illustrates an axel of the control element interface assembly of FIG. 35.
Figure 36:
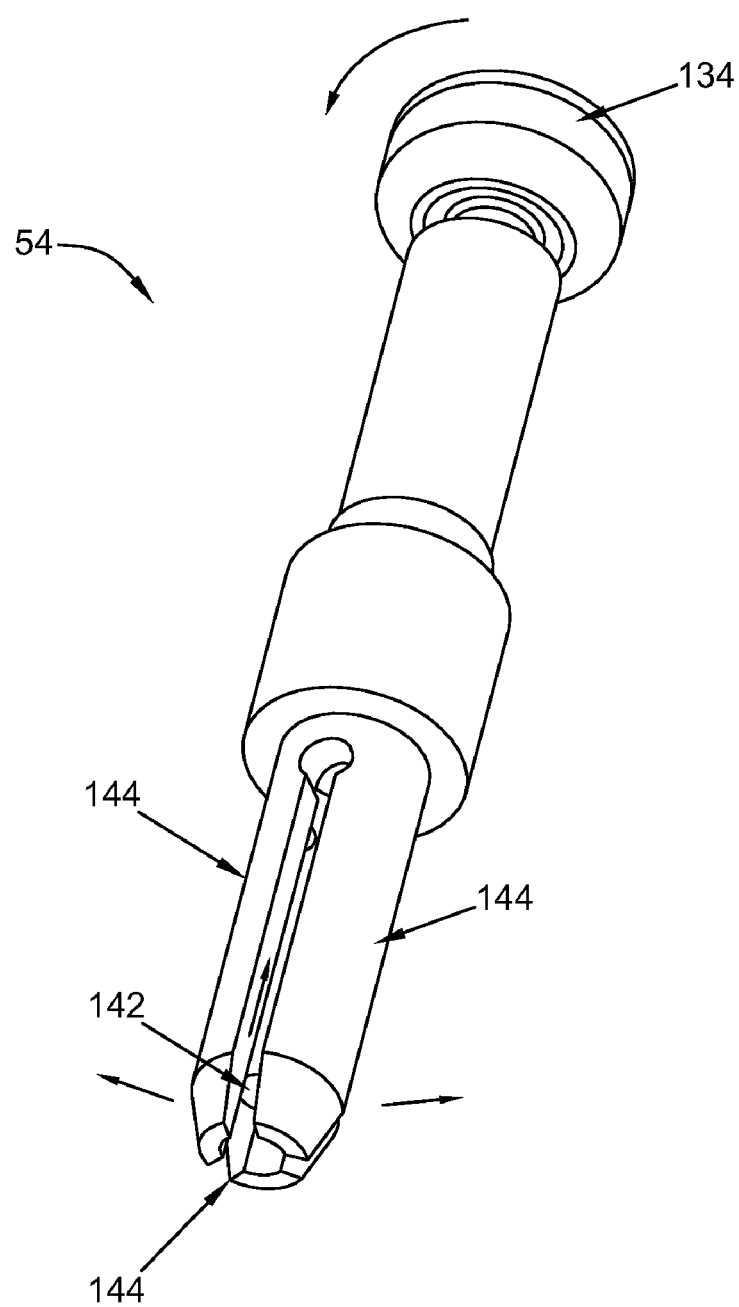
FIG. 36 illustrates a drive engagement knob in accordance with some embodiments, showing the drive engagement knob coupled to the axel of FIG. 35A.

FIGS. 35-49 depict certain aspects of a proximal portion (82) of an instrument (18) similar to that depicted in FIG. 19. Referring to FIG. 35, a control element interface assembly (132) is depicted, comprising an axel (54), a control element pulley (136), a manual adjustment knob (86), and a drive engagement knob (134). The manual adjustment knob is configured to facilitate manual adjustment of control element tensions during setup of the instrument upon the instrument driver. It is held in place against the axel (54) with a clamp screw (138), and houses a rotation range of motion limitation pin (140) which limits the range of motion of the axel subsequent to setup and tightening of the clamp screw. Referring to FIG. 35A, one embodiment of an axel (54) is depicted in isometric view without other hardware mounted upon it. Referring to FIG. 36, an axel (54) is depicted with a drive engagement knob (134) mounted upon it. The drive engagement knob (134) may take a shape similar to a screw with a long threaded portion configured to extend through the axel to engage a tapered nut (142), as shown. Twisting of the drive engagement knob (134) causes the tapered nut (142) to urge the teeth (144) of the axel outward, thereby engaging whatever structures surround the lower portion of the axel, including but not limited to a instrument driver interface socket (44).

Figure 37:
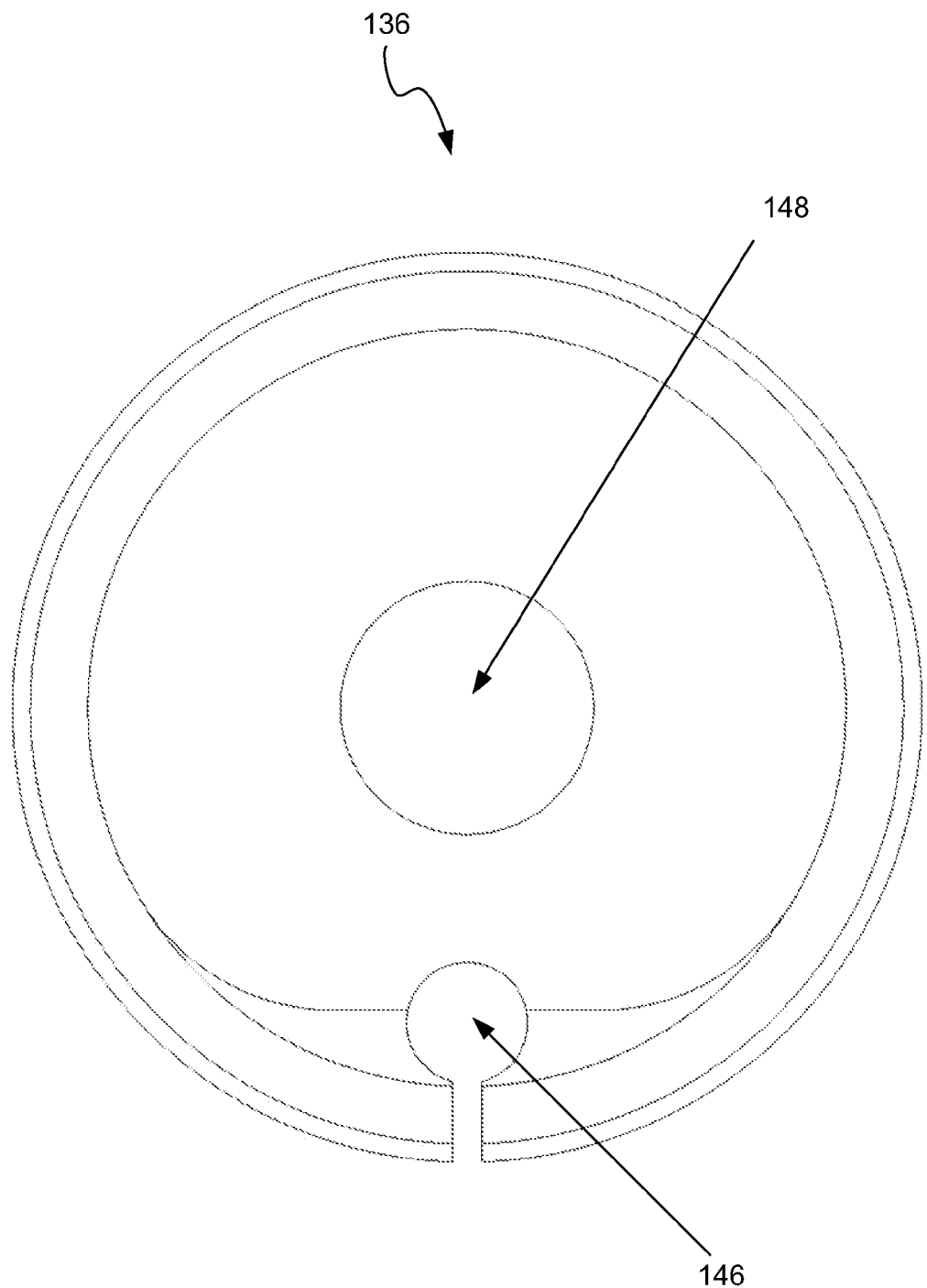
FIG. 37 illustrates a control element pulley of the control element interface assembly of FIG. 35 in accordance with some embodiments.
Figure 38:
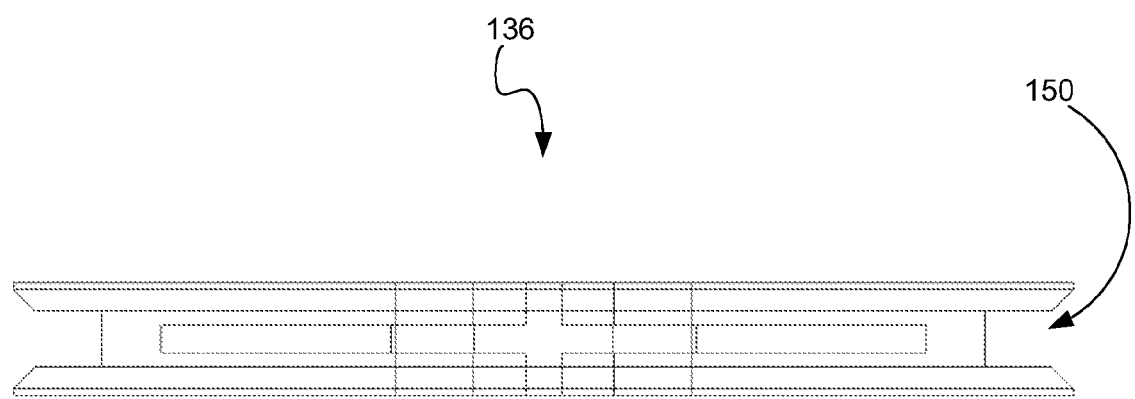
FIG. 38 illustrates a side view of the control element pulley of FIG. 37.

FIGS. 37 and 38 depict respective orthogonal views of one embodiment of a control element pulley (136). The central hole (148) in the pulley (136) is sized for a press fit upon an axel, and the control element termination engagement slot (146) is configured to capture a control element terminator, such as a lead or steel cable terminator, that is pushed into the slot before a control element is wound around the pulley (136) during manufacture or rebuilding. Referring to FIG. 38, the pulley (136) preferably has a flanged shape (150) to facilitate winding and positional maintenance of a control element.

Figure 39:
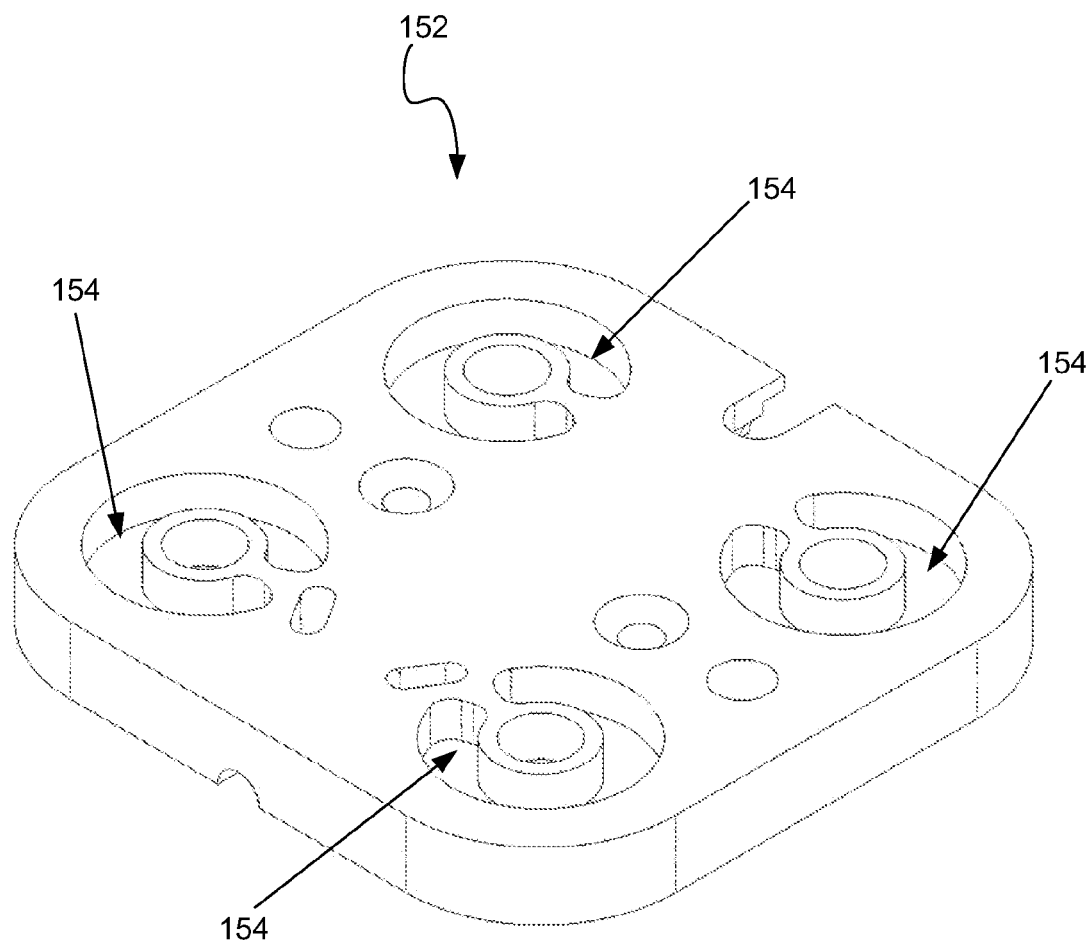
FIG. 39 illustrates a top portion of a guide instrument base in accordance with some embodiments.
Figure 40:
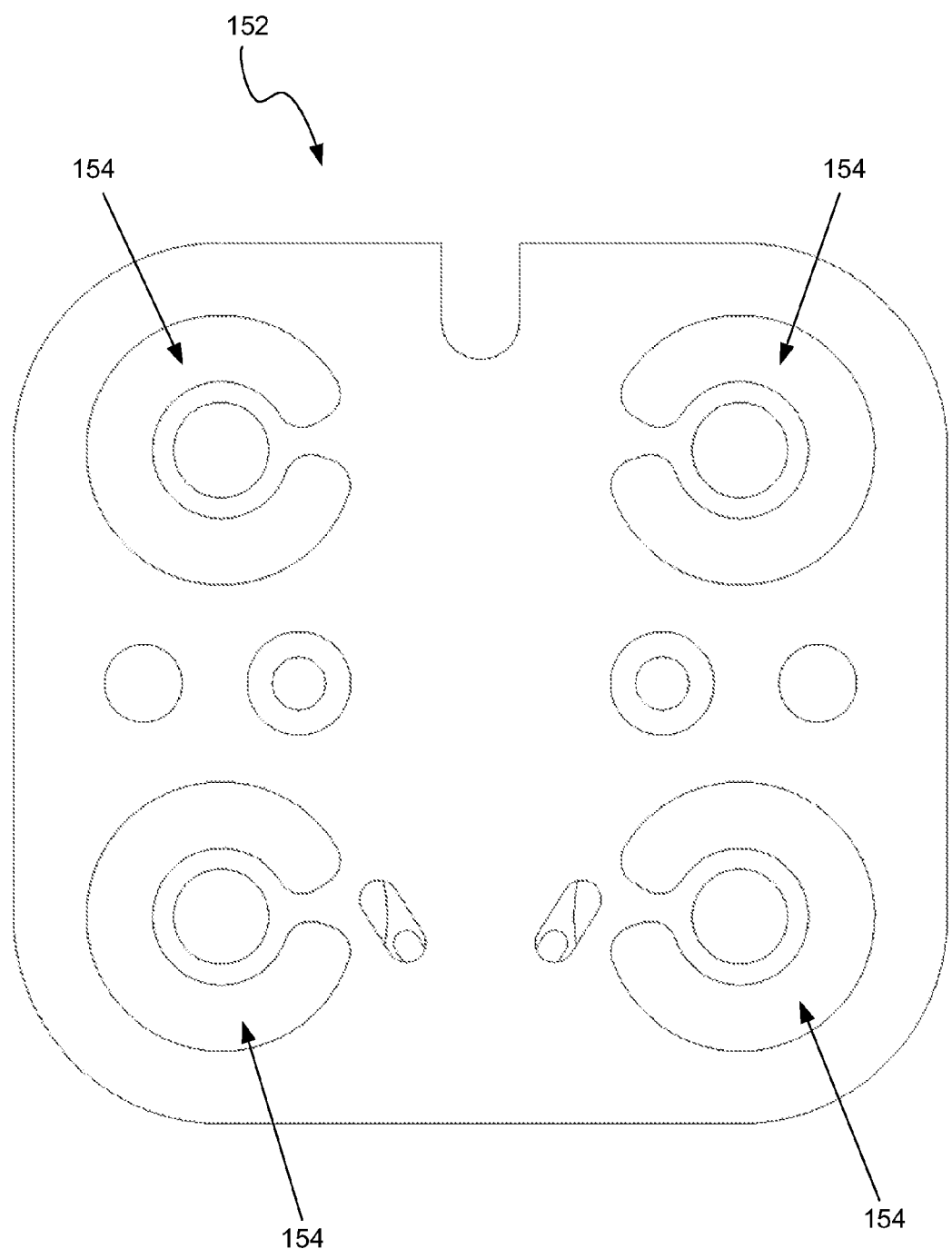
FIG. 40 illustrates a top view of the top portion of FIG. 39.
Figure 41:
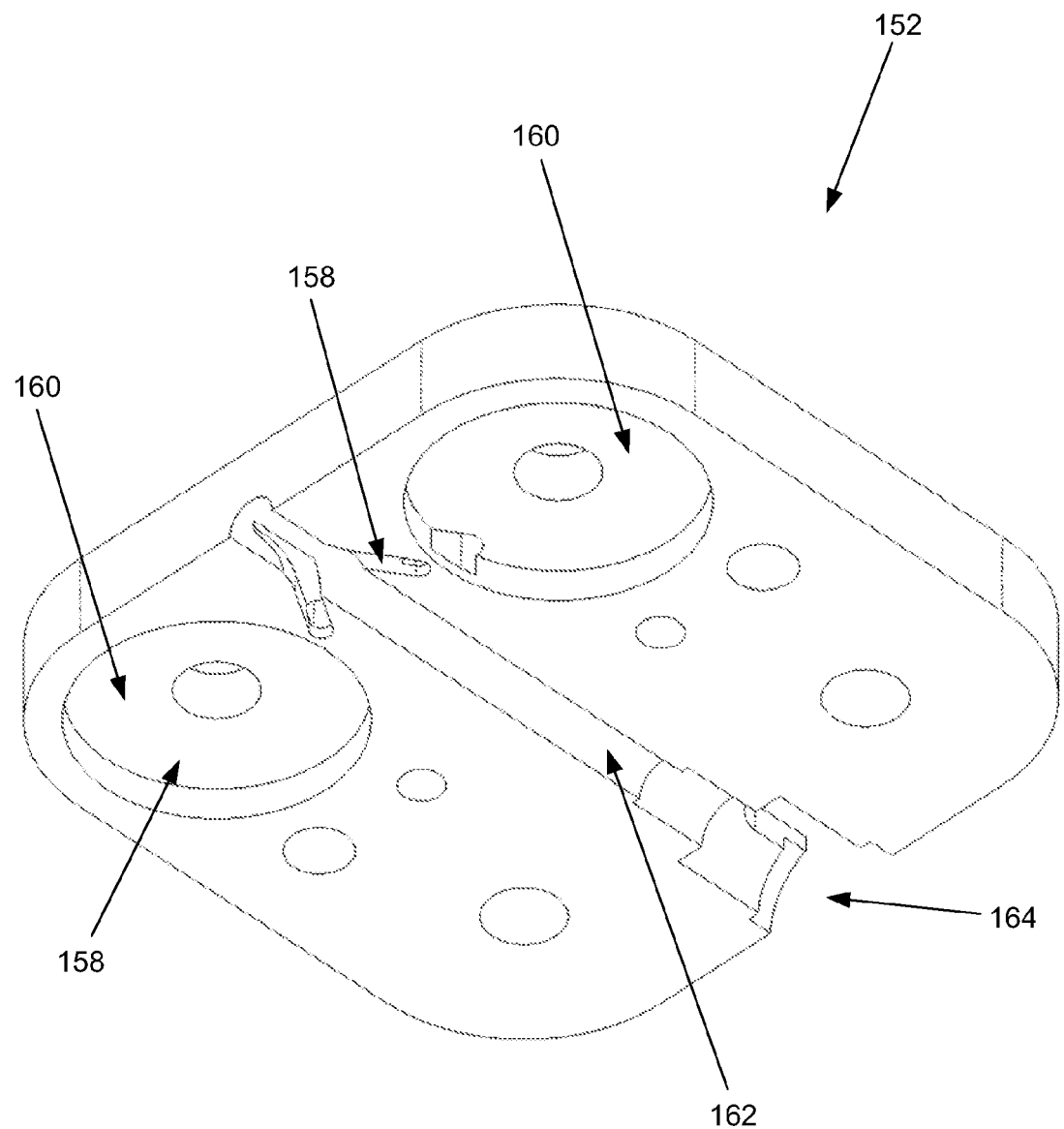
FIG. 41 illustrates an isometric bottom view of the top portion of FIG. 39.
Figure 42:
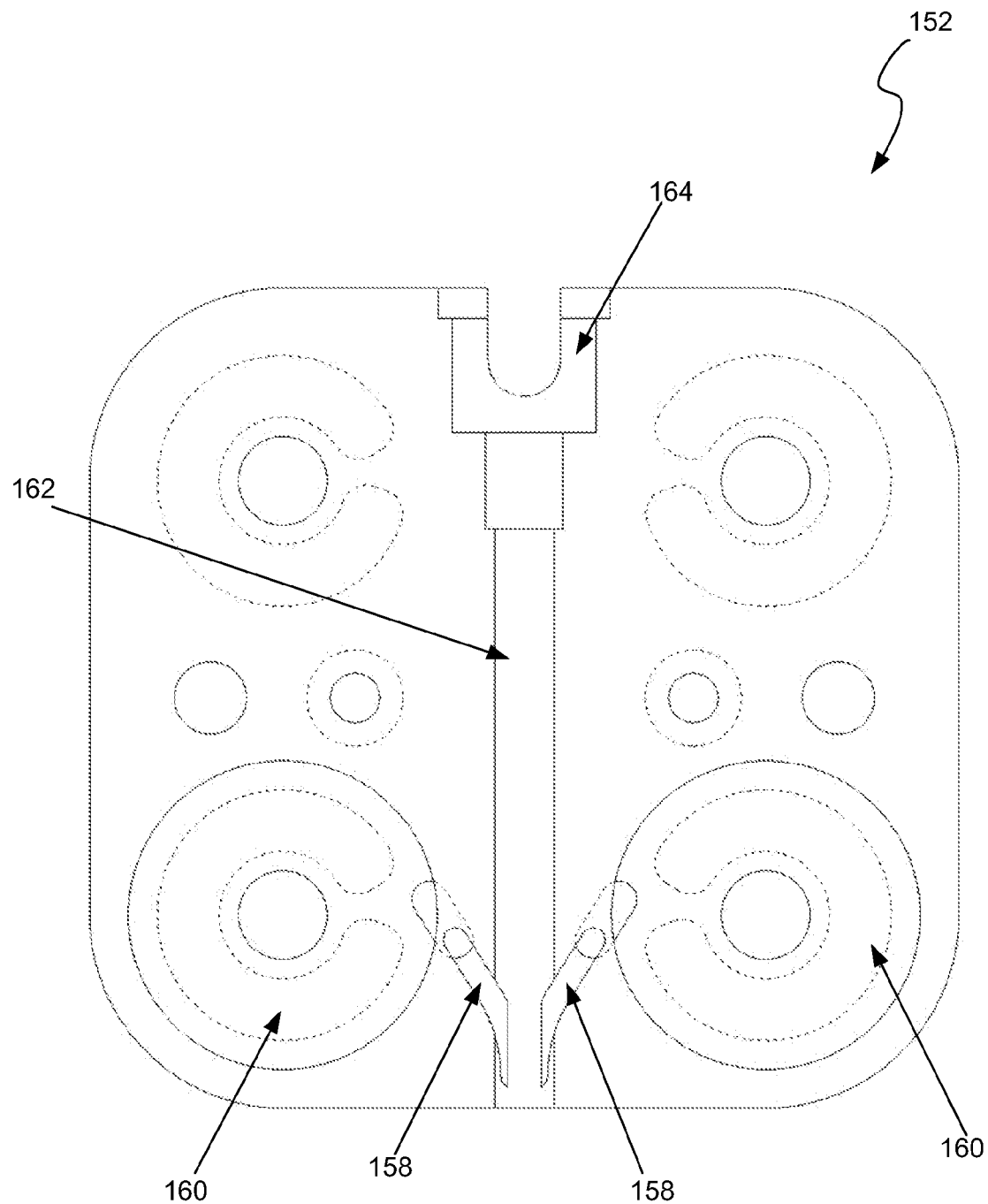
FIG. 42 illustrates a bottom view of the top portion of FIG. 39.

As shown in FIG. 39, the top portion (152) of one embodiment of a guide instrument base (48) comprises slots (154) to interface with the rotation range of motion limitation pins (140), which may be housed within a manual adjustment knob (86). FIG. 40 depicts a top view of the top portion (152). FIG. 41 depicts the same top portion (152), as viewed isometrically from underneath, to demonstrate how two pulleys may be mounted in related to the top portion (152) of the guide instrument base (48). The control element splay tracks (158) are employed to guide control elements (not shown) from apertures in a catheter member into pulleys which may be positioned within the pulley geometry accommodations (160) formed into the top portion (152) of the guide instrument base (48). Also shown in the top portion (152) is a catheter member geometry accommodation (162) and a seal geometry accommodation (164). FIG. 42 depicts an orthogonal view of the structures of FIG. 41 to better illustrate the control element splay track (158) structures positioned to guide control elements (not shown) away from a catheter member and over to a pulley associated with the top portion (152) of the guide instrument base (48).

Figure 43:
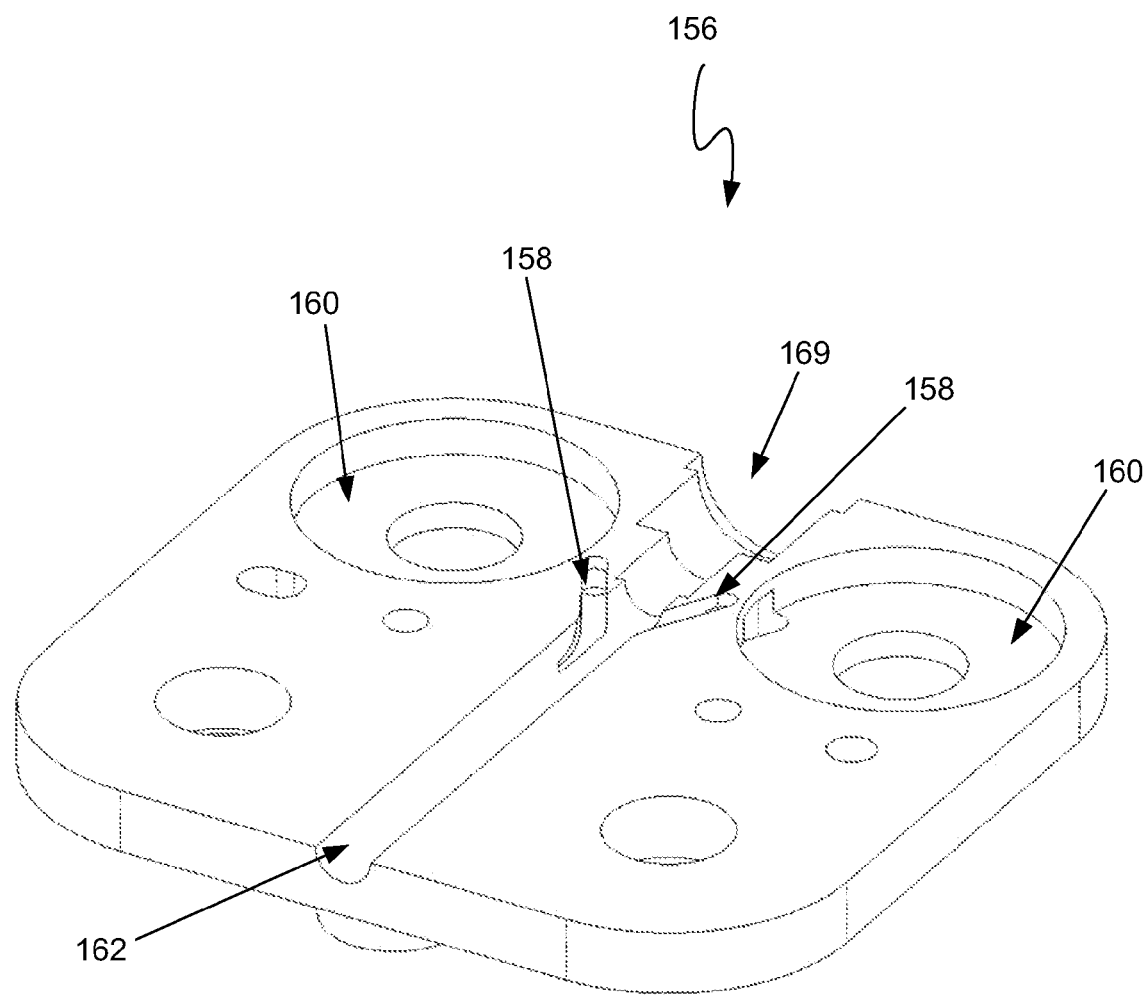
FIG. 43 illustrates an isometric view of a bottom portion of a guide instrument base in accordance with some embodiments.
Figure 44:
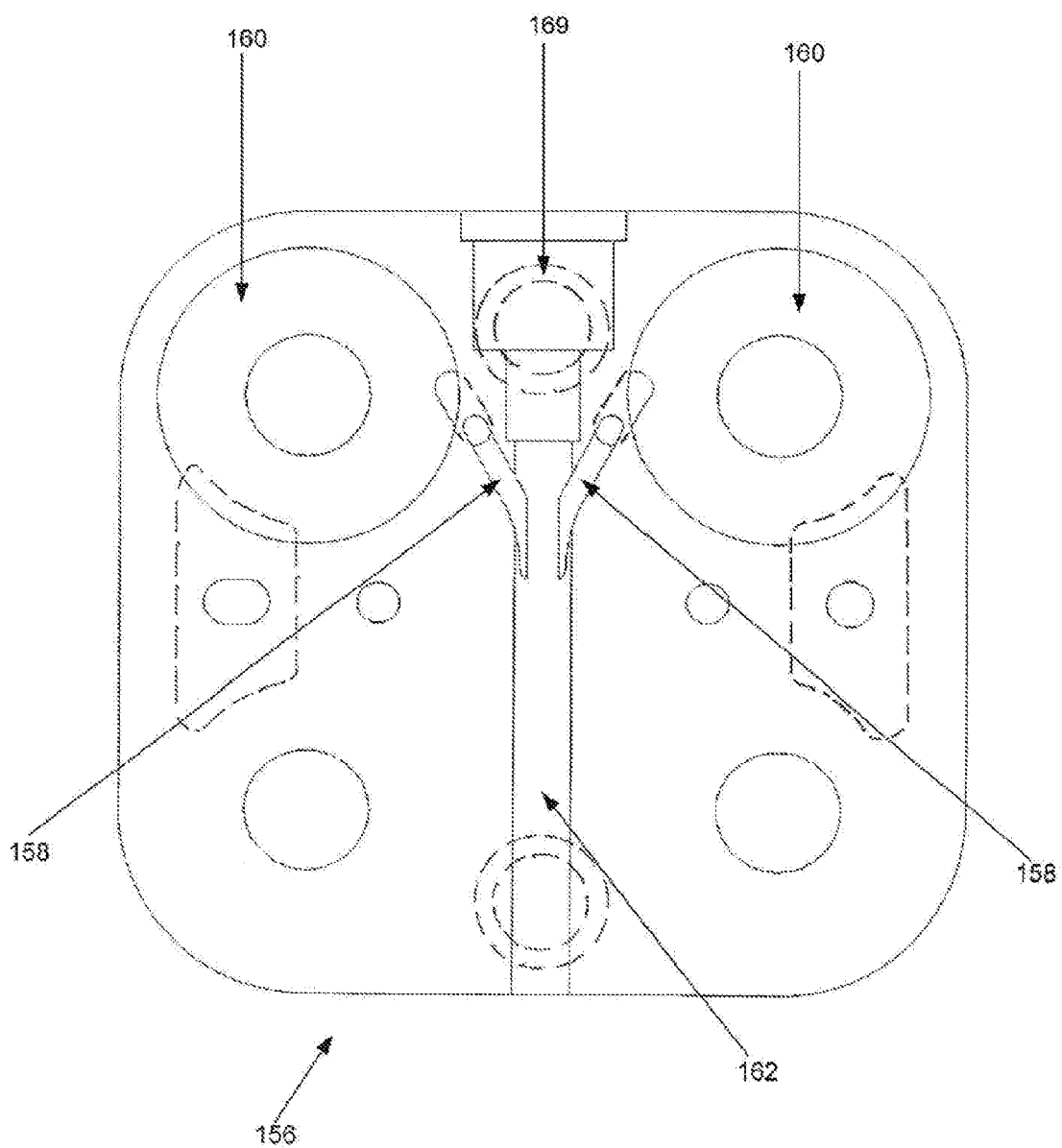
FIG. 44 illustrates a top view of the bottom portion of FIG. 43.
Figure 45:
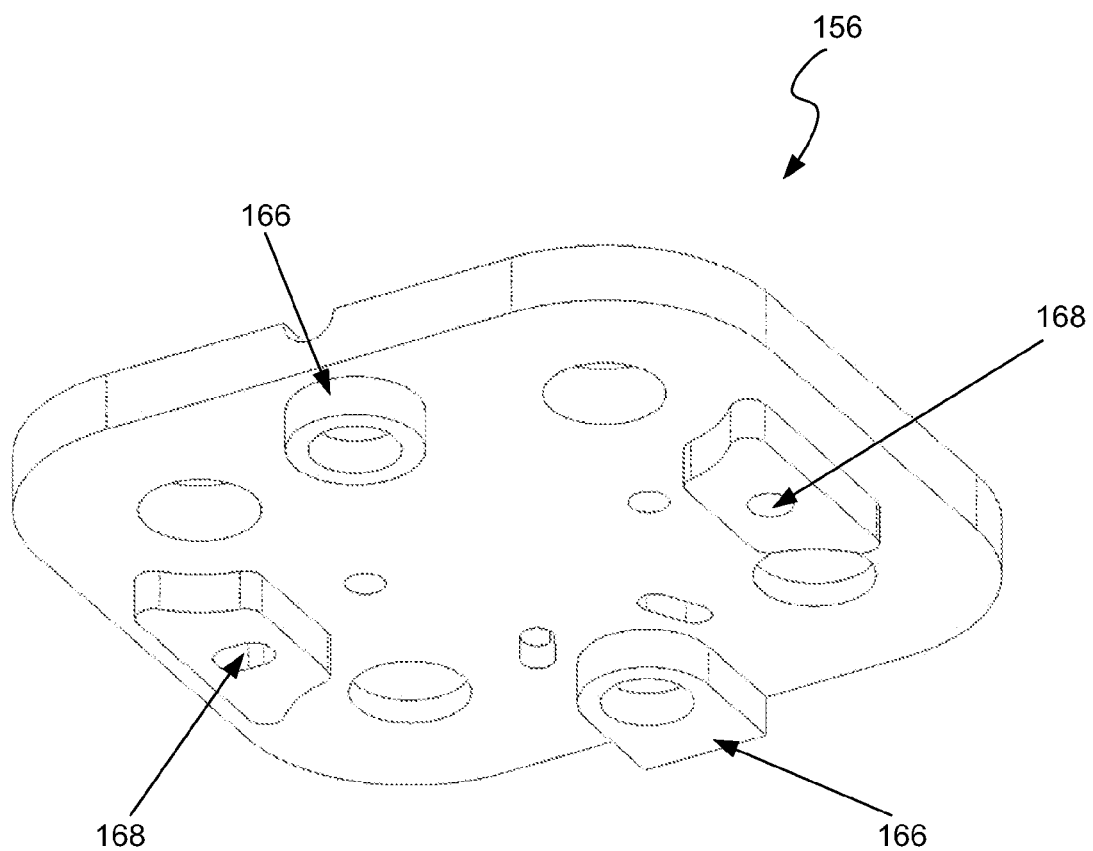
FIG. 45 illustrates an isometric bottom view of the bottom portion of FIG. 43.
Figure 46:
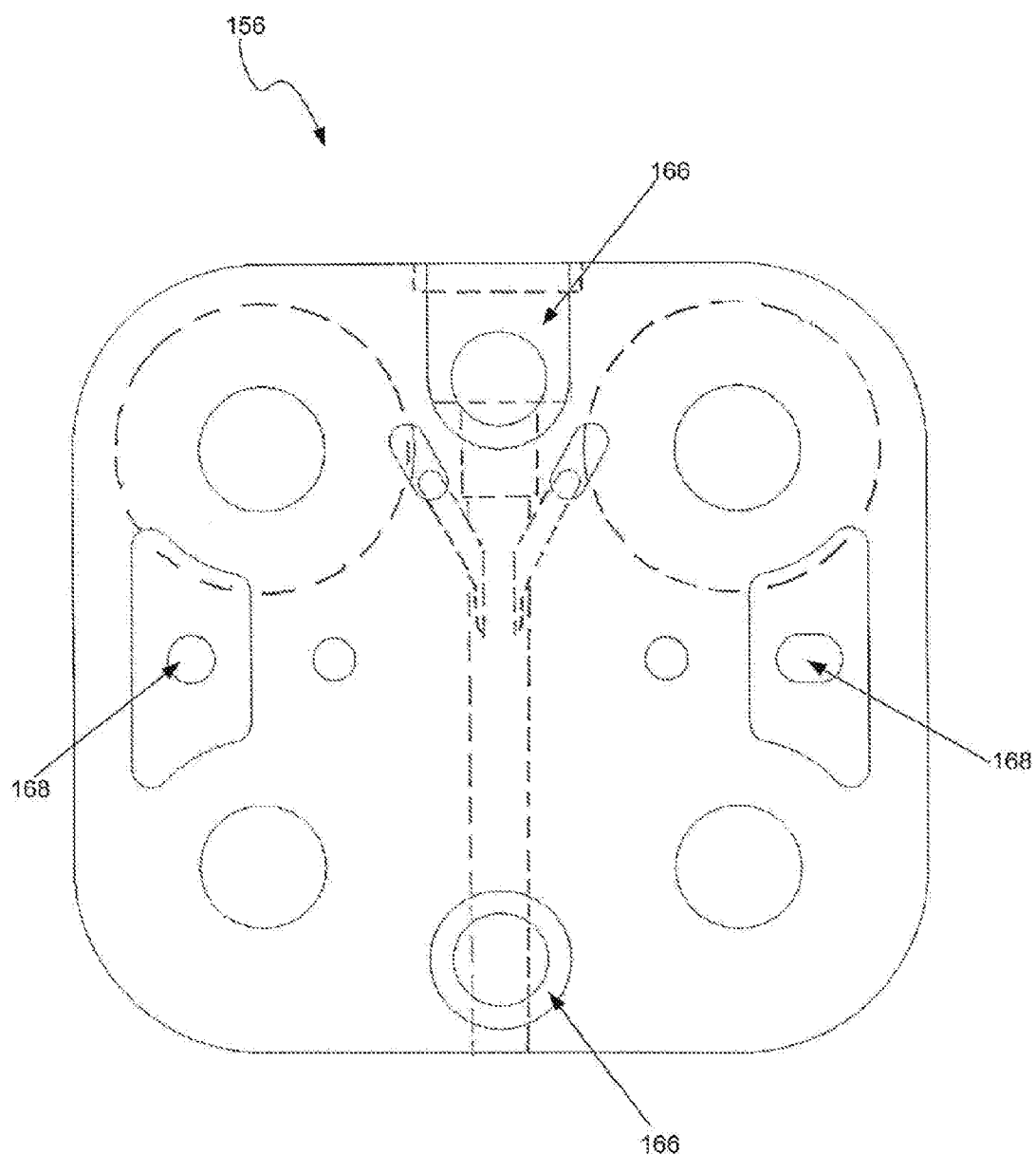
FIG. 46 illustrates a bottom view of the bottom portion of FIG. 43.

Referring to FIG. 43, a bottom portion (156) of one embodiment of a guide instrument base (48) is configured to interface with a top portion (152) such as that depicted in FIGS. 39-42. The bottom portion (156) has two additional pulley geometry accommodations (160) and associated control element splay tracks (158). The top (152) and bottom (156) portions of the guide instrument base (48) are "sandwiched" together to capture the proximal portion (88) of a catheter member (90), and therefore the bottom portion (156) also has a catheter member geometry accommodation (162) and a seal geometry accommodation (164) formed into it. FIG. 44 depicts an orthogonal view of the structures of FIG. 43 to better illustrate the control element splay track (158) structures positioned to guide control elements (not shown) away from a catheter member and to a pulley associated with the bottom portion (156) of the guide instrument base (48). FIG. 45 depicts an underside isometric view of the same bottom portion (156) shown in FIGS. 43 and 44. The bottom surface may comprise magnets (166) to facilitate mounting of the instrument upon an instrument driver. The depicted embodiment also has mounting pin interface holes (168) formed through it to accommodate mounting pins from an instrument driver. Further, the bottom surface preferably has a generally asymmetric geometry to ensure that it will only fit an underlying instrument driver snugly in one way. FIG. 46 depicts an orthogonal view of the bottom portion (156) of the guide instrument base (48) embodiment of FIG. 45.

Figure 47:
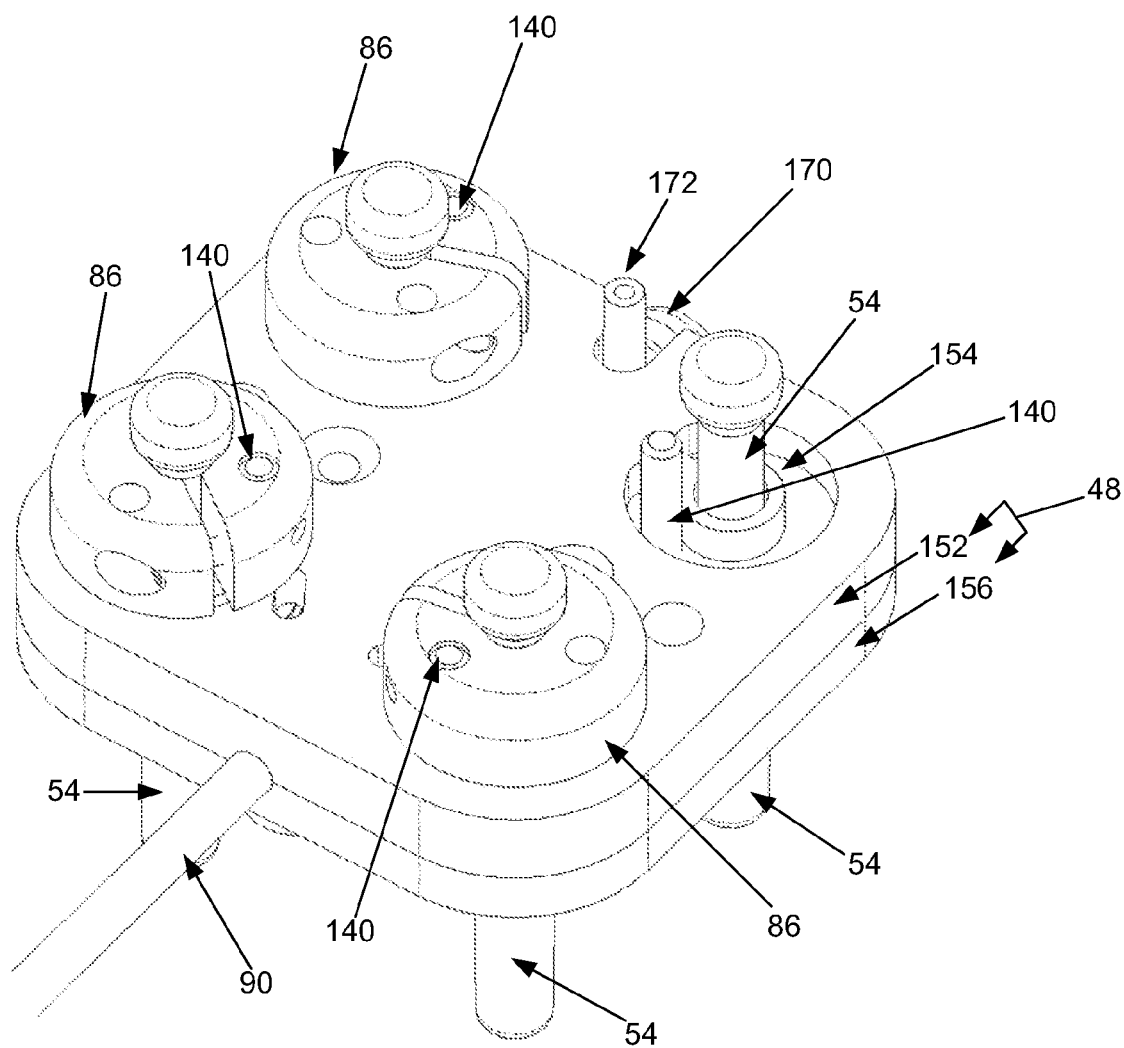
FIG. 47 illustrates an assembled instrument proximal end in accordance with some embodiments.
Figure 48:
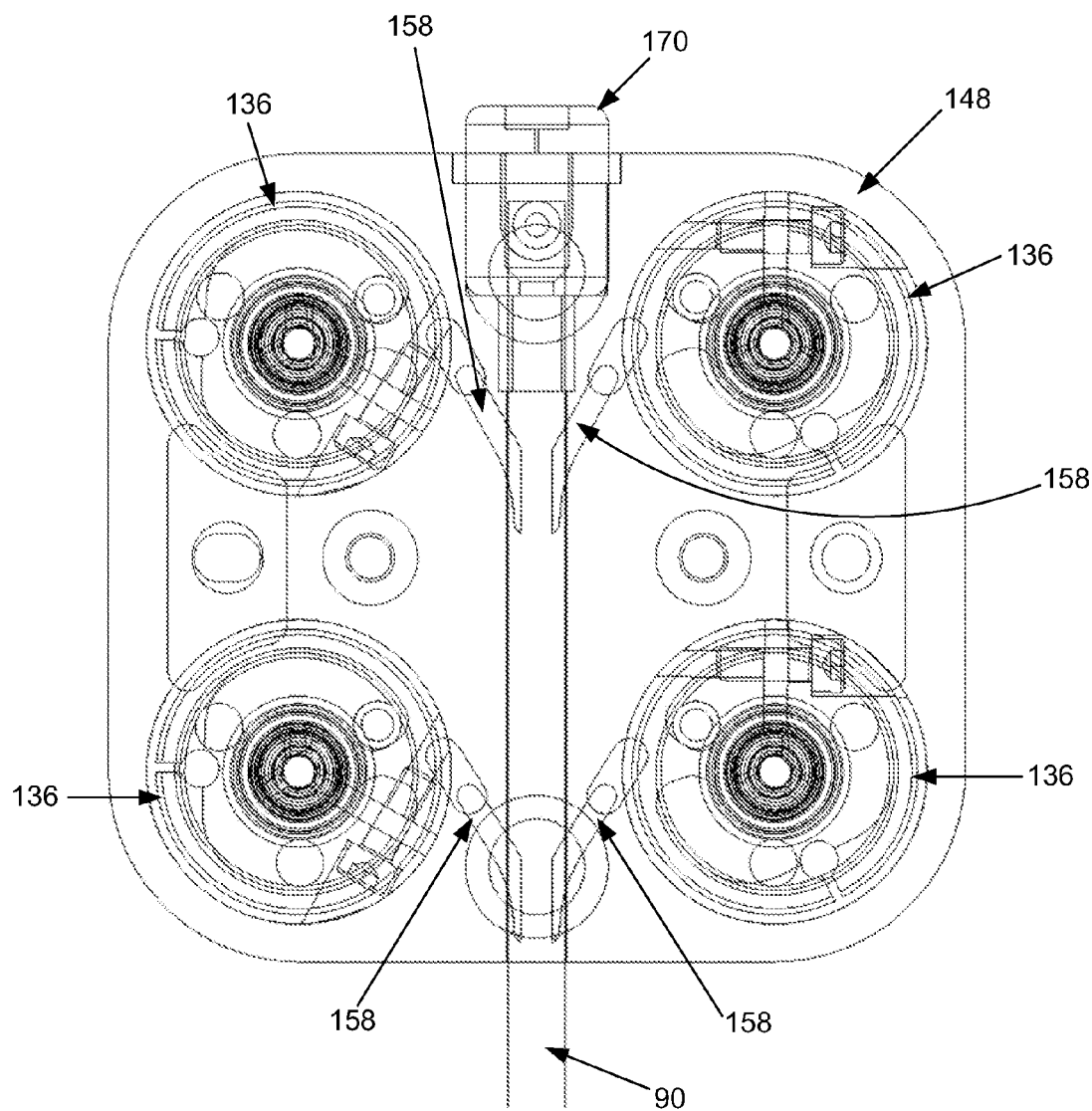
FIG. 48 illustrates a see-through view of the assembled instrument proximal end of FIG. 47.
Figure 49:
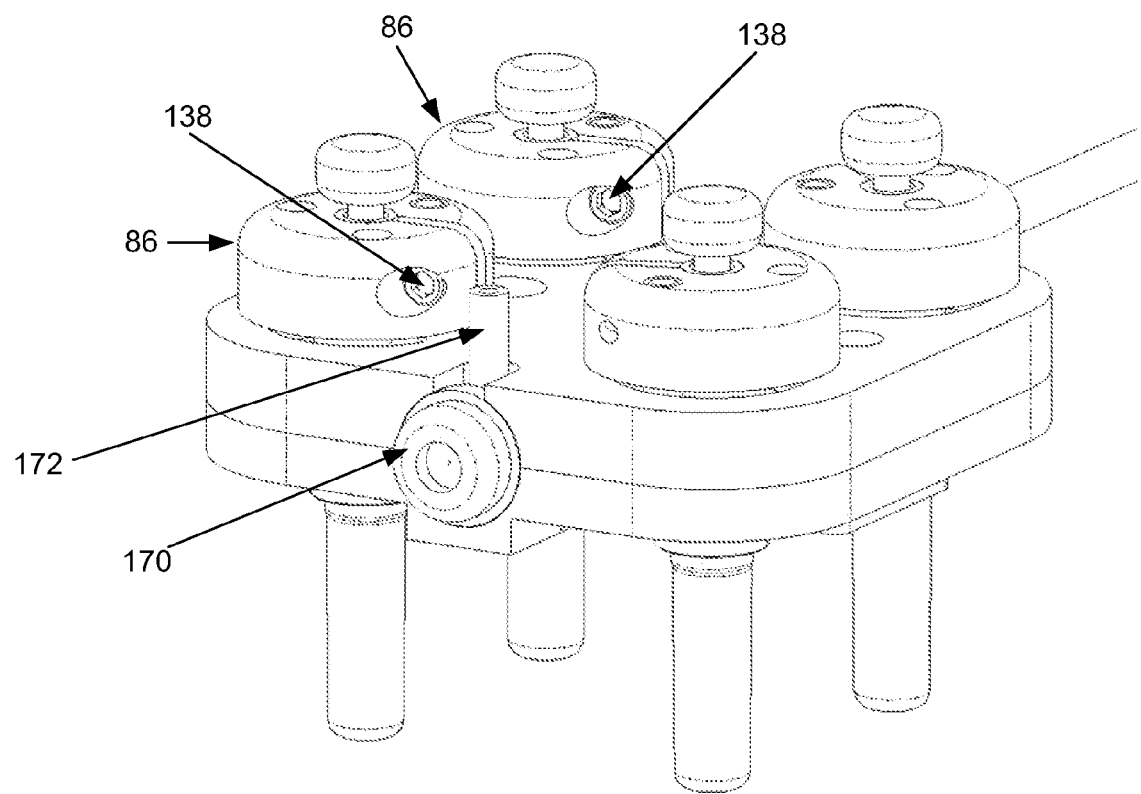
FIG. 49 illustrates a rear view of the assembled instrument proximal end of FIG. 47.

FIG. 47 illustrates a partially (although nearly completely) assembled instrument proximal end (82), including a top portion (152) and bottom portion (156) of an instrument base (48) interfaced together. The proximal end (82) houses four pulleys (not shown), a catheter member (90), and a seal (170), including and a purging port (172). Three manual adjustment knobs (86) are mounted to the guide instrument base (48) by axels (54), which are held in place by pulleys (not visible) mounted upon the axels (54). Rotational range of motion limitation pins (140) interface with the manual adjustment knobs and slots (154) in the guide instrument base (48) top portion (152). One of the four manual adjustment knobs is removed from the embodiment in FIG. 47 to illustrate the interaction between the pin (140) and slot (154). FIG. 48 shows the locations of the pulleys (136) and control element splay tracks (158) within this four-control element embodiment. Control elements (not shown) preferably comprise solid wires made from materials such as stainless steel, which are sized for the anticipated loads and geometric parameters of the particular application. They may be coated with materials such as Teflon™ to reduce friction forces. FIG. 49 illustrates a different isometric view of an instrument embodiment similar to that in FIG. 47 to better illustrate the seal (170) and purging port (172) positioning, as well as the clamp screws (138) of the manual adjustment knobs (86). The seal (170) preferably comprises a silicon rubber seal configured to accommodate insertion of working members or instruments, such as, e.g., relatively small profile guidewires (e.g, in the range of 0.035" diameter), or relatively larger profile catheters (e.g., of up to 7 French or even larger).

Referring to FIGS. 50-73, other embodiments of instruments are depicted having the respective capabilities to drive two, three, or four control elements with less than four control element interface assemblies (132) as previously discussed. For ease in illustration, many of the same components are utilized in these embodiments. As will be appreciated by those skilled in the art, such component matching is by no means required to accomplish the described functions, and many alternative arrangements are possible within the scope of the inventions disclosed herein.

Figure 50:
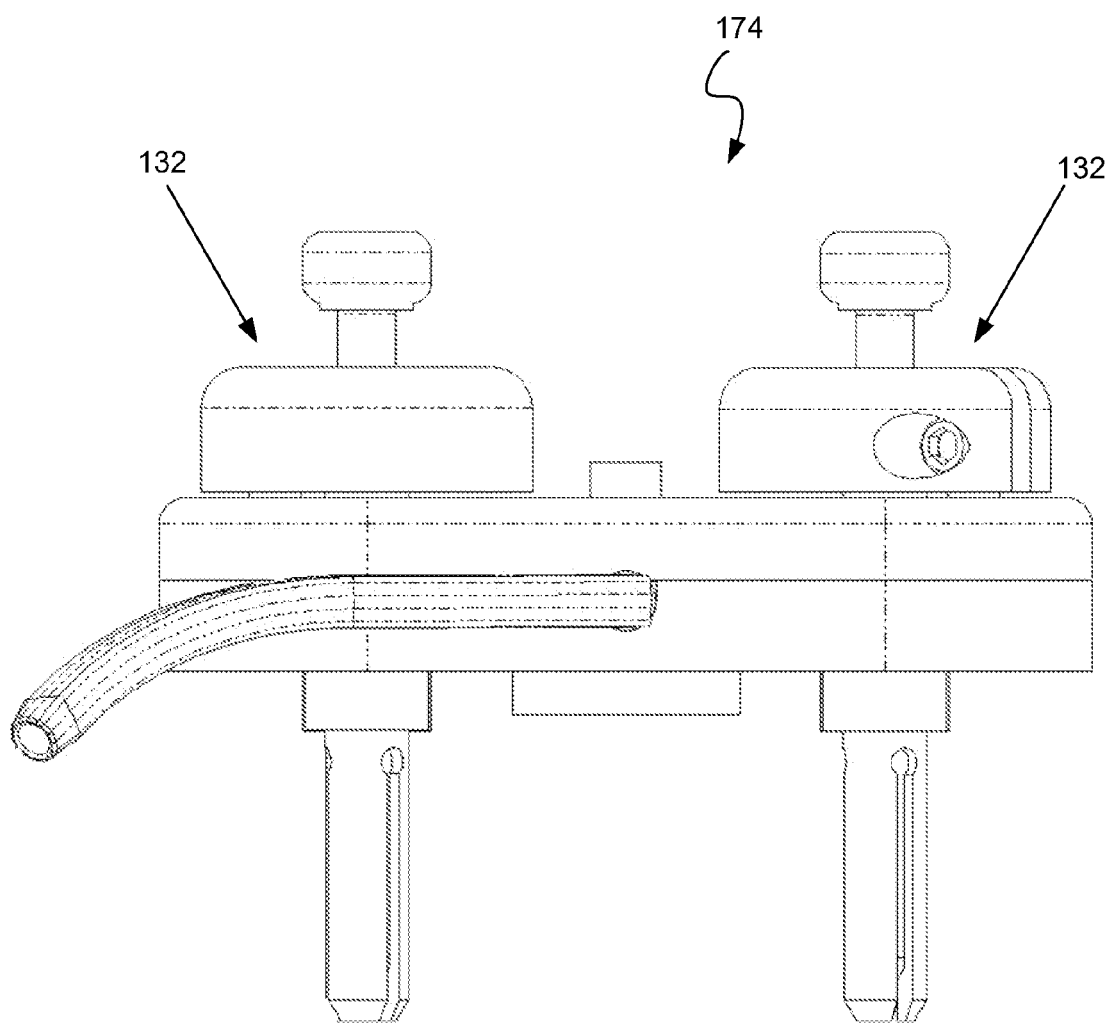
FIG. 50 illustrates a front view of an instrument in accordance with other embodiments.
Figure 51:
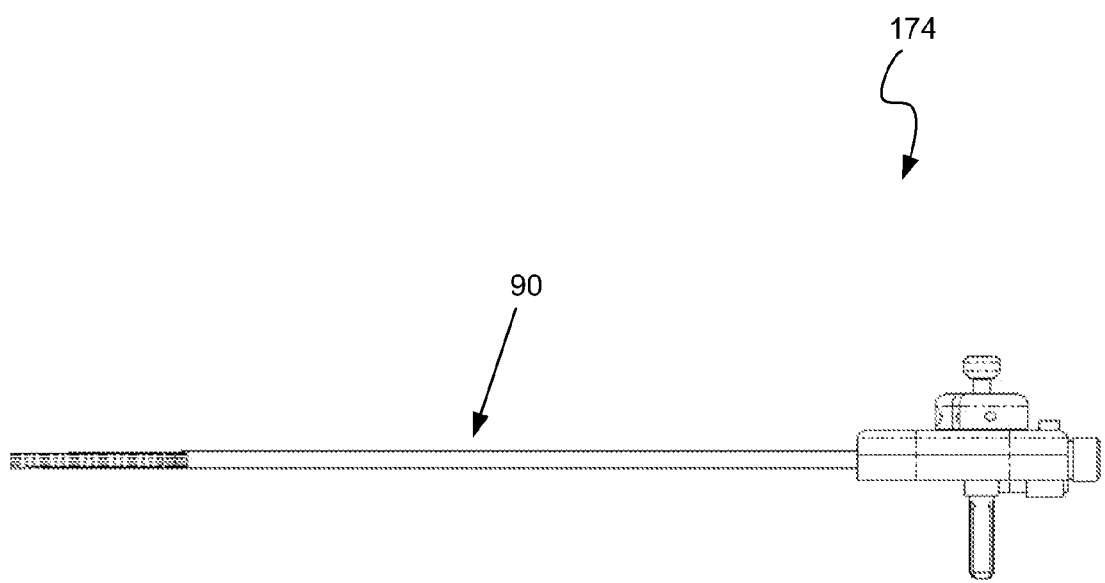
FIG. 51 illustrates a side view of the instrument of FIG. 50.
Figure 52:
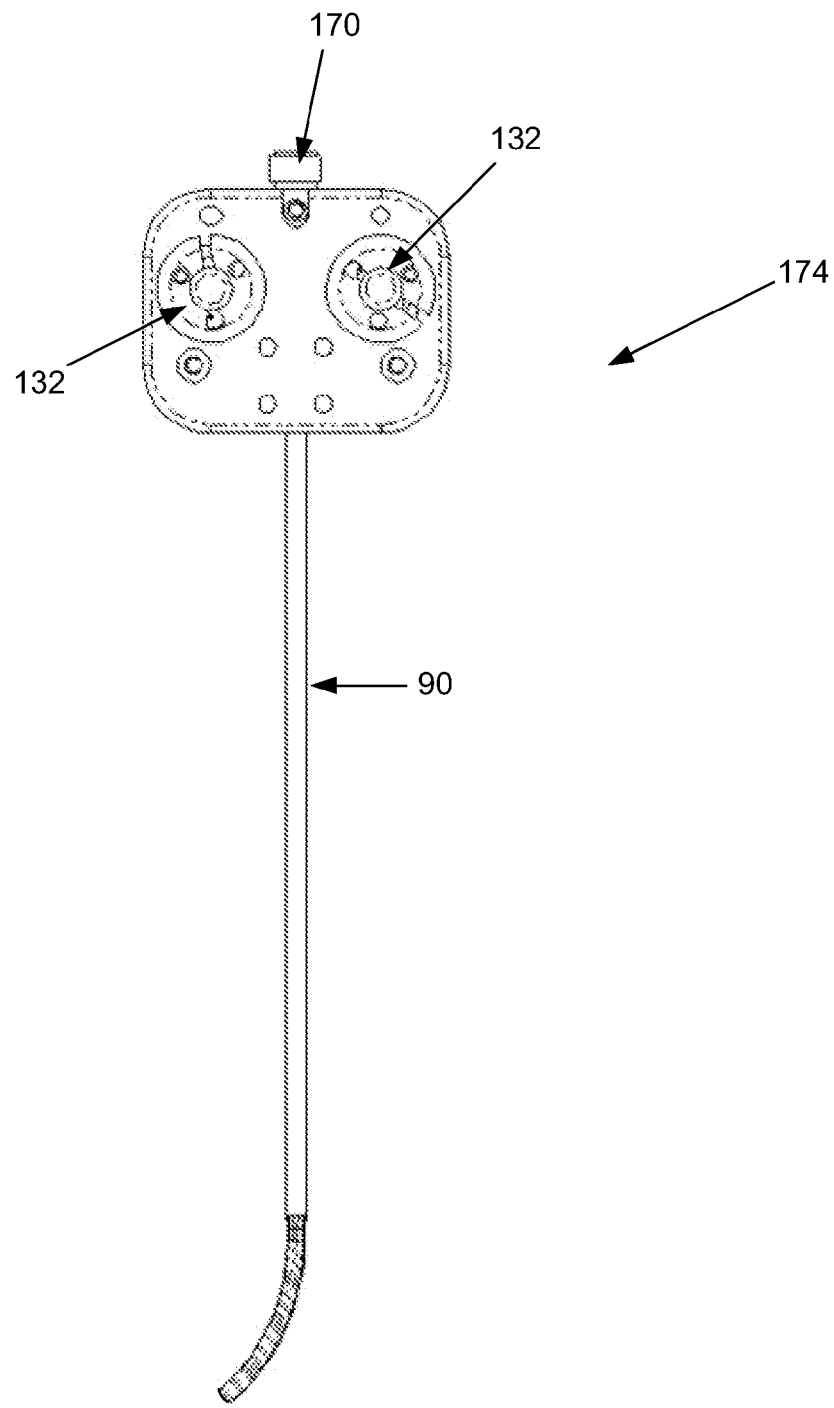
FIG. 52 illustrates a top view of the instrument of FIG. 50.
Figure 53:
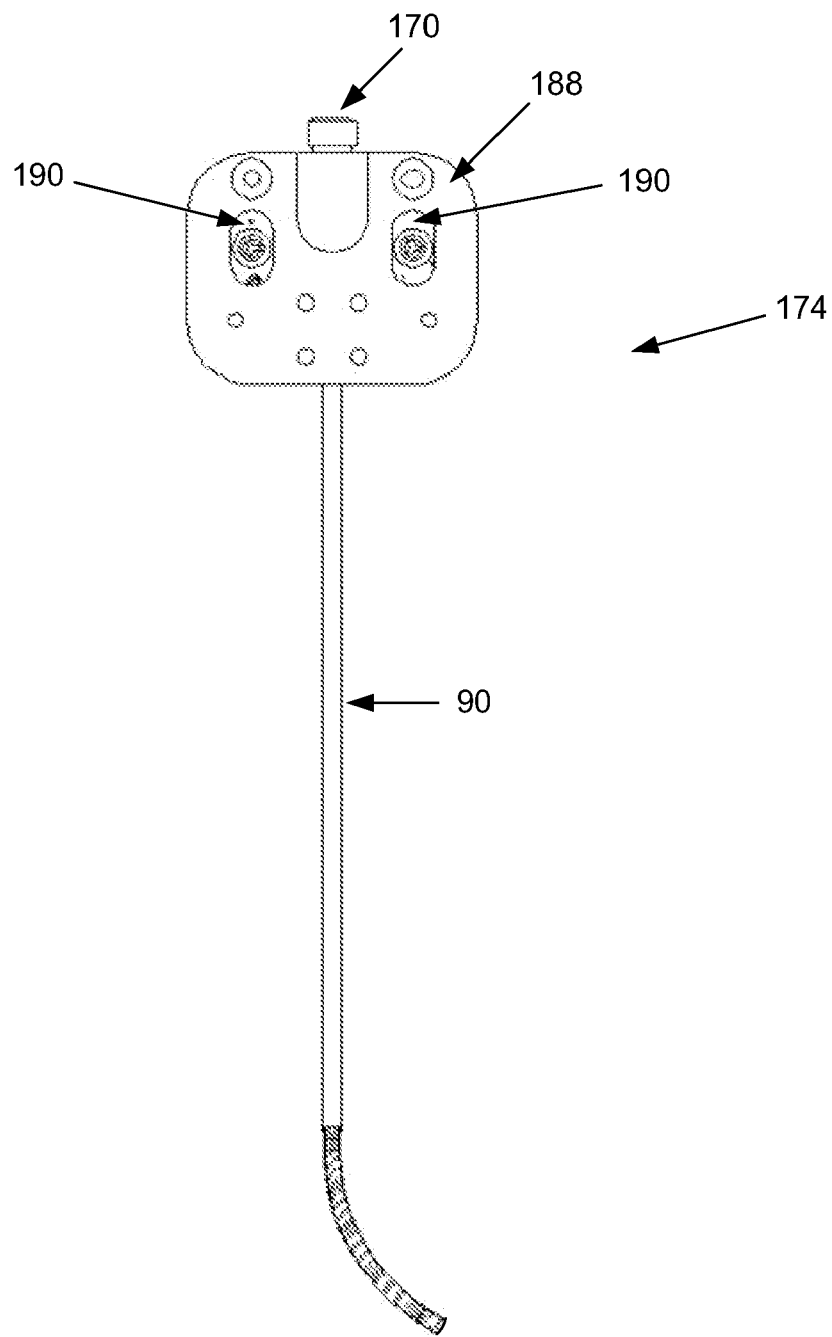
FIG. 53 illustrates a bottom view of the instrument of FIG. 50.
Figure 54:
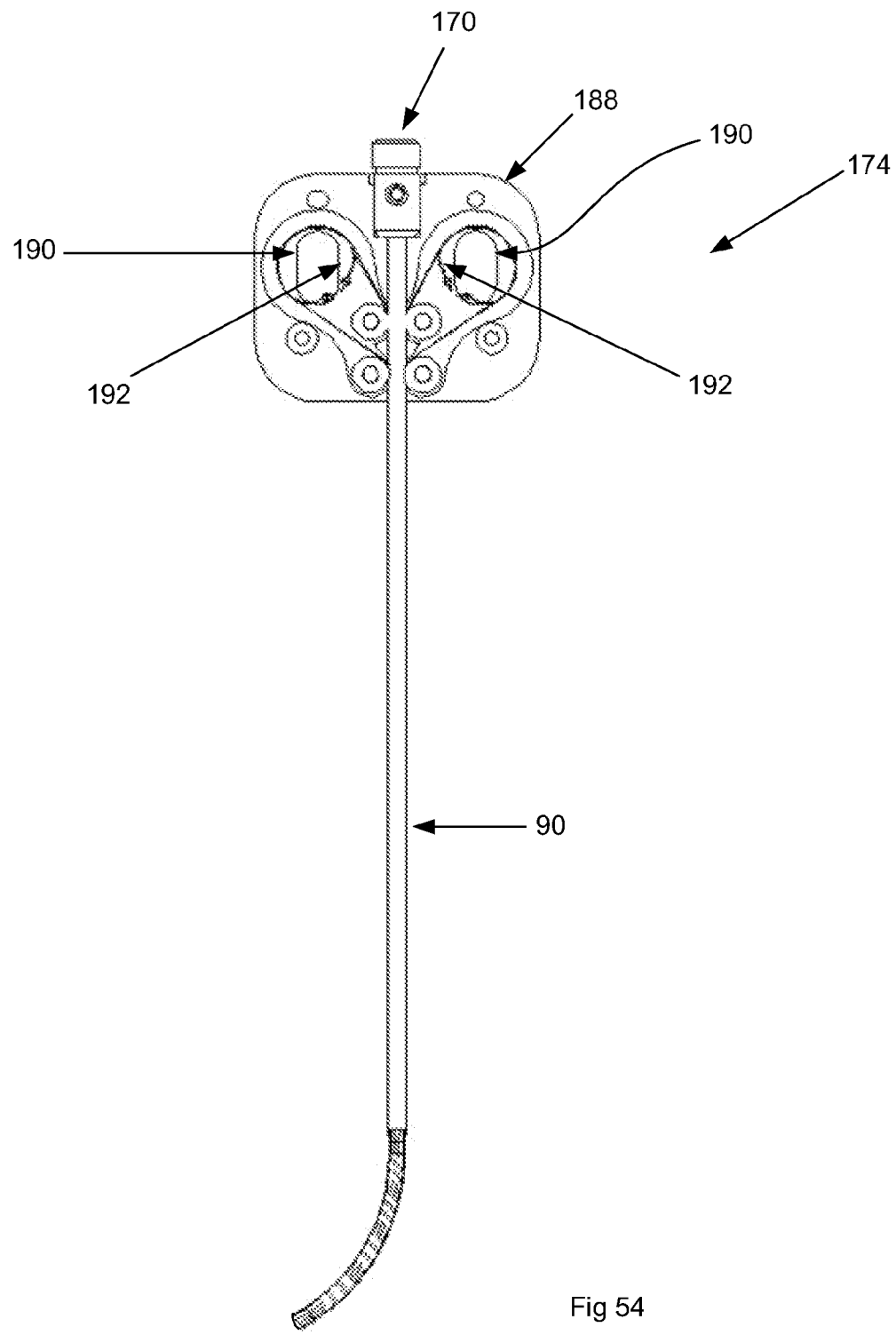
FIG. 54 illustrates a top view of the instrument of FIG. 50, showing a top view of a guide instrument base in accordance with some embodiments.

FIGS. 50, 51, and 52 illustrate an instrument (174) having two control element interface assemblies (132) is depicted in three orthogonal views. While this embodiment has only two control element interface assemblies, it is configured to drive four control elements and keep them in tension through either pre-tensioning, or active tensioning through a slotted guide instrument base (188) to a tensioning mechanism in the instrument driver (16). FIG. 53 illustrates an instrument (174) similar to that in FIG. 52, but shown from a back or bottom side orthogonal view. In particular, one side of the guide instrument base (188) forms slots (190) through which an instrument driver tensioning mechanism may keep control elements taut during operation of the instrument (174). FIG. 54 is a reverse orthogonal view of the structure in FIG. 53, with one side of the guide instrument base, and both control element interface assemblies, removed (132) to show the slots (190) and four control elements (192).

Figure 55:
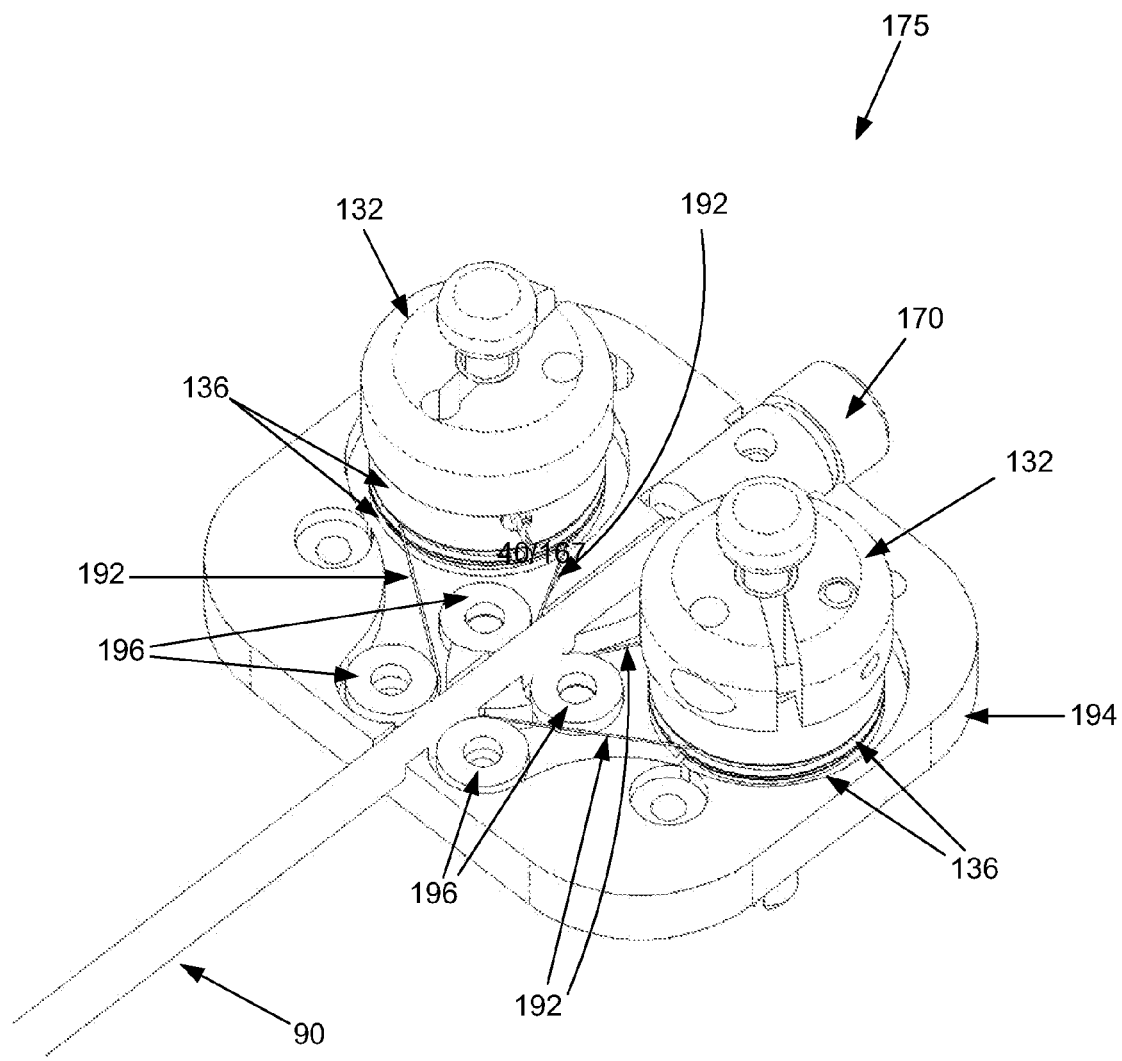
FIG. 55 illustrates an isometric view of a guide instrument base in accordance with other embodiments.
Figure 56:
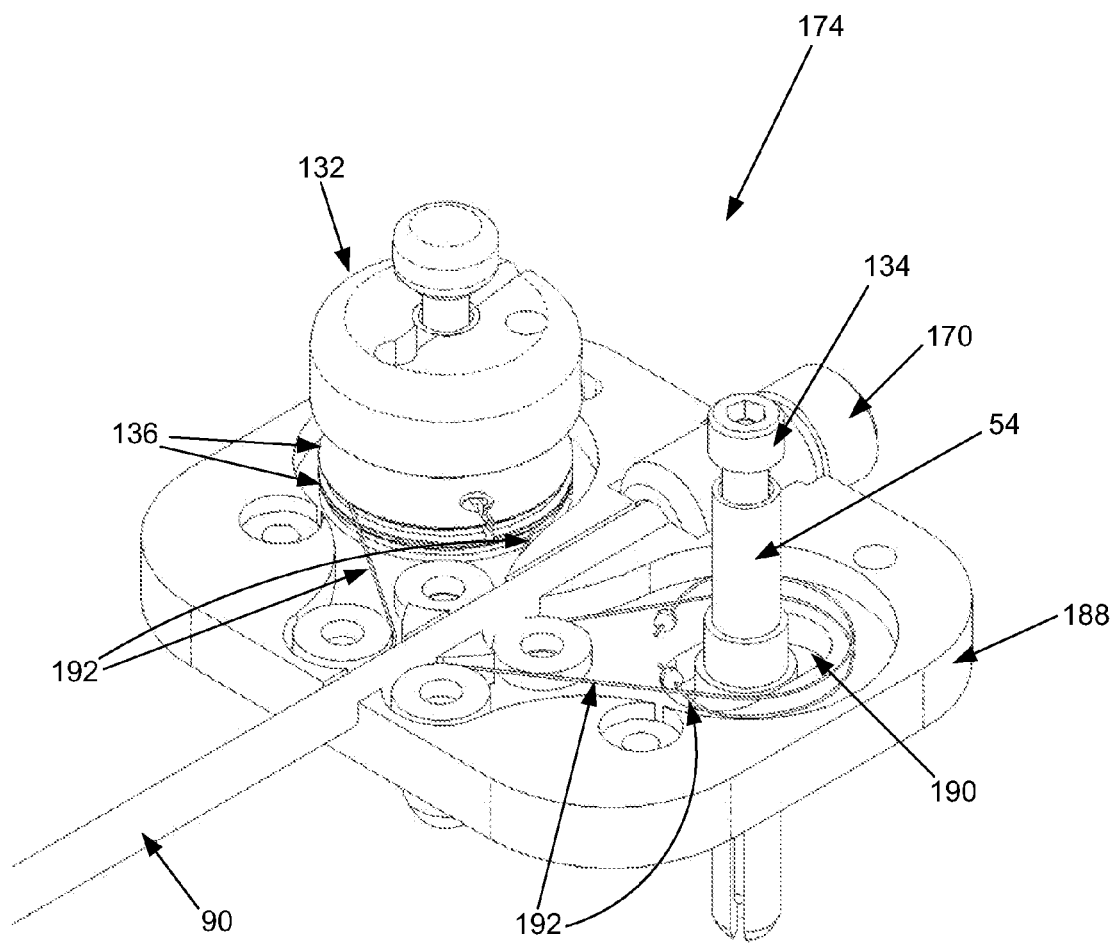
FIG. 56 illustrates an isometric view of a guide instrument base in accordance with other embodiments.

FIG. 55 illustrates an instrument (175) similar to that in FIGS. 53 and 54, with the exception that the guide instrument base (194) does not have slots—but rather has only fixed idler control element pathways to align the cables with the sets of two pulleys (136) comprising each control element interface assembly (132). In this embodiment, tension may be maintained in the control elements (192), with pre-tensioning, or pre-stressing, to prevent control element slack. FIG. 56 also illustrates an instrument (174) similar to that of FIGS. 53 and 54, including slots to allow for active tensioning of the control elements (192) from the underlying instrument driver. One of the control element interface assemblies (132) is shown intact, and one is shown only partially intact, with the axel (54) and drive engagement knob (134) depicted to show the control elements (192). A notable difference between the embodiment in FIG. 56 and that in FIG. 55 is the addition of the tensioning slots (190).

Figure 57:
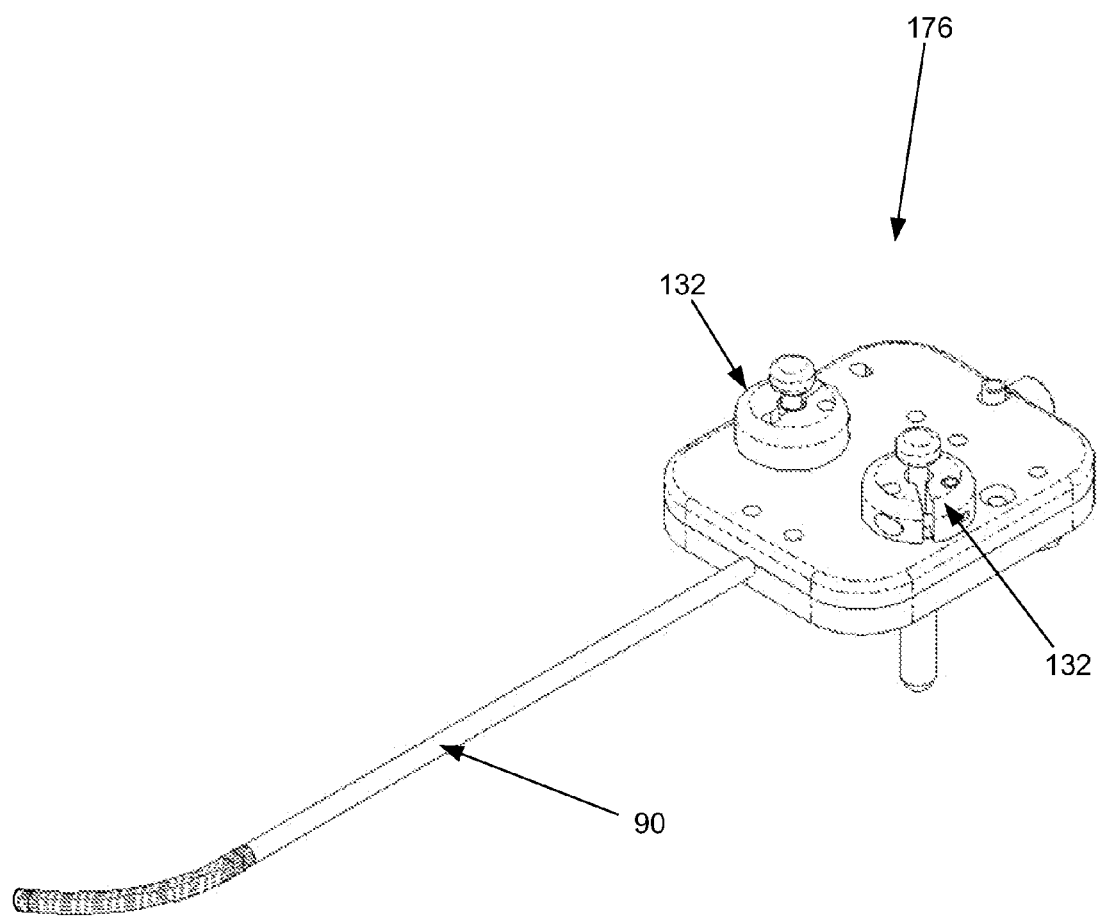
FIG. 57 illustrates an isometric view of an instrument in accordance with other embodiments.
Figure 58:
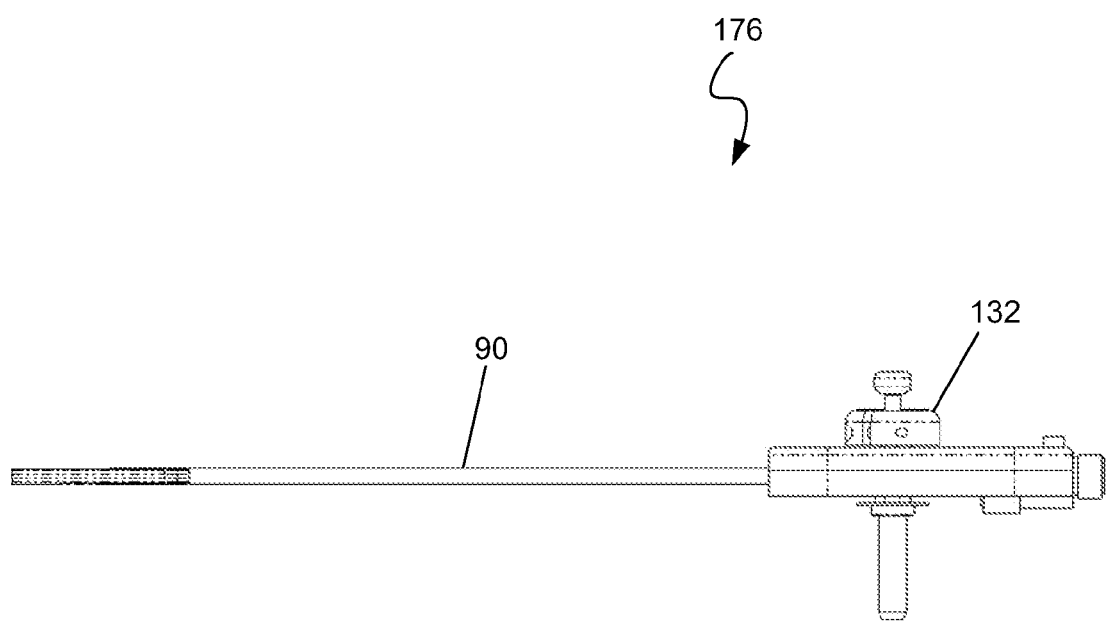
FIG. 58 illustrates a side view of the instrument of FIG. 57.
Figure 59:
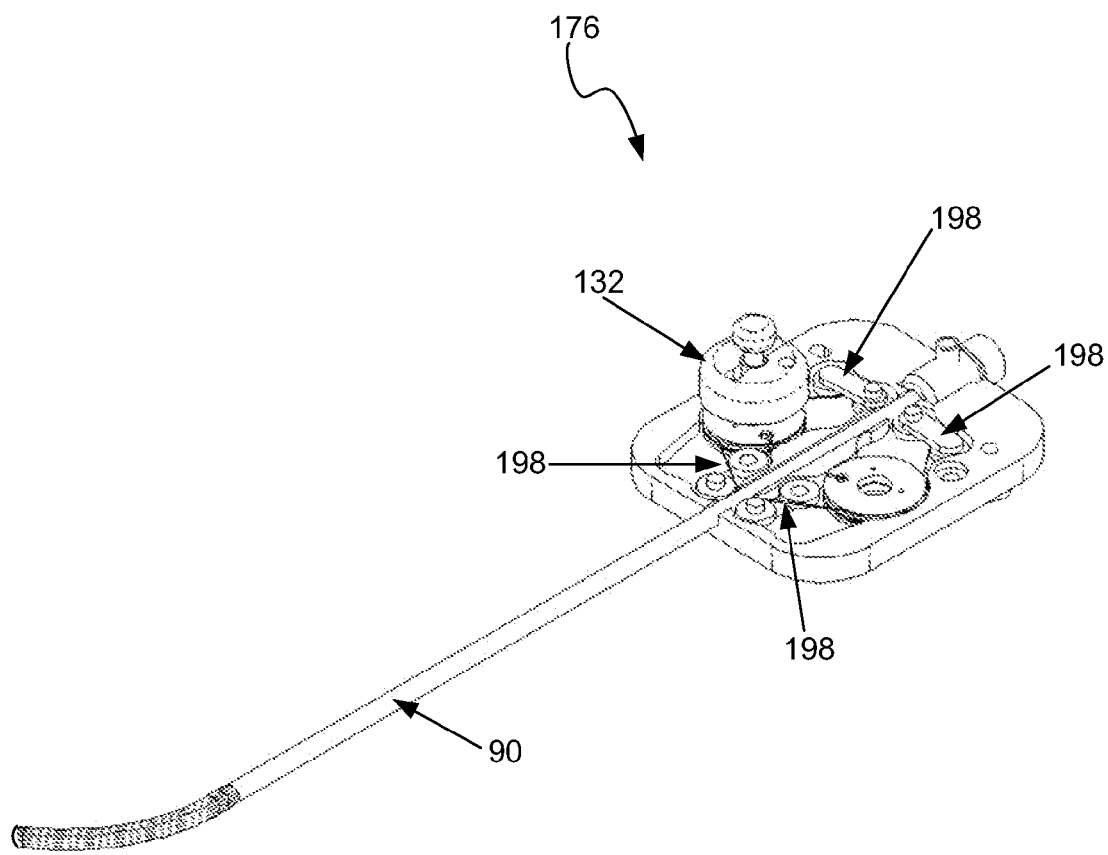
FIG. 59 illustrates an isometric view of the instrument of FIG. 57, showing a bottom portion.
Figure 60:
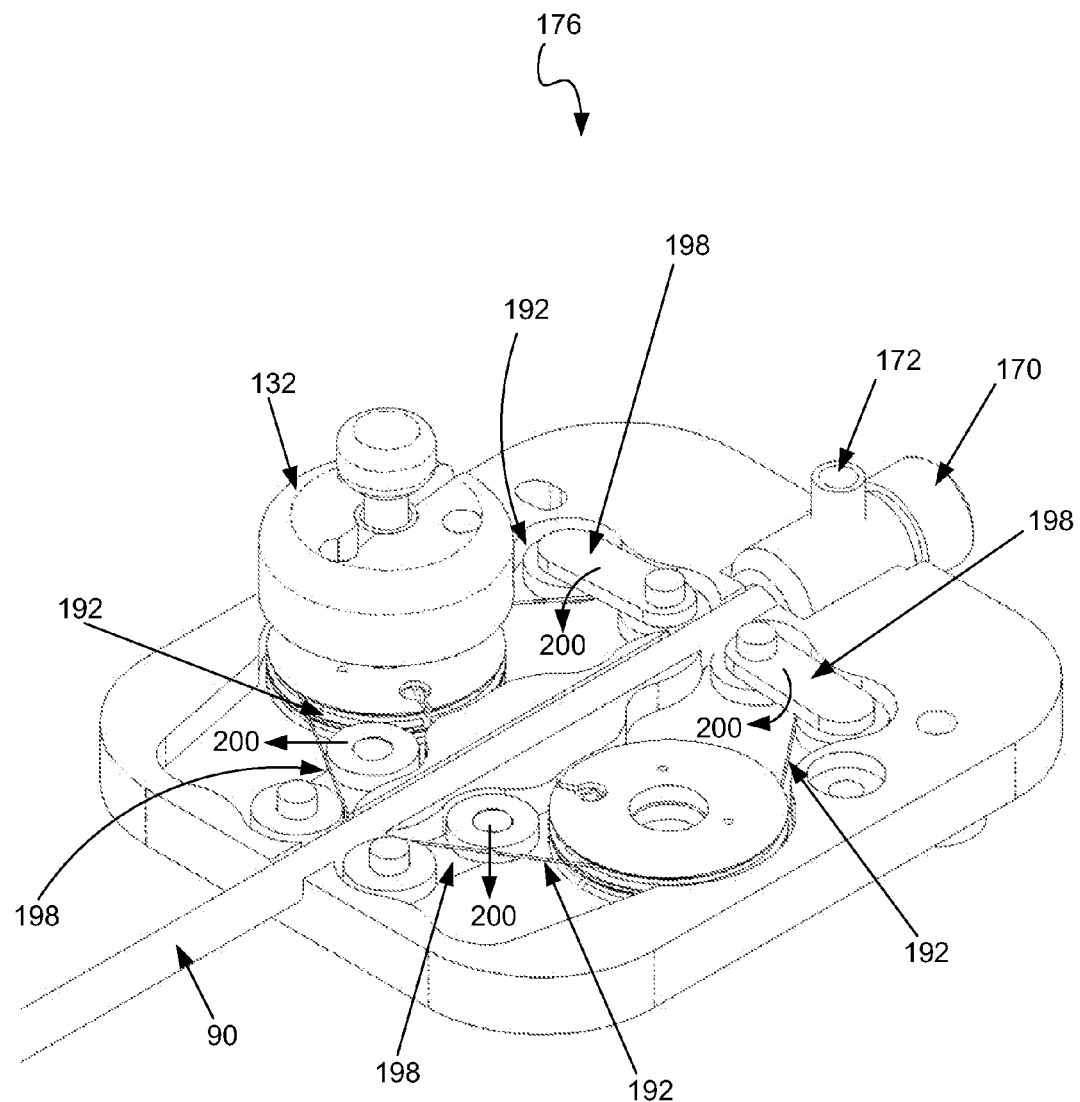
FIG. 60 illustrates a close up view of the bottom portion of FIG. 59.
Figure 61:
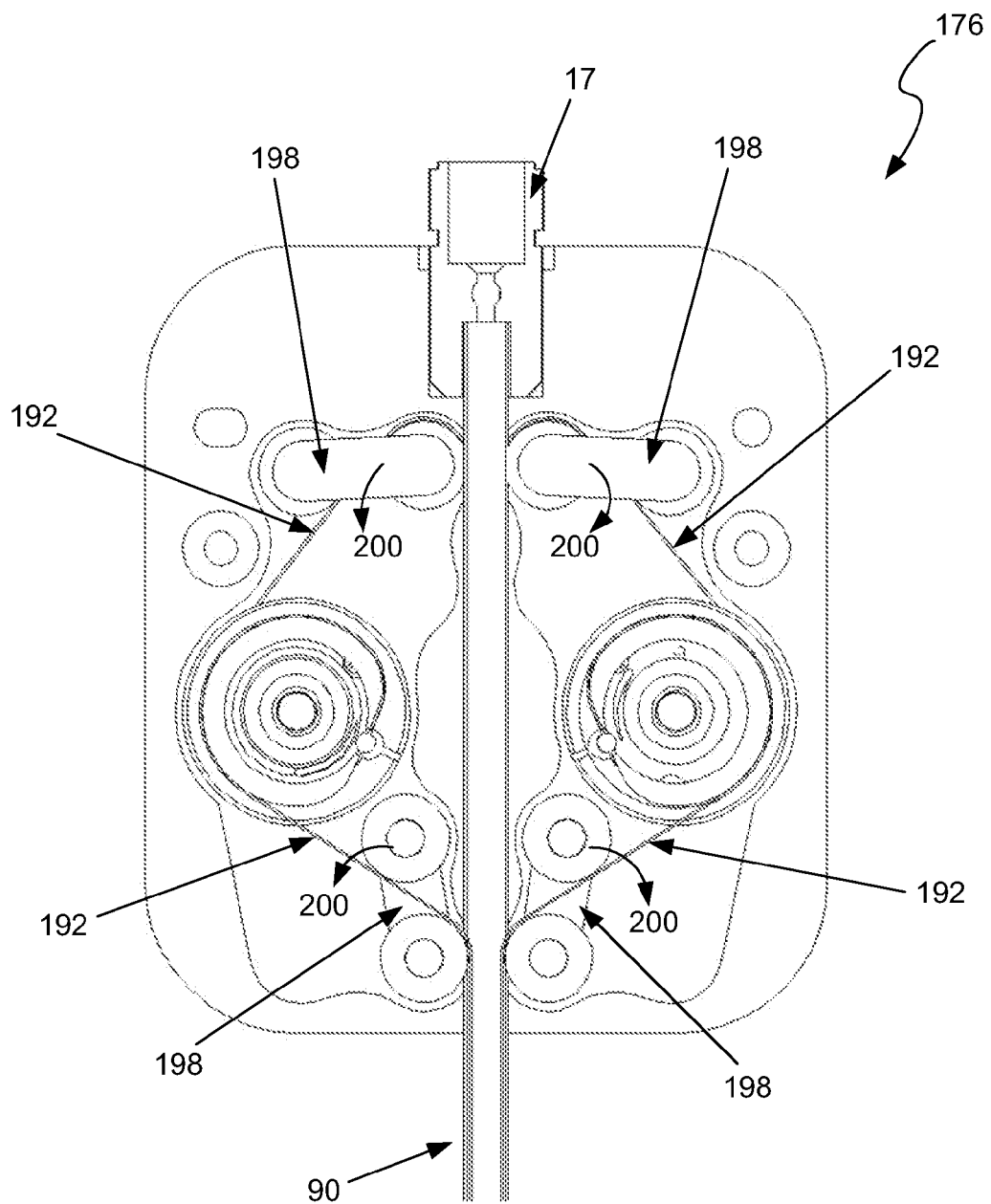
FIG. 61 illustrates another view of the bottom portion of FIG. 59.
Figure 62:
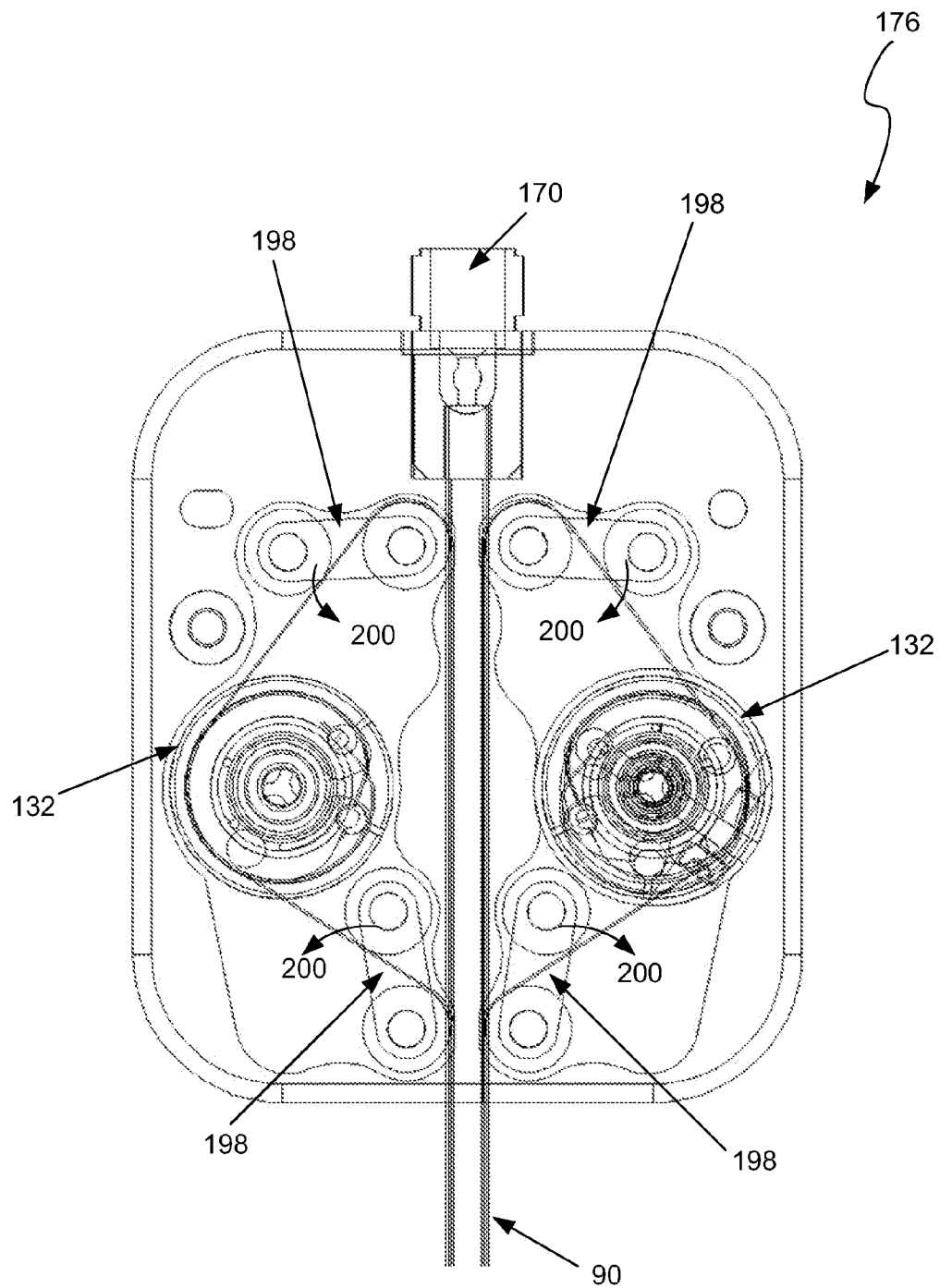
FIG. 62 illustrates a see-through view of the bottom portion of FIG. 59.

Referring to FIGS. 57 and 58, yet another instrument embodiment (176) is depicted in isometric and side views, respectively, with this embodiment having two control element interface assemblies to drive four control elements. As shown in the partial cutaway isometric view of FIG. 59, and close up cutaway view of FIG. 60, this embodiment differs from the fixed ider embodiment of FIG. 55, or the slotted embodiment of FIG. 56, in that it has four spring-loaded idlers to assist with tensioning each of the four control elements. Referring to FIG. 60, each of the control elements (192) passes through a spring loaded idler (198), which urges the control element (192) into tension by trying to rotate (200). This tensioning schema may be easiest to visualize in the orthogonal cutaway view of FIG. 61, wherein the spring loaded idlers (198) are depicted urging (200) the four control elements (192) into tension. The wireframe orthogonal view of FIG. 62 also shows the stacks of two pulleys each on each control element interface assembly (132) to accommodate four control elements (192).

Figure 63:
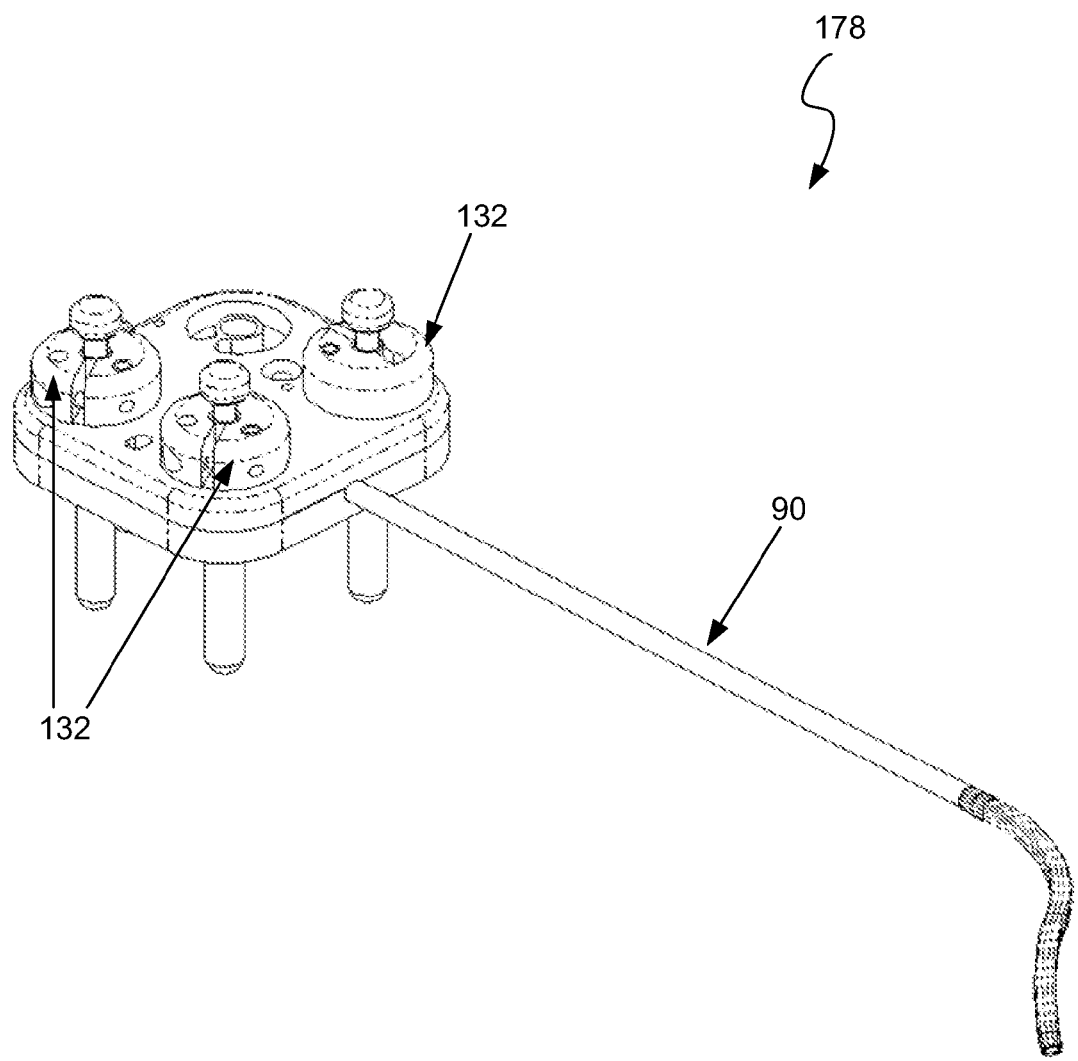
FIG. 63 illustrates an isometric view of an instrument in accordance with other embodiments.
Figure 64:
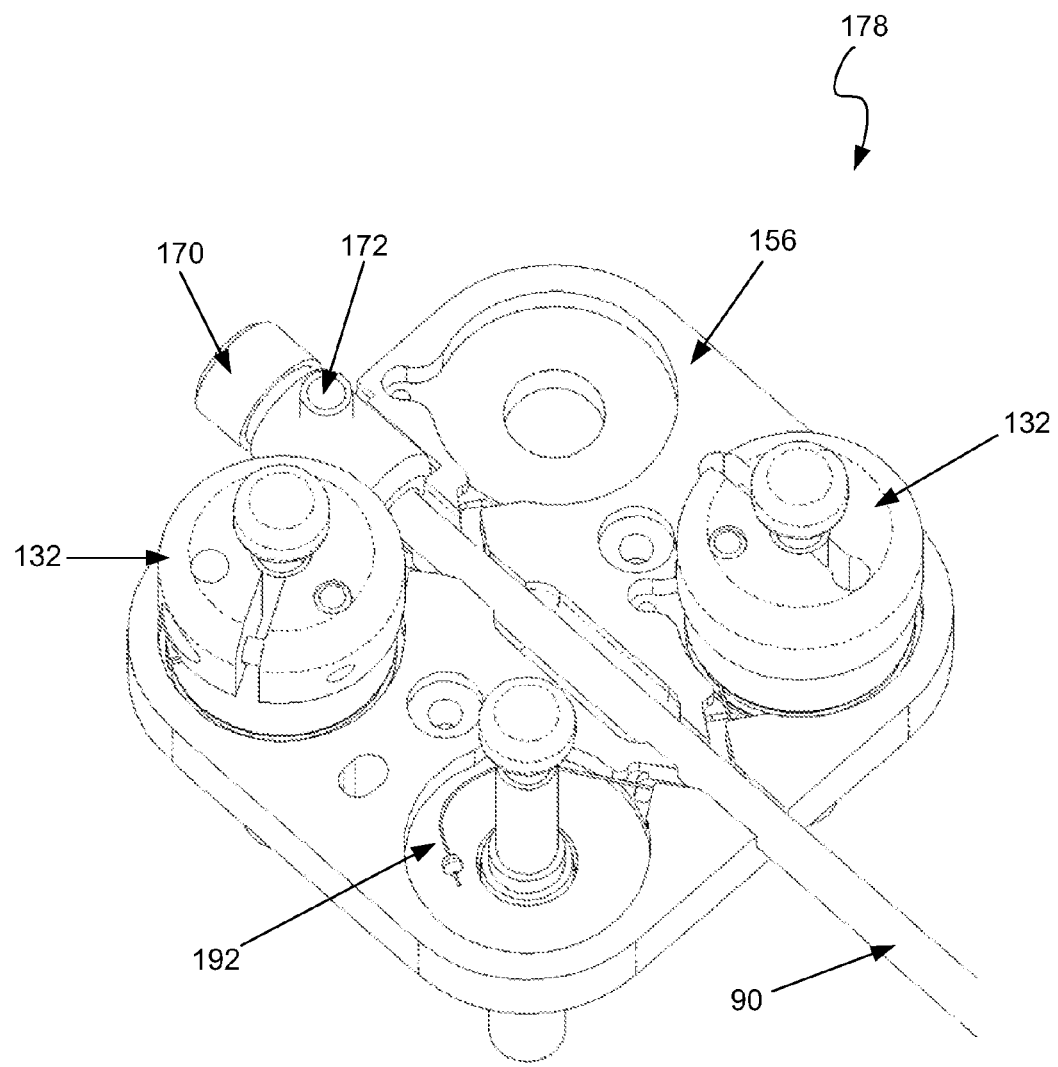
FIG. 64 illustrates an isometric view of a bottom portion of the instrument of FIG. 63.
Figure 65:
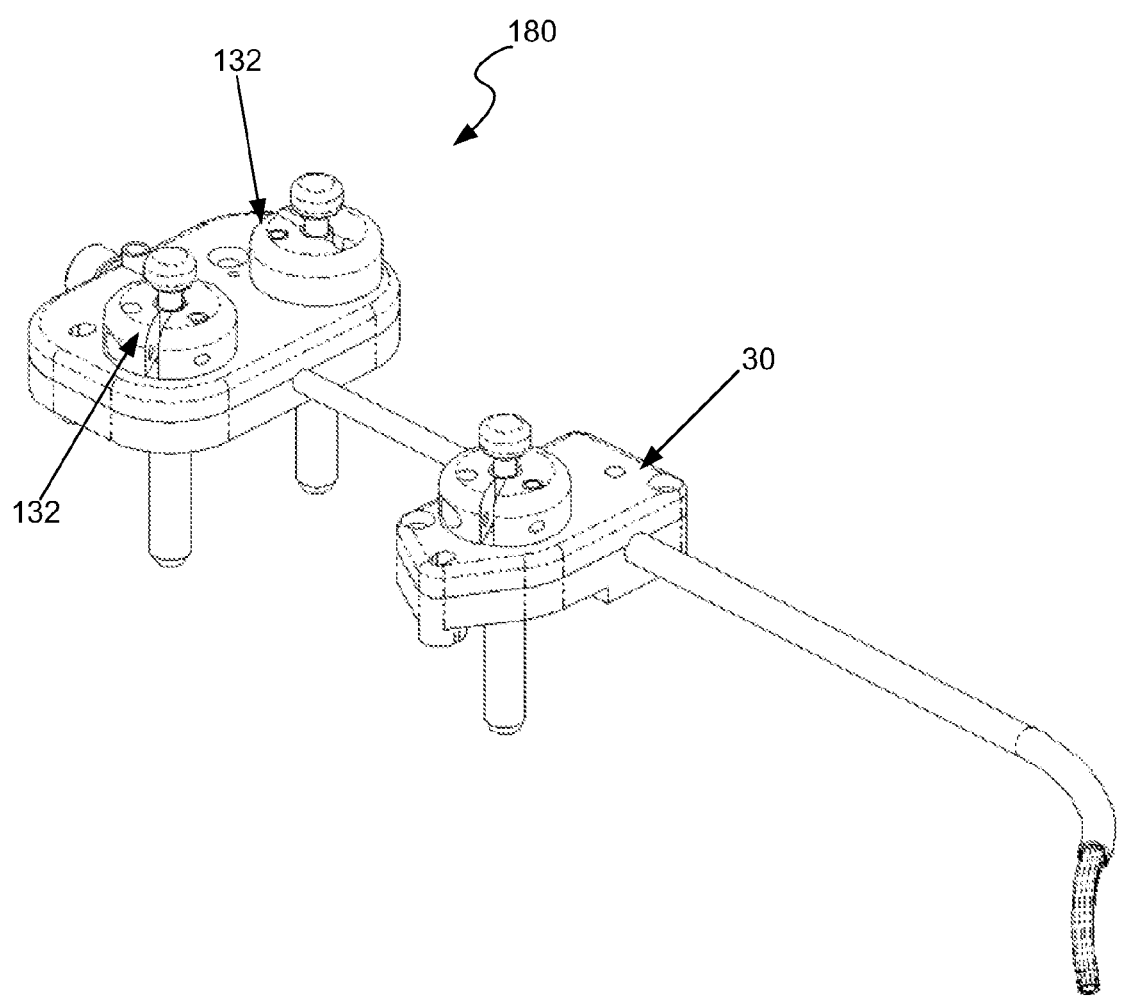
FIG. 65 illustrates an instrument having two control element interface assemblies coupled to a sheath instrument in accordance with some embodiments.
Figure 66:
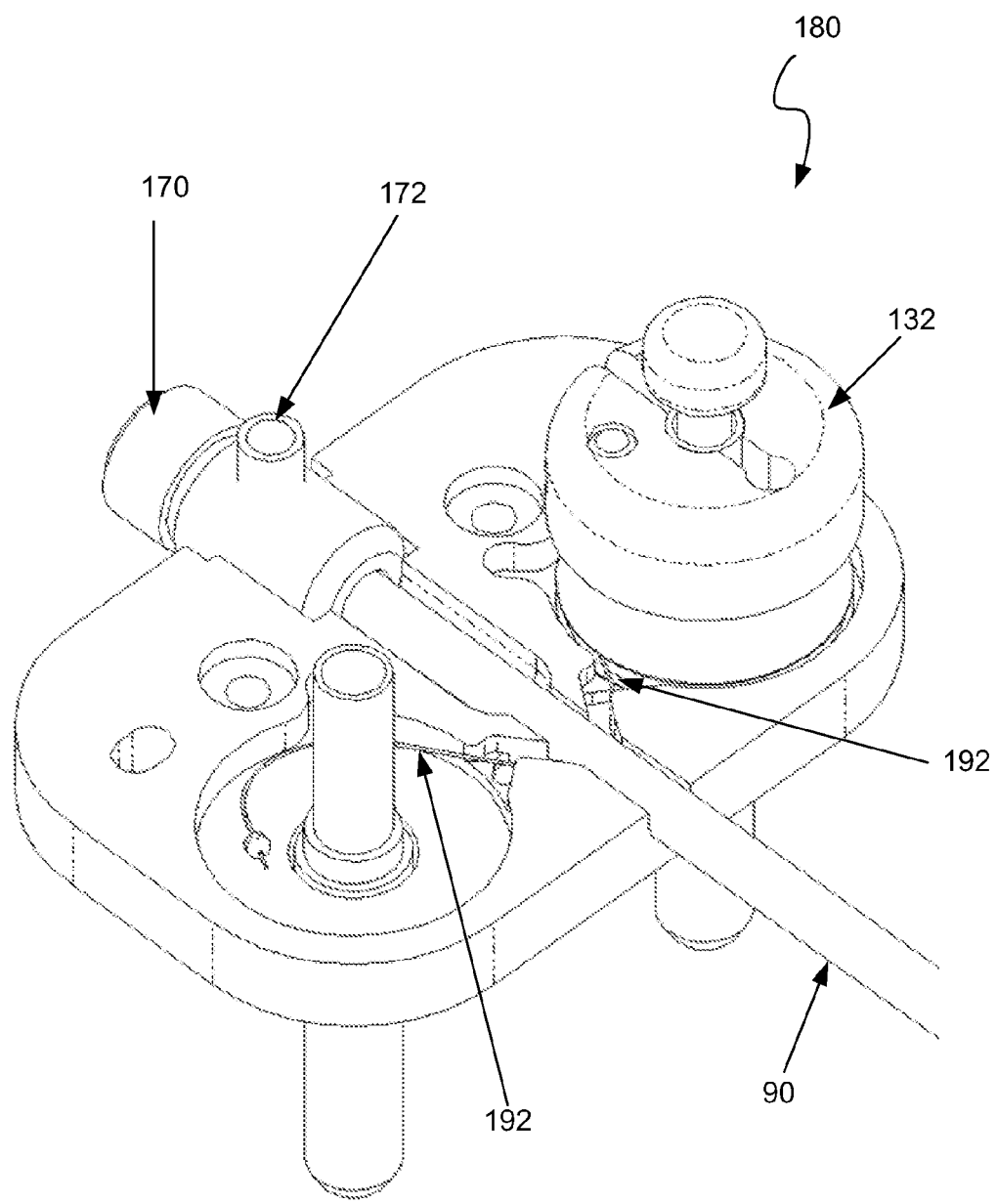
FIG. 66 illustrates an isometric view of a bottom portion of the instrument of FIG. 65.

FIGS. 63 and 64 depict another instrument embodiment (178), this one having three control element interface assemblies (132) for three independent control elements. As best seen in FIG. 64, this embodiment is similar to that of FIG. 47, for example, except that it has one less control element and one less control element interface assembly (132). FIG. 65 depicts yet another instrument embodiment (180) coupled with a sheath instrument (30). In particular, instrument (180) has two control element interface assemblies (132) and two control elements. As best seen in FIG. 66, the instrument (180) is not configured for slotted tensioning or spring-loaded tensioning. Instead, the control elements (192) of this embodiment may be actively tensioned independently, and/or pre-tensioned, to facilitate maintenance of tension for control purposes.

Figure 67:
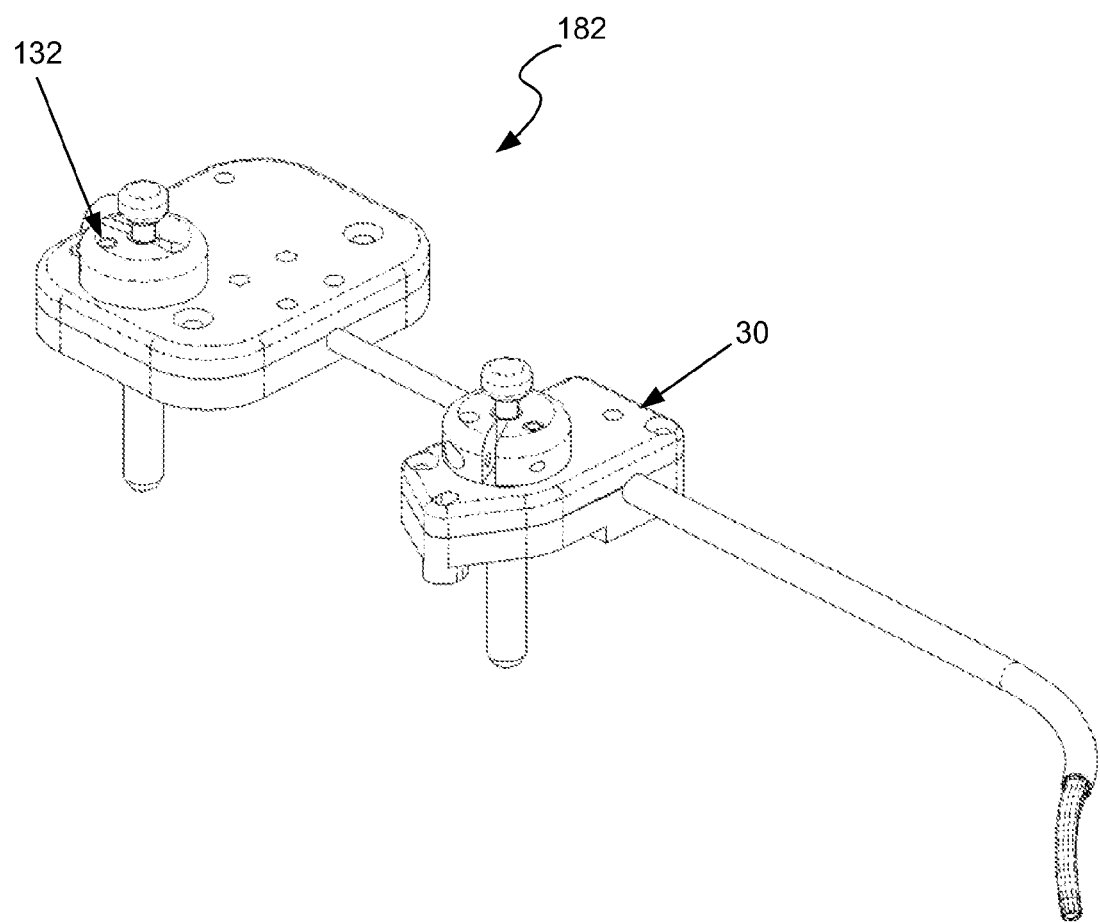
FIG. 67 illustrates an instrument having a control element interface assembly coupled to a sheath instrument in accordance with some embodiments.
Figure 68:
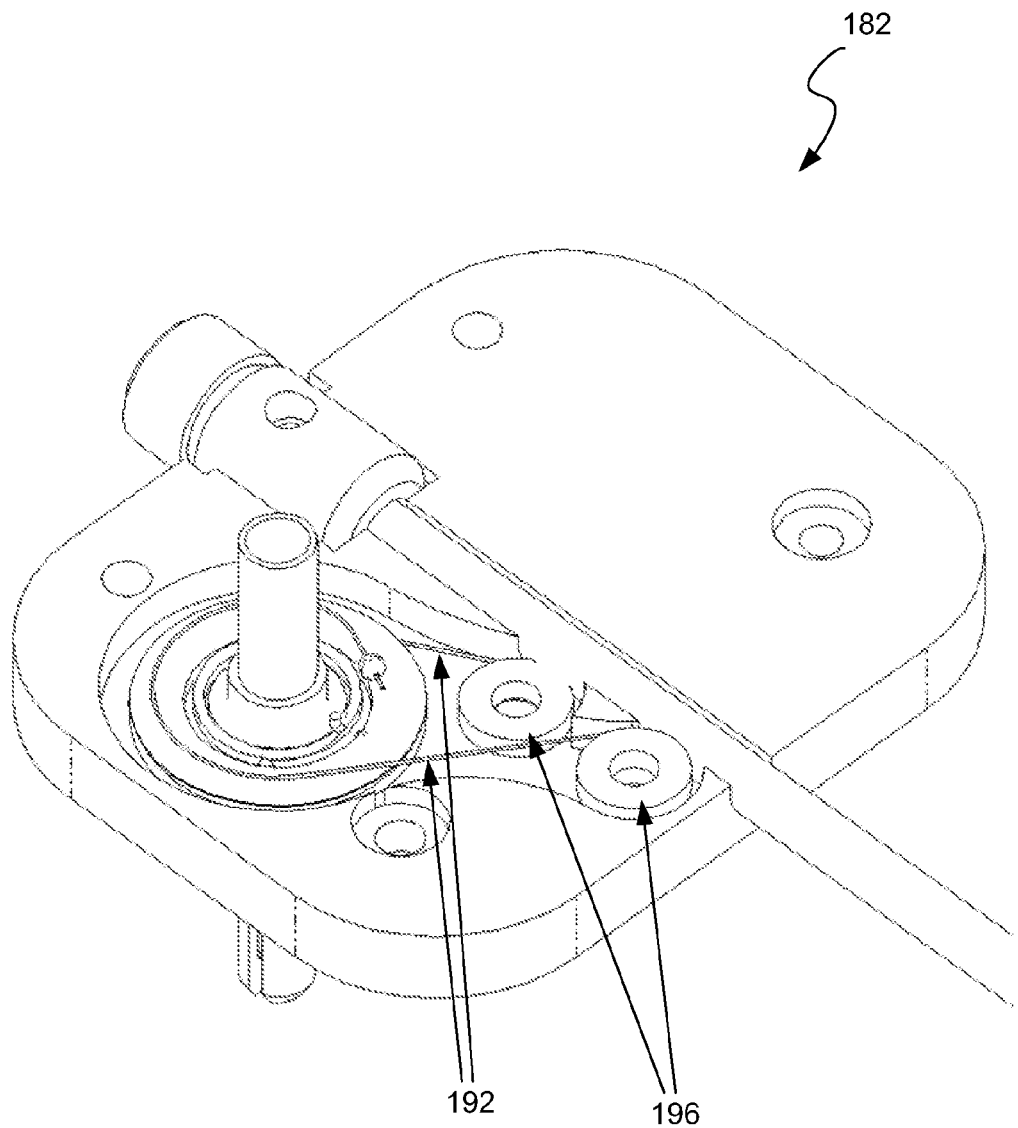
FIG. 68 illustrates an isometric view of a bottom portion of the instrument of FIG. 67.
Figure 69:
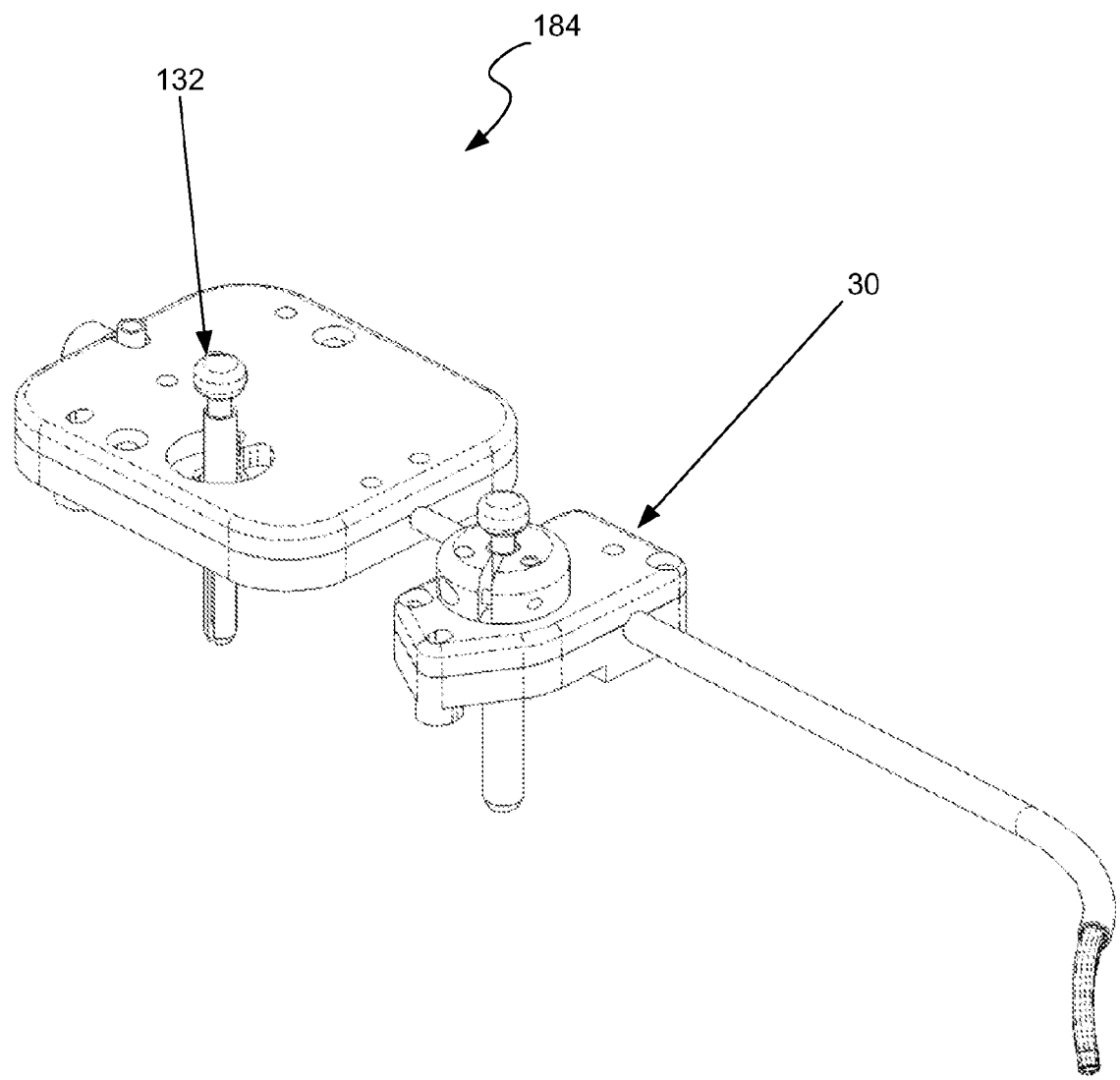
FIG. 69 illustrates an isometric view of an instrument having a control element interface assembly coupled to a sheath instrument in accordance with other embodiments.
Figure 70:
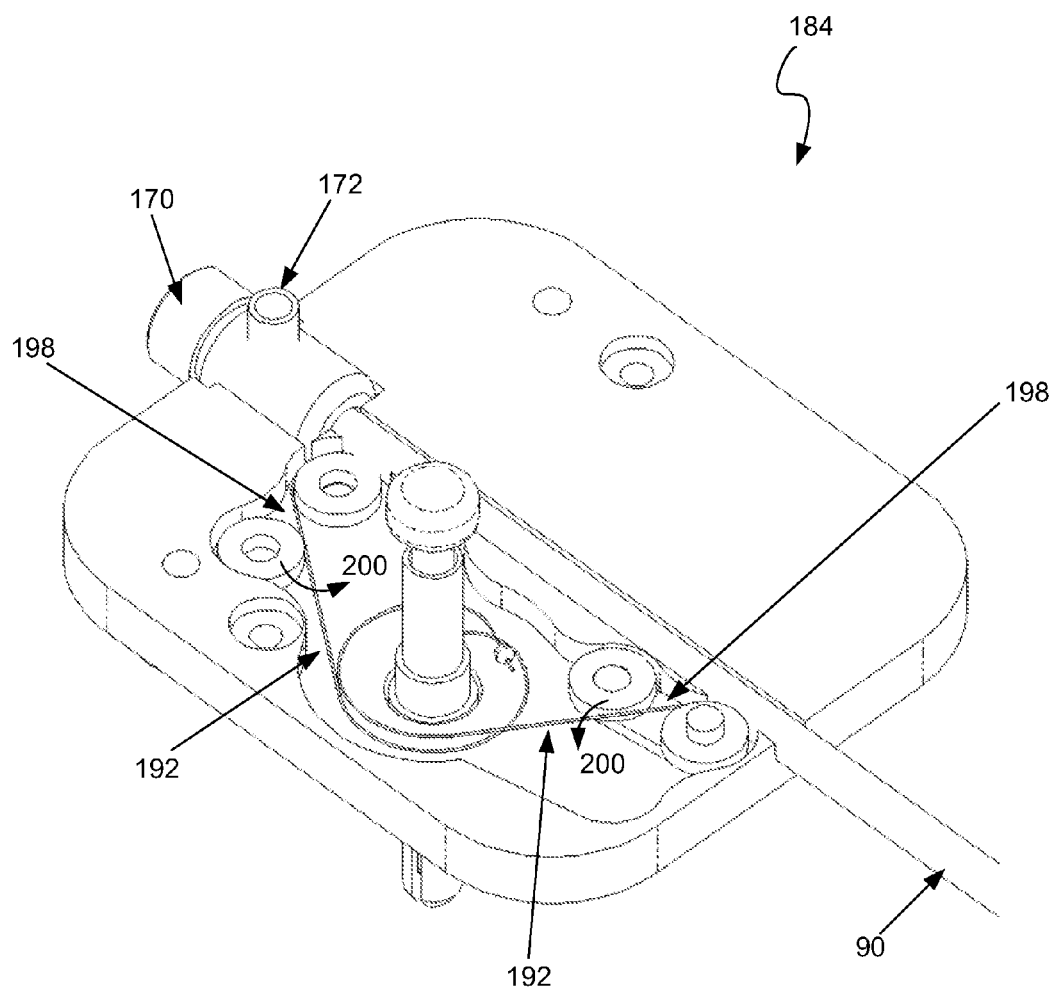
FIG. 70 illustrates an isometric view of a bottom portion of the instrument of FIG. 69.

Referring to FIG. 67, yet another instrument embodiment (182) is shown coupled with a sheath instrument (30). Instrument (182) has a single control element interface assembly (132) and two control elements. As best seen in FIG. 68, instrument (182) is also not configured for slotted tensioning or spring-loaded tensioning. Instead, the control elements (192) of this embodiment may be pre-tensioned and kept in position with the help of a fixed idler control element pathway (196) to facilitate maintenance of tension for control purposes. FIG. 69 illustrates still another instrument embodiment (184), which is shown coupled with a sheath instrument (30). Instrument (184) has a single control element interface assembly (132) and two control elements (192), with a spring-loaded idler (198) tensioning of the control elements (192), as shown in FIG. 70. As with the aforementioned spring-loaded idler tensioning instrument embodiments, the spring-loaded idlers urge (200) the control elements (192) into tension to facilitate control.

Figure 71:
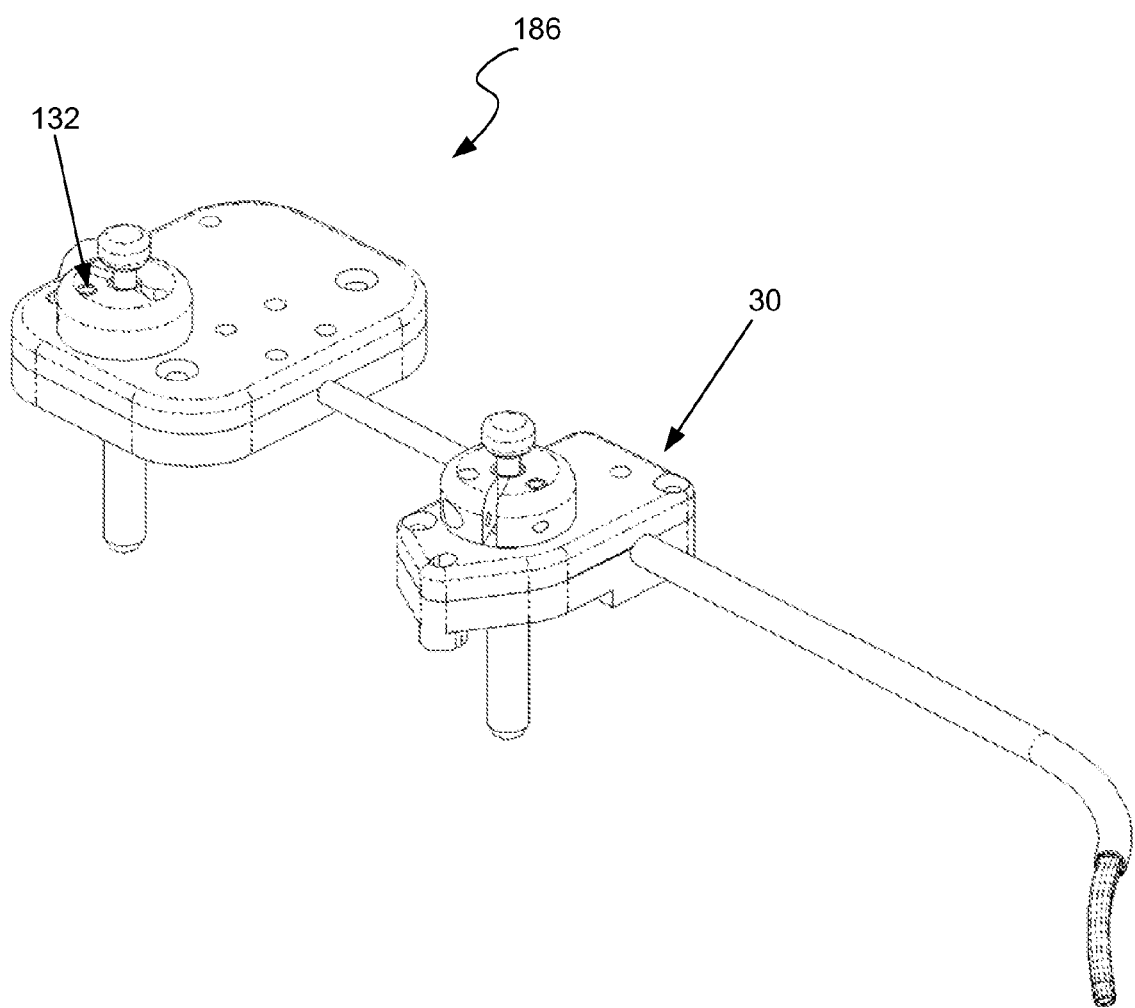
FIG. 71 illustrates an isometric view of an instrument having a control element interface assembly coupled to a sheath instrument in accordance with other embodiments.
Figure 72:
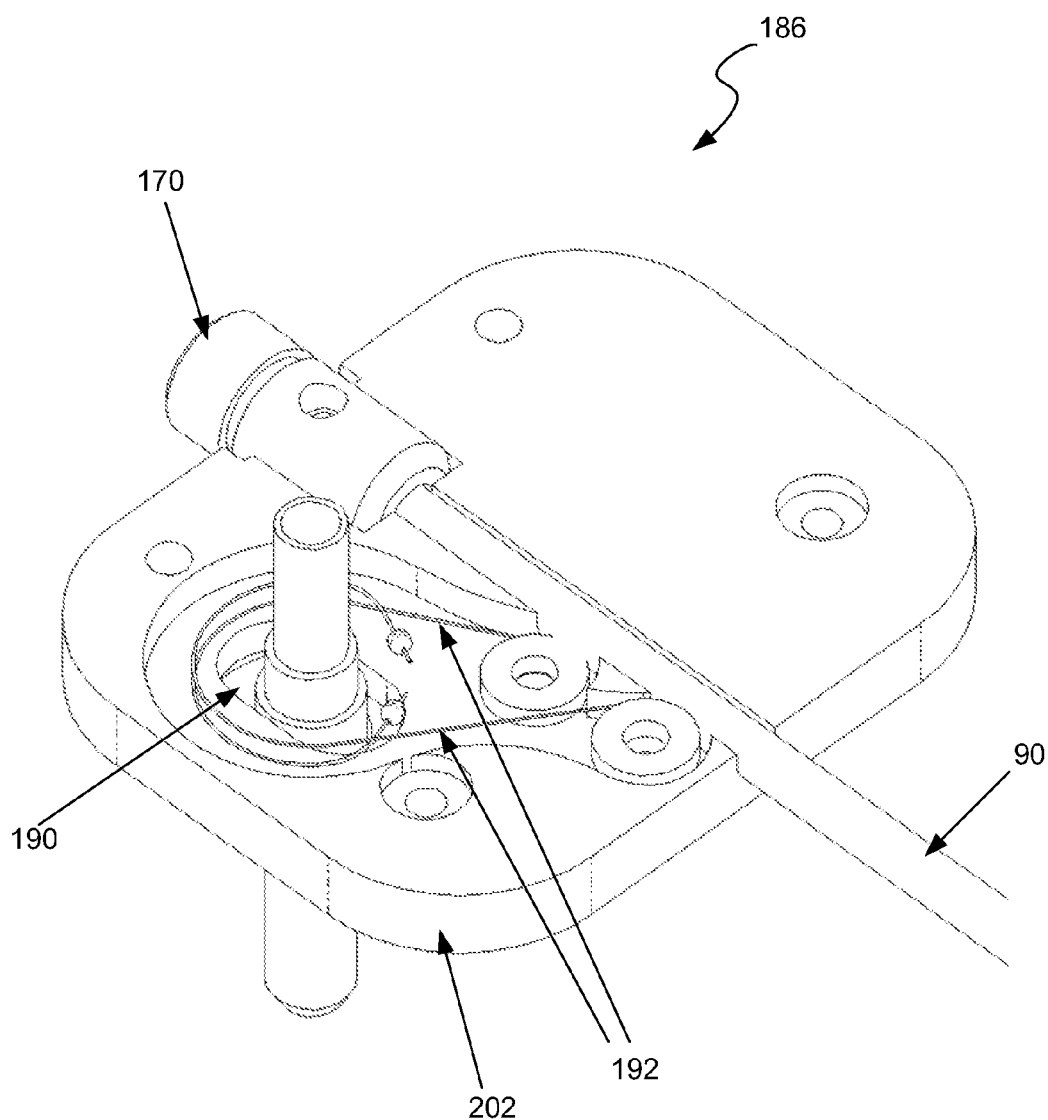
FIG. 72 illustrates an isometric view of a bottom portion of the instrument of FIG. 71.
Figure 73:
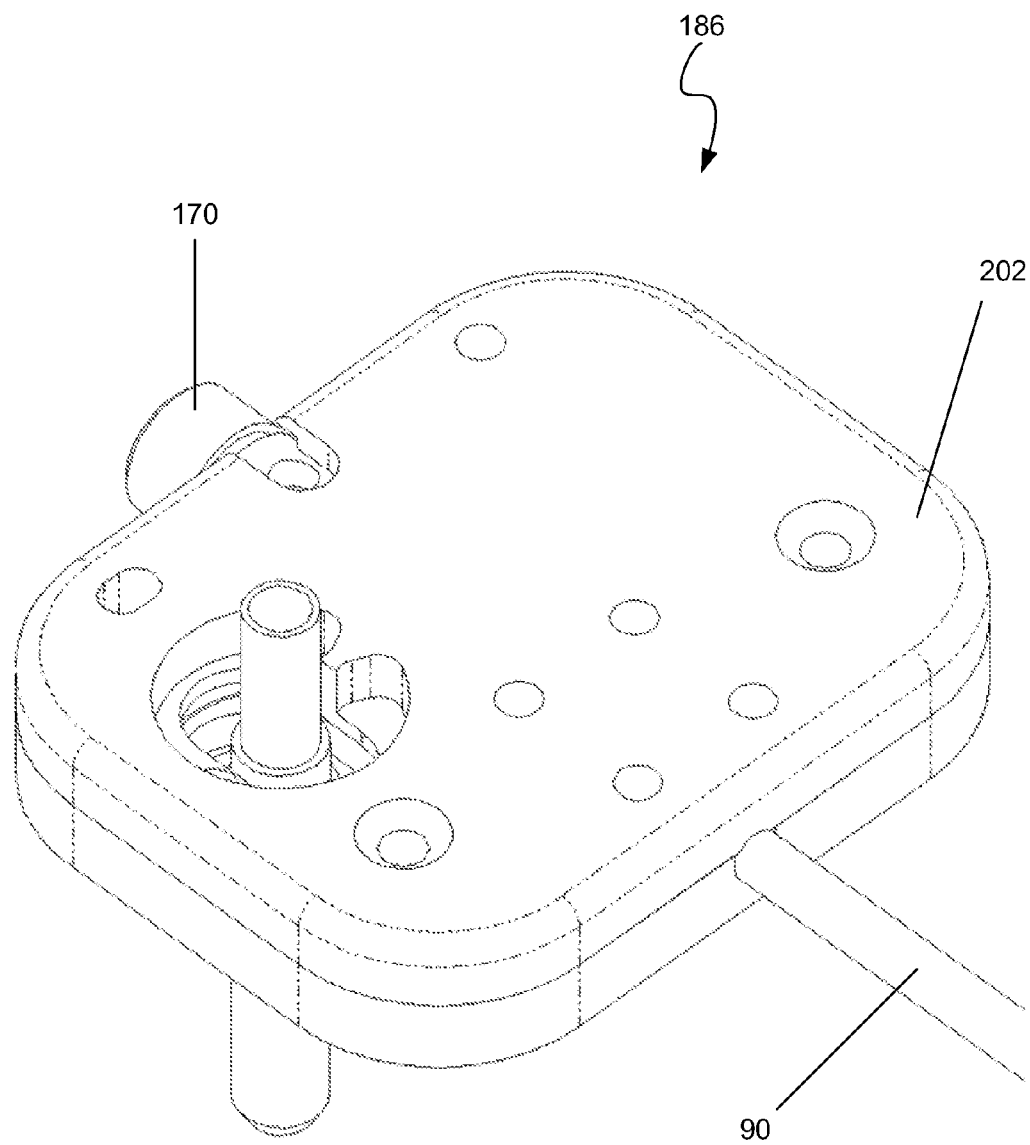
FIG. 73 illustrates an isometric view of the instrument of FIG. 71, showing a top portion placed above a bottom portion.

FIG. 71 illustrates a still further instrument embodiment (186), which is shown coupled with a sheath instrument (30). Instrument (186) has a single control element interface assembly (132) and two control elements (192), with a single-slotted guide instrument base, as shown in FIG. 72. As with the aforementioned slotted-tensioning instrument embodiments, the slot facilitates tensioning of the control elements from a mechanism in the instrument driver below. FIG. 73 depicts the embodiment of FIG. 72, with both portions of the slotted guide instrument base (202) intact. Depending upon the amount of tensioning deflection within the slot (190), it may be desirable to remove the rotational range of motion limitation pin (not shown) from the manual adjustment knob (not shown) to prevent impingement of the pin, knob, and instrument base (202), as the control element interface assembly is moved in the slot (190) relative to the rest of the instrument base (202).

Referring to FIGS. 74-93, elements of a sheath instrument embodiment will now be described. Again, for ease in illustration, many of the same components from the previously described instrument embodiments is utilized in these further embodiments, although such component matching is by no means required to accomplish the described functions.

Figure 74:
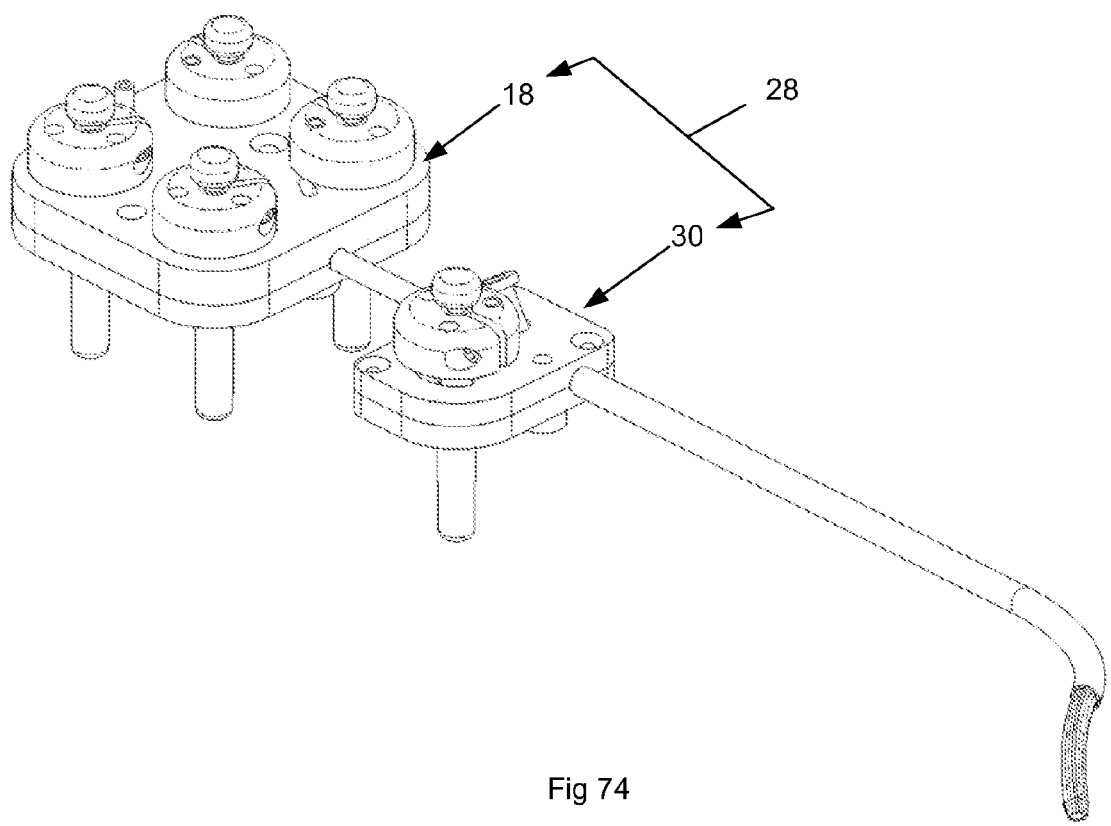
FIG. 74 illustrates an instrument coupled with a sheath instrument in accordance with some embodiments.
Figure 75:
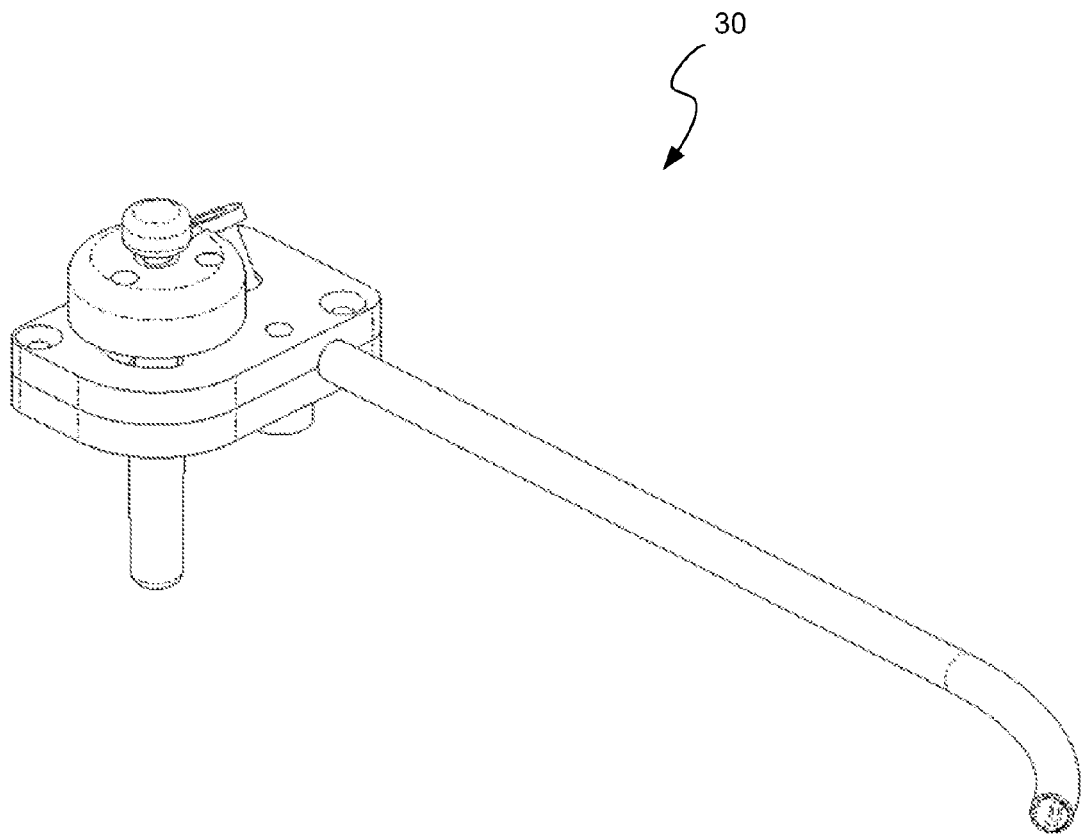
FIG. 75 illustrates an isometric view of the sheath instrument of FIG. 74.
Figure 76:
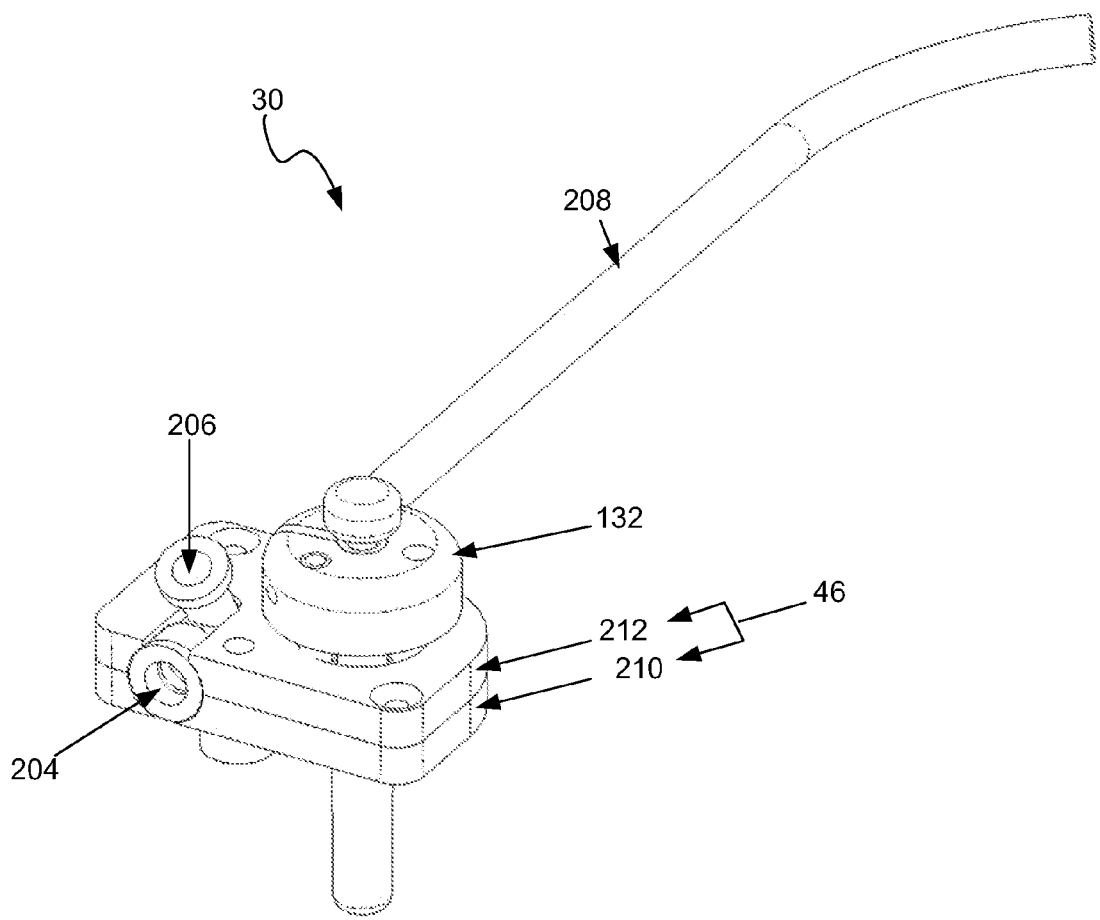
FIG. 76 illustrates an end isometric view of the sheath instrument of FIG. 74.

FIG. 74 depicts a guide instrument (18) shown coupled coaxially with a sheath instrument (30), together forming what has been described as a set of instruments (28). In FIGS. 75 and 76, the sheath instrument (30) is depicted without the guide instrument of FIG. 74. In FIG. 76, the sheath instrument (30) is depicted having one control element interface assembly (132), and preferably only one control element (not shown). From a functional perspective, in most embodiments the sheath instrument need not be as driveable or controllable as the associated guide instrument, because the sheath instrument is generally used to contribute to the remote tissue access schema by providing a conduit for the guide instrument, and to point the guide in generally the right direction. Such movement is controlled by rolling the sheath relative to the patient, bending the sheath in one or more directions with a control element, and inserting the sheath into the patient. The seal (204) is generally larger than the seal on the guide instrument due to the larger diameters of elongate members that may be inserted into the sheath instrument (30) as part of a medical procedure. Adjacent the seal (204) is an access port (206), which may be utilized to purge the instrument, or circulate fluids or instruments. The bottom (210) and top (212) portions of the sheath instrument base (48) are preferably sandwiched to house portions of the control element interface assembly, such as the single pulley in this embodiment, and the proximal portion of the sheath catheter member (208).

Figure 77:
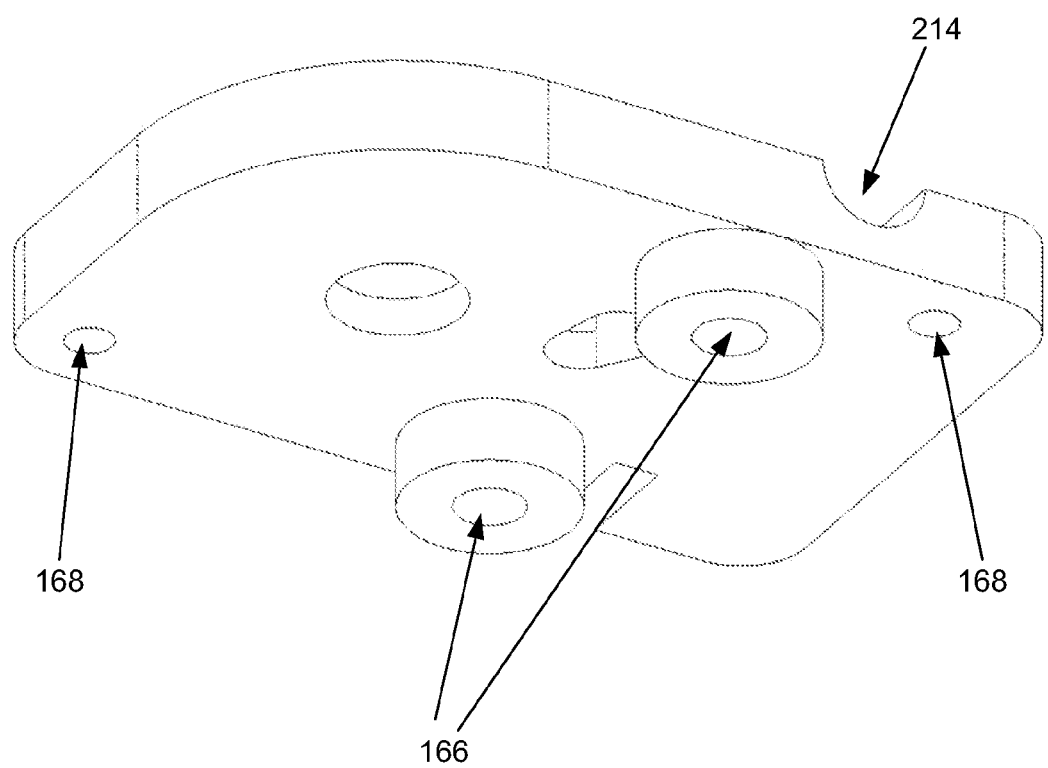
FIG. 77 illustrates a bottom isometric view of a bottom portion of the sheath instrument of FIG. 74.
Figure 78:
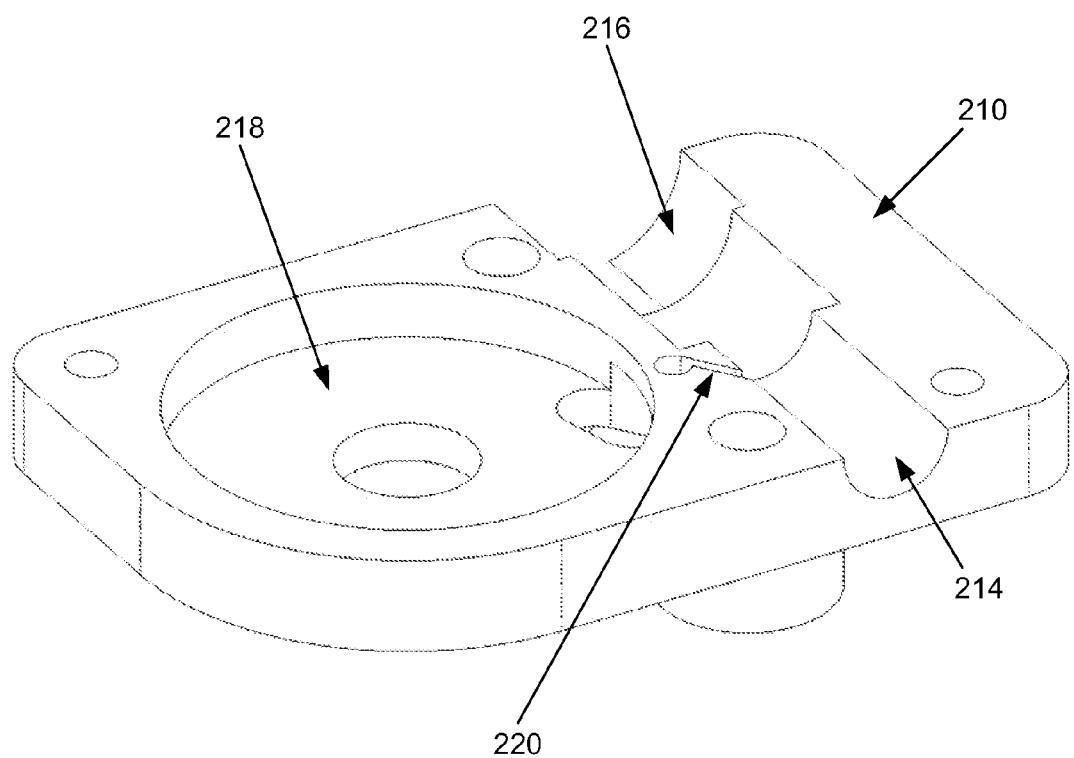
FIG. 78 illustrates a top isometric view of the bottom portion of FIG. 77.
Figure 79:
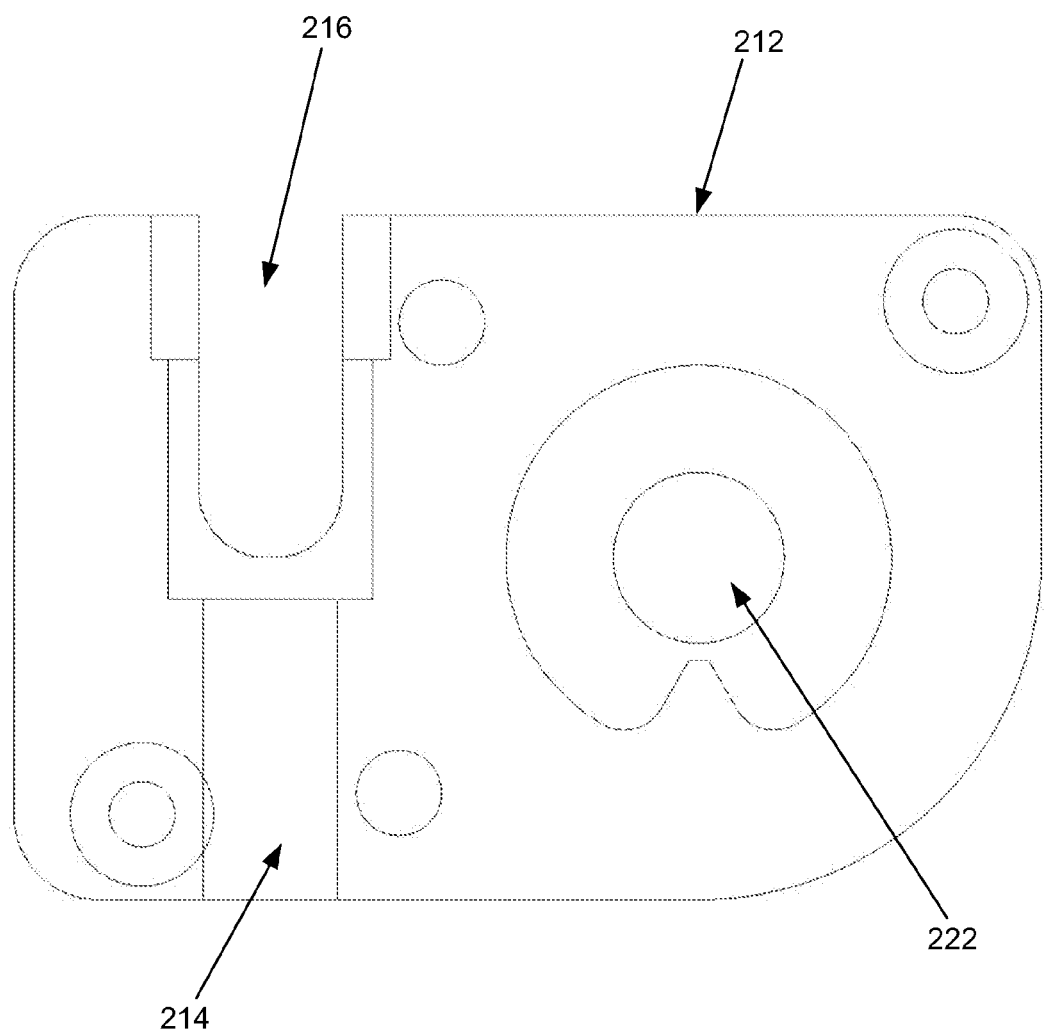
FIG. 79 illustrates a bottom view of a top portion of the sheath instrument of FIG. 74.

Referring to FIG. 77, the bottom portion of one embodiment of a sheath instrument base is depicted showing two magnets utilized to facilitate mounting against an instrument driver. Mounting pin interface holes (168) also assist in accurate interfacing with an instrument driver. The opposite surface is formed with a sheath catheter member geometry accommodation (214) to interface with the sheath catheter (not shown). FIG. 78 shows this opposite surface in further detail, having a pulley geometry accommodation (218), a seal geometry accommodation (216), and a sheath catheter geometry accommodation (214). There is also a control element splay track (220) similar to those depicted in reference to the embodiments of the guide instrument. In FIG. 79, a bottom view of a top portion (212) of one embodiment of a sheath instrument base (48) is depicted showing the sheath catheter geometry (214) and seal geometry (216) accommodations formed therein, and an axel interface hole (222) formed there through.

Figure 80:
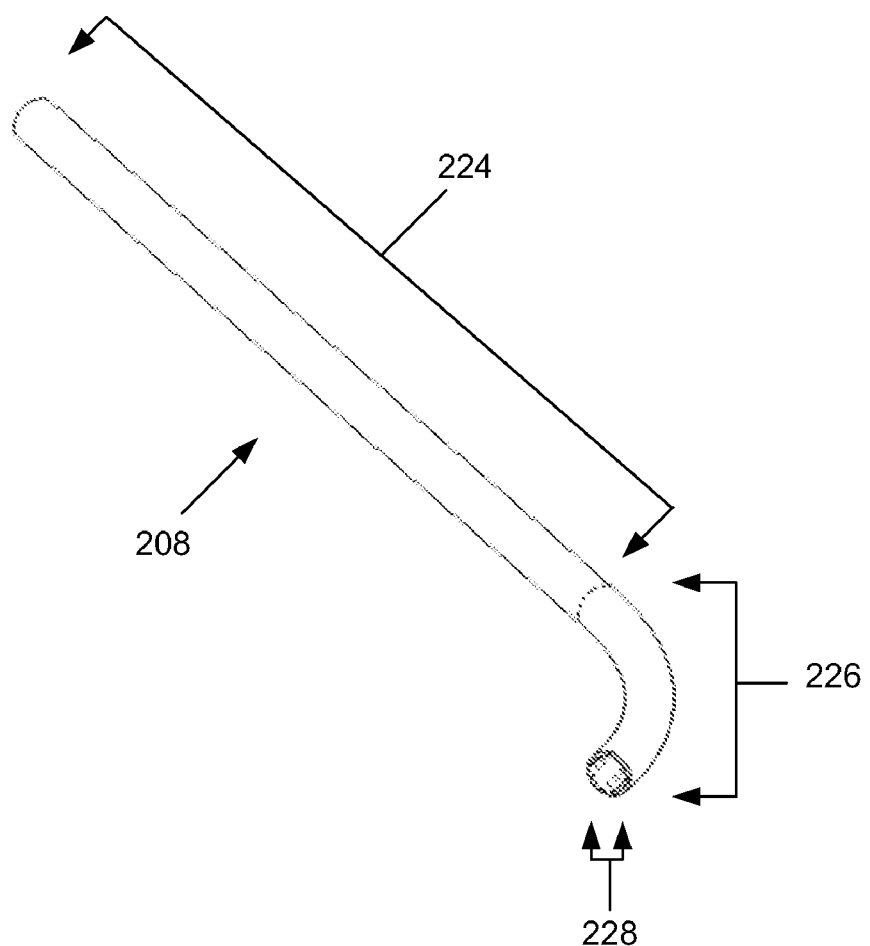
FIG. 80 illustrates a sheath catheter for use with a sheath instrument in accordance with some embodiments.

FIG. 80 illustrates yet another embodiment of the sheath catheter (208) in a pre-bent formation, which may be desirable depending upon the anatomical issue pertinent to the medical procedure. The sheath catheter (208) preferably has a construction somewhat similar to that of the aforementioned guide catheter member embodiments, with notable exceptions. For one, it preferably does not have a flexible structural element disposed within its distal end, as it is not within the preferred functionality of the sheath instrument to have very tight radius bendability, particularly given the high bendability of the associated guide instrument. Preferably both the proximal (224) and distal (226) portions comprise a low-friction inner layer, a braiding layer, and an outer layer, as described below with reference to FIG. 81. It is preferable to have more bending flexibility in the distal portion than in the proximal portion. This may be accomplished by selecting a outer layer polymeric material for the distal portion (226) having approximately half the durometer of the polymeric material utilized for the outer layer of the proximal portion (224). In the depicted embodiment, an atraumatic distal tip (228) comprising an extension of the low-friction inner layer and outer layer extends slightly beyond the termination of the braiding layer by between about ¼ inch and ⅛ inch to prevent damage to tissues in various medical procedures.

Figure 81:
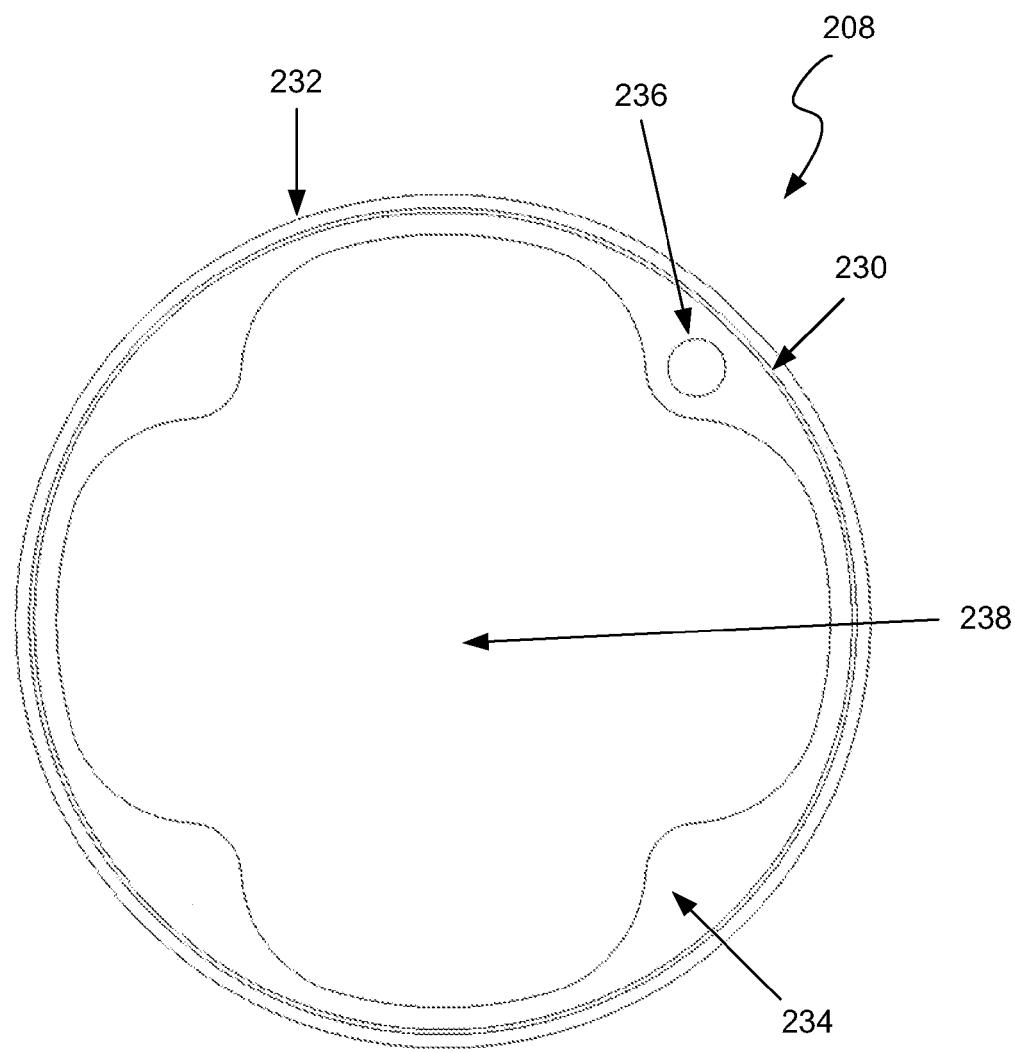
FIG. 81 illustrates a cross sectional view of the sheath catheter of FIG. 80 in accordance with some embodiments.
Figure 82:
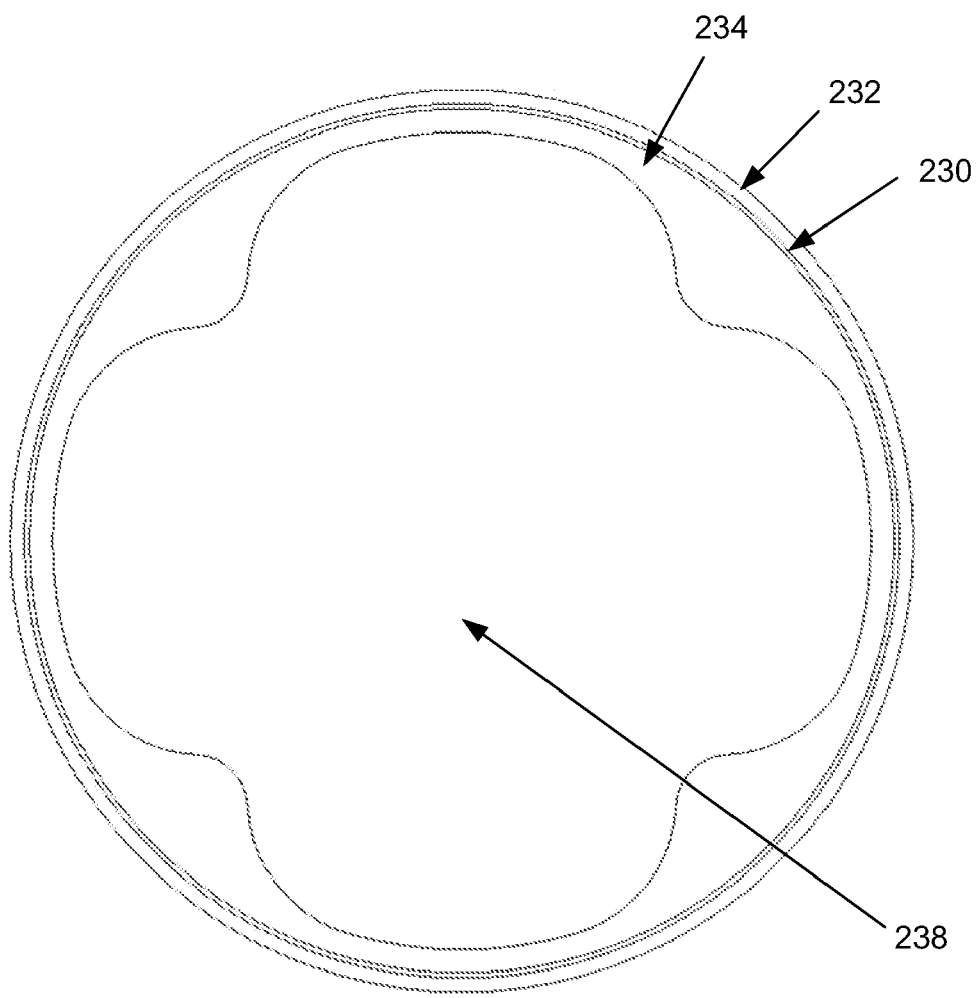
FIG. 82 illustrates a cross sectional view of another sheath catheter in accordance with other embodiments.

FIG. 81 is a cross sectional view of a proximal or distal portion of a sheath catheter member (208), similar to that shown in FIG. 80. A braiding layer (230) is surrounded by an outer layer (232) preferably comprising a polymer such as Pebax™ with a durometer between about 30 and 80, and an inner layer (234) preferably comprising a low-friction polymeric material into which one or more lumens may be optionally extruded. The embodiment of FIG. 81 depicts one control element lumen (236). The geometry of the inner layer (234) may be configured to "key" or restrictively interface with a guide catheter member outer geometry to prevent rotation of the guide catheter member as discussed below with reference to FIGS. 85-91. The central lumen (238) of the sheath catheter preferably is sized to closely fit the associated guide catheter member. FIG. 82 depicts an embodiment similar to that shown in FIG. 81, with the exception that it does not have a control element lumen. In some embodiments, it is preferable not to have a steerable sheath catheter, but instead to have a straight or pre-bent sheath catheter, or no sheath catheter at all, surrounding a portion of the guide catheter.

Figure 83:
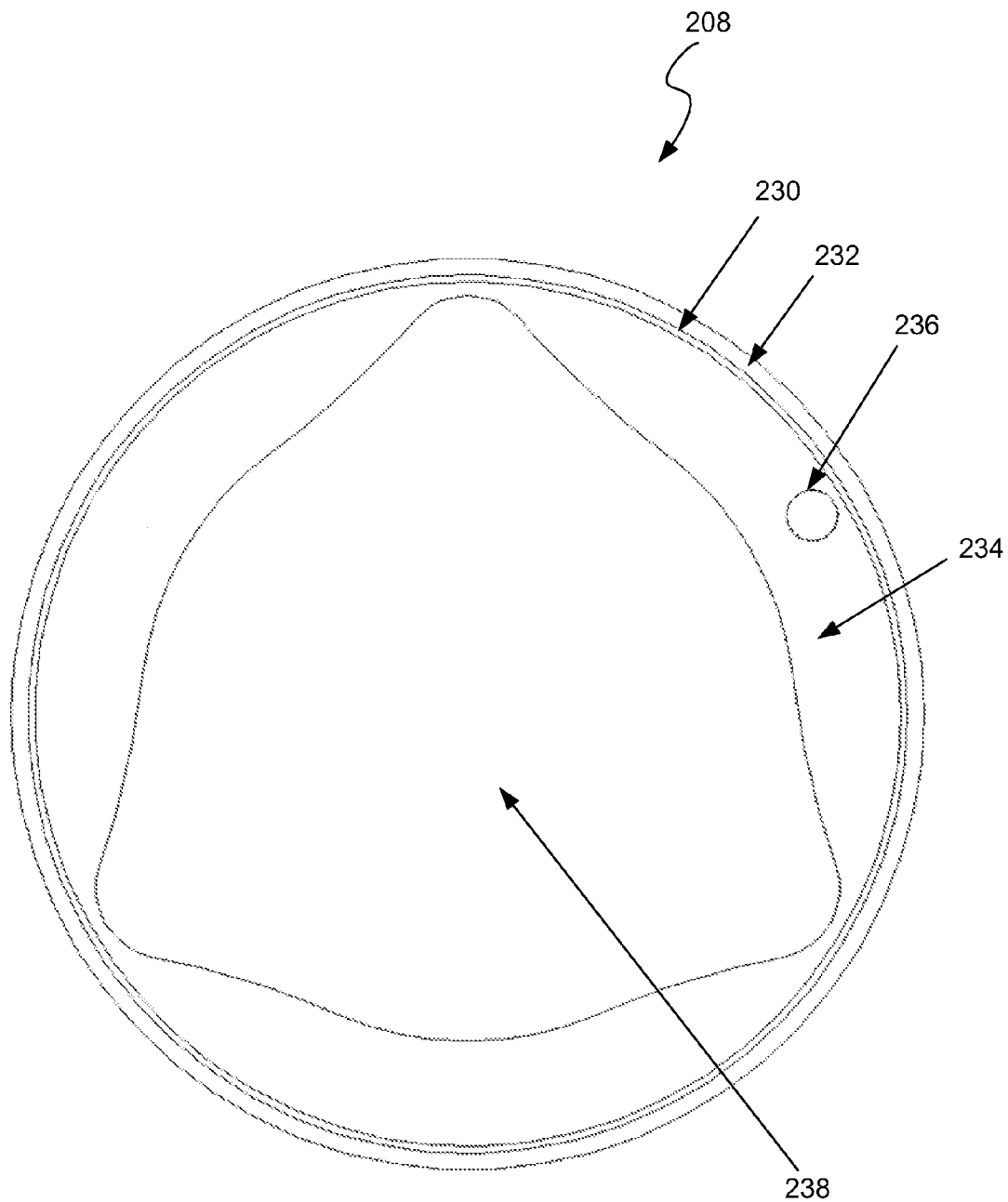
FIG. 83 illustrates a cross sectional view of another sheath catheter in accordance with other embodiments.
Figure 84:
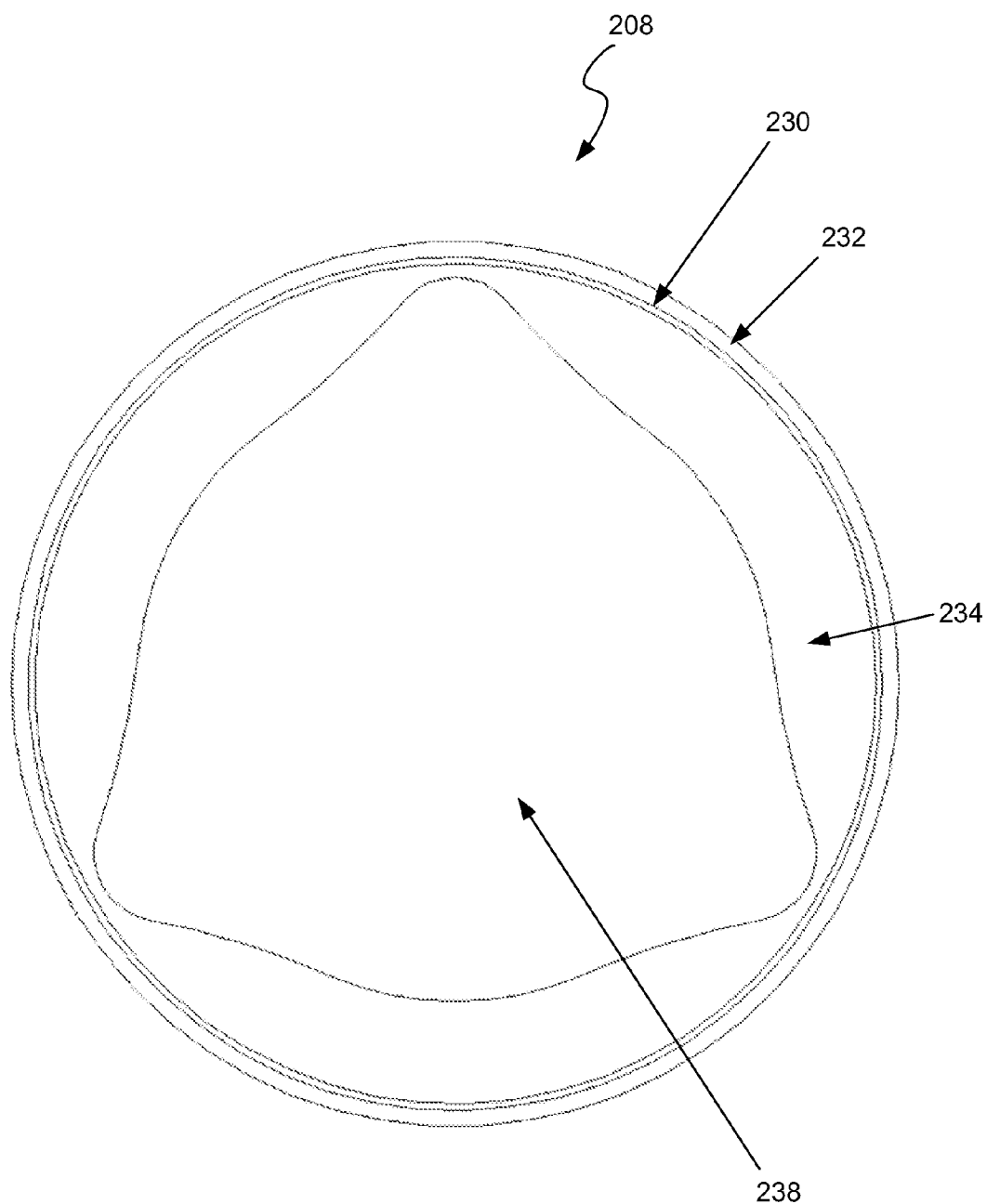
FIG. 84 illustrates a cross sectional view of another sheath catheter in accordance with other embodiments.
Figure 85:
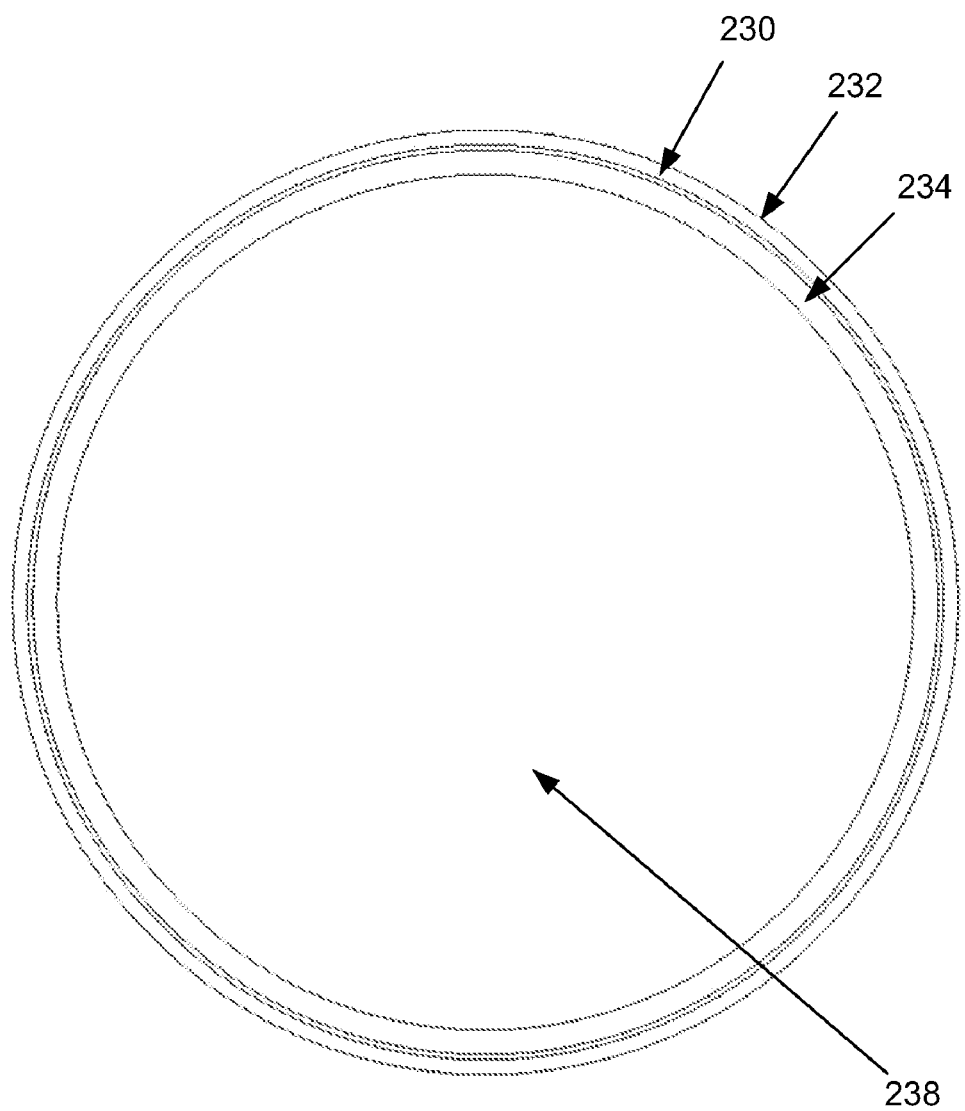
FIG. 85 illustrates a cross sectional view of another sheath catheter in accordance with other embodiments.

Referring to FIGS. 83 and 84, an embodiment of a sheath catheter member is depicted with an inner layer (234) configured to key with a 3-control-element guide geometry, such as that depicted in FIG. 21. FIG. 84 depicts a similar embodiment, without a control element lumen (236). FIG. 85 depicts an non-keyed sheath without any control element lumens to illustrate that keying and steerable control is not necessary or desired in some embodiments or procedures—particularly when more bendability of the sheath is desired. The embodiment of FIG. 85 is relatively thin walled, and while it still comprises a braiding layer (230) surrounded by an outer layer (232) and an inner layer (234) of polymeric material, it is generally more easily bendable through tortuous paths than are other more thick-walled embodiments. Further, without the keying geometry of the inner layer (234), the central lumen (238) is effectively larger.

FIGS. 86-91 illustrate cross sectional representations of various embodiments of coaxially coupled guide catheter (90) and sheath catheter (208) combinations.

Figure 86:
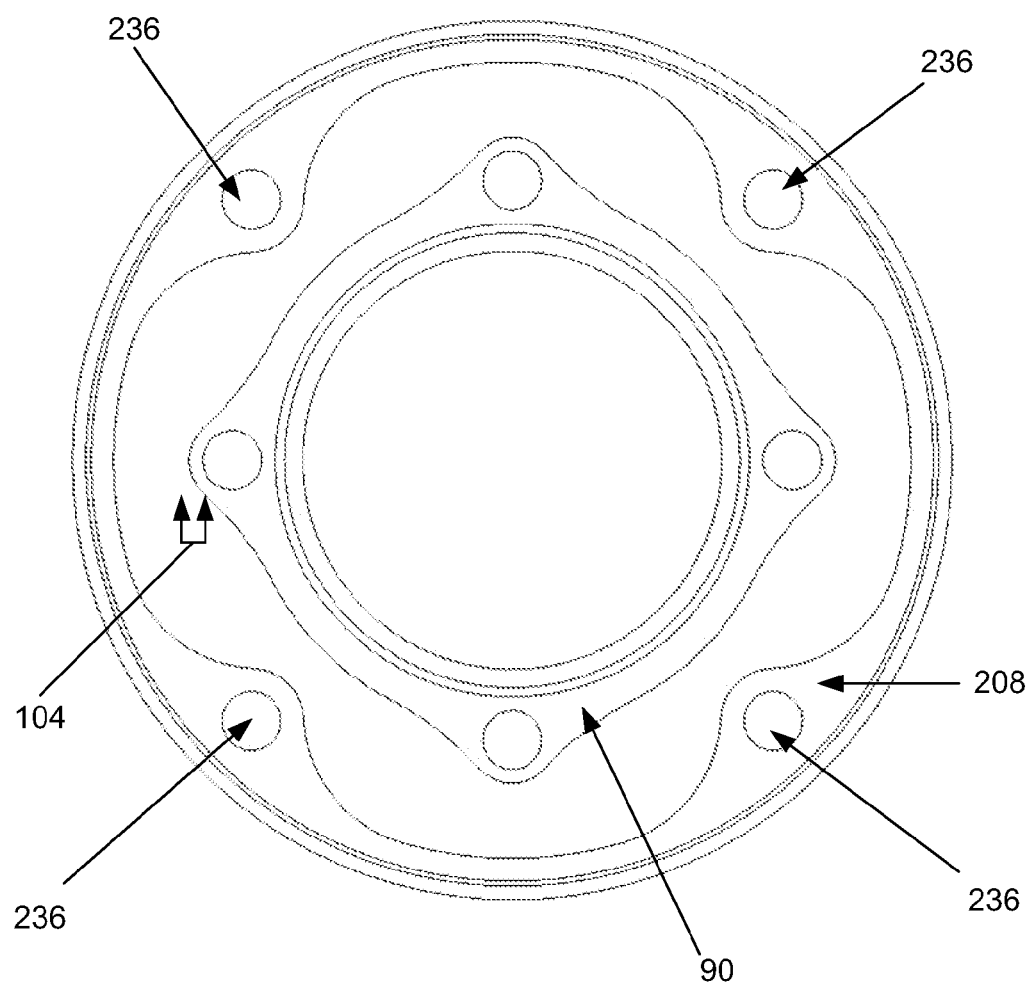
FIG. 86 illustrates a cross sectional view of a guide catheter inserted into a lumen of a sheath catheter in accordance with some embodiments.

Referring to FIG. 86, a relatively low surface profile (104) guide catheter is disposed within sheath catheter (208) having four control element lumens. The fit between the two structures is fairly loose, and some relative rotational displacement is to be expected if the guide catheter (90) is torqued significantly more than the sheath catheter (208). To help prevent such relative rotational displacement, a higher profile guide catheter (90) geometry may be utilized, as shown in FIG. 87, in order to decrease the freedom of movement between the two structures as they are bent through the pathways required by a medical procedure.

Figure 87:
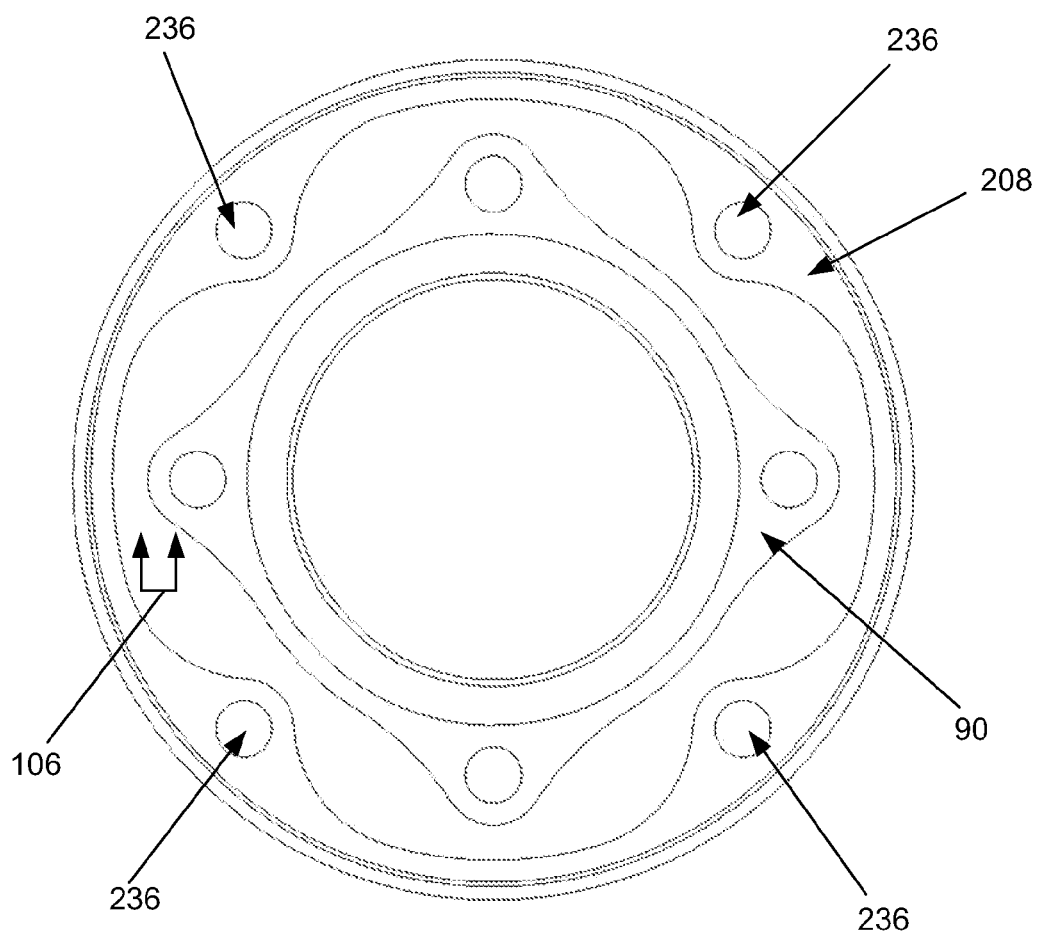
FIGS. 87-91 illustrate cross sectional views of guide catheters inserted into respective sheath catheters in accordance with other embodiments.
Figure 88:
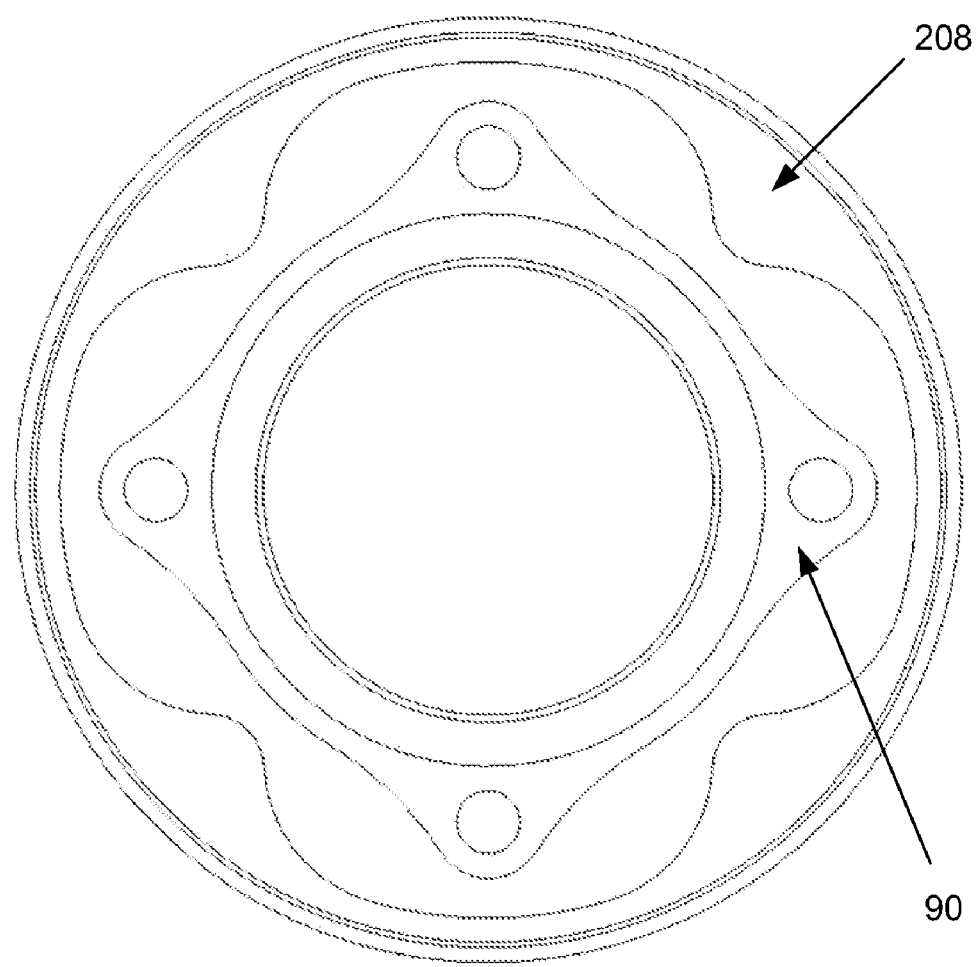

FIG. 88 depicts an embodiment similar to that in FIG. 87, but without the control element lumens. It may be desirable to have control element lumens formed into the walls of the guide catheter or sheath catheter for reasons other than passing control elements through such lumens. These lumens may function as stress relief structures to increase bendability. They may also be utilized to form preferred bending axes for the overall structure. Further, they may be utilized as working channels for flushing, drug delivery, markers, sensors, illumination fibers, vision fibers, and the like. It may be desirable to have a homogeneous patterning of control lumens across the cross section of a particular structure in order to promote homogeneous bending. For example, a sheath catheter with four control lumens, one of which is occupied by a control element in tension, may bend more homogeneously than a sheath catheter with only one or two control lumens, one of which occupied by a control element.

Figure 89:
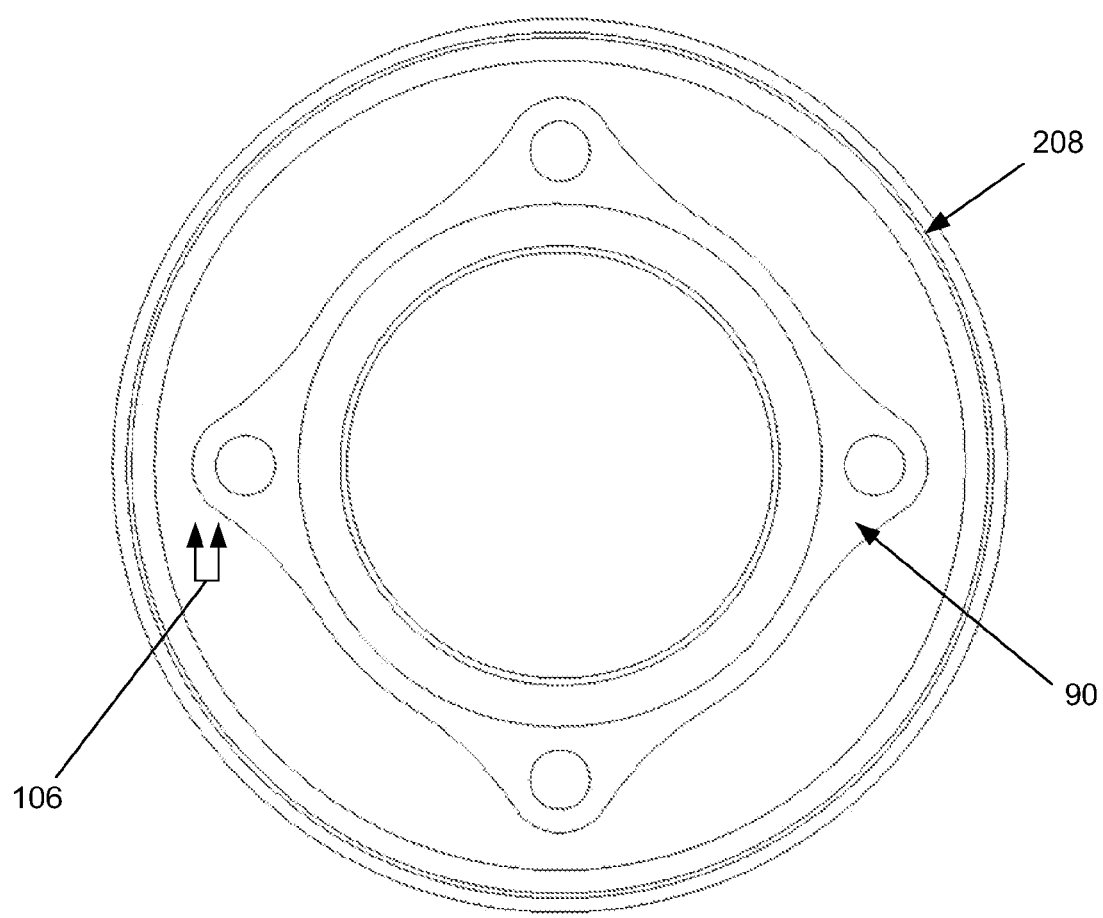
Figure 90:
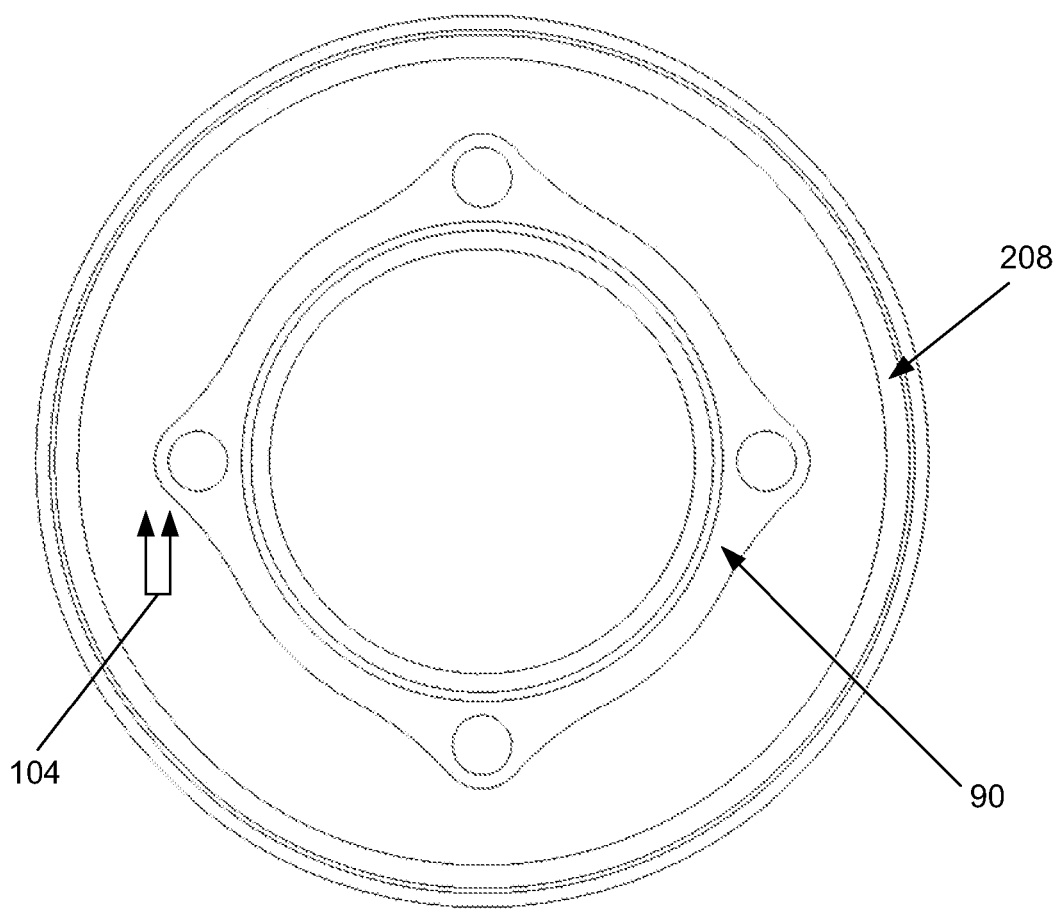
Figure 91:
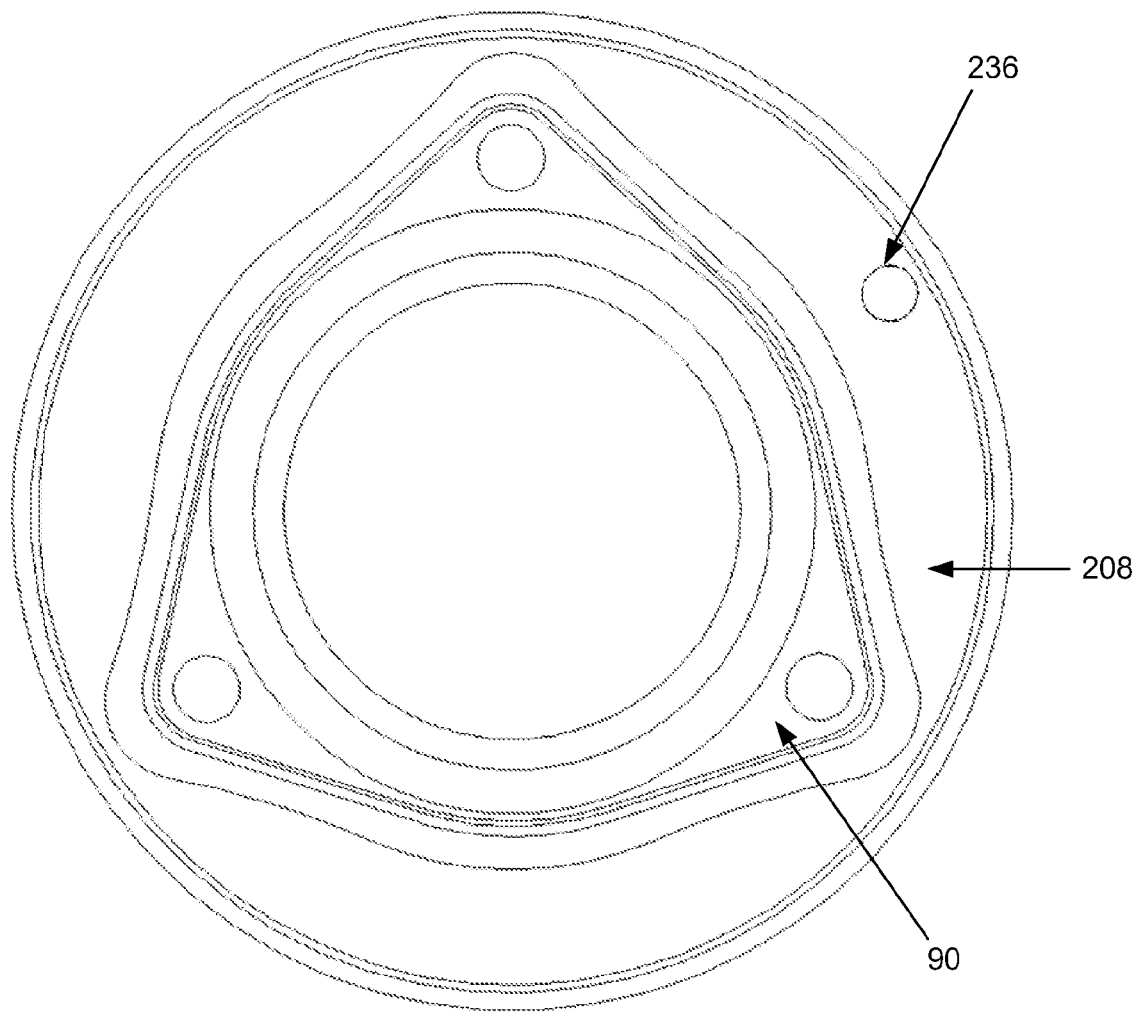
Figure 92:
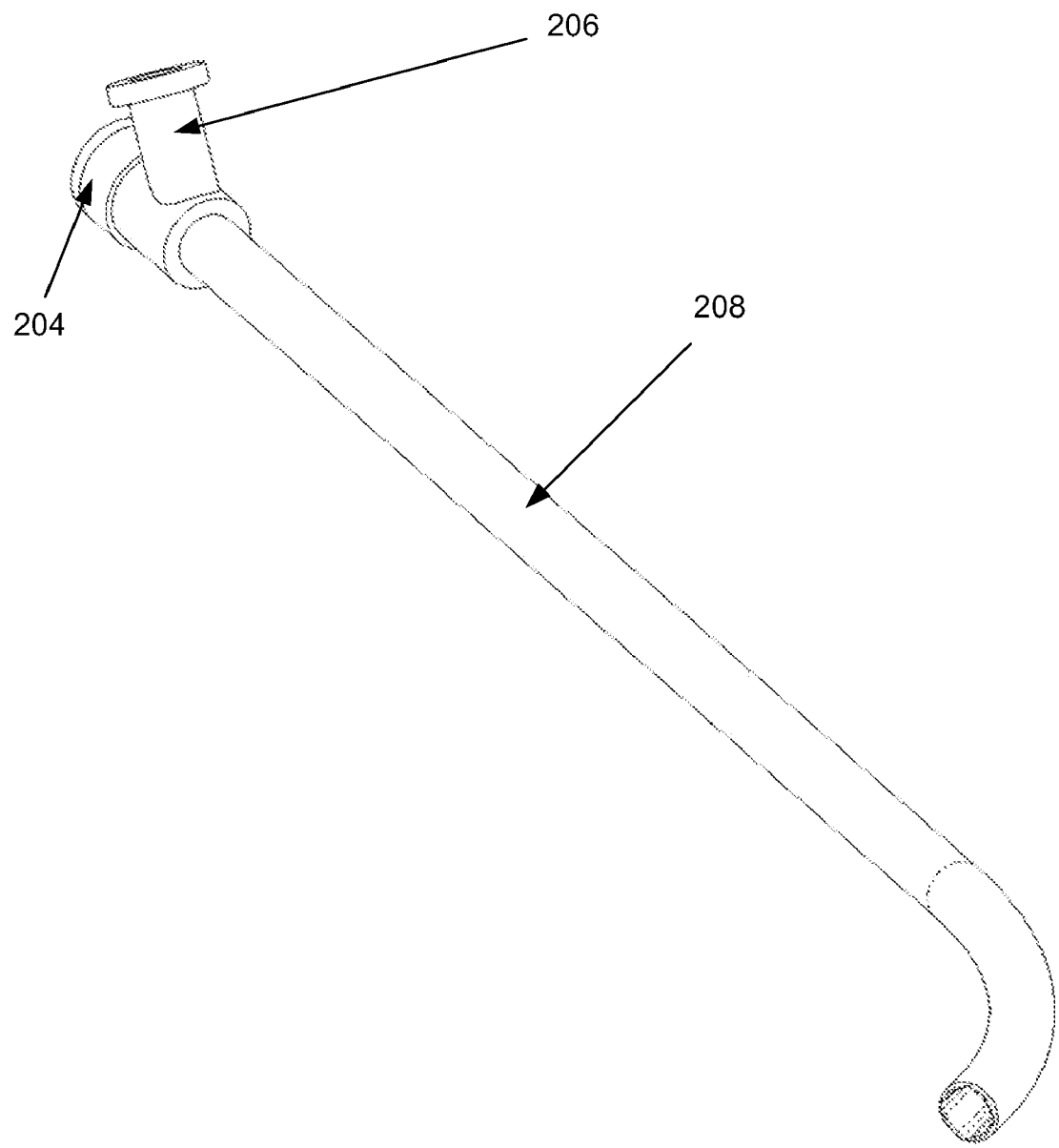
FIG. 92 illustrates a sheath catheter member coupled to a seal and an access port in accordance with some embodiments.
Figure 93:
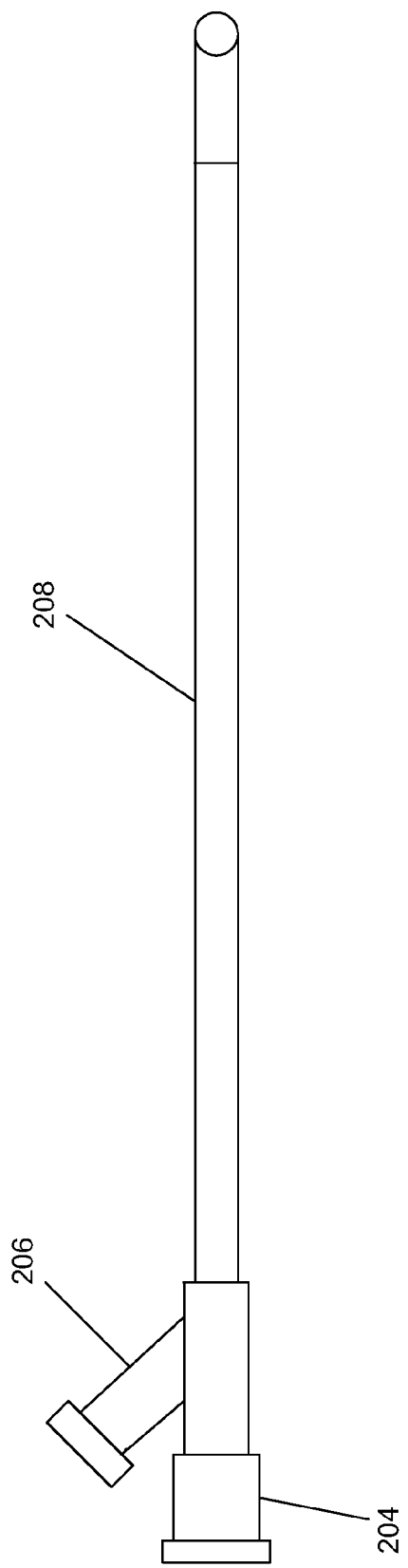
FIG. 93 illustrates a side view of the sheath catheter member of FIG. 92.
Figure 94:
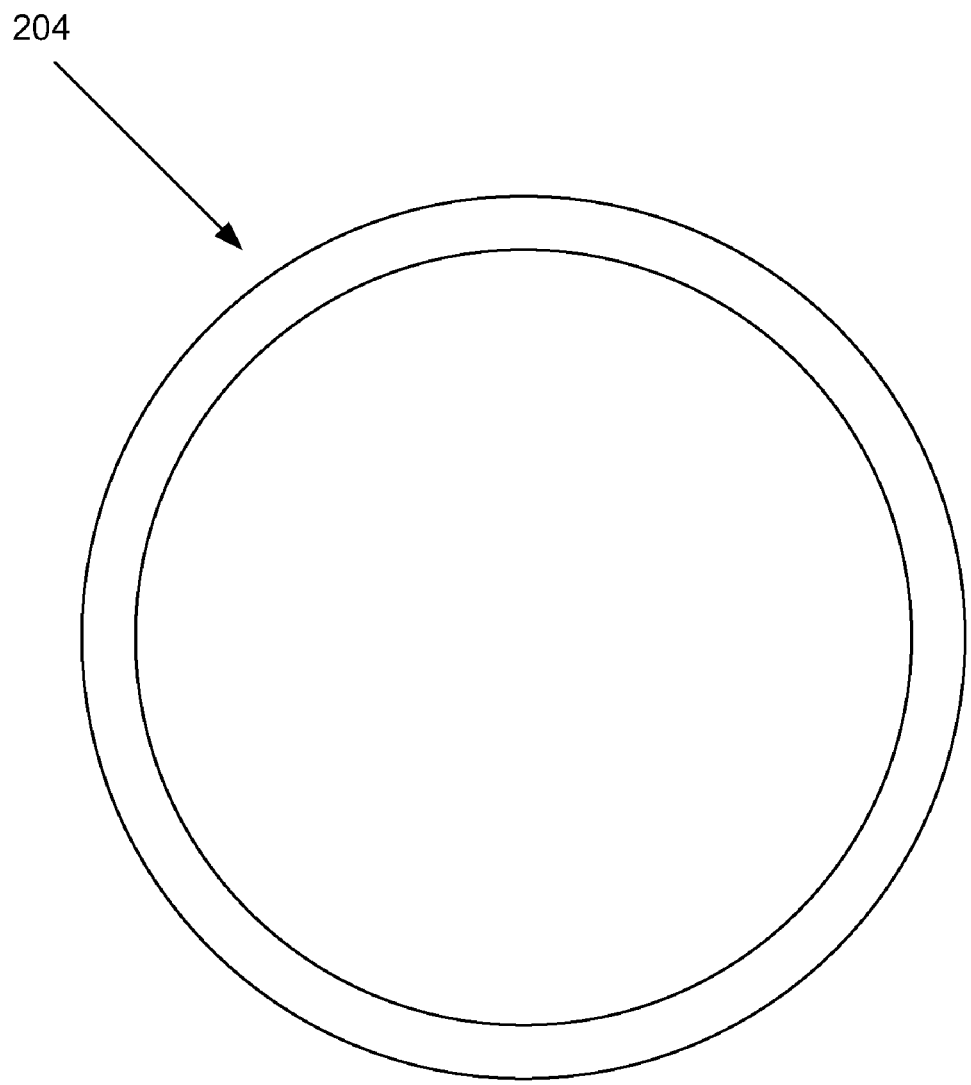
FIG. 94 illustrates an end view of the seal of FIG. 92.

Referring to FIG. 89, a relatively high surface profile (106) guide catheter (90) is depicted within a non-keyed sheath catheter, with a 4-control-element guide catheter disposed within a pre-bent sheath instrument that is not remotely steerable. FIG. 90 depicts a similar embodiment to that of FIG. 89, with the exception of an even lower surface profile (104) guide catheter (90) disposed within the non-keyed sheath catheter. FIG. 91 depicts a somewhat extreme example of keying to resist relative rotational displacement between a guide catheter (90) and a sheath catheter (208). Significant resistance to rotational displacement is traded for higher degrees of overall system bendability, as will be apparent to those skilled in the art. As shown in FIG. 92, a preferably elastomeric seal (204) and access port (206) construct may be fitted onto the sheath catheter member (208), prior to mounting within the confines of the sheath instrument base (46). FIG. 93 is a side view of the sheath catheter member (208) coupled to the seal (204) and access port (206). FIG. 94 is an end view of the seal (204).

FIGS. 95-103 depict various aspects of embodiments of an instrument driver configured for use with the above-described instrument embodiments.

Figure 95:
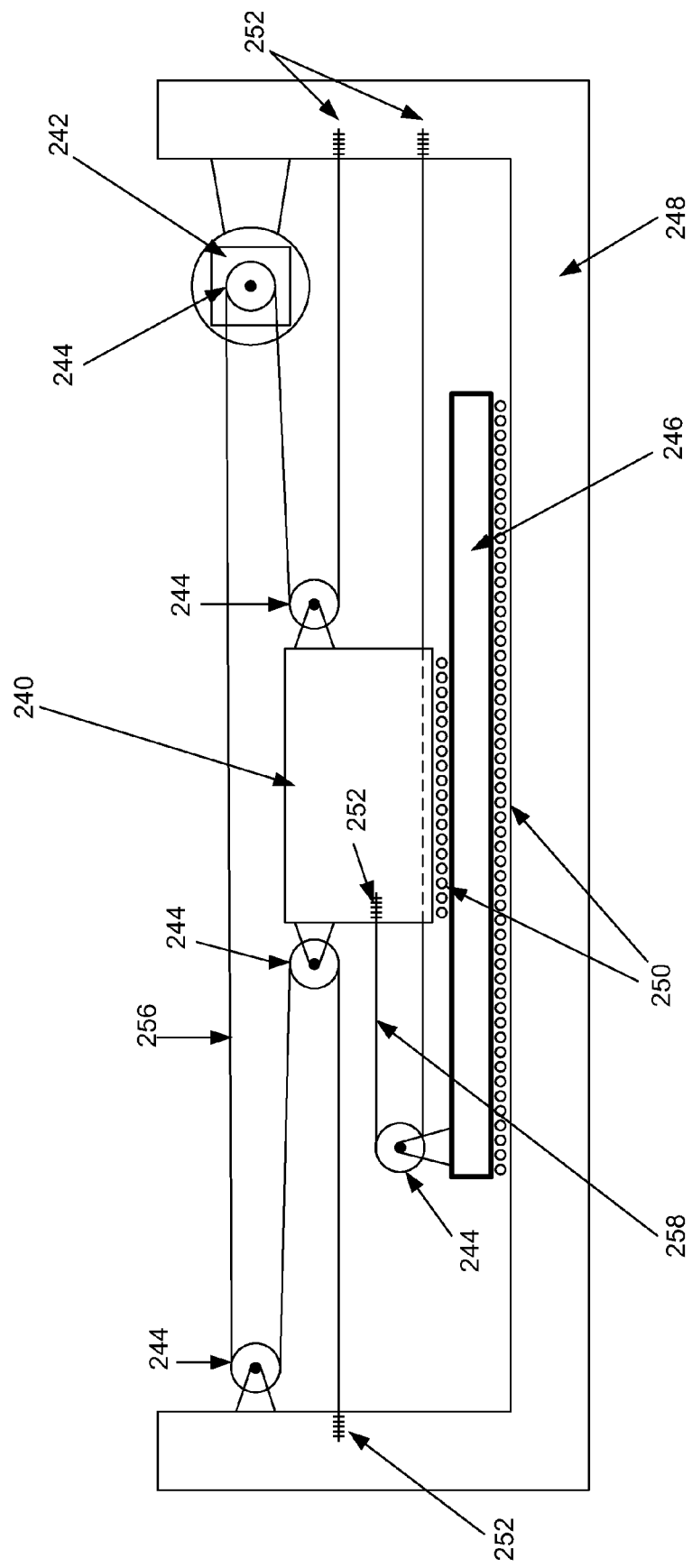
FIG. 95 illustrates an instrument driver in accordance with some embodiments.
Figure 96:
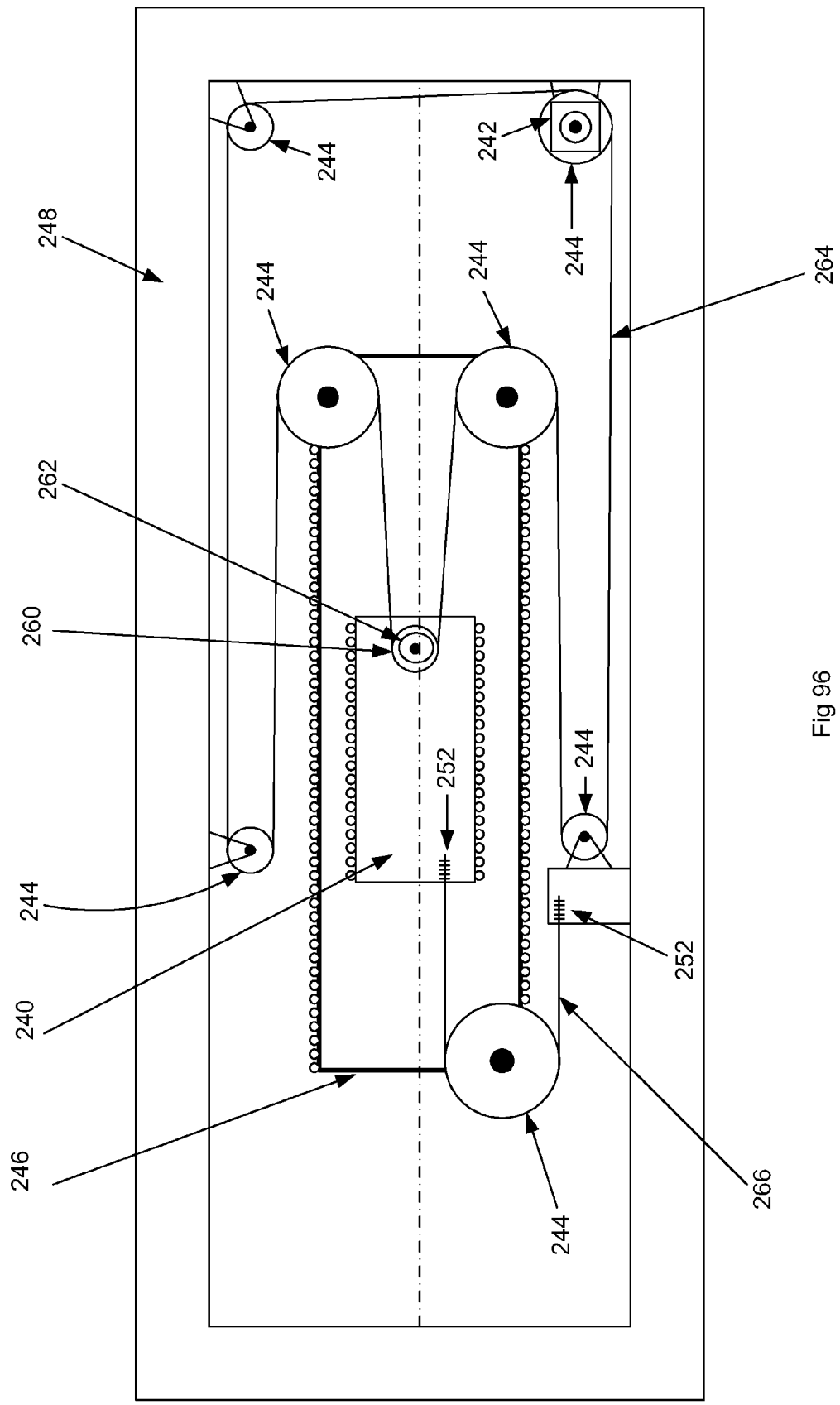
FIG. 96 illustrates an instrument driver in accordance with other embodiments.

FIGS. 95 and 96 are simplified schematics that illustrate internal features and functionalities of one embodiment of an instrument driver. In FIG. 95, a carriage (240) is slidably mounted upon a platform (246), which is slidably mounted to a base structure (248). The slidable mounting (250) at these interfaces may be accomplished with high-precision linear bearings. The depicted system has two cables (256, 258) running through a plurality of pulleys (244) to accomplish motorized, synchronized relative motion of the carriage (240) and platform (246) along the slidable interfaces (250). As will be apparent to those skilled in the art, as the motor (242) pulls on the carriage displacement cable (256) with a tension force T, the carriage (240) feels a force of 2*T. Further, as the motor pulls the carriage displacement cable (256) by a displacement X, the carriage moves by X/2, and the platform moves by half that amount, or X/4, due to its "pulleyed" synchronization cable (258).

FIG. 96 illustrates a top view of a separate (but similar) system configured to drive an instrument interface pulley (260) associated with an instrument interface socket (262) to produce both directions of rotation independently from the position of the carriage (240), to which it is coupled, along the linear pathway prescribed by the slidable interfaces (250). With a mechanical schema similar to that in FIG. 96, as the motor (242) pulls a deflection X in the instrument interface cable (264), the same deflection is seen directly at the instrument interface pulley (260), regardless of the position of the carriage (240) relative to the motor (242), due to the synchronizing cable (266) positioning and termination (252).

Figure 97:
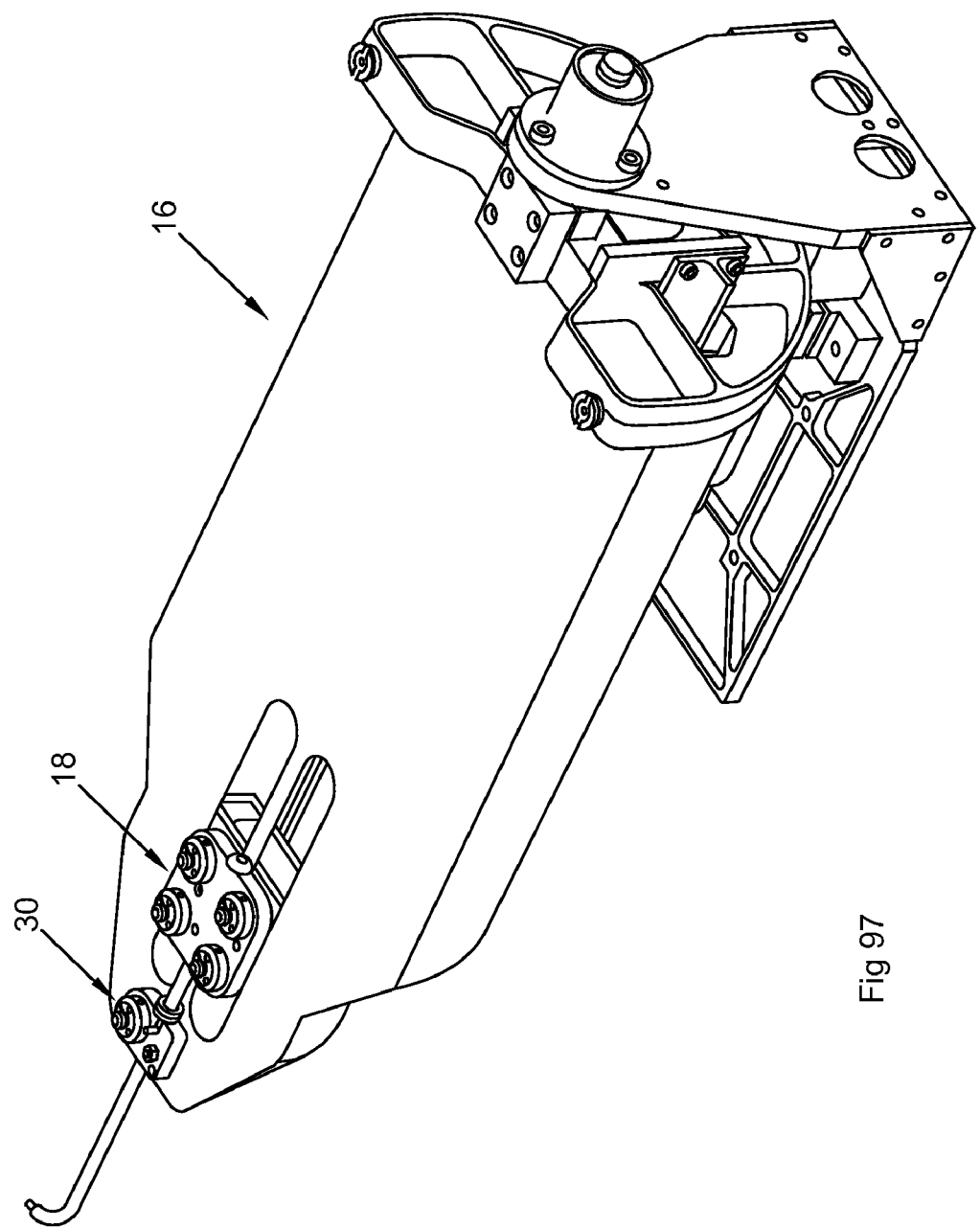
FIG. 97 illustrates an isometric view of an instrument driver coupled with a steerable guide instrument and a steerable sheath instrument in accordance with some embodiments.
Figure 98:
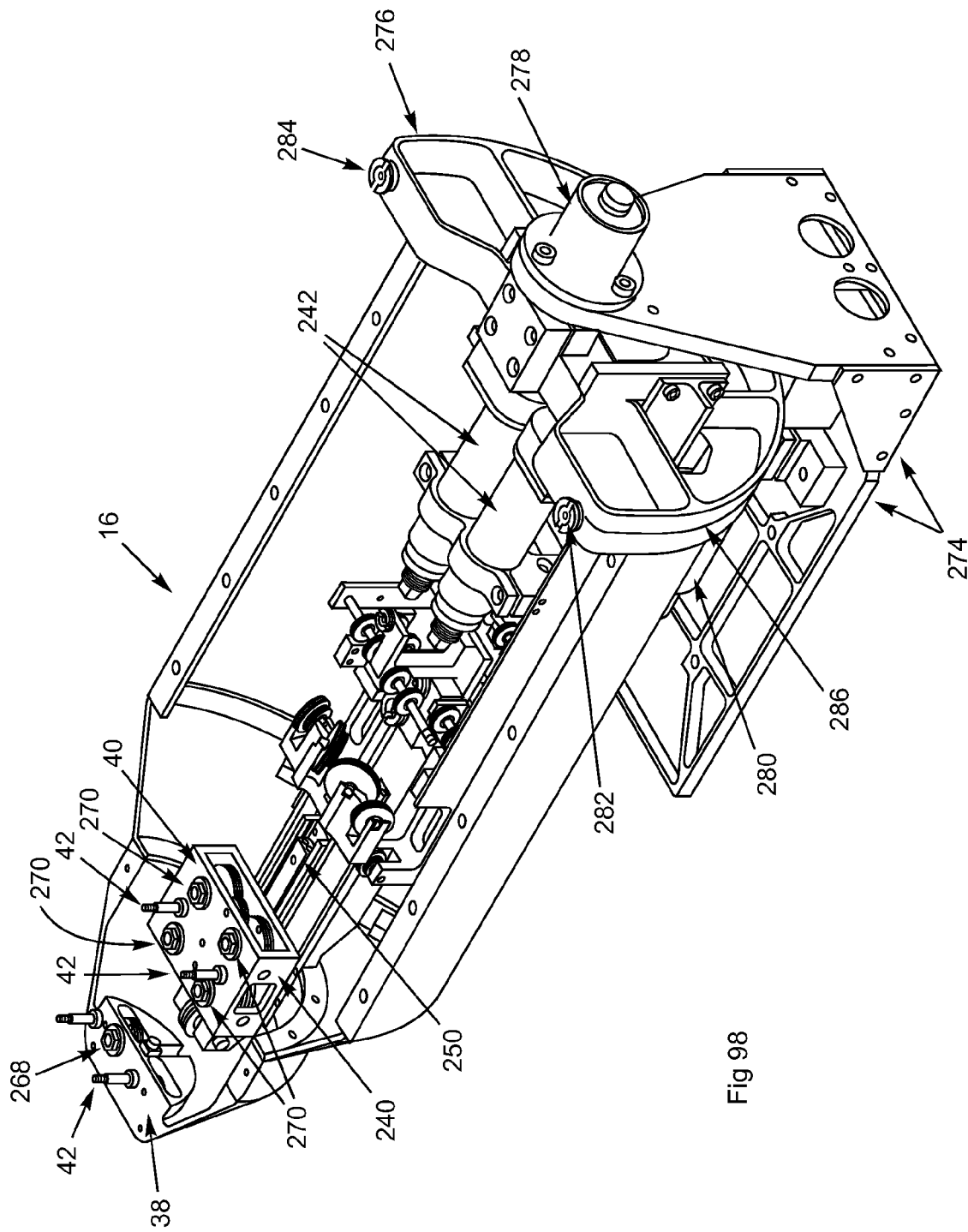
FIG. 98 illustrates components of the instrument driver of FIG. 97 in accordance with some embodiments.
Figure 99:
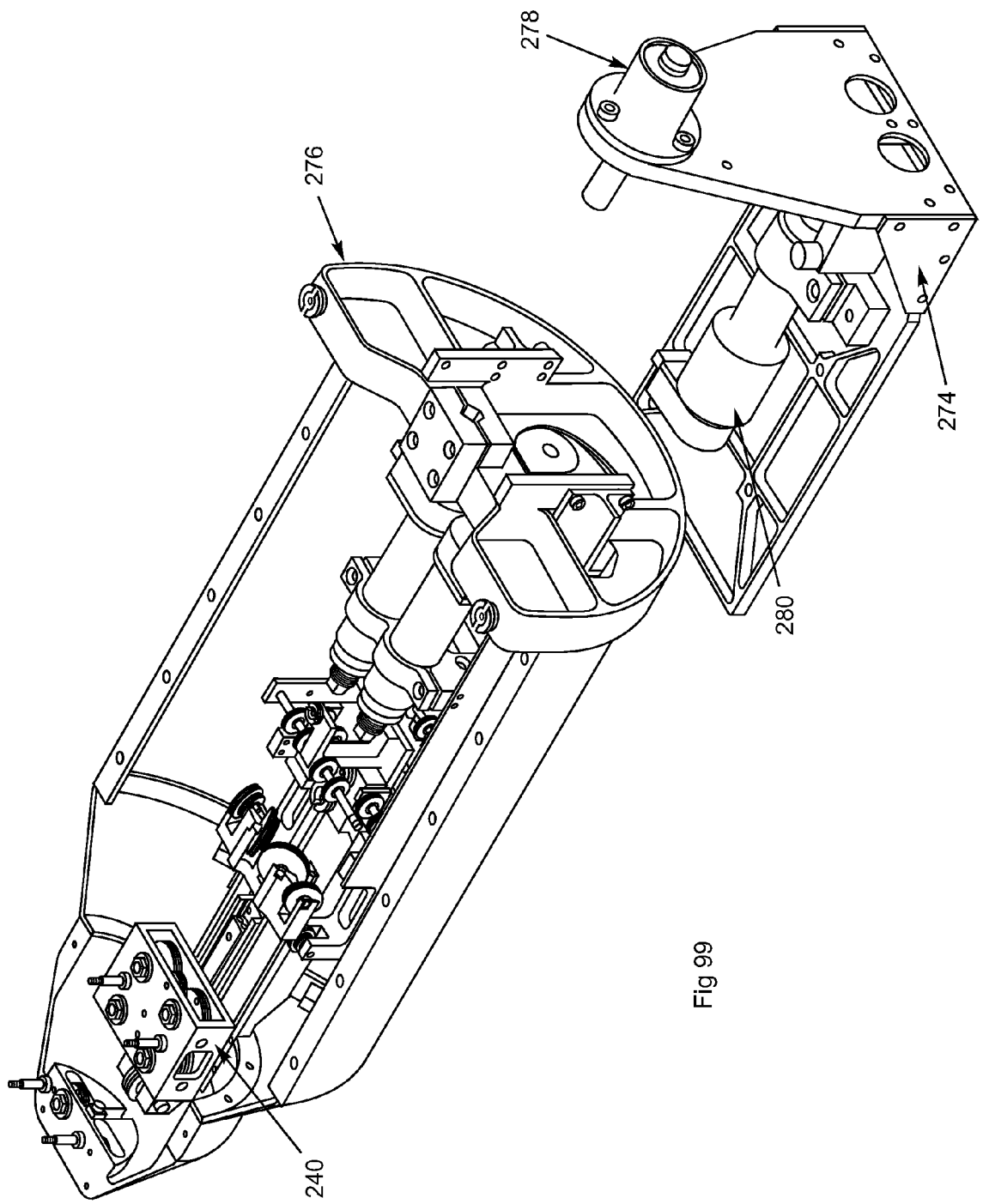
FIG. 99 illustrates the instrument driver of FIG. 98, showing the instrument driver having a roll motor.

Referring to FIGS. 97-103, systems similar to those depicted in FIGS. 95 and 96 are incorporated into various embodiments of the instrument driver. In FIG. 97, an instrument driver (16) is depicted as interfaced with a steerable guide instrument (18) and a steerable sheath instrument (30). FIG. 98 depicts an embodiment of the instrument driver (16), in which the sheath instrument interface surface (38) remains stationary, and requires only a simple motor actuation in order for a sheath to be steered using an interfaced control element via a control element interface assembly (132). This may be accomplished with a simple cable loop about a sheath socket drive pulley (272) and a capstan pulley (not shown), which is fastened to a motor, similar to the two upper motors (242) (visible in FIG. 98). The drive motor for the sheath socket drive schema is hidden under the linear bearing interface assembly.

The drive schema for the four guide instrument interface sockets (270) is more complicated, due in part to the fact that they are coupled to a carriage (240) configured to move linearly along a linear bearing interface (250) to provide for motor-driven insertion of a guide instrument toward the patient relative to the instrument driver, hospital table, and sheath instrument. The cabling and motor schema that moves the carriage (240) along the linear bearing interface (250) is an implementation of the diagrammatic view depicted in FIG. 95. The cabling and motor schema that drives each of the four depicted guide instrument interface sockets is an implementation of the diagrammatic view depicted in FIG. 96. Therefore, in the embodiments of FIGS. 98-103, wherein four separate cable drive loops serve four separate guide instrument interface sockets (270), and wherein the carriage (240) has motorized insertion, there is achieved a functional equivalent of a system such as that diagrammed in FIGS. 95 and 96, all fit into the same construct. Various conventional cable termination and routing techniques are utilized to accomplish a preferably high-density instrument driver structure with the carriage (240) mounted forward of the motors for a lower profile patient-side interface.

Still referring to FIG. 98, the instrument driver (16) is rotatably mounted to an instrument driver base (274), which is configured to interface with an instrument driver mounting brace (not shown), such as that depicted in FIG. 1, or a movable setup joint construct (not shown), such as that depicted in FIG. 2. Rotation between the instrument driver base (274) and an instrument driver base plate (276) to which it is coupled is facilitated by a heavy-duty flanged bearing structure (278). The flanged bearing structure (278) is configured to allow rotation of the body of the instrument driver (16) about an axis approximately coincident with the longitudinal axis of a guide instrument (not shown) when the guide instrument is mounted upon the instrument driver (16) in a neutral position. This rotation preferably is automated or powered by a roll motor (280) and a simple roll cable loop (286), which extends around portions of the instrument driver base plate and terminates as depicted (282, 284). Alternatively, roll rotation may be manually actuated and locked into place with a conventional clamping mechanism. The roll motor (280) position is more easily visible in FIG. 99.

Figure 100:
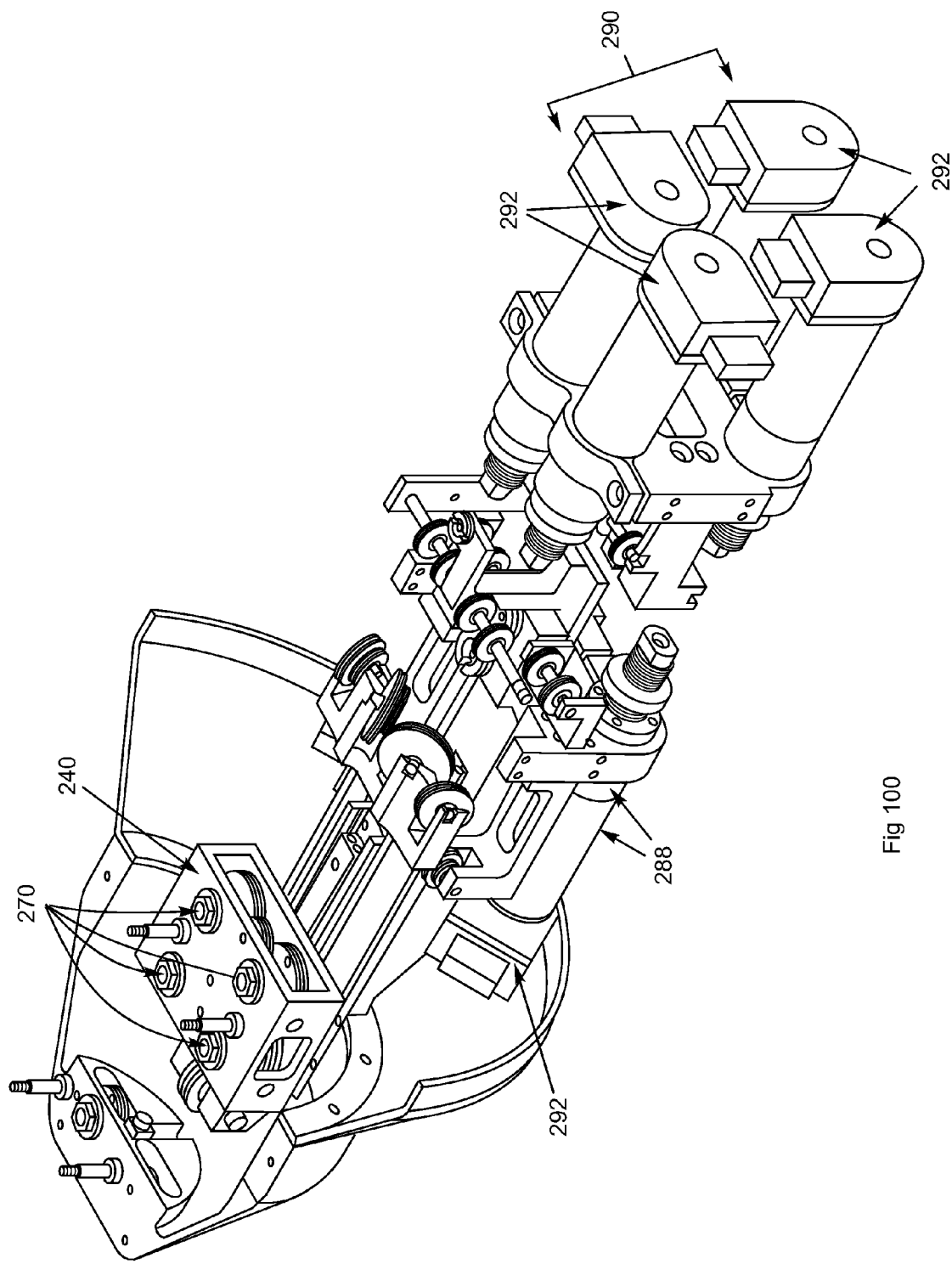
FIG. 100 illustrates components of an instrument driver in accordance with some embodiments, showing the instrument driver having four motors.

FIG. 100 illustrates another embodiment of an instrument driver, including a group of four motors (290). Each motor (290) has an associated high-precision encoder for controls purposes and being configured to drive one of the four guide instrument interface sockets (270), at one end of the instrument driver. Another group of two motors (one hidden, one visible—288) with encoders (292) are configured to drive insertion of the carriage (240) and the sheath instrument interface socket (268).

Figure 101:
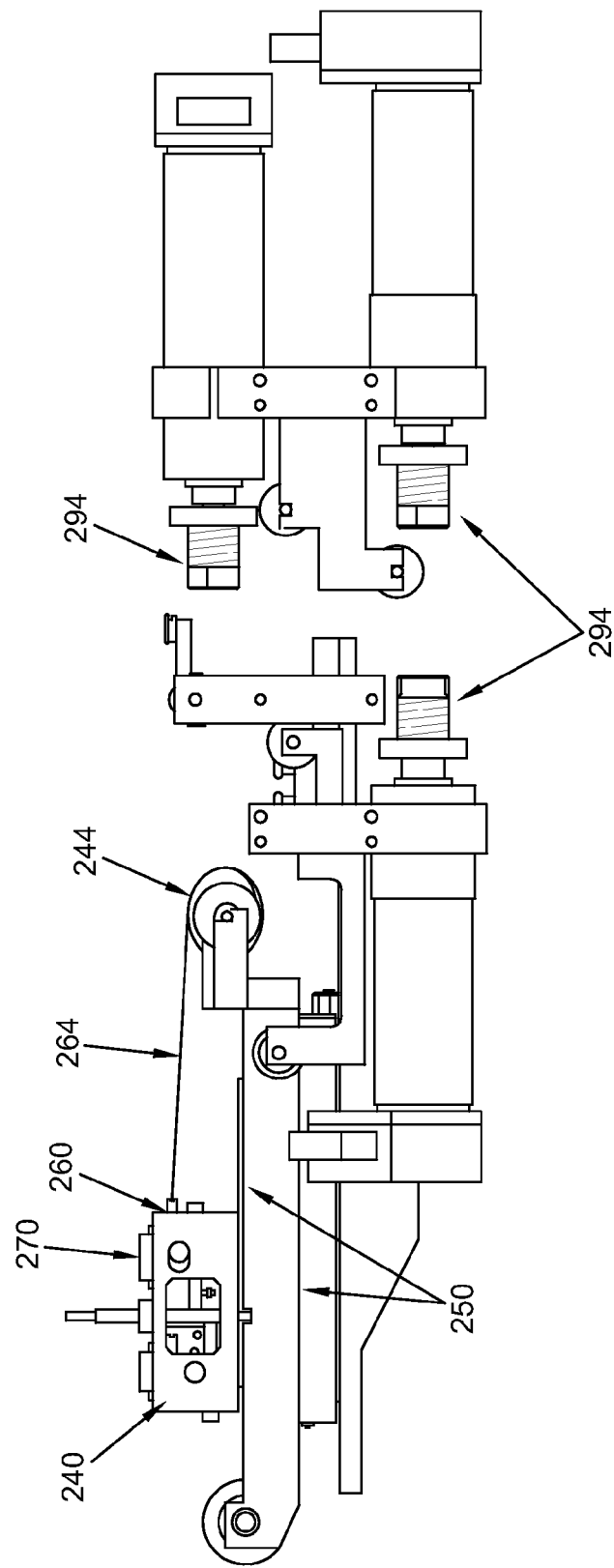
FIG. 101 illustrates a side view of components of an instrument driver in accordance with other embodiments.

Referring to FIG. 101, a further embodiment of an instrument driver is depicted to show the position of the carriage (240) relative to the linear bearing interfaces (250). Also shown is the interfacing of a portion of a instrument interface cable (264) as it bends around a pulley (244) and completes part of its loop to an instrument interface pulley (260) rotatably coupled to the carriage (240) and coupled to a guide instrument interface socket (270), around the instrument interface pulley (260), and back to a motor capstan pulley (294). To facilitate adjustment and installation of such cable loops, and due to the fact that there is generally no requirement to have a loop operating for a long period of time in one direction, thereby perhaps requiring a true unterminated loop, two ends of a cut cable loop preferably are terminated at each capstan (294).

Figure 102:
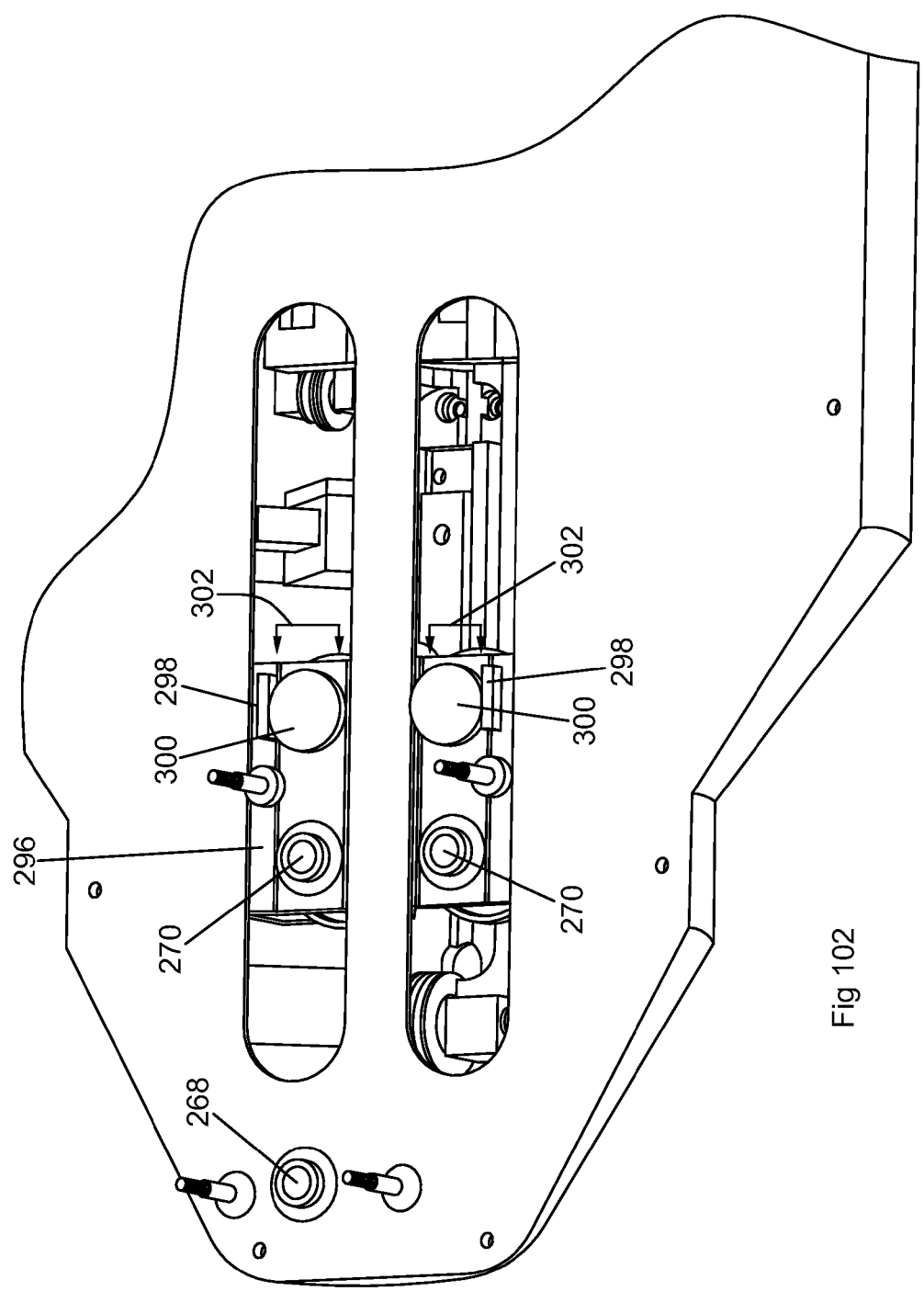
FIG. 102 illustrates a cover plate covering components of an instrument driver in accordance with some embodiments.
Figure 103:
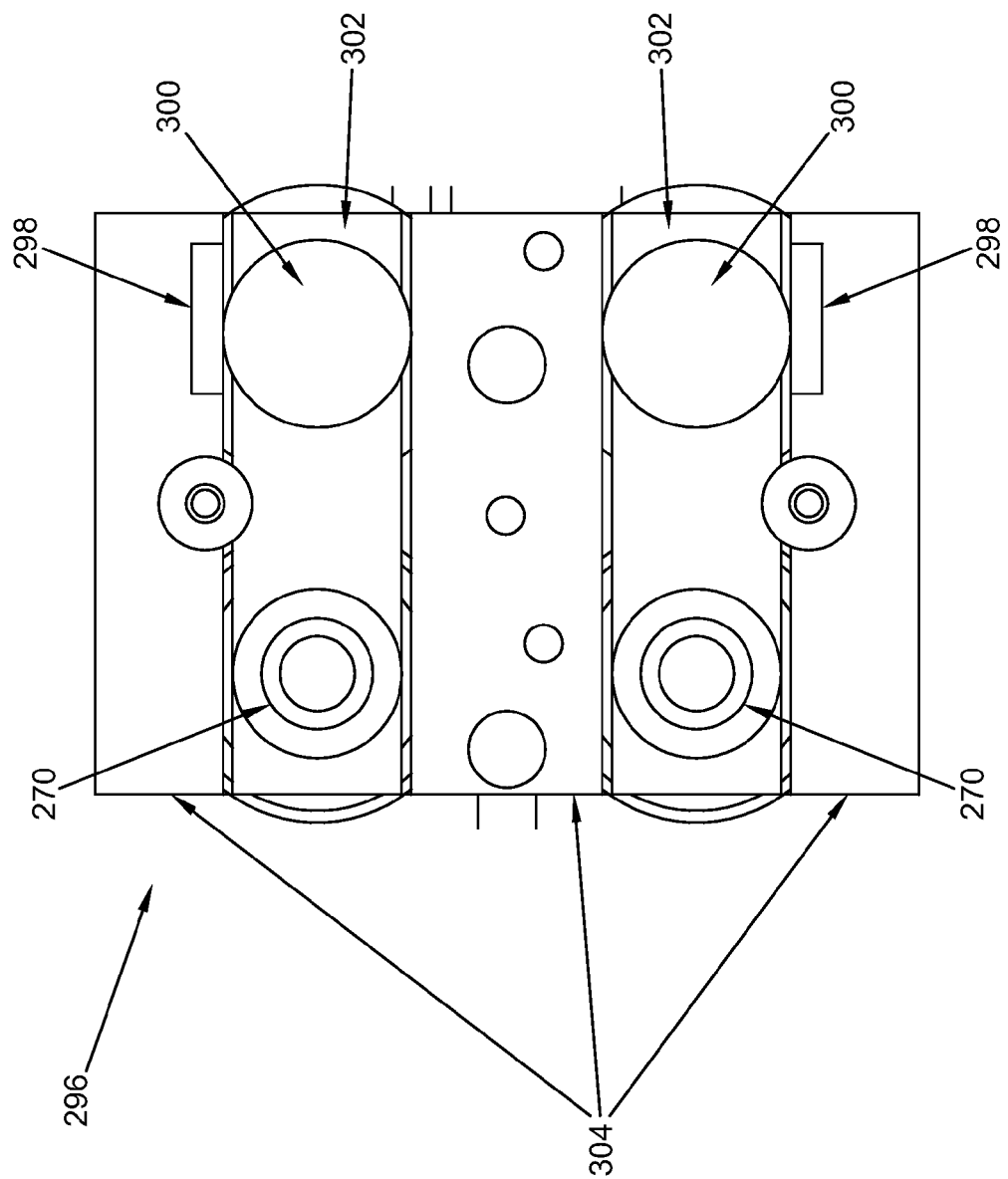
FIG. 103 illustrates components of the instrument driver of FIG. 102.

The carriage (240) depicted in the embodiments of FIGS. 97-101 generally comprises a structural box configured to house the instrument interface sockets and associated instrument interface pulleys. Referring to FIGS. 102 and 103, a split carriage (296) is depicted, comprising a main carriage body (304) similar to that of the non split carriage depicted in previous embodiments (240), and either one or two linearly movable portions (302), which are configured to slide relative to the main carriage body (304) when driven along either forward or backward relative to the main carriage body by a gear (300) placed into one of the guide instrument interface sockets, the gear (300) configured to interface with a rack (298) mounted upon the main carriage body (304) adjacent the gear (300). In an alternate embodiment, the carriage need not be split on both sides, but may have one split side and one non-split side. Further, while a carriage with four guide instrument interface sockets is suitable for driving a guide instrument with anywhere from one to four control element interface assemblies, the additional hardware required for all four control element interface assemblies may be undesirable if an instrument only requires only one or two.

Figure 104:
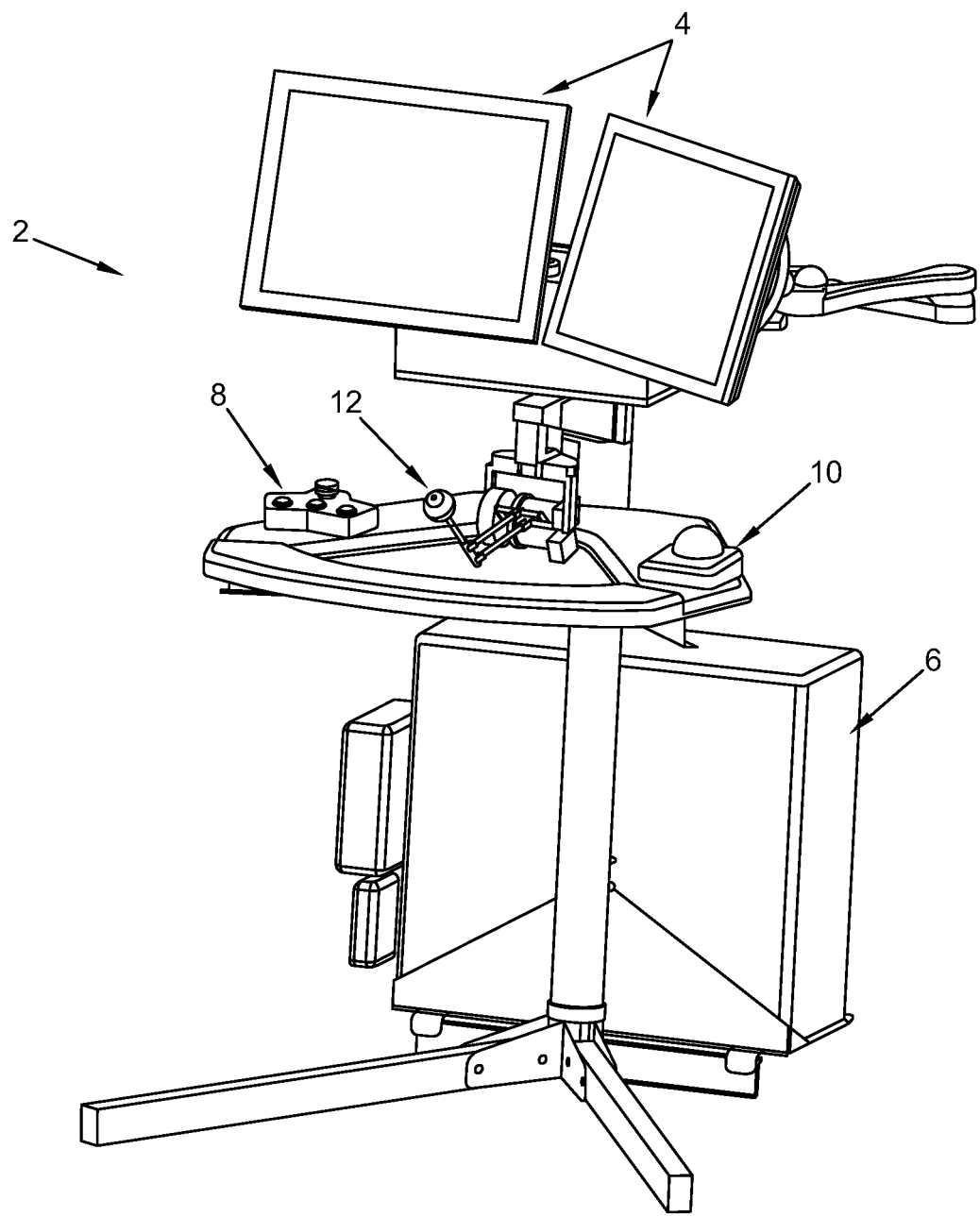
FIG. 104 illustrates an operator control station in accordance with some embodiments.
Figure 105:
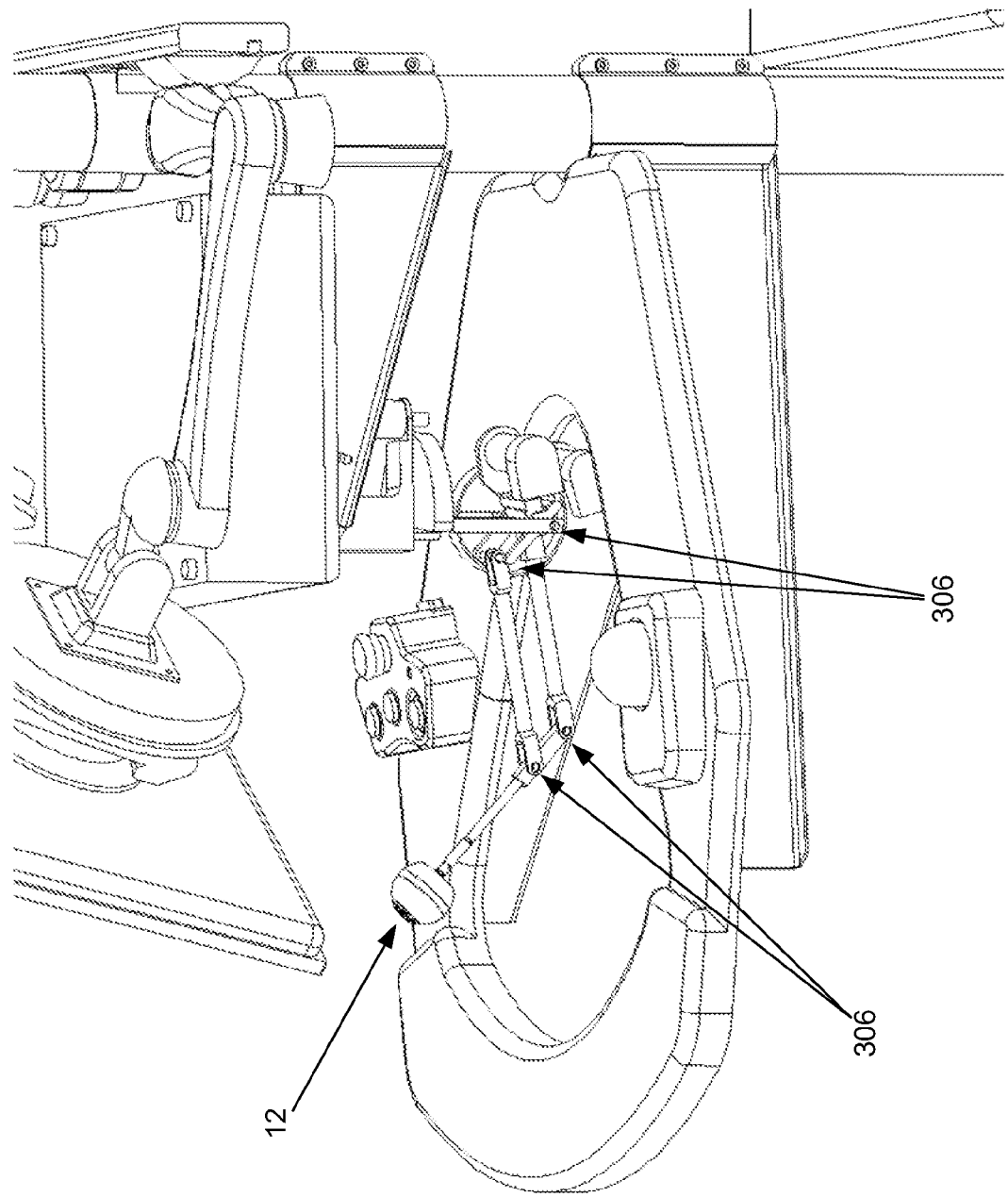
FIG. 105A illustrates a master input device in accordance with some embodiments.
FIG. 105B illustrates a master input device in accordance with other embodiments.
Figure 105:
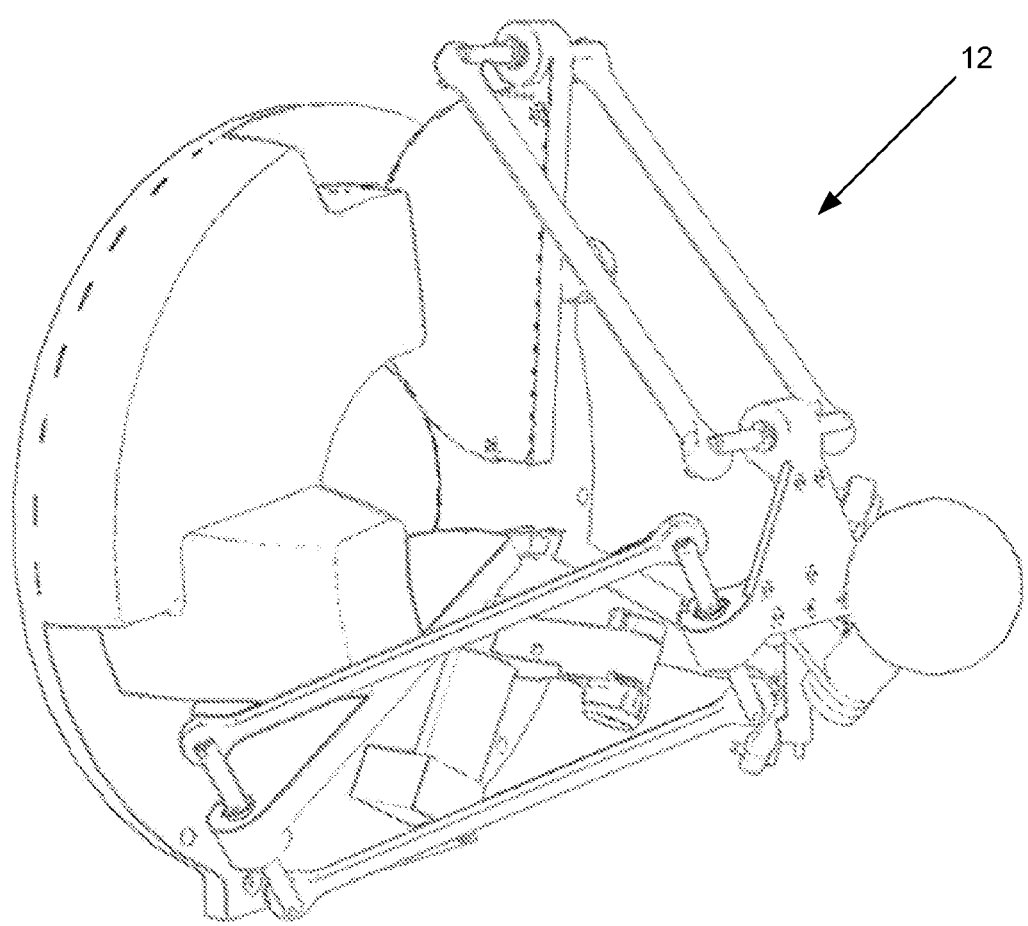

Referring to FIG. 104, an operator control station is depicted showing a control button console (8), a computer (6), a computer control interface (10), such as a mouse, a visual display system (4) and a master input device (12). In addition to "buttons" on the button console (8) footswitches and other known user control interfaces may be utilized to provide an operator interface with the system controls. Referring to FIG. 105A, in one embodiment, the master input device (12) is a multi-degree-of-freedom device having multiple joints and associated encoders (306). Further, the master input device may have integrated haptics capability for providing tactile feedback to the user. Another embodiment of a master input device (12) is depicted in FIG. 105B. Suitable master input devices are available from manufacturers such as Sensible Devices Corporation under the trade name "Phantom™", or Force Dimension under the trade name "Omega™".

Referring to FIGS. 106-109, the basic kinematics of a catheter with four control elements is reviewed.

Referring to FIGS. 106 A-B, as tension is placed only upon the bottom control element (312), the catheter bends downward, as shown in FIG. 106A. Similarly, pulling the left control element (314) in FIGS. 107 A-B bends the catheter left, pulling the right control element (310) in FIGS. 108 A-B bends the catheter right, and pulling the top control element (308) in FIGS. 109 A-B bends the catheter up. As will be apparent to those skilled in the art, well-known combinations of applied tension about the various control elements results in a variety of bending configurations at the tip of the catheter member (90). One of the challenges in accurately controlling a catheter or similar elongate member with tension control elements is the retention of tension in control elements, which may not be the subject of the majority of the tension loading applied in a particular desired bending configuration. If a system or instrument is controlled with various levels of tension, then losing tension, or having a control element in a slack configuration, can result in an unfavorable control scenario.

Referring to FIGS. 110A-E, a simple scenario is useful in demonstrating this notion. As shown in FIG. 110A, a simple catheter (316) steered with two control elements (314, 310) is depicted in a neutral position. If the left control element (314) is placed into tension greater than the tension, if any, which the right control element (310) experiences, the catheter (316) bends to the left, as shown in FIG. 110B. If a change of direction is desired, this paradigm needs to reverse, and the tension in the right control element (310) needs to overcome that in the left control element (314). At the point of a reversal of direction like this, where the tension balance changes from left to right, without slack or tension control, the right most control element (314) may gather slack which needs to be taken up before precise control can be reestablished. Subsequent to a "reeling in" of slack which may be present, the catheter (316) may be may be pulled in the opposite direction, as depicted in FIGS. 110C-E, without another slack issue from a controls perspective until a subsequent change in direction.

The above-described instrument embodiments present various techniques for managing tension control in various guide instrument systems having between two and four control elements. For example, in one set of embodiments, tension may be controlled with active independent tensioning of each control element in the pertinent guide catheter via independent control element interface assemblies (132) associated with independently-controlled guide instrument interface sockets (270) on the instrument driver (16). Thus, tension may be managed by independently actuating each of the control element interface assemblies (132) in a four-control-element embodiment, such as that depicted in FIGS. 18 and 47, a three-control-element embodiment, such as that depicted in FIGS. 63 and 64, or a two-control-element embodiment, such as that depicted in FIGS. 56 and 66.

In another set of embodiments, tension may be controlled with active independent tensioning with a split carriage design, as described in reference to FIGS. 102 and 103. For example, with an instrument embodiment similar to that depicted in FIGS. 53, 54, and 56, a split carriage with two independent linearly movable portions, such as that depicted in FIG. 103, may be utilized to actively and independently tension each of the two control element interface assemblies (132), each of which is associated with two dimensions of a given degree of freedom. For example, there can be + and − pitch on one interface assembly, + and − yaw on the other interface assembly, with slack or tension control provided for pitch by one of the linearly movable portions (302) of the split carriage (296), and slack or tension control provided for yaw by the other linearly movable portion (302) of the split carriage (296).

Similarly, with an embodiment similar to that of FIGS. 71-73, slack or tension control for a single degree of freedom, such as yaw or pitch, may be provided by a single-sided split carriage design similar to that of FIG. 103, with the exception that only one linearly movable portion would be required to actively tension the single control element interface assembly of an instrument.

In another set of embodiments, tensioning may be controlled with spring-loaded idlers configured to keep the associated control elements out of slack, as in the embodiments depicted in FIGS. 57-62 and 69-70. The control elements preferably are pre-tensioned in each embodiment to prevent slack and provide predictable performance. Indeed, in yet another set of embodiments, pre-tensioning may form the main source of tension management, as in the embodiments depicted in FIGS. 55 and 67-68. In the case of embodiments only having pre-tensioning or spring-loaded idler tensioning, the control system may need to be configured to reel in bits of slack at certain transition points in catheter bending, such as described above in relation to FIGS. 110A and 110B.

To accurately coordinate and control actuations of various motors within an instrument driver from a remote operator control station such as that depicted in FIG. 1, an advanced computerized control and visualization system is preferred. While the control system embodiments that follow are described in reference to a particular control systems interface, namely the SimuLink™ and XPC™ control interfaces available from The Mathworks Inc., and PC-based computerized hardware configurations, many other configurations may be utilized, including various pieces of specialized hardware, in place of more flexible software controls running on PC-based systems.

Referring to FIG. 111, an overview of an embodiment of a controls system flow is depicted. A master computer (400) running master input device software, visualization software, instrument localization software, and software to interface with operator control station buttons and/or switches is depicted. In one embodiment, the master input device software is a proprietary module packaged with an off-the-shelf master input device system, such as the Phantom™ from Sensible Devices Corporation, which is configured to communicate with the Phantom™ hardware at a relatively high frequency as prescribed by the manufacturer. Other suitable master input devices, such as that (12) depicted in FIG. 105B are available from suppliers such as Force Dimension of Lausanne, Switzerland. The master input device (12) may also have haptics capability to facilitate feedback to the operator, and the software modules pertinent to such functionality may also be operated on the master computer (400). Preferred embodiments of haptics feedback to the operator are discussed in further detail below.

Figure 112B:
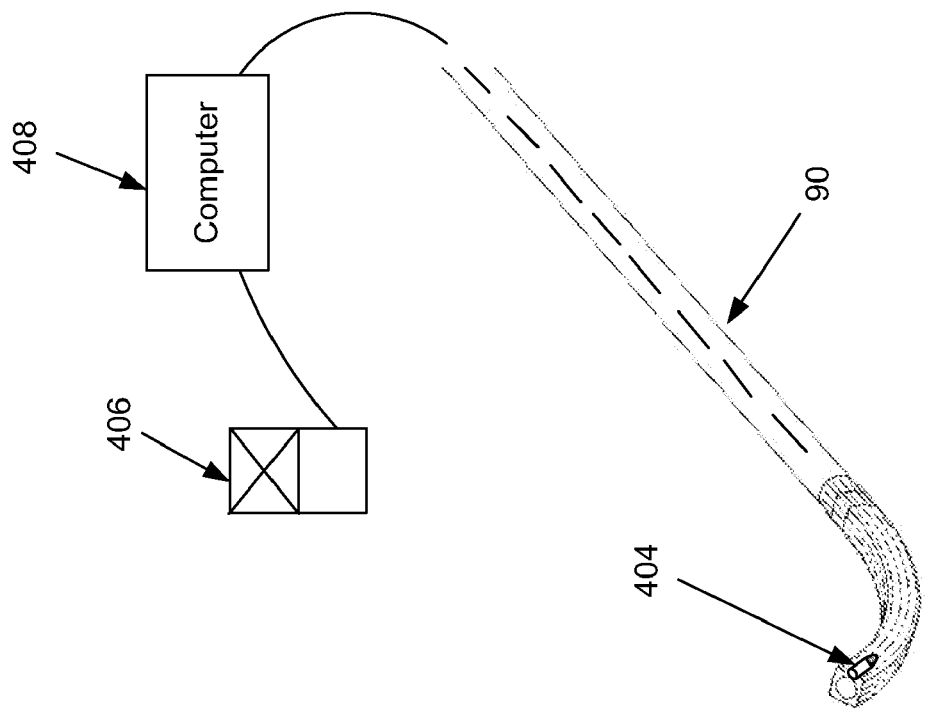
FIG. 112B illustrates a localization sensing system in accordance with other embodiments.
Figure 112A:
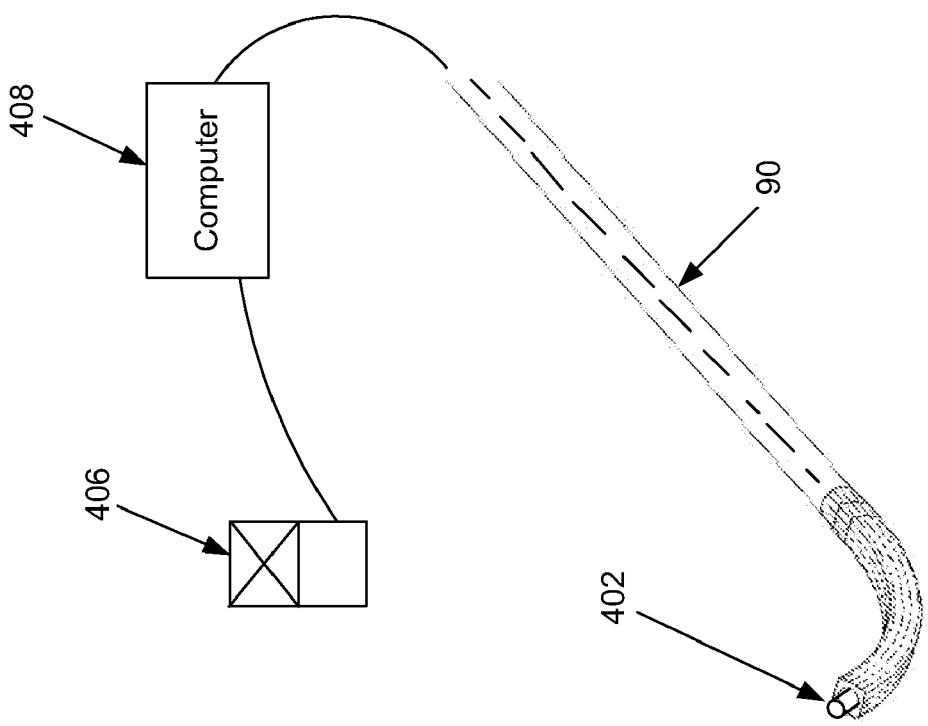
FIG. 112A illustrates a localization sensing system having an electromagnetic field receiver in accordance with some embodiments.

The term "localization" is used in the art in reference to systems for determining and/or monitoring the position of objects, such as medical instruments, in a reference coordinate system. In one embodiment, the instrument localization software is a proprietary module packaged with an off-the-shelf or custom instrument position tracking system, such as those available from Ascension Technology Corporation, Biosense Webster, Inc., Endocardial Solutions, Inc., Boston Scientific (EP Technologies), and others. Such systems may be capable of providing not only real-time or near real-time positional information, such as X-Y-Z coordinates in a Cartesian coordinate system, but also orientation information relative to a given coordinate axis or system. Referring to FIGS. 112A and 112B, various localization sensing systems may be utilized with the various embodiments of the robotic catheter system disclosed herein. In other embodiments not comprising a localization system to determine the position of various components, kinematic and/or geometric relationships between various components of the system may be utilized to predict the position of one component relative to the position of another. Some embodiments may utilize both localization data and kinematic and/or geometric relationships to determine the positions of various components.

As shown in FIG. 112A, one preferred localization system comprises an electromagnetic field transmitter (406) and an electromagnetic field receiver (402) positioned within the central lumen of a guide catheter (90). The transmitter (406) and receiver (402) are interfaced with a computer operating software configured to detect the position of the detector relative to the coordinate system of the transmitter (406) in real or near-real time with high degrees of accuracy. Referring to FIG. 112B, a similar embodiment is depicted with a receiver (404) embedded within the guide catheter (90) construction. Preferred receiver structures may comprise three or more sets of very small coils spatially configured to sense orthogonal aspects of magnetic fields emitted by a transmitter. Such coils may be embedded in a custom configuration within or around the walls of a preferred catheter construct.

For example, in one embodiment, two orthogonal coils are embedded within a thin polymeric layer at two slightly flattened surfaces of a catheter (90) body approximately ninety degrees orthogonal to each other about the longitudinal axis of the catheter (90) body, and a third coil is embedded in a slight polymer-encapsulated protrusion from the outside of the catheter (90) body, perpendicular to the other two coils. Due to the very small size of the pertinent coils, the protrusion of the third coil may be minimized. Electronic leads for such coils may also be embedded in the catheter wall, down the length of the catheter body to a position, preferably adjacent an instrument driver, where they may be routed away from the instrument to a computer running localization software and interfaced with a pertinent transmitter.

Figure 113:
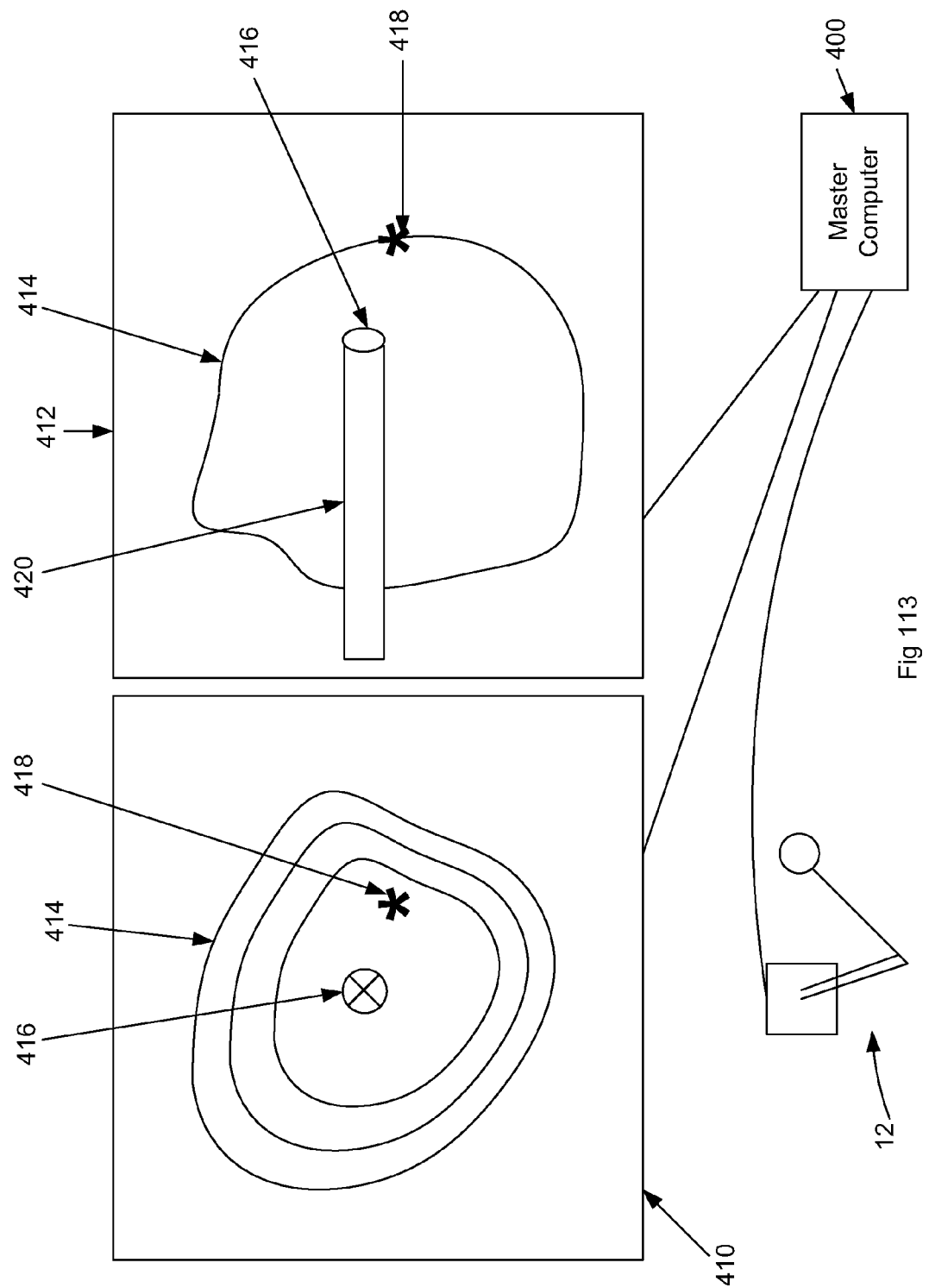
FIG. 113 illustrates a user interface for a master input device in accordance with some embodiments.

Referring back to FIG. 111, in one embodiment, visualization software runs on the master computer (400) to facilitate real-time driving and navigation of one or more steerable instruments. In one embodiment, visualization software provides an operator at an operator control station, such as that depicted in FIG. 1 (2), with a digitized "dashboard" or "windshield" display to enhance instinctive drivability of the pertinent instrumentation within the pertinent tissue structures. Referring to FIG. 113, a simple illustration is useful to explain one embodiment of a preferred relationship between visualization and navigation with a master input device (12). In the depicted embodiment, two display views (410, 412) are shown. One preferably represents a primary (410) navigation view, and one may represent a secondary (412) navigation view. To facilitate instinctive operation of the system, it is preferable to have the master input device coordinate system at least approximately synchronized with the coordinate system of at least one of the two views. Further, it is preferable to provide the operator with one or more secondary views which may be helpful in navigating through challenging tissue structure pathways and geometries.

Using the operation of an automobile as an example, if the master input device is a steering wheel and the operator desires to drive a car in a forward direction using one or more views, his first priority is likely to have a view straight out the windshield, as opposed to a view out the back window, out one of the side windows, or from a car in front of the car that he is operating. The operator might prefer to have the forward windshield view as his primary display view, such that a right turn on the steering wheel takes him right as he observes his primary display, a left turn on the steering wheel takes him left, and so forth. If the operator of the automobile is trying to park the car adjacent another car parked directly in front of him, it might be preferable to also have a view from a camera positioned, for example, upon the sidewalk aimed perpendicularly through the space between the two cars (one driven by the operator and one parked in front of the driven car), so the operator can see the gap closing between his car and the car in front of him as he parks. While the driver might not prefer to have to completely operate his vehicle with the sidewalk perpendicular camera view as his sole visualization for navigation purposes, this view is helpful as a secondary view.

Referring still to FIG. 113, if an operator is attempting to navigate a steerable catheter in order to, for example, contact a particular tissue location with the catheter's distal tip, a useful primary navigation view (410) may comprise a three dimensional digital model of the pertinent tissue structures (414) through which the operator is navigating the catheter with the master input device (12), along with a representation of the catheter distal tip location (416) as viewed along the longitudinal axis of the catheter near the distal tip. This embodiment illustrates a representation of a targeted tissue structure location (418), which may be desired in addition to the tissue digital model (414) information. A useful secondary view (412), displayed upon a different monitor, in a different window upon the same monitor, or within the same user interface window, for example, comprises an orthogonal view depicting the catheter tip representation (416), and also perhaps a catheter body representation (420), to facilitate the operator's driving of the catheter tip toward the desired targeted tissue location (418).

In one embodiment, subsequent to development and display of a digital model of pertinent tissue structures, an operator may select one primary and at least one secondary view to facilitate navigation of the instrumentation. By selecting which view is a primary view, the user can automatically toggle a master input device (12) coordinate system to synchronize with the selected primary view. In an embodiment with the leftmost depicted view (410) selected as the primary view, to navigate toward the targeted tissue site (418), the operator should manipulate the master input device (12) forward, to the right, and down. The right view will provide valued navigation information, but will not be as instinctive from a "driving" perspective.

To illustrate: if the operator wishes to insert the catheter tip toward the targeted tissue site (418) watching only the rightmost view (412) without the master input device (12) coordinate system synchronized with such view, the operator would have to remember that pushing straight ahead on the master input device will make the distal tip representation (416) move to the right on the rightmost display (412). Should the operator decide to toggle the system to use the rightmost view (412) as the primary navigation view, the coordinate system of the master input device (12) is then synchronized with that of the rightmost view (412), enabling the operator to move the catheter tip (416) closer to the desired targeted tissue location (418) by manipulating the master input device (12) down and to the right.

The synchronization of coordinate systems described herein may be conducted using fairly conventional mathematic relationships. For example, in one embodiment, the orientation of the distal tip of the catheter may be measured using a 6-axis position sensor system such as those available from Ascension Technology Corporation, Biosense Webster, Inc., Endocardial Solutions, Inc., Boston Scientific (EP Technologies), and others. A 3-axis coordinate frame, C, for locating the distal tip of the catheter, is constructed from this orientation information. The orientation information is used to construct the homogeneous transformation matrix, $T_{C0}^{G0}$, which transforms a vector in the Catheter coordinate frame "C" to the fixed Global coordinate frame "G" in which the sensor measurements are done (the subscript $C_0$ and superscript $G_0$ are used to represent the 0'th, or initial, step). As a registration step, the computer graphics view of the catheter is rotated until the master input and the computer graphics view of the catheter distal tip motion are coordinated and aligned with the camera view of the graphics scene. The 3-axis coordinate frame transformation matrix $T_{Gref}^{G0}$ for the camera position of this initial view is stored (subscripts $G_{ref}$ and superscript $C_{ref}$ stand for the global and camera "reference" views). The corresponding catheter "reference view" matrix for the catheter coordinates is obtained as:

$$T_{Cref}^{C0} = T_{G0}^{C0} T_{Gref}^{G0} T_{Cref}^{Gref} = (T_{C0}^{G0})^{-1} T_{Gref}^{G0} T_{C1}^{Gref}$$

Also note that the catheter's coordinate frame is fixed in the global reference frame G, thus the transformation matrix between the global frame and the catheter frame is the same in all views, i.e., $T_{C0}^{G0} = T_{Cref}^{Gref} = T_{Ci}^{Gi}$ for any arbitrary view i.

The coordination between primary view and master input device coordinate systems is achieved by transforming the master input as follows: Given any arbitrary computer graphics view of the representation, e.g. the i'th view, the 3-axis coordinate frame transformation matrix $T_{Gi}^{G0}$ of the camera view of the computer graphics scene is obtained form the computer graphics software. The corresponding catheter transformation matrix is computed in a similar manner as above:

$$T_{Ci}^{C0} = T_{G0}^{C0} T_{Gi}^{G0} T_{Ci}^{Gi} = (T_{C0}^{G0})^{-1} T_{Gi}^{G0} T_{Ci}^{Gi}$$

The transformation that needs to be applied to the master input which achieves the view coordination is the one that transforms from the reference view that was registered above, to the current ith view, i.e., $T_{Cref}^{Ci}$. Using the previously computed quantities above, this transform is computed as:

$$T_{Cref}^{Ci} = T_{C0}^{Ci} T_{Cref}^{C0}$$

The master input is transformed into the commanded catheter input by application of the transformation $T_{Cref}^{Ci}$. Given a command input $$r_{master} = \begin{bmatrix} x_{master} \\ y_{master} \\ y_{master} \end{bmatrix},$$

one may calculate:

$$r_{catheter} = \begin{bmatrix} x_{catheter} \\ y_{catheter} \\ y_{catheter} \end{bmatrix} = T_{Cref}^{Ci} \begin{bmatrix} x_{master} \\ y_{master} \\ y_{master} \end{bmatrix}.$$

Under such relationships, coordinate systems of the primary view and master input device may be aligned for instinctive operation.

Referring back to embodiment of FIG. 111, the master computer (400) also comprises software and hardware interfaces to operator control station buttons, switches, and other input devices which may be utilized, for example, to "freeze" the system by functionally disengaging the master input device as a controls input, or provide toggling between various scaling ratios desired by the operator for manipulated inputs at the master input device (12). The master computer (400) has two separate functional connections with the control and instrument driver computer (422): one (426) for passing controls and visualization related commands, such as desired XYZ) in the catheter coordinate system) commands, and one (428) for passing safety signal commands. Similarly, the control and instrument driver computer (422) has two separate functional connections with the instrument and instrument driver hardware (424): one (430) for passing control and visualization related commands such as required-torque-related voltages to the amplifiers to drive the motors and encoders, and one (432) for passing safety signal commands.

In one embodiment, the safety signal commands represent a simple signal repeated at very short intervals, such as every 10 milliseconds, such signal chain being logically read as "system is ok, amplifiers stay active". If there is any interruption in the safety signal chain, the amplifiers are logically toggled to inactive status and the instrument cannot be moved by the control system until the safety signal chain is restored. Also shown in the signal flow overview of FIG. 111 is a pathway (434) between the physical instrument and instrument driver hardware back to the master computer to depict a closed loop system embodiment wherein instrument localization technology, such as that described in reference to FIGS. 112A-B, is utilized to determine the actual position of the instrument to minimize navigation and control error, as described in further detail below.

FIGS. 114-124 depict various aspects of one embodiment of a SimuLink™ software control schema for an embodiment of the physical system, with particular attention to an embodiment of a "master following mode." In this embodiment, an instrument is driven by following instructions from a master input device, and a motor servo loop embodiment, which comprises key operational functionality for executing upon commands delivered from the master following mode to actuate the instrument.

Figure 114:
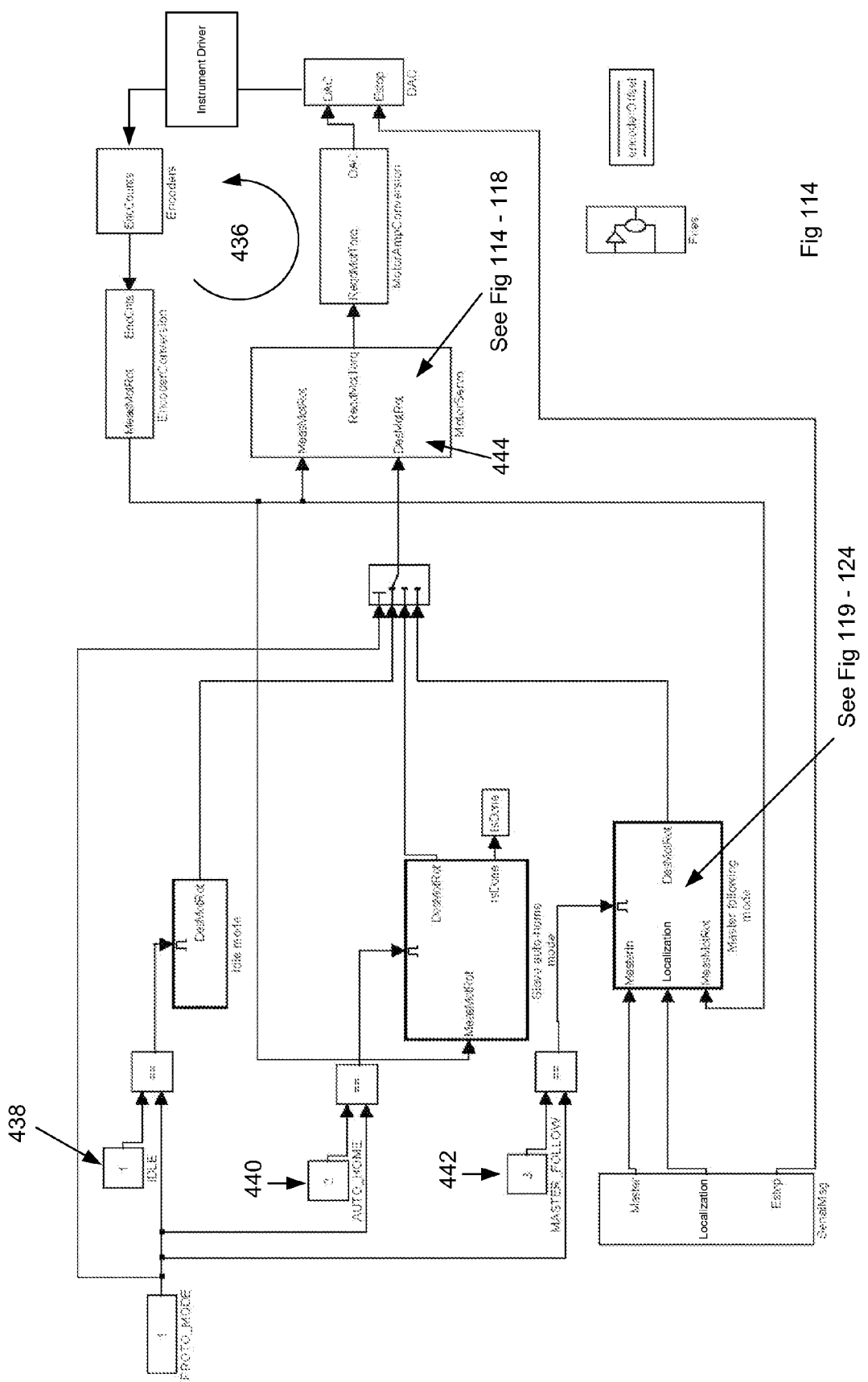
FIGS. 114-124 illustrate software control schema in accordance with various embodiments.

FIG. 114 depicts a high-level view of an embodiment wherein any one of three modes may be toggled to operate the primary servo loop (436). In idle mode (438), the default mode when the system is started up, all of the motors are commanded via the motor servo loop (436) to servo about their current positions, their positions being monitored with digital encoders associated with the motors. In other words, idle mode (438) deactivates the motors, while the remaining system stays active. Thus, when the operator leaves idle mode, the system knows the position of the relative components. In auto home mode (440), cable loops within an associated instrument driver, such as that depicted in FIG. 97, are centered within their cable loop range to ensure substantially equivalent range of motion of an associated instrument, such as that depicted in FIG. 17, in both directions for a various degree of freedom, such as + and − directions of pitch or yaw, when loaded upon the instrument driver. This is a setup mode for preparing an instrument driver before an instrument is engaged.

In master following mode (442), the control system receives signals from the master input device, and in a closed loop embodiment from both a master input device and a localization system, and forwards drive signals to the primary servo loop (436) to actuate the instrument in accordance with the forwarded commands. Aspects of this embodiment of the master following mode (442) are depicted in further detail in FIGS. 119-124. Aspects of the primary servo loop and motor servo block (444) are depicted in further detail in FIGS. 115-118.

Figure 119:
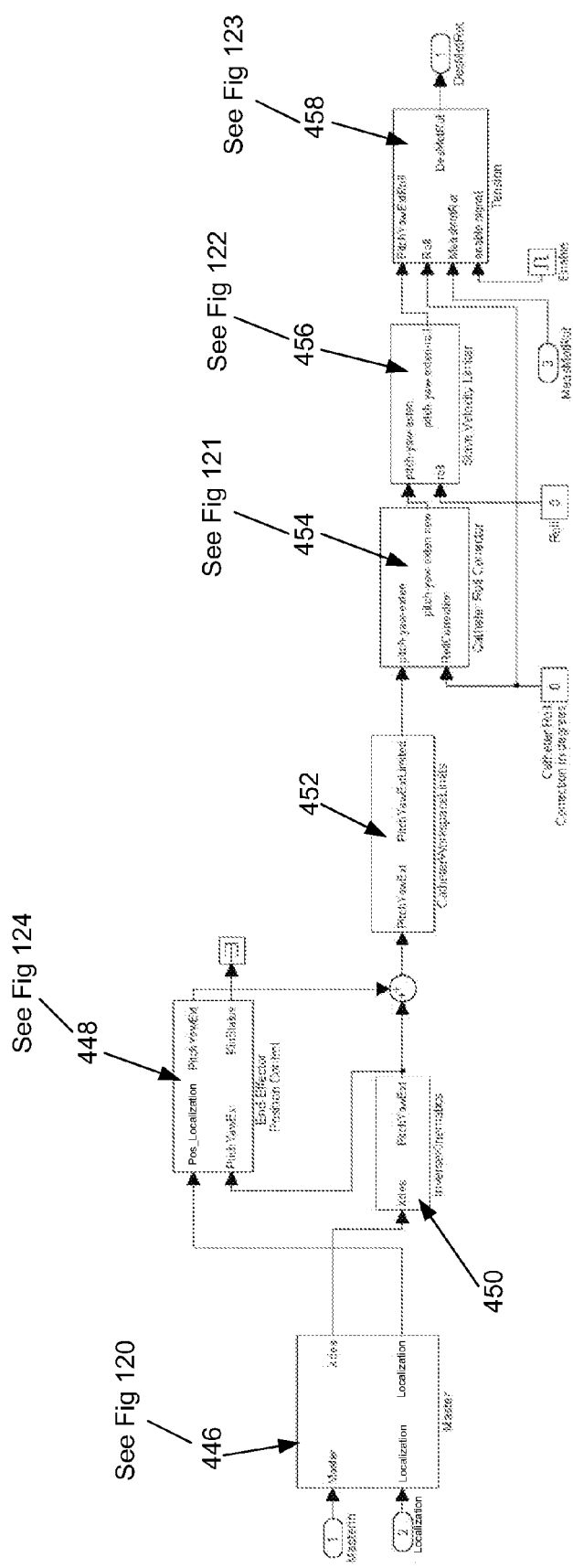
Figure 120:
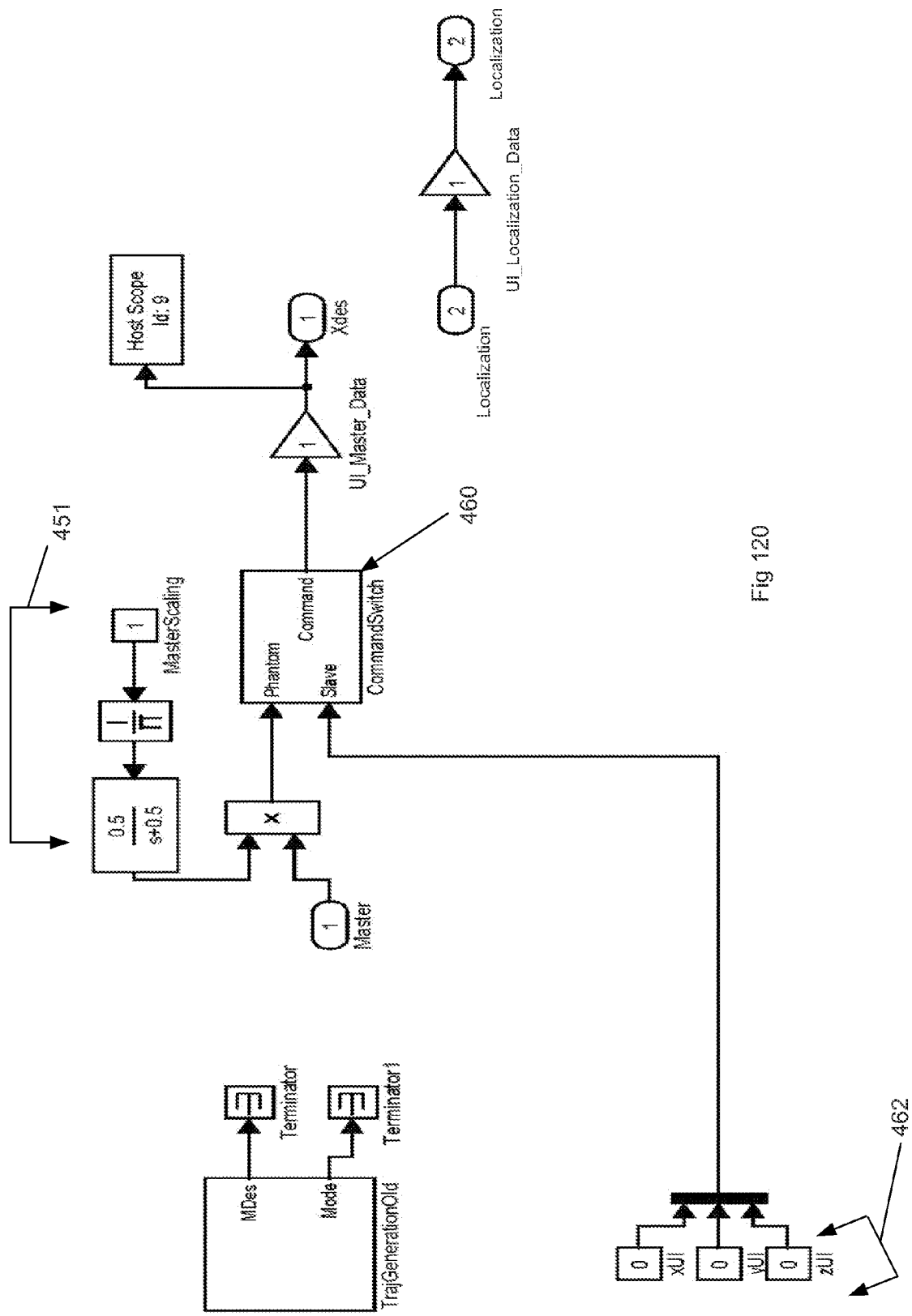

Referring to FIG. 119, a more detailed functional diagram of an embodiment of master following mode (442) is depicted. As shown in FIG. 119, the inputs to functional block (446) are XYZ position of the master input device in the coordinate system of the master input device which, per a setting in the software of the master input device may be aligned to have the same coordinate system as the catheter, and localization XYZ position of the distal tip of the instrument as measured by the localization system in the same coordinate system as the master input device and catheter. Referring to FIG. 120 for a more detailed view of functional block (446) of FIG. 119, a switch (460) is provided at block to allow switching between master inputs for desired catheter position, to an input interface (462) through which an operator may command that the instrument go to a particular XYZ location in space. Various controls features may also utilize this interface to provide an operator with, for example, a menu of destinations to which the system should automatically drive an instrument, etc. Also depicted in FIG. 120 is a master scaling functional block (464) which is utilized to scale the inputs coming from the master input device with a ratio selectable by the operator. The command switch (460)

functionality includes a low pass filter to weight commands switching between the master input device and the input interface (462), to ensure a smooth transition between these modes.

Referring back to FIG. 119, desired position data in XYZ terms is passed to the inverse kinematics block (450) for conversion to pitch, yaw, and extension (or "insertion") terms in accordance with the predicted mechanics of materials relationships inherent in the mechanical design of the instrument.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and − directions. Other motorized tension relationships may drive other instruments, active tensioning, or insertion or roll of the catheter instrument. The relationship between actuated inputs and the catheter's end point position as a function of the actuated inputs is referred to as the "kinematics" of the catheter.

Figure 126:
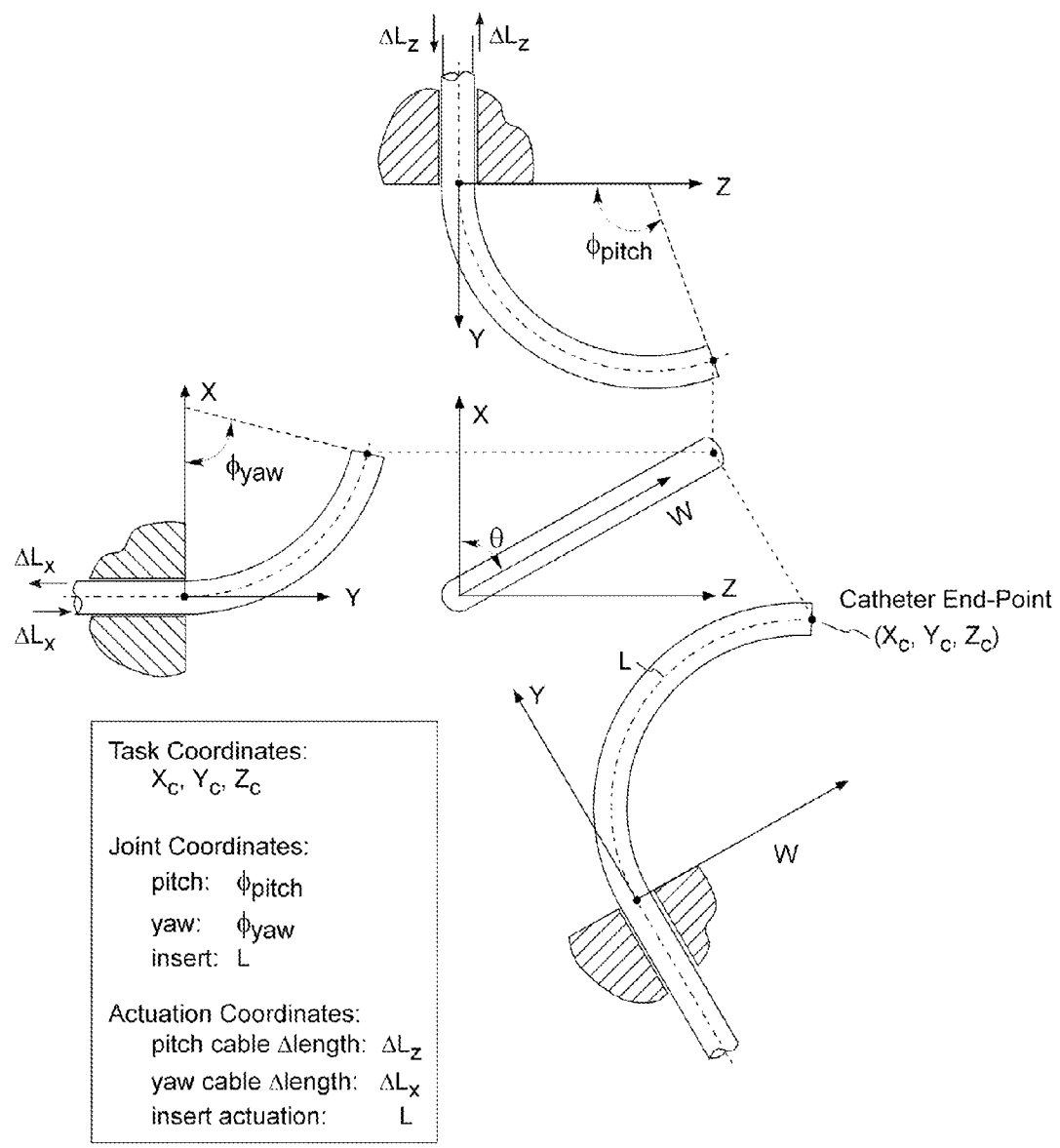
FIG. 126 illustrates task coordinates, joint coordinates, and actuation coordinates in accordance with some embodiments.

Referring to FIG. 125, the "forward kinematics" expresses the catheter's end-point position as a function of the actuated inputs while the "inverse kinematics" expresses the actuated inputs as a function of the desired end-point position. Accurate mathematical models of the forward and inverse kinematics are essential for the control of a robotically controlled catheter system. For clarity, the kinematics equations are further refined to separate out common elements, as shown in FIG. 125. The basic kinematics describes the relationship between the task coordinates and the joint coordinates. In such case, the task coordinates refer to the position of the catheter end-point while the joint coordinates refer to the bending (pitch and yaw, for example) and length of the active catheter. The actuator kinematics describes the relationship between the actuation coordinates and the joint coordinates. The task, joint, and bending actuation coordinates for the robotic catheter are illustrated in FIG. 126. By describing the kinematics in this way we can separate out the kinematics associated with the catheter structure, namely the basic kinematics, from those associated with the actuation methodology.

The development of the catheter's kinematics model is derived using a few essential assumptions. Included are assumptions that the catheter structure is approximated as a simple beam in bending from a mechanics perspective, and that control elements, such as thin tension wires, remain at a fixed distance from the neutral axis and thus impart a uniform moment along the length of the catheter.

Figure 127:
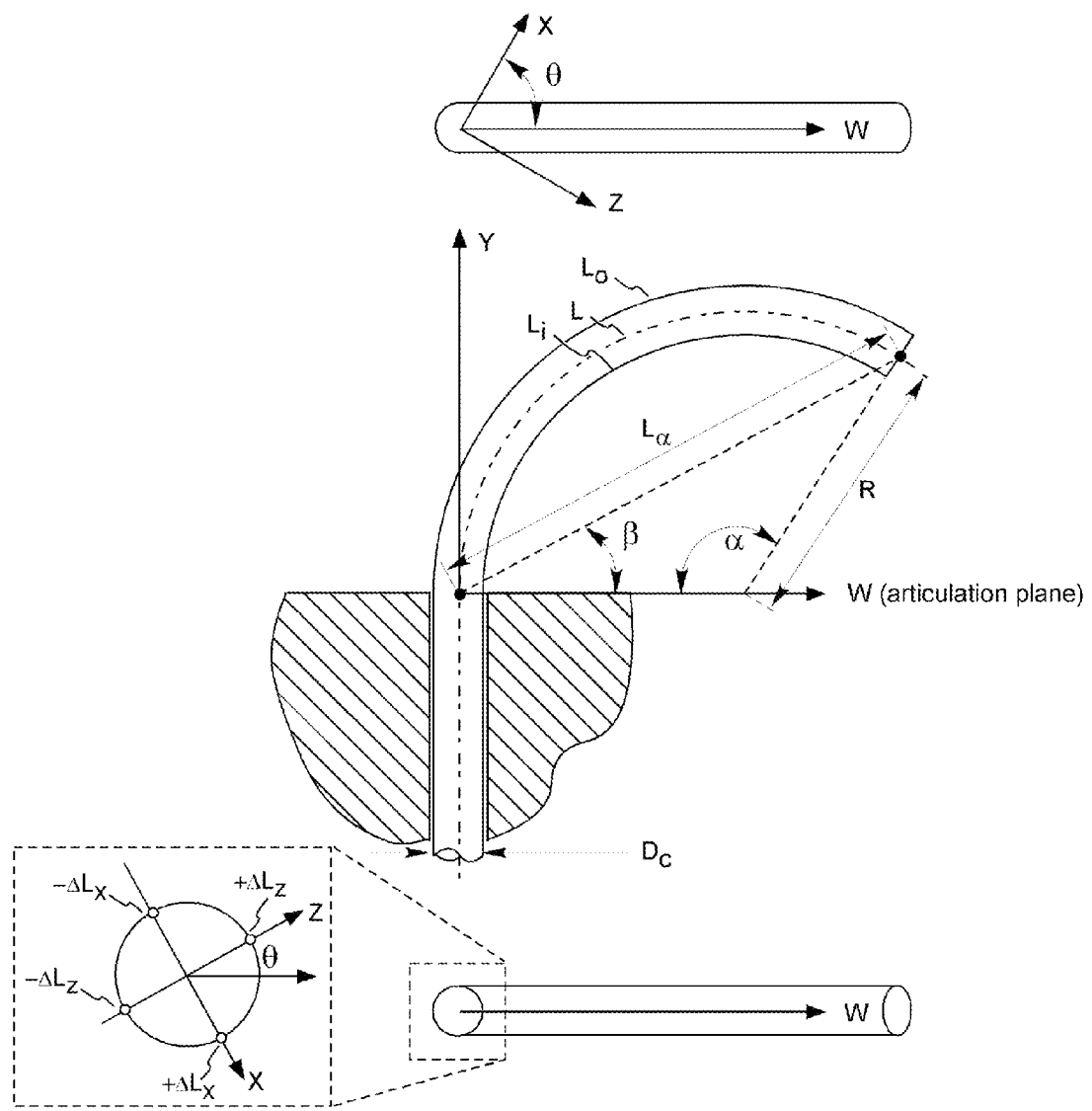
FIG. 127 illustrates variables associated with a geometry of a catheter in accordance with some embodiments.

In addition to the above assumptions, the geometry and variables shown in FIG. 127 are used in the derivation of the forward and inverse kinematics. The basic forward kinematics, relating the catheter task coordinates ($X_c$, $Y_c$, $Z_c$) to the joint coordinates ($\phi_{pitch}$, $\phi_{pitch}$, L), is given as follows:

$$X_c = w\cos(\theta)$$
$$Y_c = R\sin(\alpha)$$
$$Z_c = w\sin(\theta)$$

where $$w = R(1 - \cos(\alpha))$$

-continued $$\alpha = [(\phi_{pitch})^2 + (\phi_{yaw})^2]^{1/2} \quad \text{(total bending)}$$
$$R = \frac{L}{\alpha} \quad \text{(bend radius)}$$
$$\theta = \text{atan2}(\phi_{pitch}, \phi_{yaw}) \quad \text{(roll angle)}$$

The actuator forward kinematics, relating the joint coordinates ($\phi_{pitch}$, $\phi_{pitch}$, L) to the actuator coordinates ($\Delta L_x$, $\Delta L_z$, L) is given as follows:

$$\phi_{pitch} = \frac{2\Delta L_z}{D_c}$$
$$\phi_{yaw} = \frac{2\Delta L_x}{D_c}$$

As illustrated in FIG. 125, the catheter's end-point position can be predicted given the joint or actuation coordinates by using the forward kinematics equations described above.

Calculation of the catheter's actuated inputs as a function of end-point position, referred to as the inverse kinematics, can be performed numerically, using a nonlinear equation solver such as Newton-Raphson. A more desireable approach, and the one used in this illustrative embodiment, is to develop a closed-form solution which can be used to calculate the required actuated inputs directly from the desired end-point positions.

As with the forward kinematics, we separate the inverse kinematics into the basic inverse kinematics, which relates joint coordinates to the task coordinates, and the actuation inverse kinematics, which relates the actuation coordinates to the joint coordinates. The basic inverse kinematics, relating the joint coordinates ($\phi_{pitch}$, $\phi_{pitch}$, L), to the catheter task coordinates (Xc, Yc, Zc) is given as follows:

$$\phi_{pitch} = \alpha \sin(\theta)$$
$$\phi_{yaw} = \alpha \cos(\theta)$$
$$L = R\alpha$$

$$\rightarrow \text{where} \rightarrow \quad \begin{aligned} \theta &= \text{atan2}(Z_c, X_c) \\ R &= \frac{l \sin\beta}{\sin 2\beta} \\ \alpha &= \pi - 2\beta \end{aligned} \quad \begin{aligned} \beta &= \text{atan2}(Y_c, W_c) \\ W_c &= (X_c^2 + Z_c^2)^{1/2} \\ l &= (W_c^2 + Y_c^2)^{1/2} \end{aligned}$$

The actuator inverse kinematics, relating the actuator coordinates ($\Delta L_x$, $\Delta L_z$, L) to the joint coordinates ($\phi_{pitch}$, $\phi_{pitch}$, L) is given as follows:

$$\Delta L_x = \frac{D_c \phi_{yaw}}{2}$$
$$\Delta L_z = \frac{D_c \phi_{pitch}}{2}$$

Figure 124:
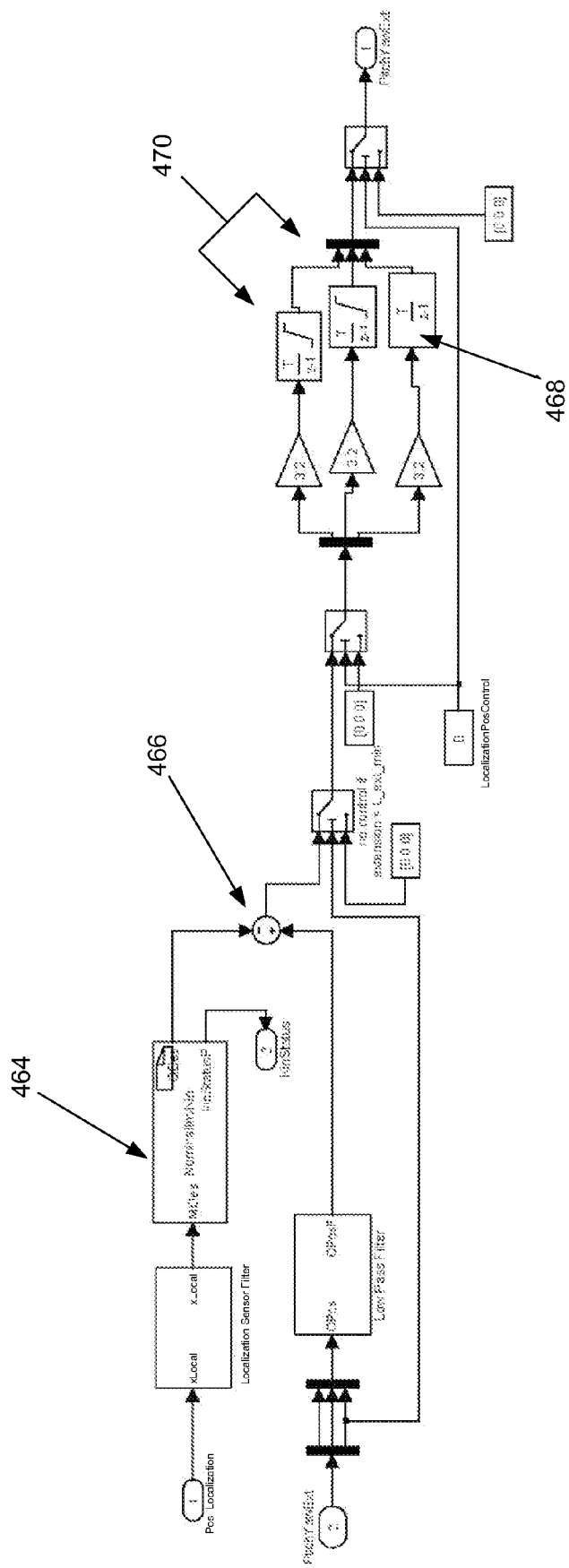

Referring back to FIG. 119, pitch, yaw, and extension commands are passed from the inverse kinematics (450) to a position control block (448) along with measured localization data. FIG. 124 provides a more detailed view of the position control block (448). After measured XYZ position data comes in from the localization system, it goes through a inverse kinematics block (464) to calculate the pitch, yaw, and extension the instrument needs to have in order to travel to where it needs to be. Comparing (466) these values with filtered desired pitch, yaw, and extension data from the master input device, integral compensation is then conducted with limits on pitch and yaw to integrate away the error. In this embodiment, the extension variable does not have the same limits (468), as do pitch and yaw (470). As will be apparent to those skilled in the art, having an integrator in a negative feedback loop forces the error to zero. Desired pitch, yaw, and extension commands are next passed through a catheter workspace limitation (452), which may be a function of the experimentally determined physical limits of the instrument beyond which componentry may fail, deform undesirably, or perform unpredictably or undesirably. This workspace limitation essentially defines a volume similar to a cardioid-shaped volume about the distal end of the instrument. Desired pitch, yaw, and extension commands, limited by the workspace limitation block, are then passed to a catheter roll correction block (454).

Figure 121:
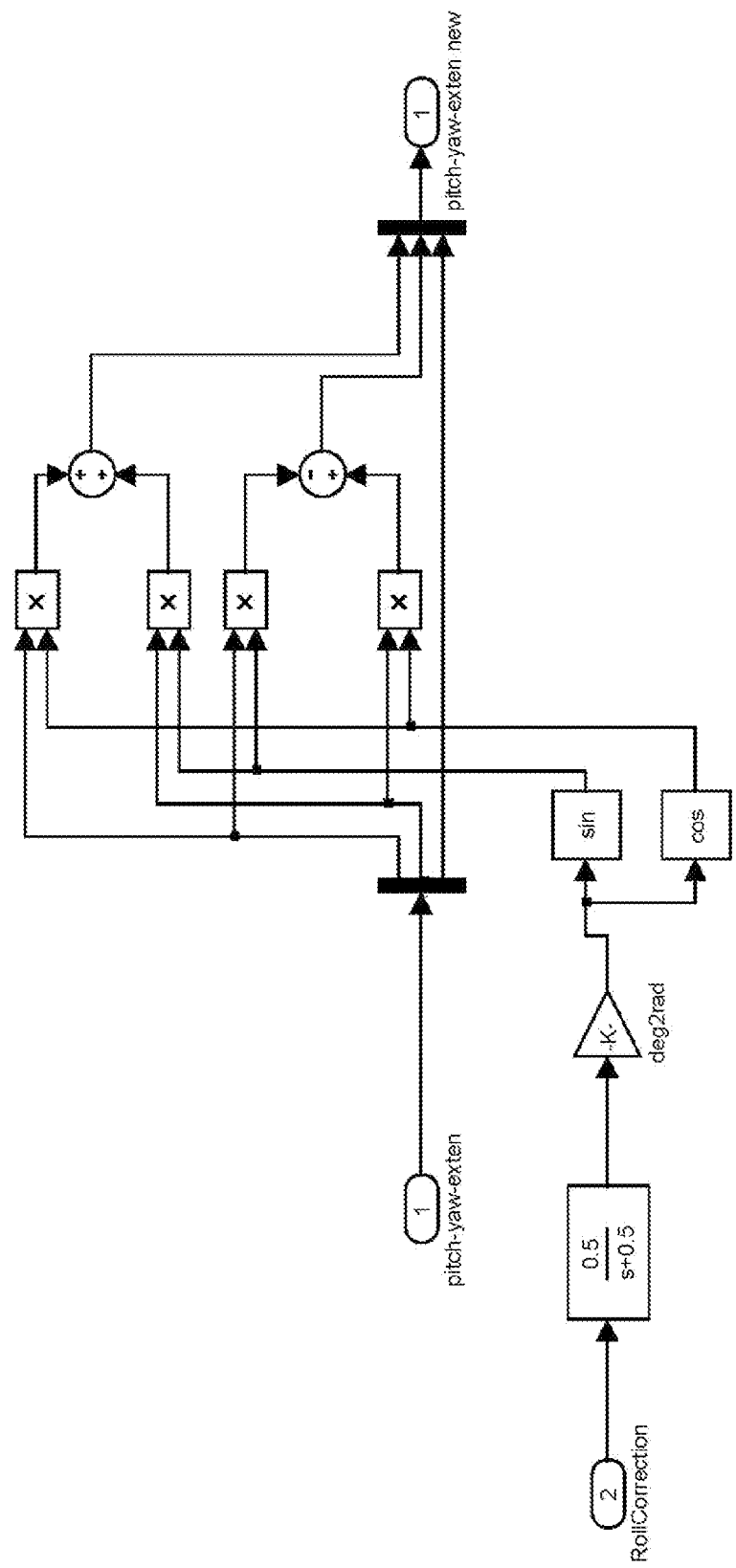

This functional block is depicted in further detail in FIG. 121, and essentially comprises a rotation matrix for transforming the pitch, yaw, and extension commands about the longitudinal, or "roll", axis of the instrument—to calibrate the control system for rotational deflection at the distal tip of the catheter that may change the control element steering dynamics. For example, if a catheter has no rotational deflection, pulling on a control element located directly up at twelve o'clock should urge the distal tip of the instrument upward. If, however, the distal tip of the catheter has been rotationally deflected by, say, ninety degrees clockwise, to get an upward response from the catheter, it may be necessary to tension the control element that was originally positioned at a nine o'clock position. The catheter roll correction schema depicted in FIG. 121 provides a means for using a rotation matrix to make such a transformation, subject to a roll correction angle, such as the ninety degrees in the above example, which is input, passed through a low pass filter, turned to radians, and put through rotation matrix calculations.

In one embodiment, the roll correction angle is determined through experimental experience with a particular instrument and path of navigation. In another embodiment, the roll correction angle may be determined experimentally in-situ using the accurate orientation data available from the preferred localization systems. In other words, with such an embodiment, a command to, for example, bend straight up can be executed, and a localization system can be utilized to determine at which angle the defection actually went—to simply determine the in-situ roll correction angle.

Figure 122:
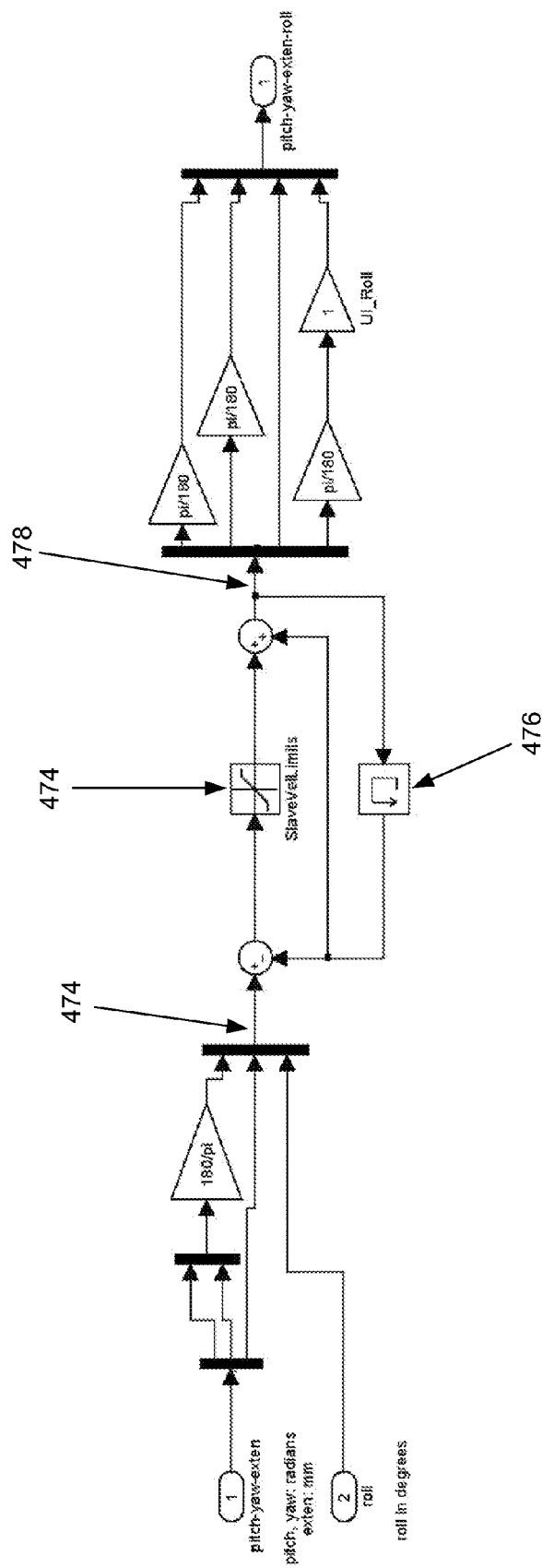

Referring briefly back to FIG. 119, roll corrected pitch and yaw commands, as well as unaffected extension commands, are output from the roll correction block (454) and may optionally be passed to a conventional velocity limitation block (456). Referring to FIG. 122, pitch and yaw commands are converted from radians to degrees, and automatically controlled roll may enter the controls picture to complete the current desired position (472) from the last servo cycle. Velocity is calculated by comparing the desired position from the previous servo cycle, as calculated with a conventional memory block (476) calculation, with that of the incoming commanded cycle. A conventional saturation block (474) keeps the calculated velocity within specified values, and the velocity-limited command (478) is converted back to radians and passed to a tension control block (458).

Figure 123:
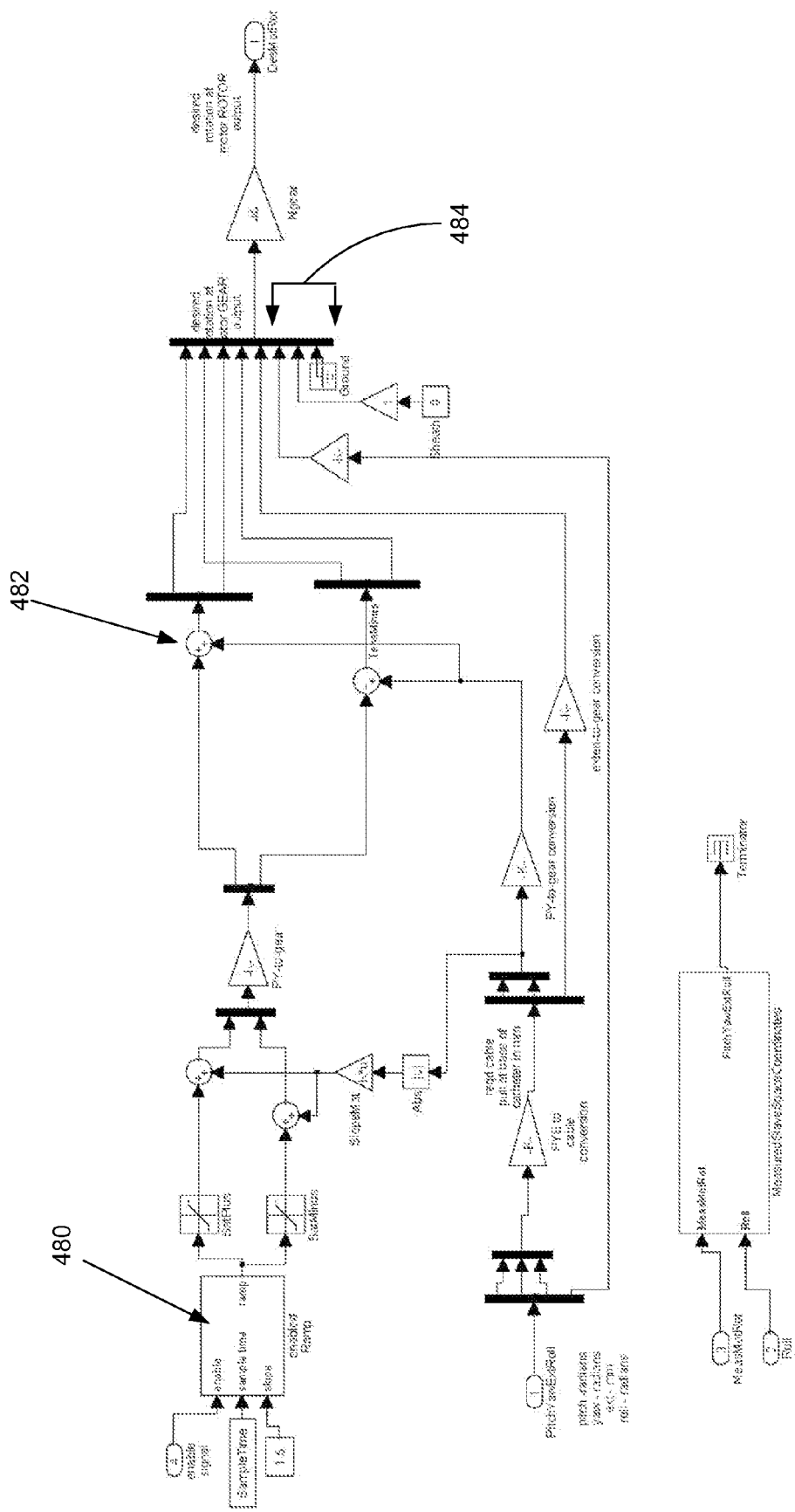

Tension within control elements may be managed depending upon the particular instrument embodiment, as described above in reference to the various instrument embodiments and tension control mechanisms. As an example, FIG. 123 depicts a pre-tensioning block (480) with which a given control element tension is ramped to a present value. An adjustment is then added to the original pre-tensioning based upon a preferably experimentally-tuned matrix pertinent to variables, such as the failure limits of the instrument construct and the incoming velocity-limited pitch, yaw, extension, and roll commands. This adjusted value is then added (482) to the original signal for output, via gear ratio adjustment, to calculate desired motor rotation commands for the various motors involved with the instrument movement. In this embodiment, extension, roll, and sheath instrument actuation (484) have no pre-tensioning algorithms associated with their control. The output is then complete from the master following mode functionality, and this output is passed to the primary servo loop (436).

Referring back to FIG. 114, incoming desired motor rotation commands from either the master following mode (442), auto home mode (440), or idle mode (438) in the depicted embodiment are fed into a motor servo block (444), which is depicted in greater detail in FIGS. 115-118.

Figure 115:
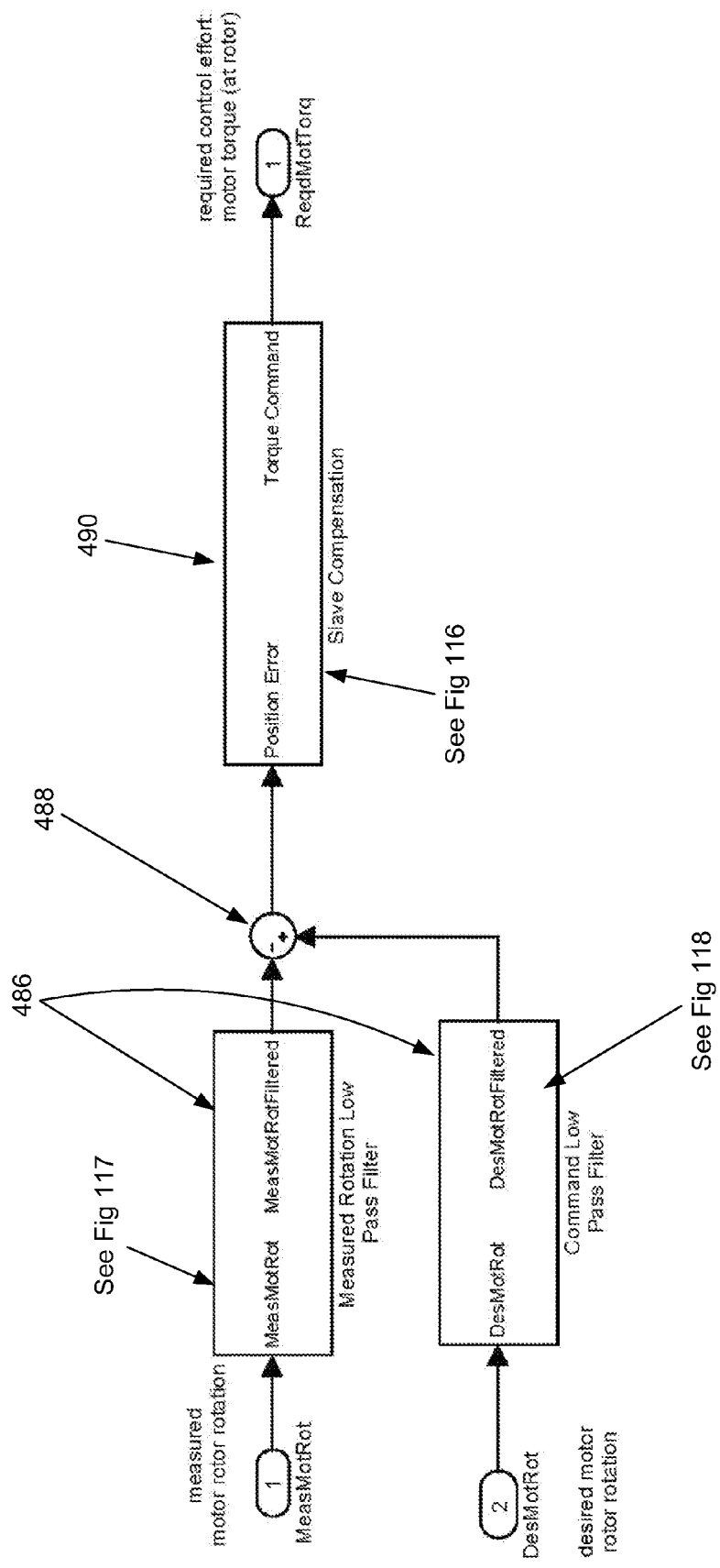
Figure 117:
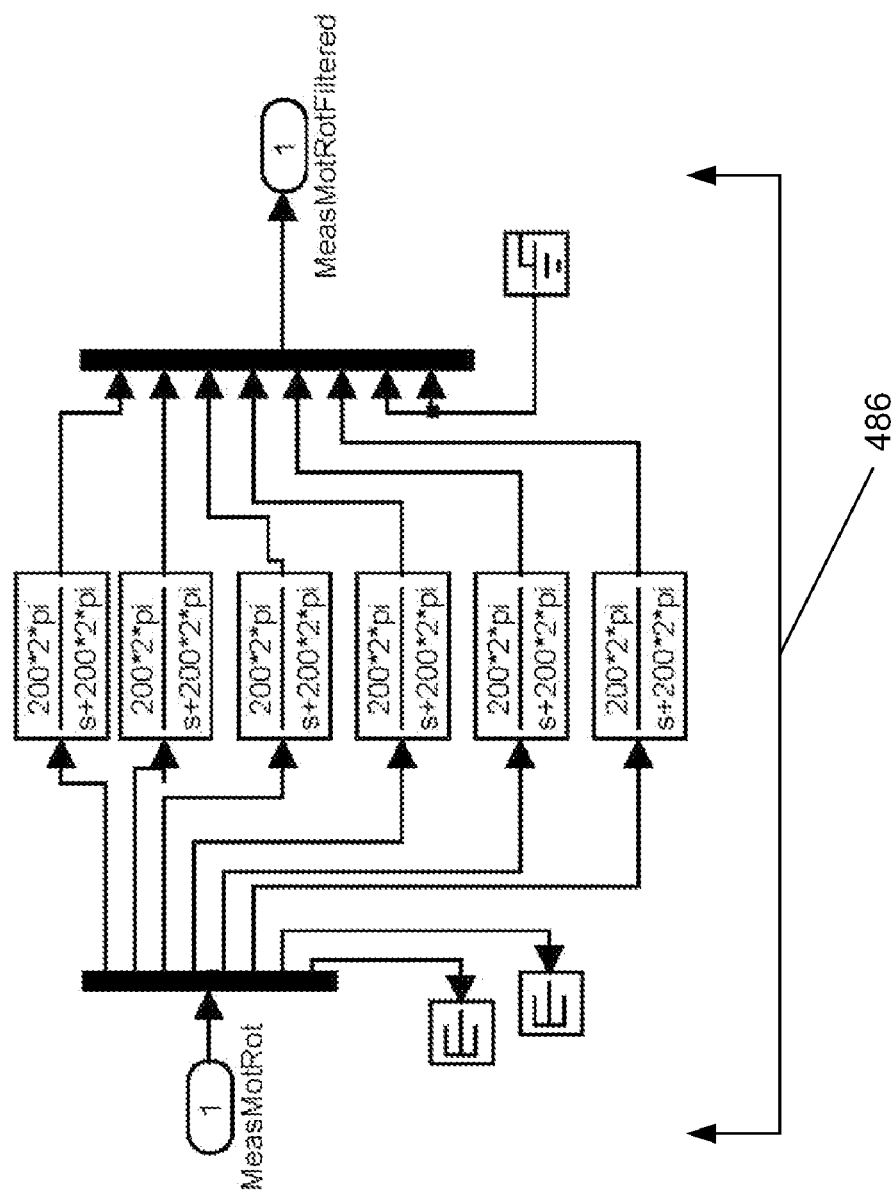
Figure 118:
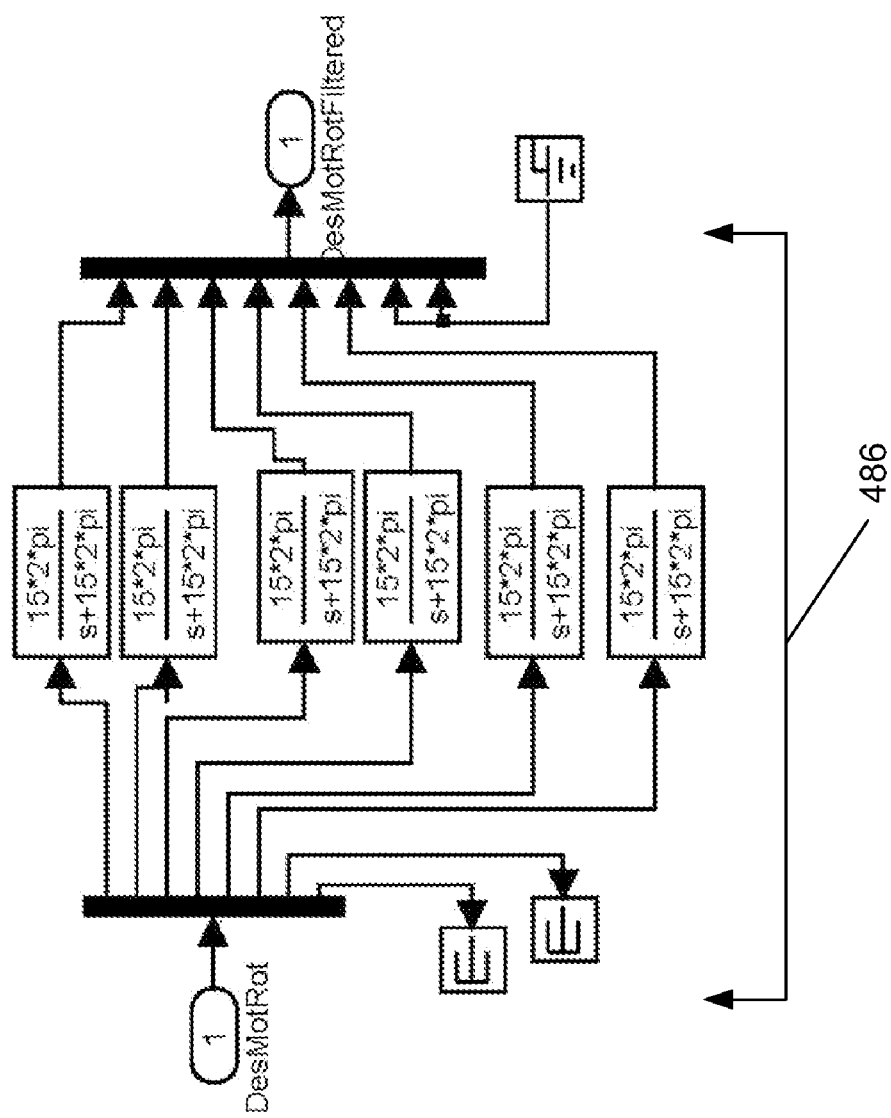

Referring to FIG. 115, incoming measured motor rotation data from digital encoders and incoming desired motor rotation commands are filtered using conventional quantization noise filtration at frequencies selected for each of the incoming data streams to reduce noise while not adding undue delays which may affect the stability of the control system. As shown in FIGS. 117 and 118, conventional quantization filtration is utilized on the measured motor rotation signals at about 200 hertz in this embodiment, and on the desired motor rotation command at about 15 hertz. The difference (488) between the quantization filtered values forms the position error which may be passed through a lead filter, the functional equivalent of a proportional derivative ("PD")+low pass filter. In another embodiment, conventional PID, lead/lag, or state space representation filter may be utilized. The lead filter of the depicted embodiment is shown in further detail in FIG. 116.

Figure 116:
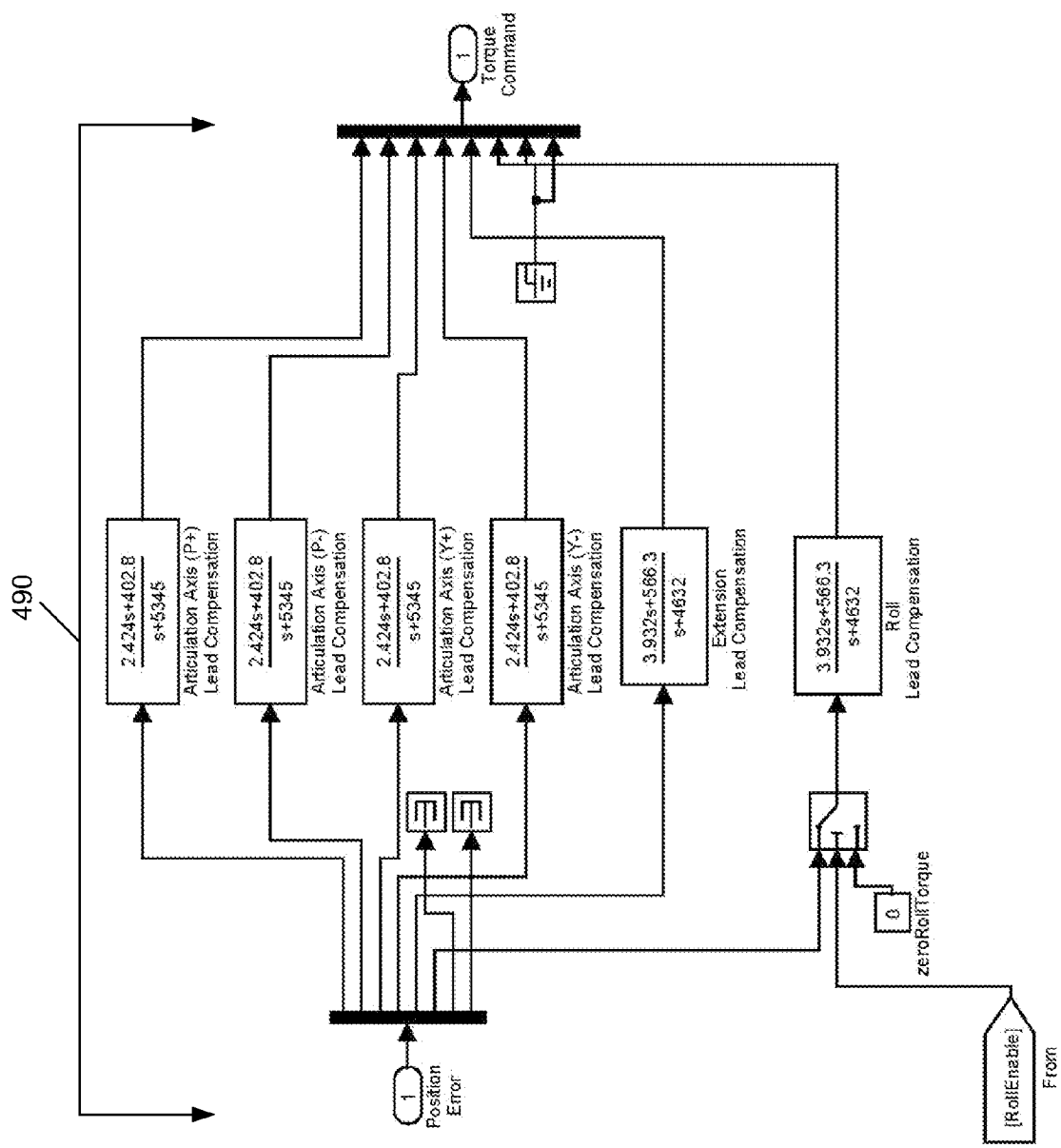

In particular, the lead filter embodiment in FIG. 116 comprises a variety of constants selected to tune the system to achieve desired performance. The depicted filter addresses the needs of one embodiment of a 4-control element guide catheter instrument with independent control of each of four control element interface assemblies for +/− pitch and +/− yaw, and separate roll and extension control. As demonstrated in the depicted embodiment, insertion and roll have different inertia and dynamics as opposed to pitch and yaw controls, and the constants selected to tune them is different. The filter constants may be theoretically calculated using conventional techniques and tuned by experimental techniques, or wholly determined by experimental techniques, such as setting the constants to give a sixty degree or more phase margin for stability and speed of response, a conventional phase margin value for medical control systems.

In an embodiment where a tuned master following mode is paired with a tuned primary servo loop, an instrument and instrument driver, such as those described above, may be "driven" accurately in three-dimensions with a remotely located master input device. Other preferred embodiments incorporate related functionalities, such as haptic feedback to the operator, active tensioning with a split carriage instrument driver, navigation utilizing direct visualization and/or tissue models acquired in-situ and tissue contact sensing, and enhanced navigation logic.

Figure 128:
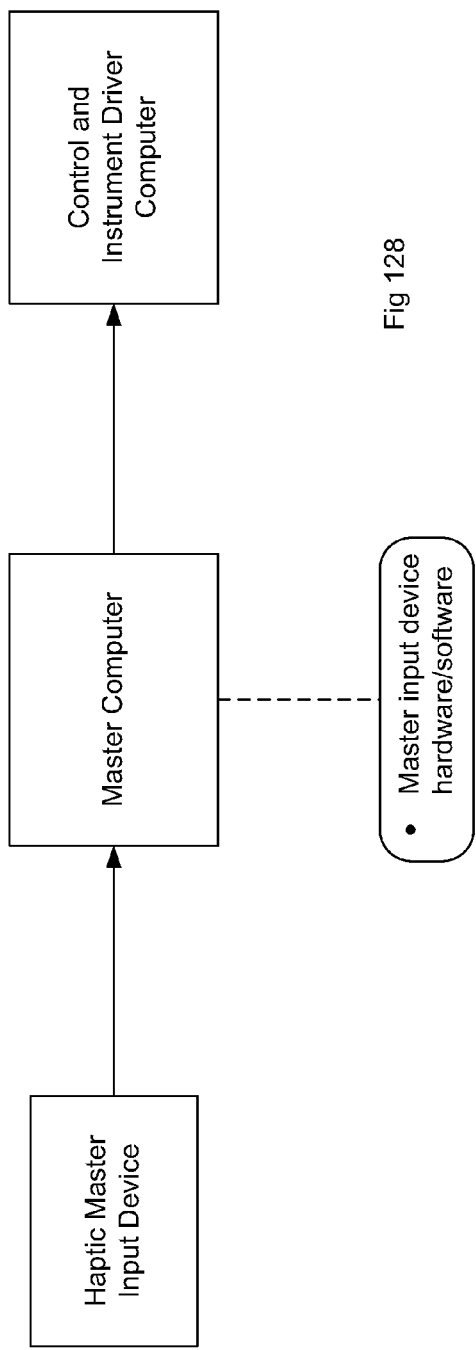
FIG. 128 illustrates a block diagram of a system having a haptic master input device.

Referring to FIG. 128, in one embodiment, the master input device may be a haptic master input device, such as those available from Sensible Devices, Inc., under the trade name Phantom™, and the hardware and software required for operating such a device may at least partially reside on the master computer. The master XYZ positions measured from the master joint rotations and forward kinematics are generally passed to the master computer via a parallel port or similar link and may subsequently be passed to a control and instrument driver computer. With such an embodiment, an internal servo loop for the Phantom™ generally runs at a much higher frequency in the range of 1,000 Hz, or greater, to accurately create forces and torques at the joints of the master.

Figure 129:
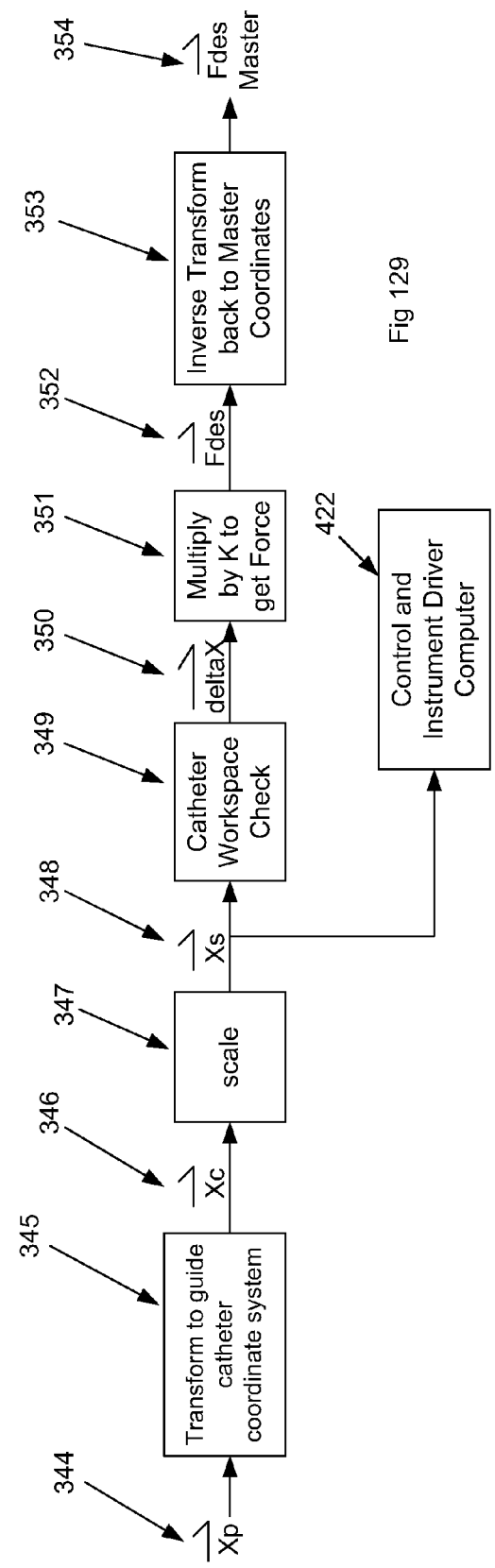
FIG. 129 illustrates a method for generating a haptic signal in accordance with some embodiments.

Referring to FIG. 129, a sample flowchart of a series of operations leading from a position vector applied at the master input device to a haptic signal applied back at the operator is depicted. A vector (344) associated with a master input device move by an operator may be transformed into an instrument coordinate system, and in particular to a catheter instrument tip coordinate system, using a simple matrix transformation (345). The transformed vector (346) may then be scaled (347) per the preferences of the operator, to produce a scaled-transformed vector (348). The scaled-transformed vector (348) may be sent to both the control and instrument driver computer (422) preferably via a serial wired connection, and to the master computer for a catheter workspace check (349) and any associated vector modification (350). this is followed by a feedback constant multiplication (351) chosen to produce preferred levels of feedback, such as force, in order to produce a desired force vector (352), and an inverse transform (353) back to the master input device coordinate system for associated haptic signaling to the operator in that coordinate system (354).

A conventional Jacobian may be utilized to convert a desired force vector (352) to torques desirably applied at the various motors comprising the master input device, to give the operator a desired signal pattern at the master input device. Given this embodiment of a suitable signal and execution pathway, feedback to the operator in the form of haptics, or touch sensations, may be utilized in various ways to provide added safety and instinctiveness to the navigation features of the system, as discussed in further detail below.

FIG. 130 is a system block diagram including haptics capability. As shown in summary form in FIG. 130, encoder positions on the master input device, changing in response to motion at the master input device, are measured (355), sent through forward kinematics calculations (356) pertinent to the master input device to get XYZ spatial positions of the device in the master input device coordinate system (357), then transformed (358) to switch into the catheter coordinate system and (perhaps) transform for visualization orientation and preferred controls orientation, to facilitate "instinctive driving."

The transformed desired instrument position (359) may then be sent down one or more controls pathways to, for example, provide haptic feedback (360) regarding workspace boundaries or navigation issues, and provide a catheter instrument position control loop (361) with requisite catheter desired position values, as transformed utilizing inverse kinematics relationships for the particular instrument (362) into yaw, pitch, and extension, or "insertion", terms (363) pertinent to operating the particular catheter instrument with open or closed loop control.

Referring to FIGS. 131-136, relationships pertinent to tension control via a split carriage design such as that depicted in FIGS. 102-103 are depicted to illustrate that such a design may isolate tension control from actuation for each associated degree of freedom, such as pitch or yaw of a steerable catheter instrument.

Referring to FIG. 131, some of the structures associated with a split carriage design, such as the embodiments depicted in FIGS. 102 and 103, include a linearly movable portion (302), a guide instrument interface socket (270), a gear (300), and a rack (298). Applying conventional geometric relationships to the physical state of the structures related in FIG. 131, the equations (364, 365) of FIG. 132 may be generated. Utilizing forward kinematics of the instrument, such as those described above in reference to a pure cantilever bending model for a catheter instrument, the relationships of FIG. 133 may be developed for the amount of bending as a function of cable pull and catheter diameter ("Dc") (366), and for tension (367), defined as the total amount of common pull in the control elements. Combining the equations of FIGS. 132 and 133, one arrives at the relationships (368, 369) depicted in FIG. 134, wherein desired actuation and desired tensioning are decoupled by the mechanics of the involved structures. Desired actuation (368) of the guide instrument interface socket (270) depicted in FIG. 131 is a function of the socket's angular rotational position. Desired tensioning (369) of the associated control elements is a function of the position of the tensioning gear (300) versus the rack (298).

Figures 135, 136:
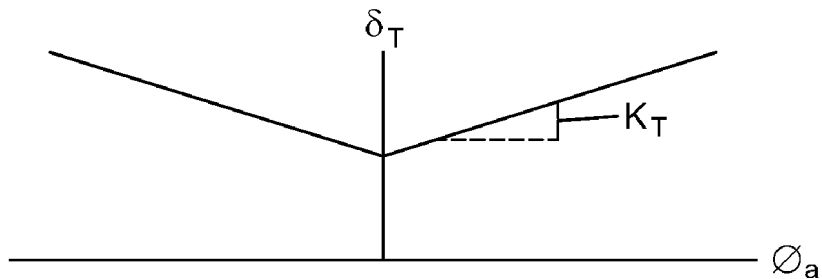

Referring to FIG. 135, with a single degree of freedom actuated, such as +/− pitch or +/− yaw, and active tensioning via a split carriage mechanism, desired tension is linearly related to the absolute value of the amount of bending, as one would predict per the discussion above in reference to FIGS. 110A-E. The prescribed system never goes into slack—desired tension is always positive, as shown in FIG. 135. Referring to FIG. 136, a similar relationship applies for a two degree of freedom system with active tensioning—such as a four-cable system with +/− pitch and +/− yaw as the active degrees of freedom and active tensioning via a split carriage design. Since there are two dimensions, coupling terms (370) are incorporated to handle heuristic adjustments to, for example, minimize control element slacking and total instrument compression.

As discussed in reference to FIG. 113, in one embodiment, a tissue structure model (414) may be utilized to enhance navigation. It is particularly desirable to utilize actual data, acquired in situ, from the patient onto which a procedure is to be conducted, due to anatomic variation among the patient population which may be significant, depending generally upon the subject tissue structures. For example, the geometry of the left atrium of the human heart varies significantly from patient to patient, according to published reports and experimental verification in animals.

In one embodiment, focused magnetic resonance imaging, gated for heart cycle motion, and preferably gated for respiratory cycle motion, may be utilized along with conventional image cropping and thresholding techniques to produce a three dimensional tissue structure model. One of the challenges with such an imaging modality as applied to modeling active tissue structures such as those of the heart is the gating. In one embodiment, the gating comprises waiting for cardiac resting periods during diastole which are also correlated to substantially limited respiratory-induced motion. Acquiring a three-dimensional image of a left atrium, for example, utilizing gated magnetic resonance, may require an unacceptable amount of acquisition time, not to mention the generally large and expensive instrumentation required to accomplish the acquisition and fusion into a usable tissue structure model. Such a modality, however, may be preferred where cardiac and/or respiratory cyclic motion is negligible, and wherein an image or series of images may be acquired and synthesized into a usable tissue structure model comparatively quickly.

Figure 137:
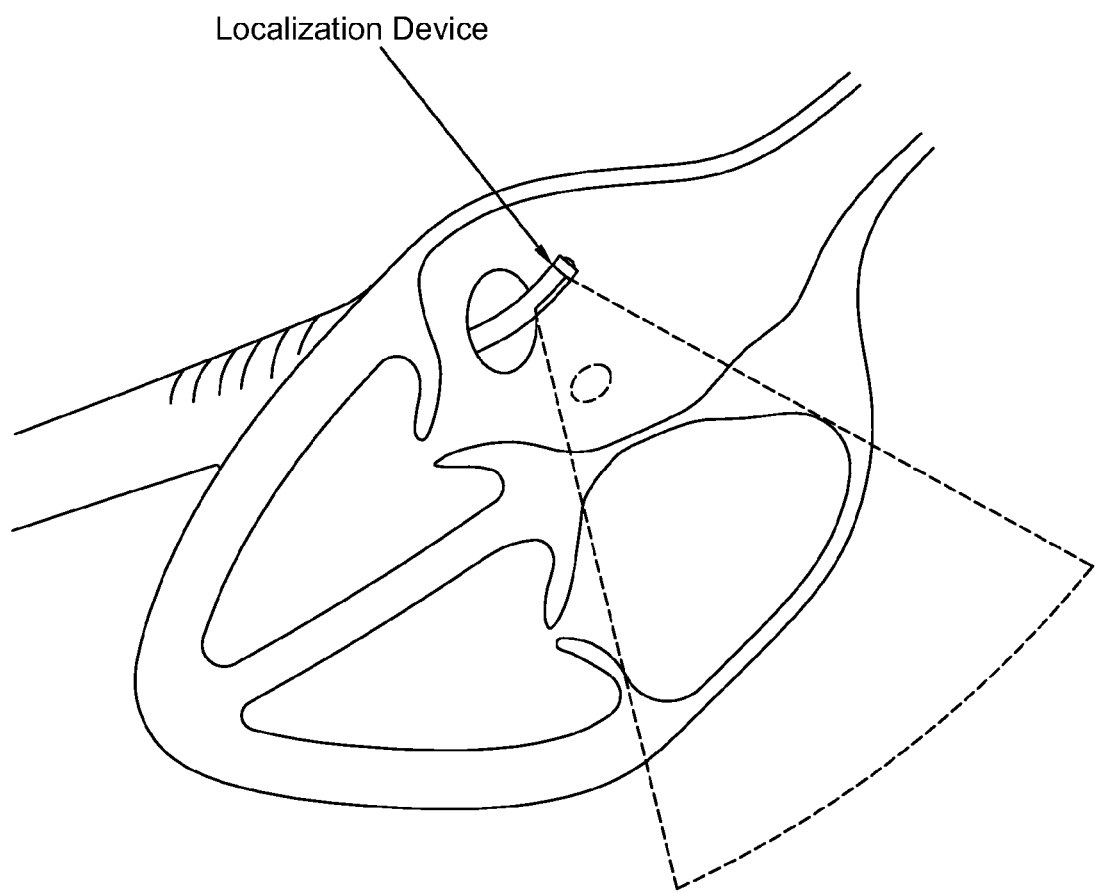
FIG. 137 illustrates a localization device being used in a heart in accordance with some embodiments.
Figure 138:
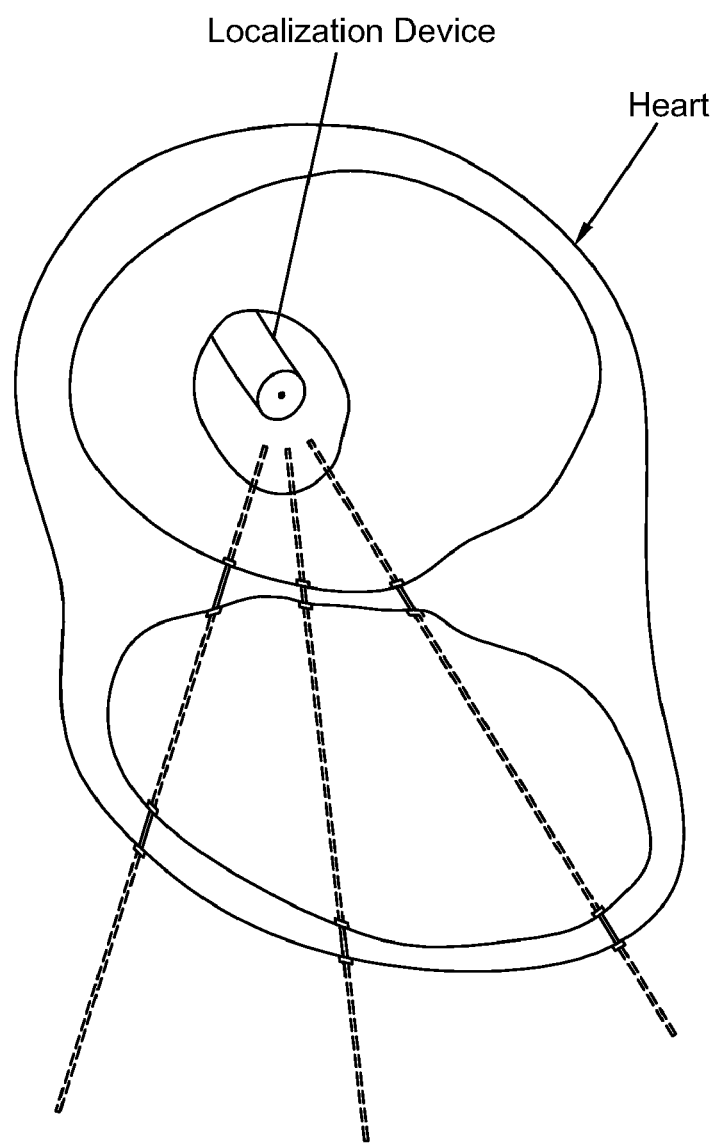
FIG. 138 illustrates a cross sectional view of the heart of FIG. 137, showing the heart being imaged by a localization device in accordance with some embodiments.
Figure 139:
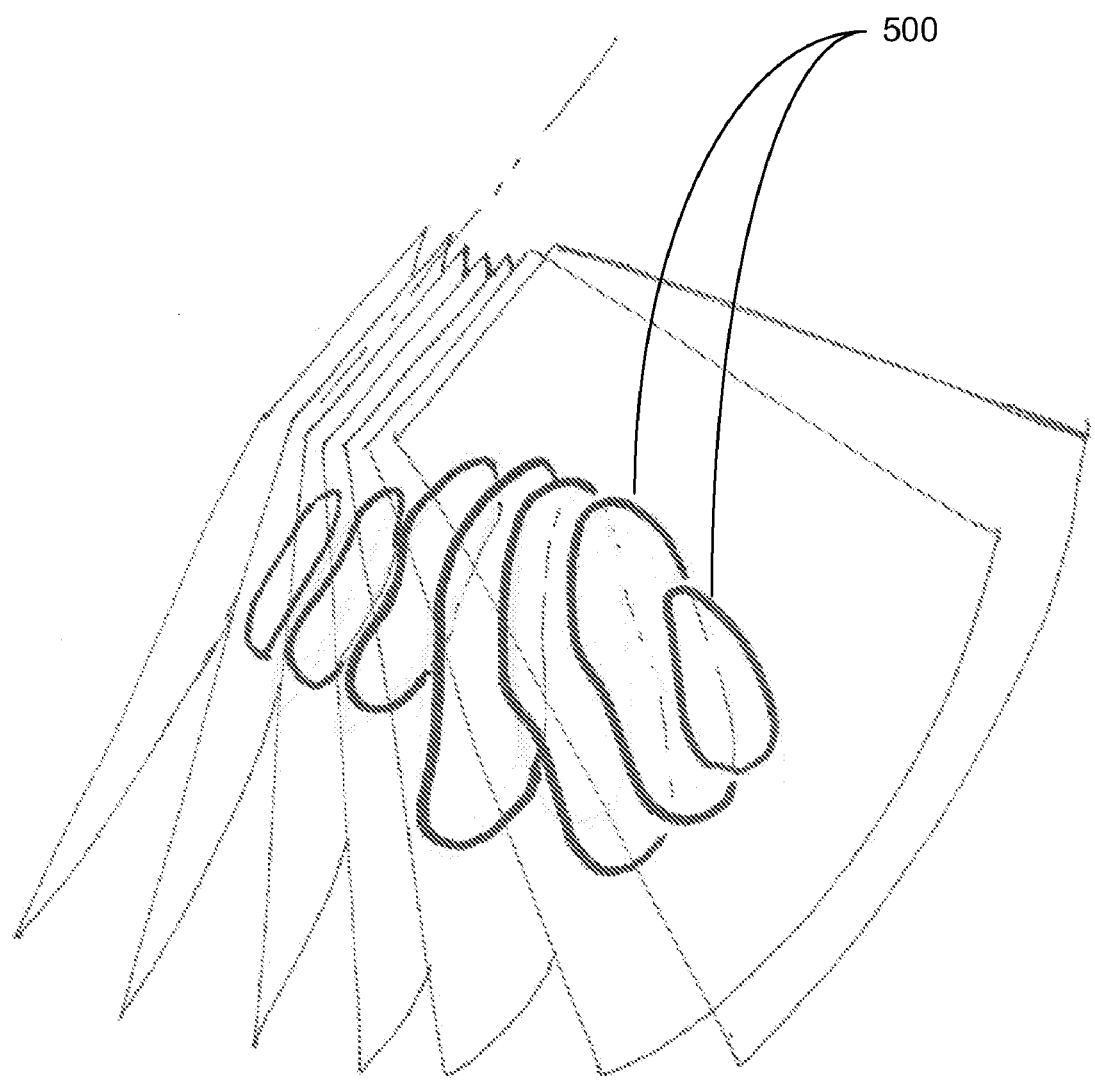
FIG. 139 illustrates images generated using the localization device of FIG. 137.

Referring to FIGS. 137-139 a technique is depicted through which a tissue structure model may be synthesized given appropriate hardware, such as an ultrasound transducer mounted upon a catheter or similar structure, and a localization system mounted upon the same structure to enable the capture of not only ultrasound slice data, but also the position and orientation of the transducer at the time of each slice acquisition. In other embodiments, a similar robotic system does not include a localization system, in which case kinematic and/or geometric relationships may be used to predict the location of the imaging device.

FIG. 137 depicts a human heart with a side-firing ultrasound catheter, such as those available under the trade name AcuNav™ by Siemens AG, entering the left atrium via the inferior vena cava blood vessel. Coupled to the ultrasound catheter, at or near the location of the ultrasound transducer, is a localization device, such as a set of orthogonally oriented electromagnetic receiving coils, to determine the position and orientation of the ultrasound transducer at each acquired "slice" of acquired reflected data. FIG. 138 is a view along the longitudinal axis of the distal end of the ultrasound catheter illustrating that, by rotating the ultrasound catheter, multiple slices (500) of reflected ultrasound image data, comprising multiple structural tissue mass location points, may be acquired, along with the position and orientation of the ultrasound transducer for each slice of reflected ultrasound data. With such an embodiment and a targeted tissue structure that is cyclically mobile, such as the heart, each of the slices preferably is acquired during the resting period of diastole to prevent motion-based image distortion.

In post-acquisition processing, the acquired image slice data and associated position and orientation data may be utilized to construct a three-dimensional tissue structure model, such as that represented by the series of slices in FIG. 139. As will be apparent to those skilled in the art, to achieve a finer "mesh" of points for image formation, more slices may be acquired and assembled as shown in FIG. 139. Utilizing conventional image thresholding techniques available, for example, on most ultrasound mainframe devices, such as that sold under the trade name Sequoia™ by Siemens AG, points of transition between blood or other fluid-filled cavity and tissue mass may be clearly resolved to establish transition points such as those depicted in FIG. 138.

Figure 140:
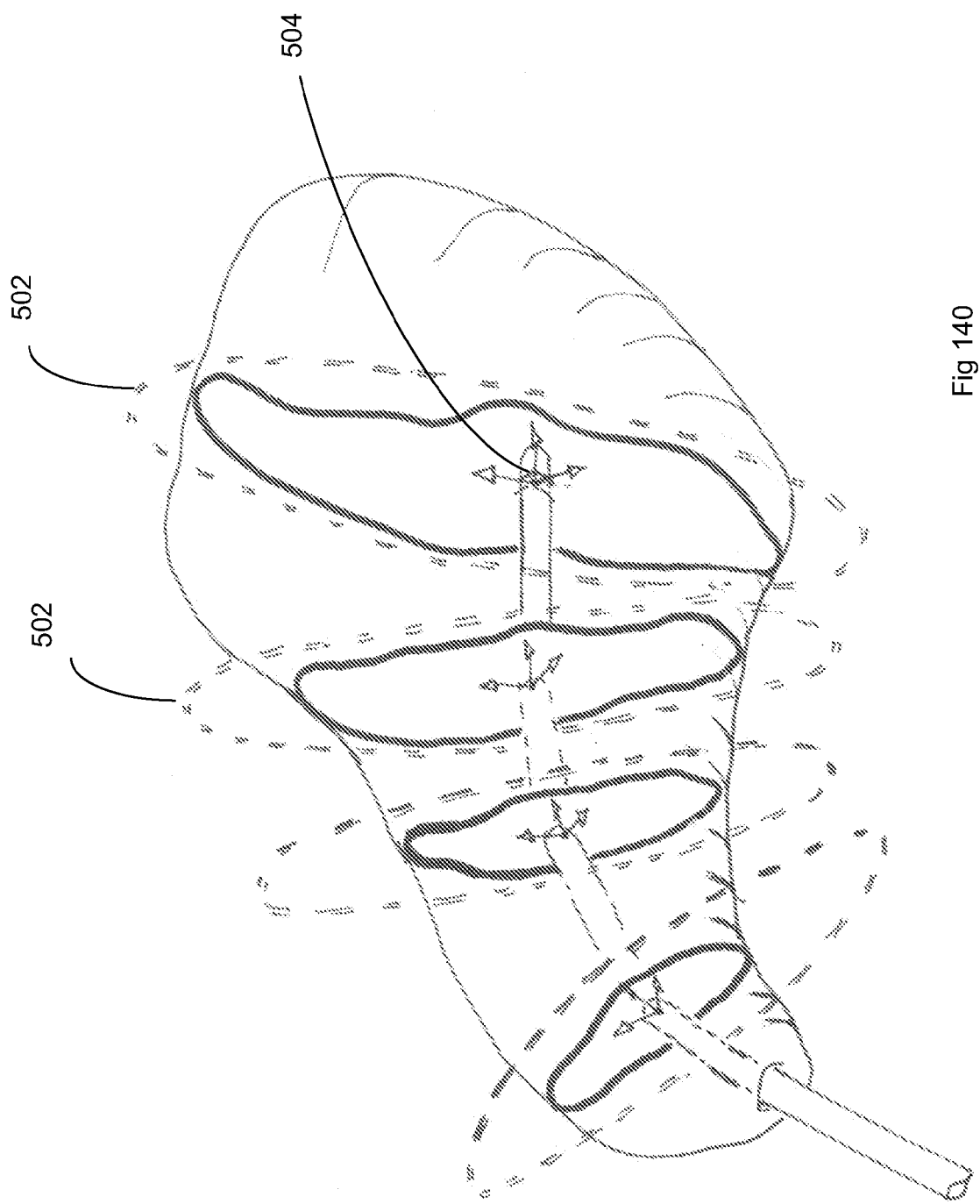
FIG. 140 illustrates an ultrasound image acquisition device being used to acquire a plurality of image slices in accordance with some embodiments.
Figure 141:
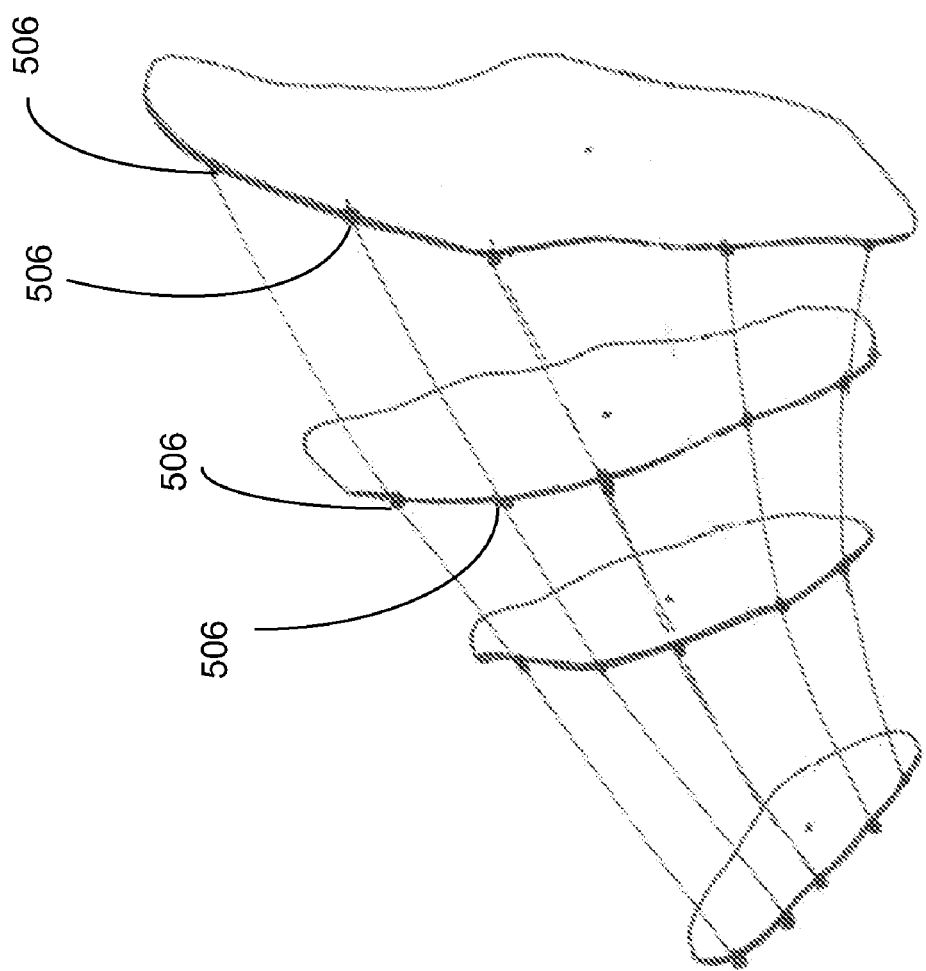
FIG. 141 illustrates cavity threshold points obtained from the slices of FIG. 140.

Referring to FIGS. 140-148, various aspects of another embodiment for acquiring a compiling a tissue structure image is depicted. Referring to FIG. 140, applying similar principles as applied in reference to the embodiment of FIGS. 137-139, a perimetrically-firing ultrasound image acquisition device, such as that sold under the trade name UltraICE™ by Boston Scientific Corporation, may be utilized in concert with a localization system to acquire a series of perimetric slices (502) and associated position and orientation data for the transducer (504) to assemble a series of tissue-cavity threshold points (506) related in space, as depicted in FIG. 141. As illustrated in FIG. 140, a series of related slices (502) is gathered as the transducer is inserted, retrieved, or both, through a cavity. As with the embodiment above, in the case of mobile heart tissue, each of the slices preferably is acquired during the resting period of diastole to prevent motion-based image distortion. Further, a finer resolution tissue structure image may be created with higher density image acquisition as the transducer is repositioned within the targeted cavity, as will be apparent to those skilled in the art.

Figure 144:
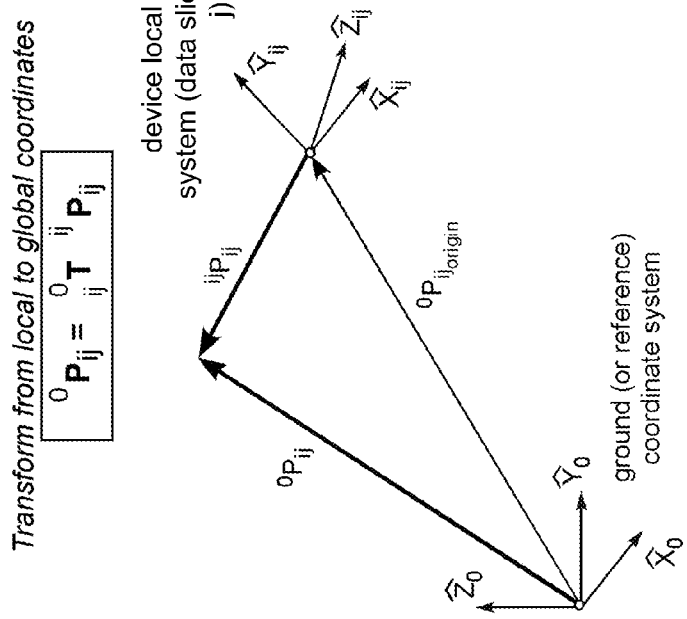
Figure 145B:
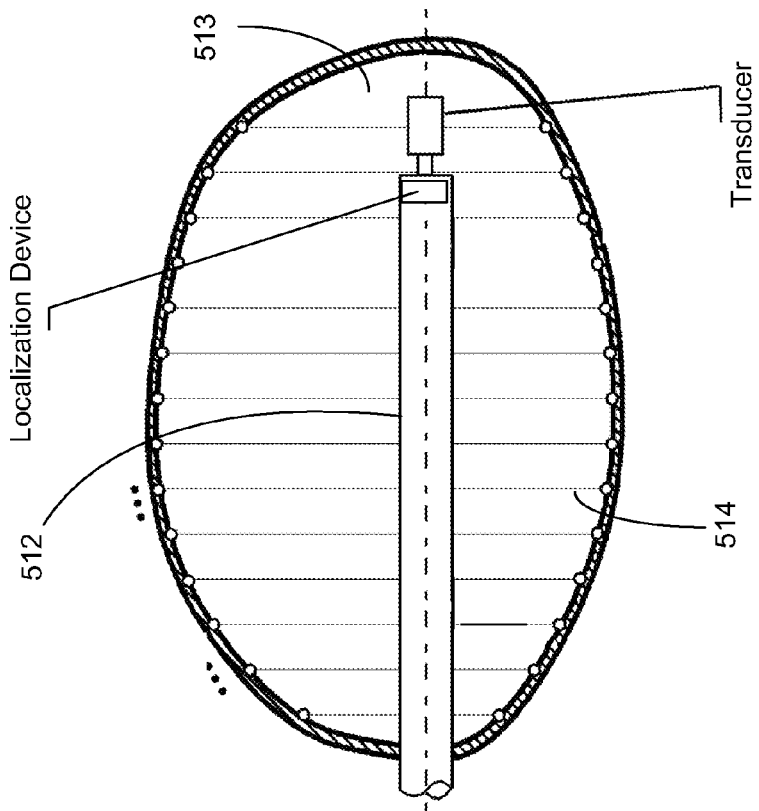
Figure 145A:
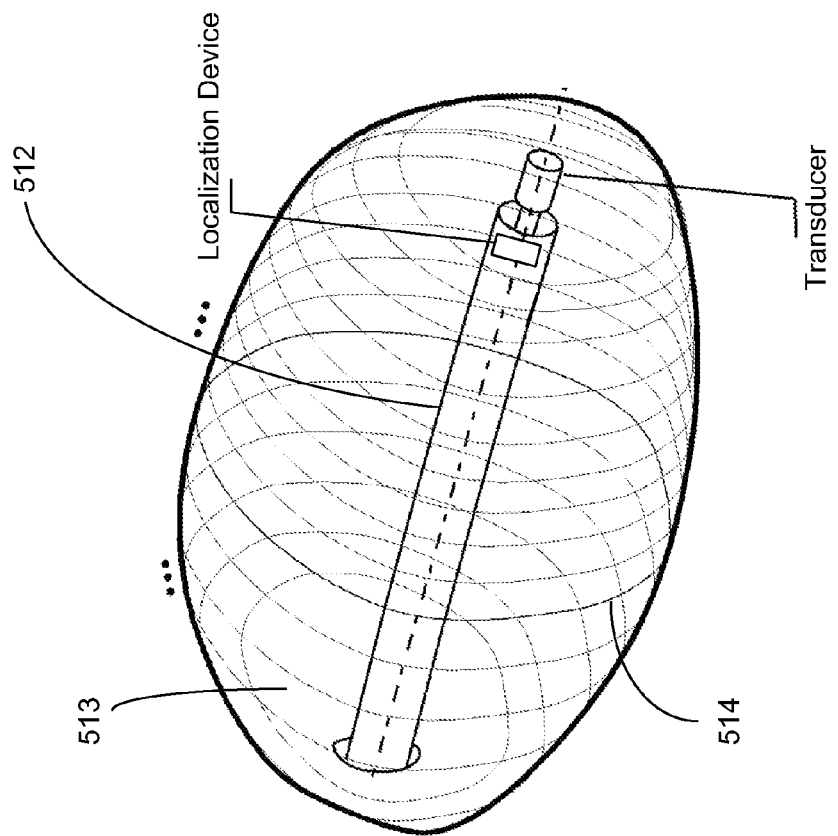

Referring to FIG. 142, a close-up isometric view of a circumferentially-firing ultrasound catheter device (508) comprising a localization device (509) and an ultrasound transducer (510) is depicted within a tissue cavity acquiring a slice of data with an illustrative measured point at a detected density threshold at the transition between empty cavity and tissue wall. FIG. 143 depicts two views down the longitudinal axis of such a catheter system to depict acquisition of a series of density transition points about the catheter which form a slice which may be compiled into a larger three-dimensional image of the subject cavity. Referring to FIG. 144, the conventional transformation mathematics which may be utilized to transform position and orientation data within the acquiring catheter tip frame of reference to the ground frame of reference, or some other desired frame of reference. FIGS. 145A and 145B depict two different views of a catheter (512) inserting straight through a tissue cavity (513) and acquiring a series of data slices (514) along the way.

Figure 146B:
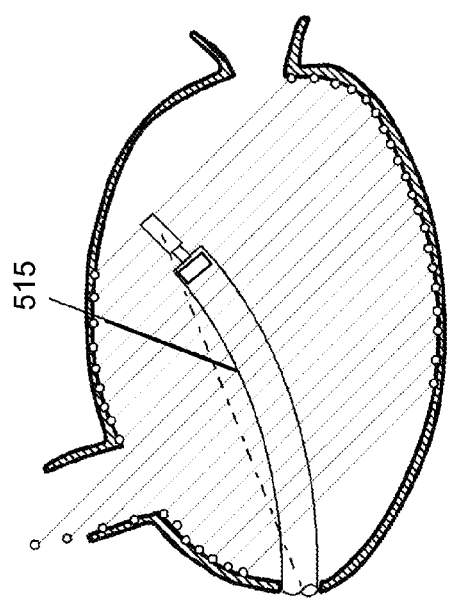
Figure 146D:
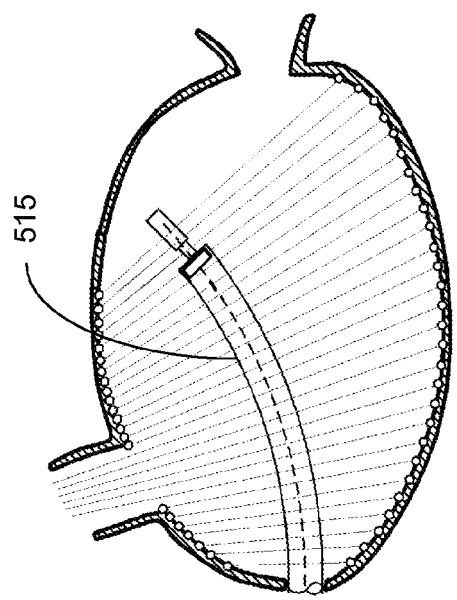
Figure 146A:
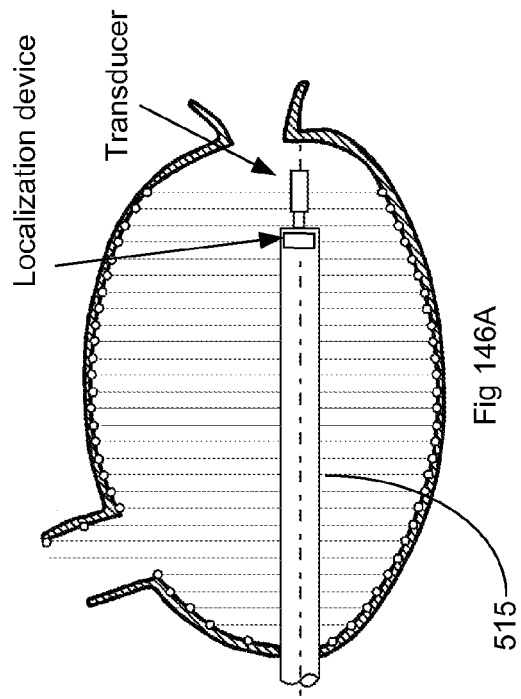
Figure 146C:
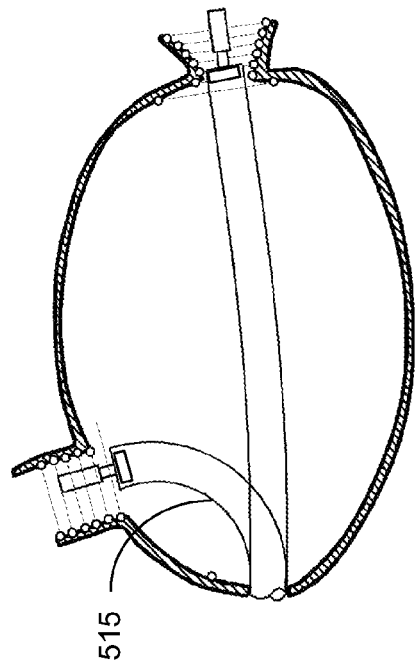
Figure 147:
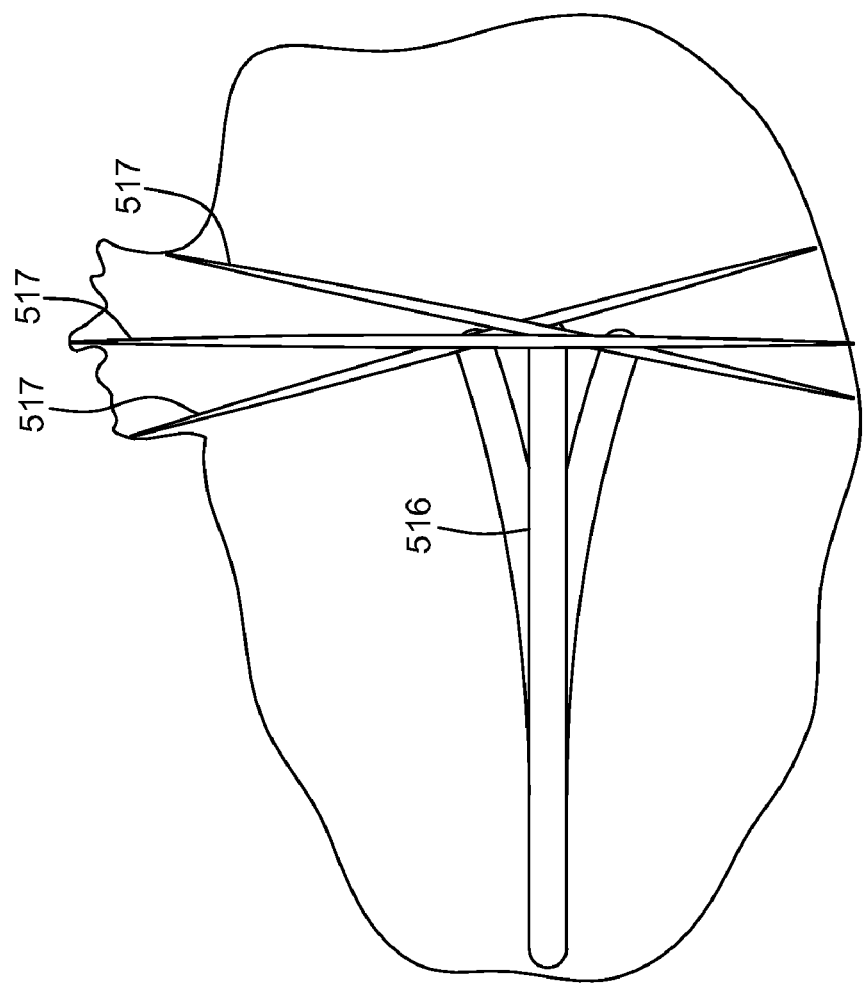

FIGS. 146A-D depict respective variations for imaging a given tissue structure geometry with the subject embodiment. In the embodiment depicted in FIG. 146A, a circumferentially-firing ultrasound catheter (515) is inserted straight through a cavity without regard to incoming slice data. In FIG. 146B, a variation is depicted wherein the catheter structure carrying the ultrasound transducer and localization device is bent as it moves through the subject tissue cavity to provide a series of slices occupying substantially parallel planes. FIG. 146C depicts a variation wherein the catheter structure carrying the ultrasound transducer and localization device is directed into specific sub-portions of the subject tissue mass. In one embodiment, such directing may be the result of real-time or near-real-time image analysis by the operator. For example, fluoroscopy or other conventional imaging techniques may be utilized to position the catheter into such a location in one embodiment. In another embodiment, the catheter may be automatically or semi-automatically guided to such as position, as discussed below. As shown in FIG. 146D, the catheter may be inserted and steered through the subject tissue cavity such that the planes of the slices of data acquired are not parallel. Given the known position and orientation of the ultrasound transducer from an associated localization system, it is by no means a requirement that the planes within a given image stack be parallel. Indeed, in some embodiments, it may be desirable to controllably bend an imaging catheter (516) near a location of interest to acquire multiple images (517) of a particular portion of the subject tissue, as depicted in FIG. 147. Such controlled bending through a preset range of motion as additional image slices are acquired may be termed "bend detailing" a particular portion of the subject tissue structures.

Figure 148A:
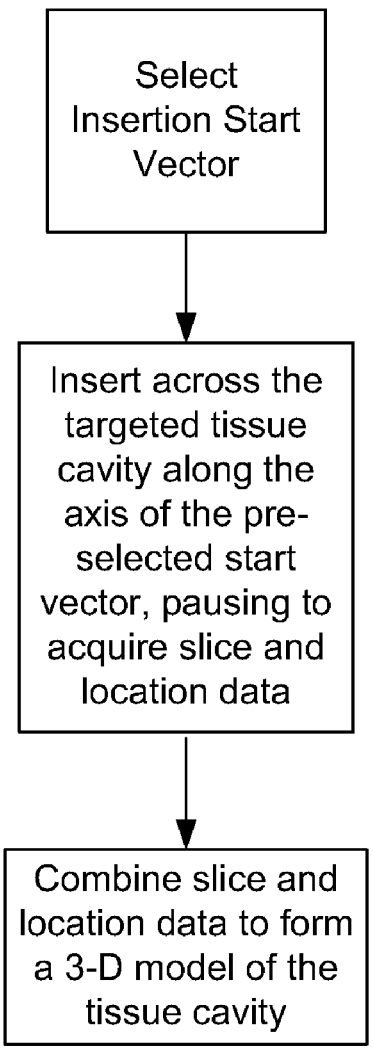
Figure 148B:
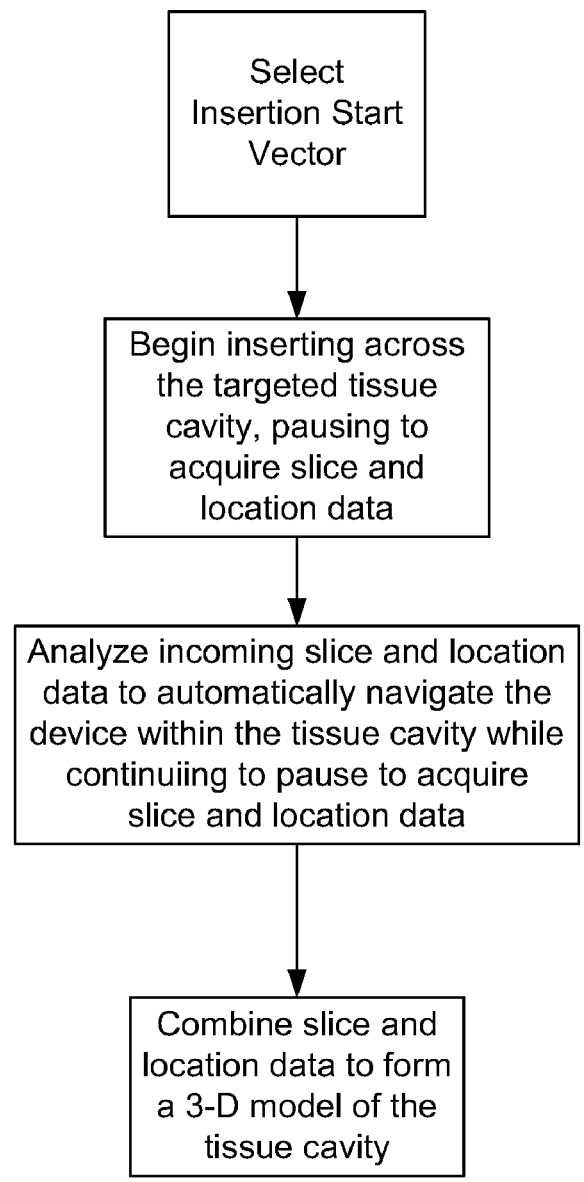
Figure 148C:
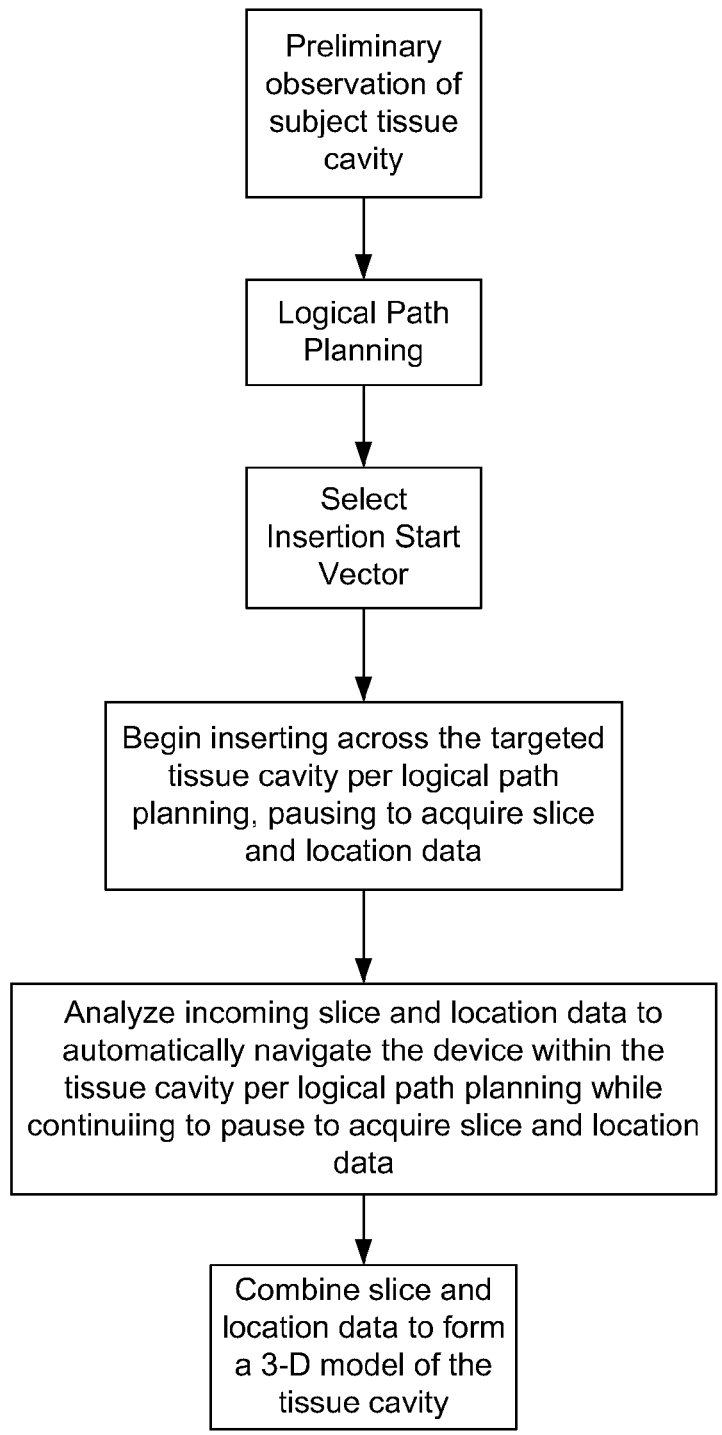

Referring to FIGS. 148A-C, several acquisition protocol embodiments are depicted for implementing the aforementioned acquisition system embodiment. In a simple embodiment (148A), an insertion vector is selected, subsequent to which an ultrasound transducer is inserted across a subject tissue cavity, pausing to acquire slice and position/orientation data along the way, leading to the combination of slice and location/orientation data into a three-dimensional model. In another embodiment (148B), rather than following a predetermined program for inserting across the subject cavity and acquiring data slices, a closed-loop system analyzes incoming slice data and applies preprogrammed logic to automatically navigate as the image acquisition continues. FIG. 148C depicts an embodiment similar to that of FIG. 148B, with the exception that logical path planning is integrated into the controls logic operating the catheter instrument driver to provide automated or semi-automated image acquisition functionality. For example, the system may watch acquired images time-of-flight between emitted radiation and detected reflection of such radiation to steer the instrument directly down the middle of the cavity, as interpreted utilizing the time-of-flight data. This may be referred to as "time-of-flight center drive". In another embodiment, significant changes in time-of-flight data for a given sector of an image series over a given period of time or distance may be interpreted as a change in tissue surface geometry worth higher density localized imaging, or even an automatic bending to take the transducer closer to the site of interest—or to rotate the transducer for higher-resolution imaging of the particular area without insertion adjustment, as described above in reference to FIG. 147.

Figure 149:
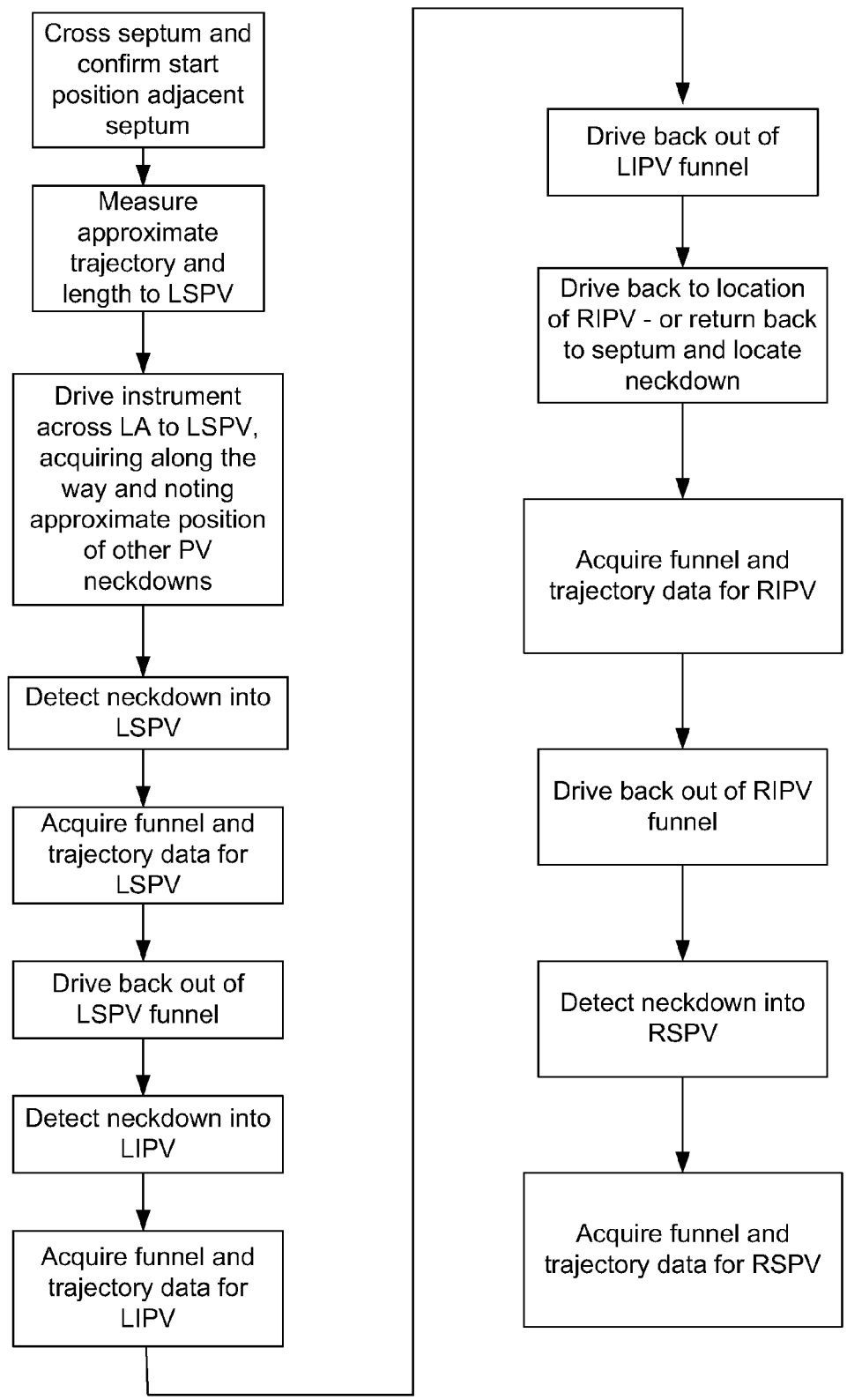
Figure 150:
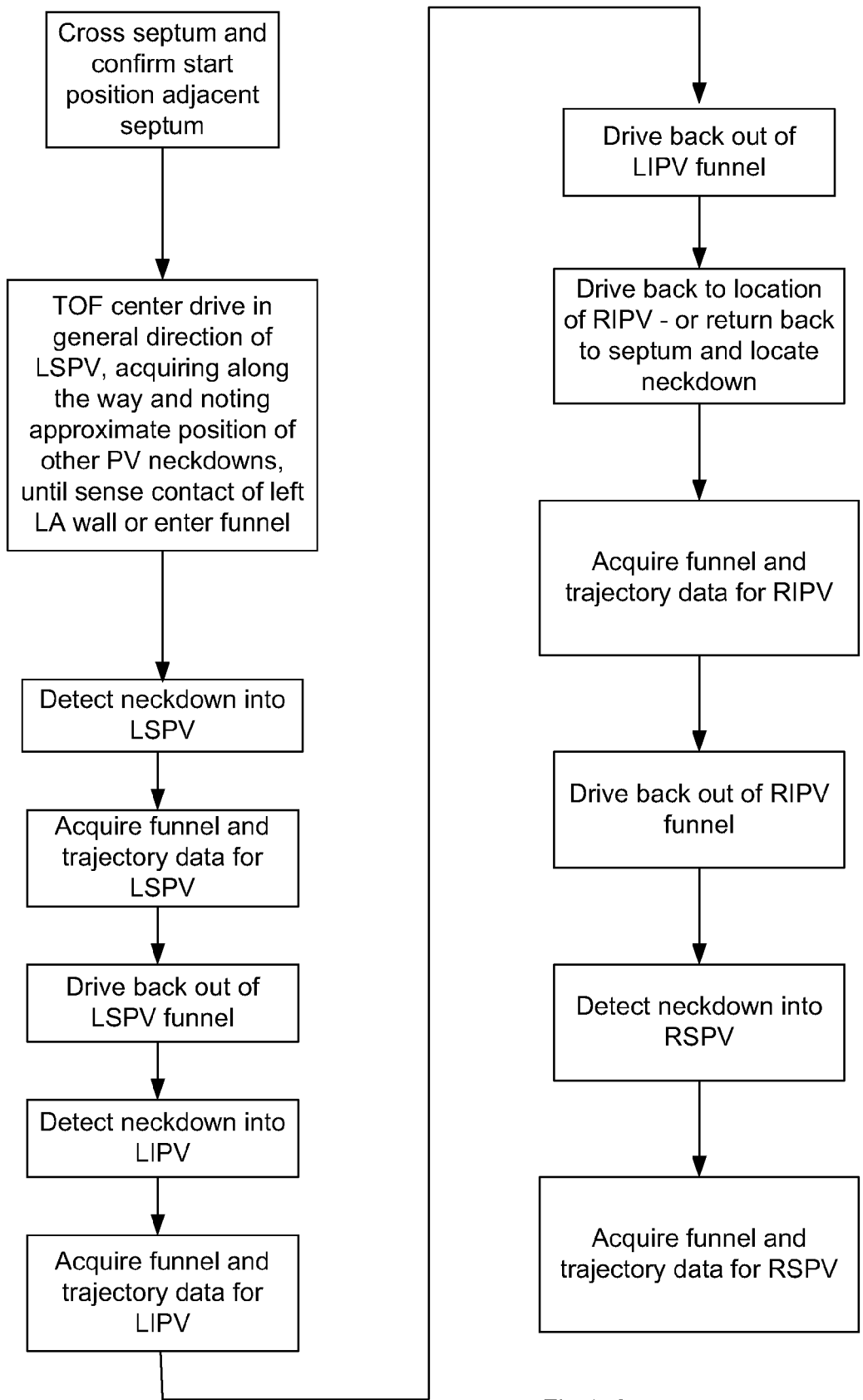

FIGS. 149 and 150 depict respective embodiments for acquiring a three-dimensional tissue structure model of a human left atrium.

Referring to FIG. 149, subsequent to crossing the septal wall, confirming an acquisition start position adjacent the septum, and measuring the approximate trajectory and insertion length to reach the left superior pulmonary vein funnel into the left atrium with the instrument utilizing a conventional technology such as fluoroscopy or ultrasound, the instrument may be driven across the left atrium cavity along the approximate trajectory, gathering slices along the way and noting, via time of flight calculations and anatomy logic, approximate positioning of any other pulmonary vein funnel neckdown positions. As the instrument reaches the end of the predicted trajectory to the left inferior pulmonary vein funnel, neckdown into the funnel may be detected using time of flight calculations and added data from bend-detailing, as described above in reference to FIG. 147. After the neckdown is detected, the instrument may be driven into the funnel and funnel shape and trajectory data acquired for the left superior pulmonary vein structure. In one embodiment, a preset insertion limit prevents insertion beyond a set value into a pulmonary vein funnel structure. In another embodiment (such as that described in reference to FIG. 150), a tissue contact sensing means may be utilized to provide feedback to an operator or automated drive system that a tissue structure has been physically encountered by the instrument, and that the instrument insertion should be limited, as directed by the pertinent controls logic.

Referring still to FIG. 149, subsequent to acquiring funnel shape and trajectory data for a first pulmonary vein funnel of the left atrium, a similar procedure may be utilized to do the same for second, third, and fourth pulmonary vein funnels. After driving back out of the left superior pulmonary vein funnel, preferably along the trajectory utilized to minimally invasively enter the funnel, the neckdown into the left inferior pulmonary vein funnel is detected utilizing similar techniques, such as bend-detailing, and funnel and trajectory data pertinent to the left inferior pulmonary vein is acquired. Subsequently, the instrument may be driven back to the location of the right pulmonary vein neckdowns, preferably starting with the more easily accessed, in most patients, right inferior pulmonary vein neckdown. To increase the amount and variation of data comprising the ultimate left atrium model, data slices may be continually gathered as the instrument is driven back, forth, and around the left atrium.

After locating the right inferior pulmonary vein funnel, the instrument may be driven into the funnel and data acquired for the trajectory and shape, as discussed above in reference to the left pulmonary vein funnels. Similar, shape and trajectory data may be acquired for the right superior pulmonary vein funnel, which in most patients, is the most difficult to access due to its location relative to the septum. Should bend-detailing or acquisition of slices and time of flight analysis as facilitated by driving the instrument around within the atrium be ineffective in location any of the pulmonary vein neck down locations, conventional systems, such as fluoroscopy or intracardiac ultrasound, may be utilized during the depicted acquisition procedure to assist in generally driving the instrument to the location of the pertinent tissue structures, after which the appropriate portion of the depicted procedure may be resumed in a more automated fashion.

Referring to FIG. 150, another embodiment of a procedure for acquiring a three-dimensional image of a left atrium is depicted, this embodiment differing from that of FIG. 149 in that the pertinent system also incorporates a contact sensing means at the distal tip of the instrument for sensing contact between the instrument tip and the subject tissue structures. With such added functionality and logic to incorporate the information from it, the subject system may be configured to stop or indicate to the operator that a tissue structure or wall has been engaged. Such a feature may be utilized to streamline the acquisition process. For example, rather than planning a trajectory based upon data from imaging modalities such as fluoroscopy or ultrasound, the instrument merely may be pointed in roughly the appropriate direction across the left atrium toward the left pulmonary veins, and insertion driving and data slice acquisition engaged. The contact sensing feedback may be logically utilized to stop insertion of the instrument at or near the left wall of the left atrium, or within the bends of the pulmonary veins as they narrow away from the funnels of the left atrium.

A number of references have reported methods for determining contact between medical device instrumentation and tissue. For example, U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342 disclose various aspects of determining electrode-tissue contact by measuring changes in impedance between an instrument electrode and a reference electrode. In an embodiment of the subject invention wherein the instrument comprises suitably positioned electrodes, techniques such as those disclosed in the art may be utilized. Other preferred embodiments of contact sensing means are described in reference to FIGS. 151-157.

Figure 151:
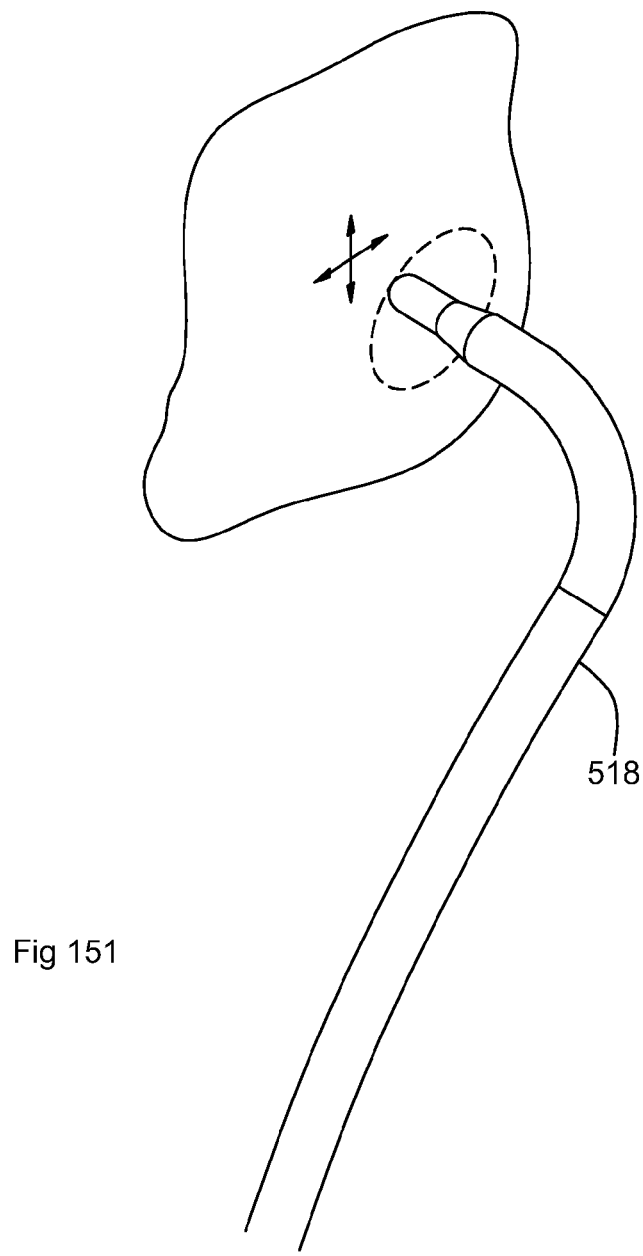

Referring to FIG. 151, an instrument (518) operated by an instrument driver and a closed-loop control system incorporating a localization technology to measure actual instrument position is depicted. When the instrument tip is driven through a range of motion, such as + pitch to − pitch, then back to neutral and + yaw to − yaw, at some cyclic interval, loads encountered by tissue structure contact, as opposed to free cavity space in blood, for example, will tend to increase the error detected between the measured tip position determined by the localization system, and the predicted tip location, determined via the inverse kinematics of the instrument structure. Other cyclic patterns of motion may also be utilized, such as repeated spiral motion, circular motion, etc. Depending upon the experimentally determined systematic error between the predicted and measured tip locations in free space given a particular instrument structure, a threshold may be utilized, beyond which error is considered an indicator of tissue contact. Depending upon the cyclic motion pattern selected, the direction of contact between the instrument and another object may also be detected by observing the directionality of error between predicted and measured instrument position.

Figure 152:
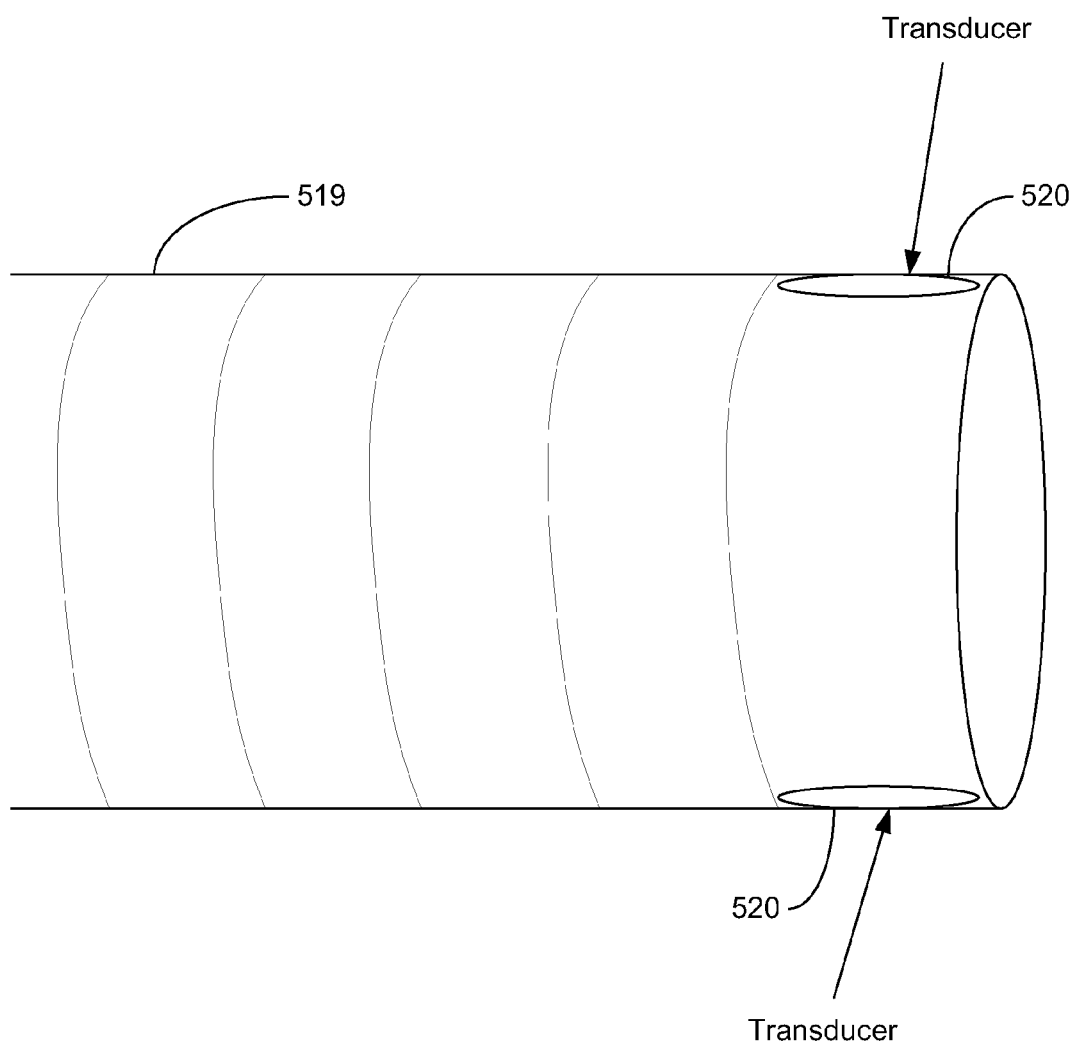

Referring to FIG. 152, a distal tip of an instrument (519) is depicted having two vibratory devices (520). In one embodiment, one device is a vibratory transmitter, such as a piezoelectric crystal adjacent a membrane, and the other device is a vibratory receiver comprising, for example, a membrane adjacent another piezoelectric crystal. In another embodiment, both devices, a single device, or more than two devices may comprise both transmitters and receivers. In free cavity space, the instrument will vibrate more freely than it will when in mechanical contact with a tissue structure, and in this embodiment, the difference is detected and logically interpreted as a tissue structure contact indicator.

Figure 153:
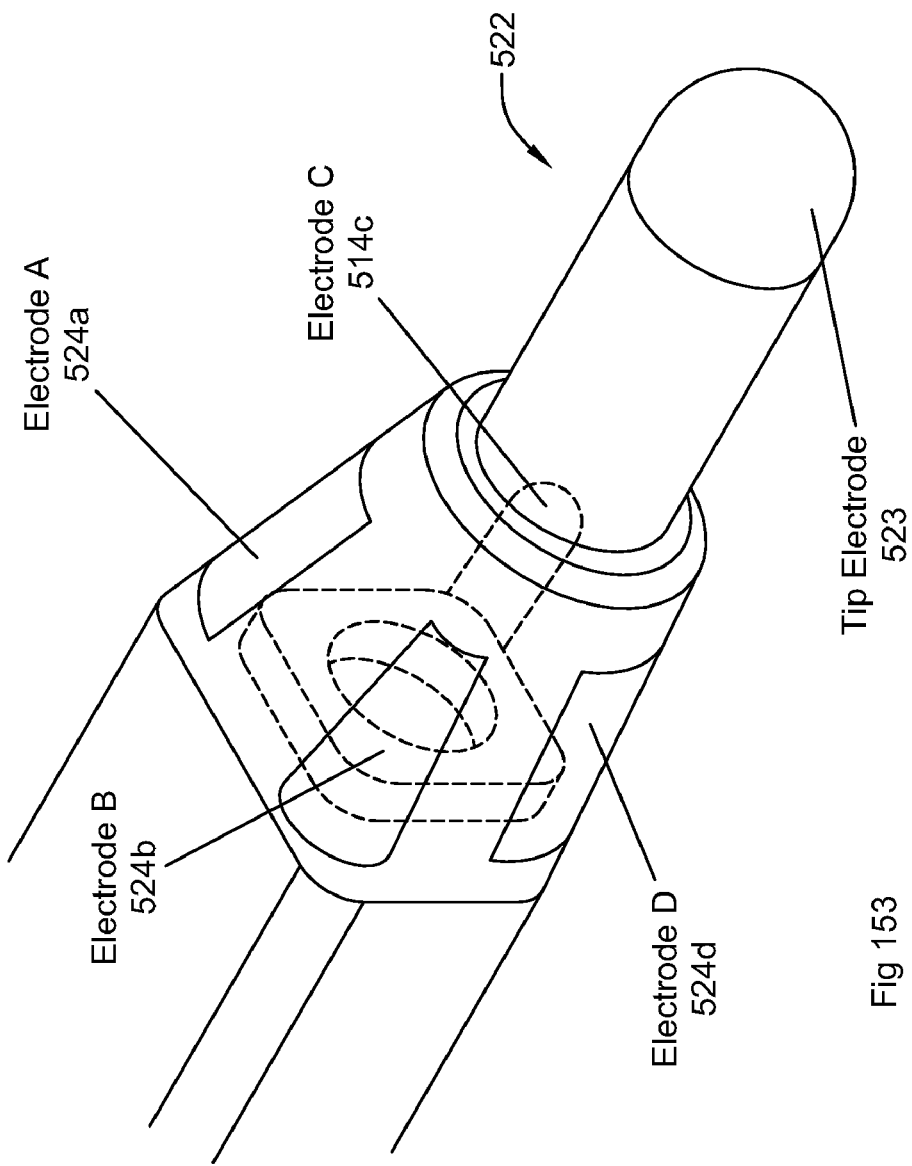
Figure 154:
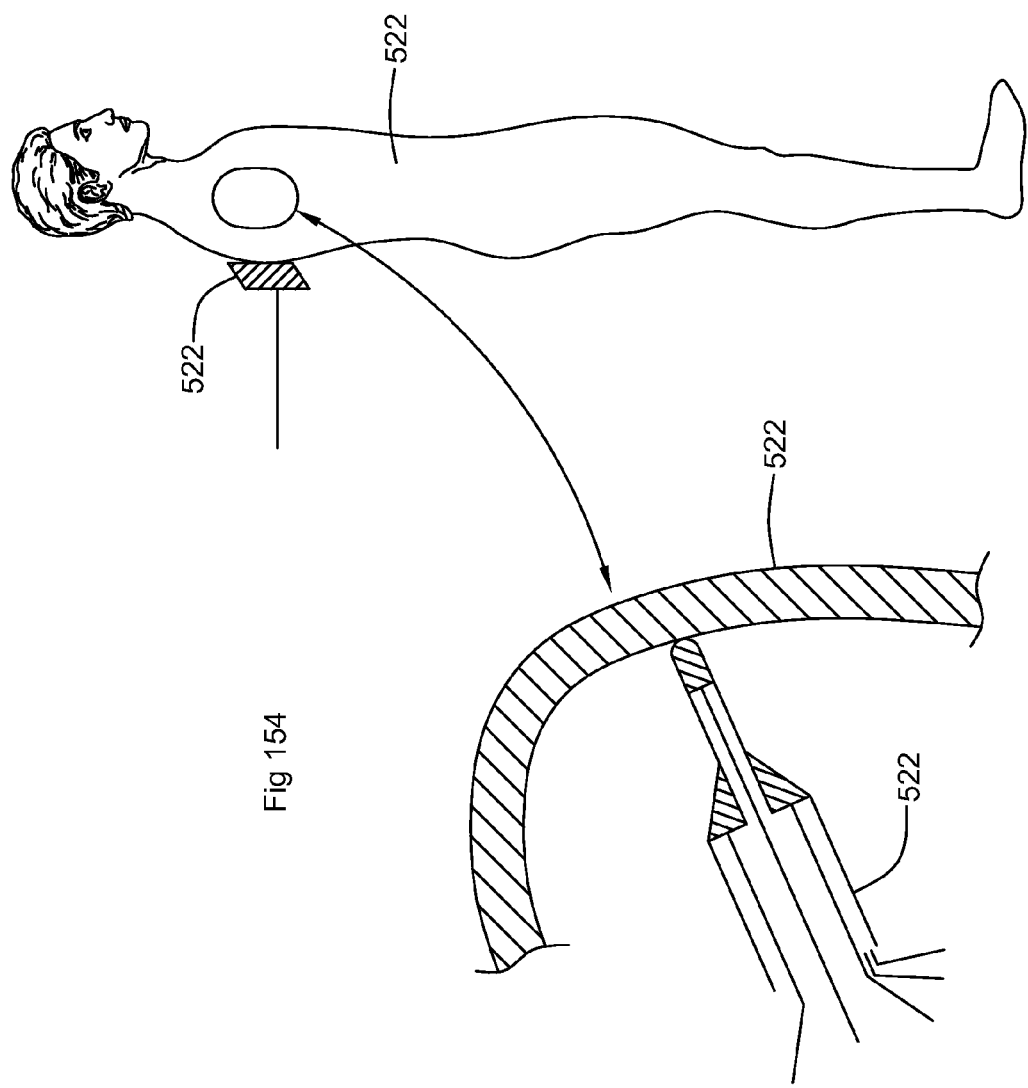
Figure 155:
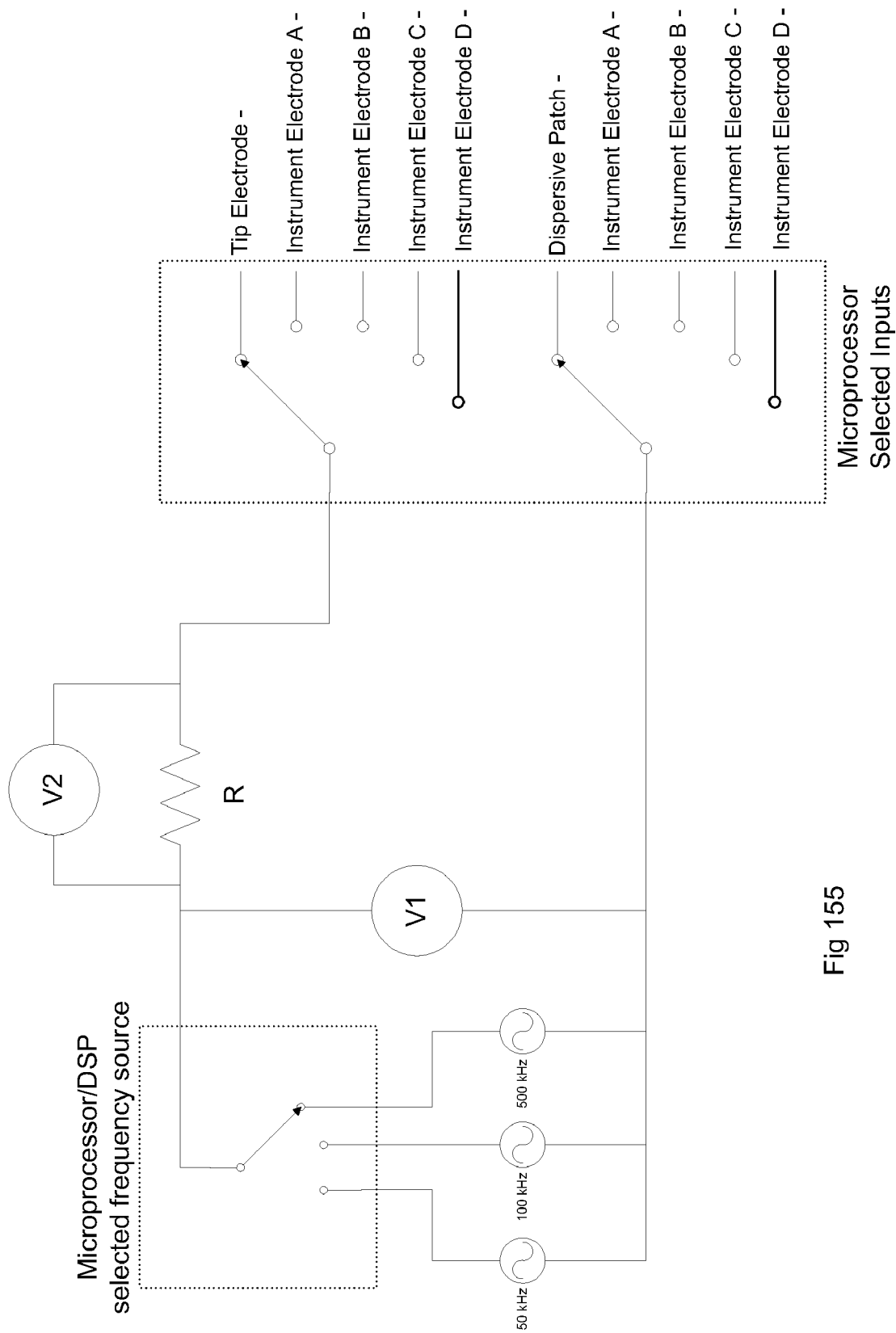

Referring to FIGS. 153-155, another embodiment of a tissue contact sensing means is depicted wherein impedance monitoring through multiple paths at multiple frequencies may be utilized as an indicator of tissue contact. Conductivity measured through blood varies relatively little with frequency modulation, whereas conductivity does vary more significantly with frequency modulation when measured through a tissue structure. By quickly switching frequencies and taking measurements at various frequencies, using, for example, a microprocessor, one can make a determination regarding contact with tissue or not based upon the associated modulation in conductivity or impedance.

Such a technique may be combined with conductivity path modulation. Conventionally, impedance is measured between an instrument tip electrode and a dispersive ground mounted, for example, upon the skin of a patient's back. With such a configuration, conductivity increases, and impedance decreases, when the instrument is in contact with, for example, the heart wall. Another measurement path of interest is conductivity between an instrument tip electrode and another electrode inside of the same chamber, but at a more proximal instrument location. As blood is relatively highly conductive, conductivity will be at a maximum when the tip electrode is not in contact with tissue, and will decrease when the tip electrode touches a tissue wall, resulting in obscuring at least a portion of the tip electrode. Indeed, previous studies have shown conductivity or impedance measurements take with such a configuration can be utilized to predict contact before it actually occurs, and that depth of tip electrode penetration may also be predicted given the relationship between conductivity and obstruction of the tip electrode by tissue.

FIG. 153 depicts a further instrument embodiment (522) having a distal tip configured to facilitate such functionality. The instrument (522) has a tip electrode disposed distally, and four electrodes (524*a-d*) disposed more proximally at corner positions to facilitate contact with tissue structures as the instrument is positioned adjacent a tissue structure in a near parallel or tangential manner. FIG. 154 depicts the instrument (522) adjacent a tissue structure (523) with reference to a dispersive patch electrode (524) located upon the skin of a patient's back. With such a configuration, impedance may be monitored between any pair of electrodes, with various frequencies, to provide a configuration combining not only frequency modulation to detect tissue-electrode contact, but also conductivity comparison path modulation to detect tissue-electrode contact.

Referring to FIG. 155, a schematic is depicted for utilizing fast switching hardware, such as microprocessors, to collect data with each of the pertinent combinations. Each cycle of acquisition through the various combinations yields impedance difference monitoring based upon path switching and frequency switching, which may be compiled and logically associated with determinations of tissue contact or not, and even the location of the instrument which is predicted to be in contact with tissue. Many other variations of electrode arrays may be utilized in addition to the configuration depicted in FIG. 153, and frequency may be modulated between more than three frequencies, as depicted in FIG. 155, to produce additional data for each combination acquisition cycle.

FIGS. 156 and 157 depict another embodiment of a means for detecting contact between an instrument electrode and a tissue structure, such as a cardiac wall. The electrocardiogram ("ECG") signal acquired by an instrument electrode positioned in free blood in the heart shows a discernable signal, but from a signal processing perspective, is less sharp and lower in amplitude due to the attenuation of high frequency signal content, as compared with similar signals detected when the electrode is in contact with a cardiac wall. When the ECG signal is differentiated with respect to time, the resulting differentiated signal has higher amplitude when the electrode is in contact, as compared with a slower-rising curve for a not-in-contact scenario. In one embodiment, a microcontroller or digital signal processor ("DSP") is utilized to perform sampling, differentiation, and analysis of acquired ECG waveforms. In another embodiment, the shape of incoming ECG waveforms is monitored to detect not only contact, but proximity to contact as the waveform shape changes with proximity to the pertinent tissue structure.

Referring to FIG. 157, similar signal processing means are utilized to compare an intracardiac ECG signal (527) with a body surface ECG signal (528), which essentially represents a superposition of the various ECG waveforms from subportions of the heart. The fit between the intracardiac ECG signal is compared with the body surface ECG signal to determine whether the intracardiac ECG signal does indeed appear to be a portion of the combined signal represented by the body surface ECG signal. If the superposition match does not meet an experimentally determined threshold, the result is logically related to a state of non-contact between the intracardiac electrode and the heart wall tissue structures.

When the intracardiac electrode is in contact with a particular wall of the heart, the intracardiac ECG signal is crisp, detailed, and fits well into a portion of the superimposed combined body surface ECG signal, as depicted in FIG. 157. In another embodiment, the body surface ECG signal may be split into, for example, four subportions, each of which may be compared in a similar manner to the intracardiac ECG signal for a determination of not only contact, but also a confirmation of position within the heart as associated with the four subportions. For example, the body surface ECG signal may be subdivided into four portions representative of the four chambers of the heart, or even four portions of the same chamber.

In a generic form, the aforementioned "master following mode" may be logically configured to follow directly each command as it comes through the control system from the master input device. In one closed loop control embodiment, however, a logic layer is configured to interpret data incoming from a master input device and a localization system in light of the integrated tissue structure model and certain system settings information pertinent to the particular procedure at hand, to make modifications to commands forwarded to the master following and subsequent main servo loop controls logic, resulting in movements of the physical instrument.

Referring to FIGS. 158-160, some relatively simplistic examples illustrate challenges addressed by interpreted master following. The exemplary instrument embodiment depicted in each of these figures comprises a localization device and a contact sensing device. Many combinations or instrument componentry may be utilized with an interpreted master following logic layer to provide an operator with enhanced navigation functionality, depending upon the functional objectives.

As shown in FIG. 158, an instrument (530) has a distal end carrying a localization device (532) is positioned adjacent an irregular tissue wall which is represented in the system's visualization and control systems by a preferably three-dimensional tissue structure model acquired utilizing one of the aforementioned modalities. Supposing that the operator's objective is to move the instrument distal tip as indicated in FIG. 158, an operator's preferred movement path depends upon his preferred action in between the two locations. For example, if the operator merely wishes to touch the instrument (530) to the tissue wall in each location without contacting any tissue in between, the operator may prefer a path of efficiency around the irregularity in the tissue structure, such as that depicted by a dashed line (531). Following this path, the operator may drive the instrument between the respective positions/locations.

Additionally or alternately, the operator may wish to lightly touch the instrument (530) against the tissue structure and keep the instrument in contact as the instrument is driven between the locations depicted in FIG. 159 via a series of hops between the two locations, rather than a constant dragging type of contact as described in the aforementioned embodiment. Further, in another embodiment, as depicted in FIG. 160, the operator may wish to move the instrument between positions, while maintaining the instrument substantially normal to the tissue structure wall, perhaps due to the preferred orientation of a distal instrument feature, e.g., an electrode.

In addition, the operator may wish to have safety functionality built into the controls logic to, for example, prevent the instrument from damaging the subject tissue structures by excessively dragging along the tissue with an excessive load, overloading or overstressing a particular portion of a tissue structure with a concentrated load, or occupying a region that may cause tissue damage, such as an active valve entrance.

Such operator objectives are addressed in various embodiments of an interpreted master following logic layer interposed into the controls logic. In one embodiment, interpreted master following interprets commands that would normally lead to dragging along the tissue structure surface as commands to execute a succession of smaller "hops" to and from the tissue structure surface, while logging each contact as a new point to add to the tissue structure surface model. Hops are preferably executed by backing the instrument out the same trajectory it came into contact with the tissue structure, then moving normally along the wall per the tissue structure model, and re-approaching with a similar trajectory. In addition to saving to memory each new XYZ surface point, in one embodiment. the system saves the trajectory of the instrument with which the contact was made by saving the localization orientation data and control element tension commands to allow the operator to re-execute the same trajectory at a later time if so desired. By saving the trajectories and new points of contact confirmation, a more detailed contour map is formed from the tissue structure model, which may be utilized in the procedure and continually enhanced. The length of each hop may be configured, as well as the length of non-contact distance in between each hop contact.

In one embodiment, interpreted master following performs a variety of safety checking steps to ensure that the operator does not accidentally damage the subject tissue structure by driving into it or through it with the instrument. For example, the controls logic may be configured to disallow driving of the instrument beyond or into the subject tissue structure, as determined utilizing a tissue structure model with localization data and/or contact sensing. Such a mode may be manually overridden with an operator command in certain scenarios, for example, in order to purposefully puncture a tissue wall such as the septum at the location of the fossa ovalis. In one embodiment, the controls logic may be configured to prevent instrument electrode activation while the operator is attempting to move the instrument, or may attempt to prevent electrode activation in the same location for more than a predetermined time or amount of energy delivered.

In another embodiment, interpreted master following assists the operator in automating various clinical procedures. For example, where the instrument comprises a distal ablation electrode, the controls may be configured to automatically fit a circular ablation pattern through three contact points selected by the operator. Further, an operator may select a hopping, intermittent electrode burning pattern to automatically apply has he merely moves the master input device linearly. Haptics functionality may be utilized to provide the operator with various feedback to assist in clinical procedures. For example, a haptic "groove" may be created along the insertion axis of the instrument to assist the operator in driving the instrument with the master input device. Further, previously selected points of desired contact may be haptically turned in to "gravity wells" to assist the operator in directing the instrument to such locations.

A control system embodiment, such as described above, facilitates precision steerability of a catheter-based instrument in order to conduct a medical procedure. As an exemplary application, a myocardial ablation procedure to address atrial fibrillation will now be described with reference to FIGS. 161-174.

Figure 161:
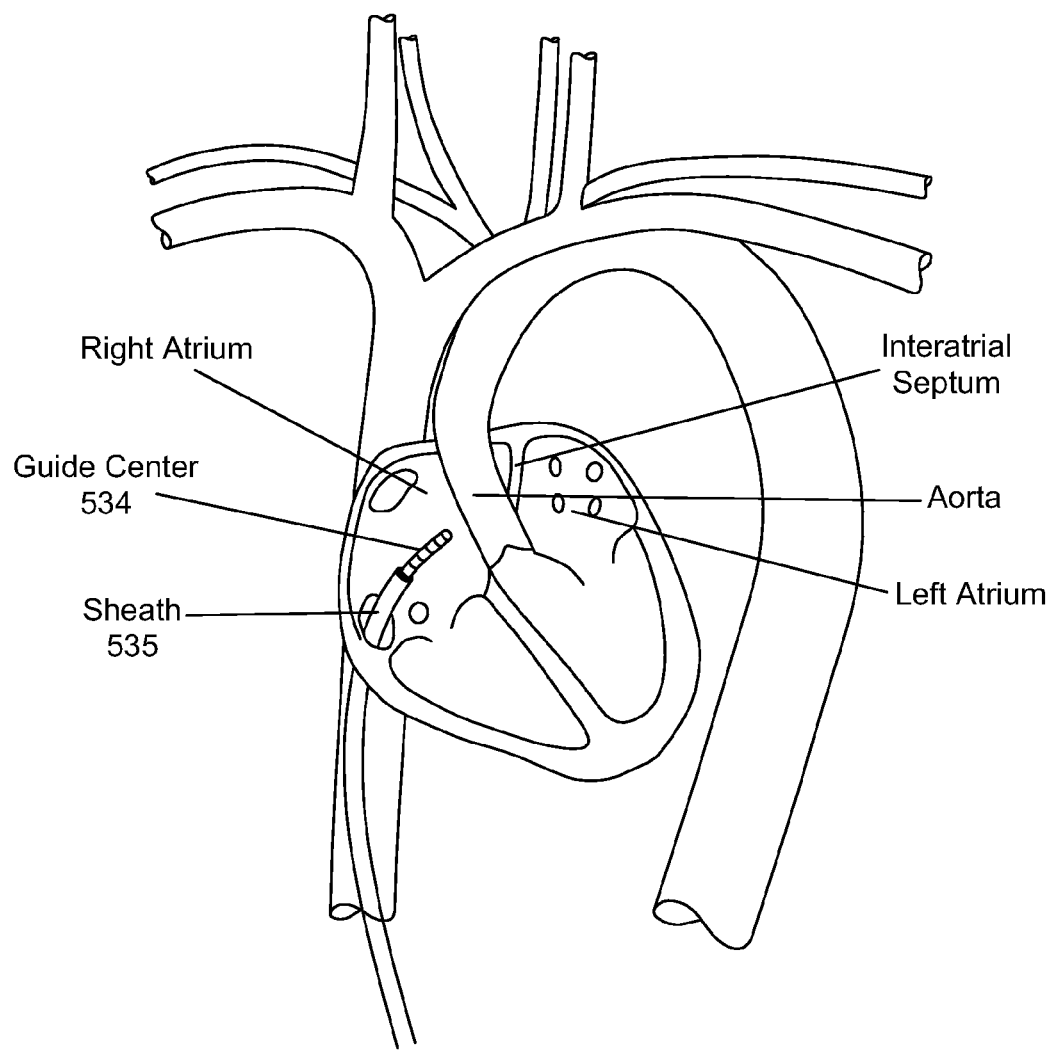
Figure 162:
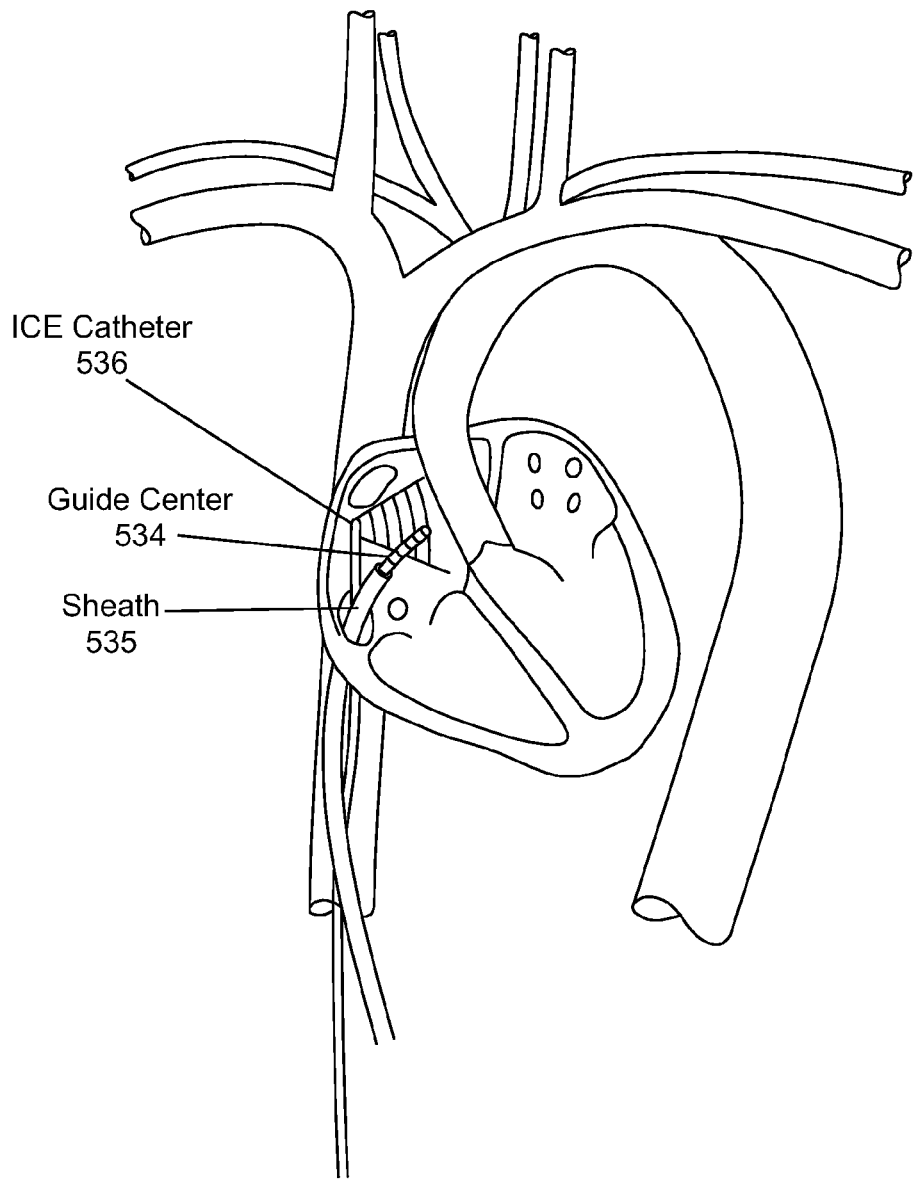
Figure 163:
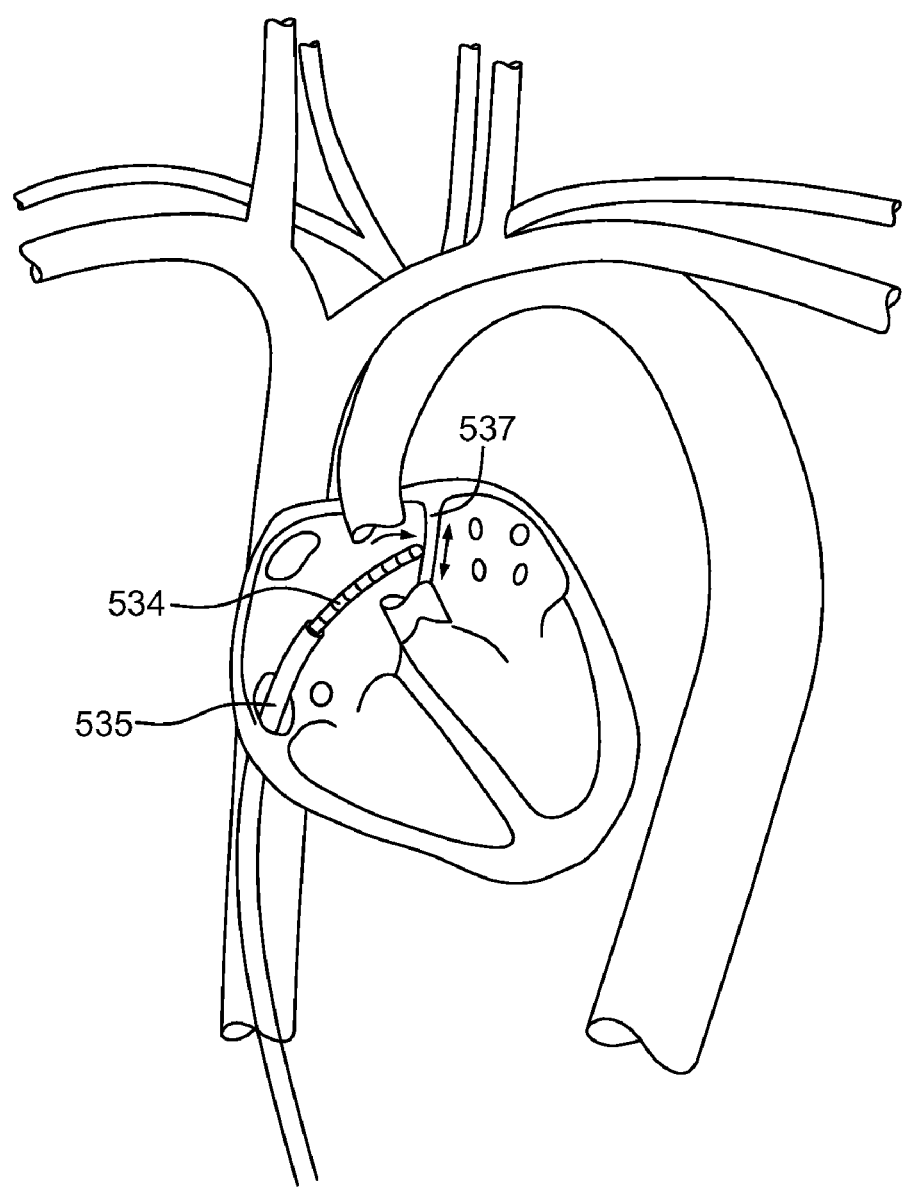
Figure 164:
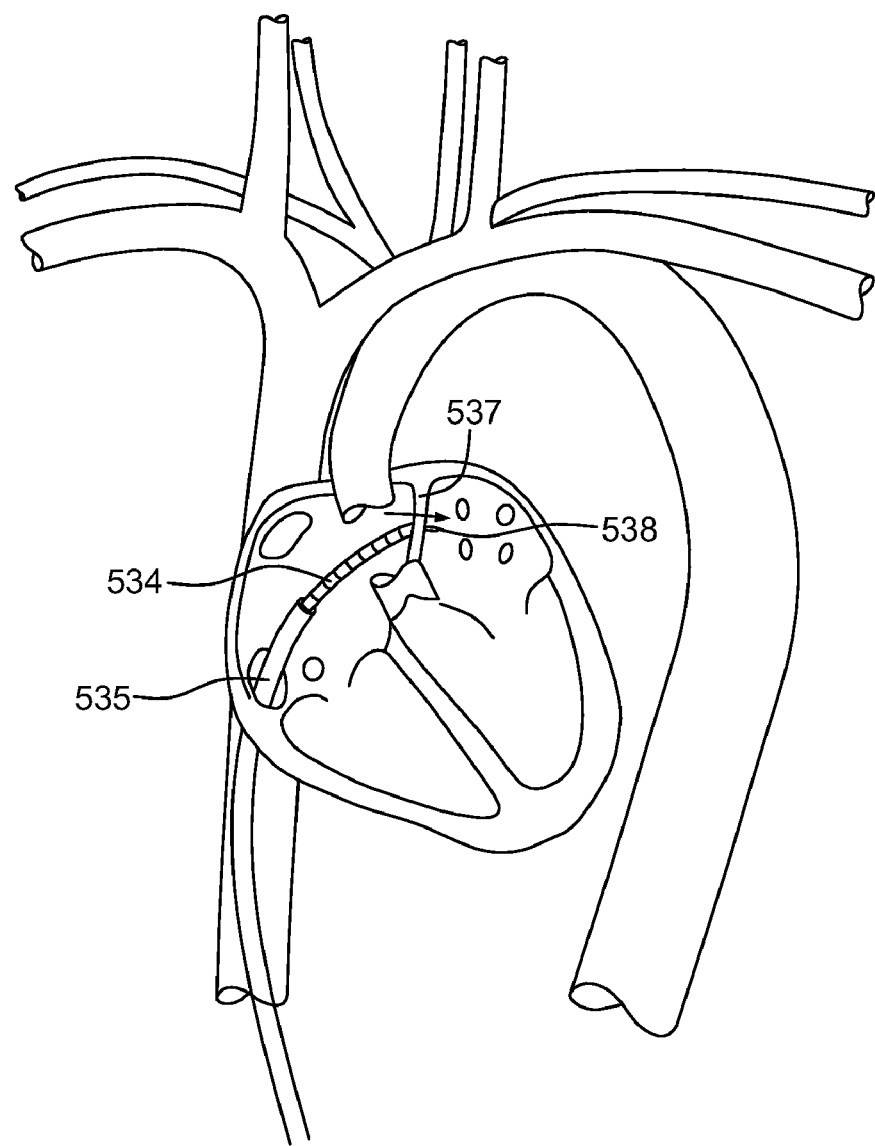
Figure 165:
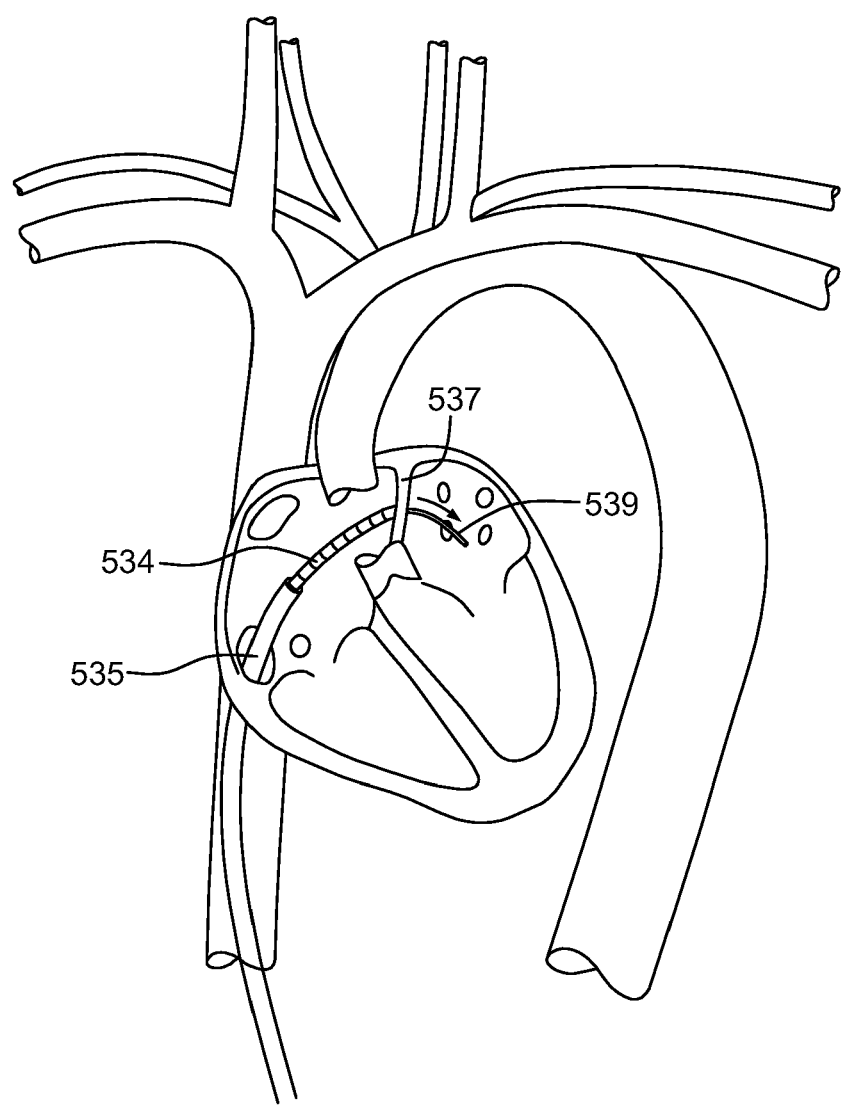
Figure 166:
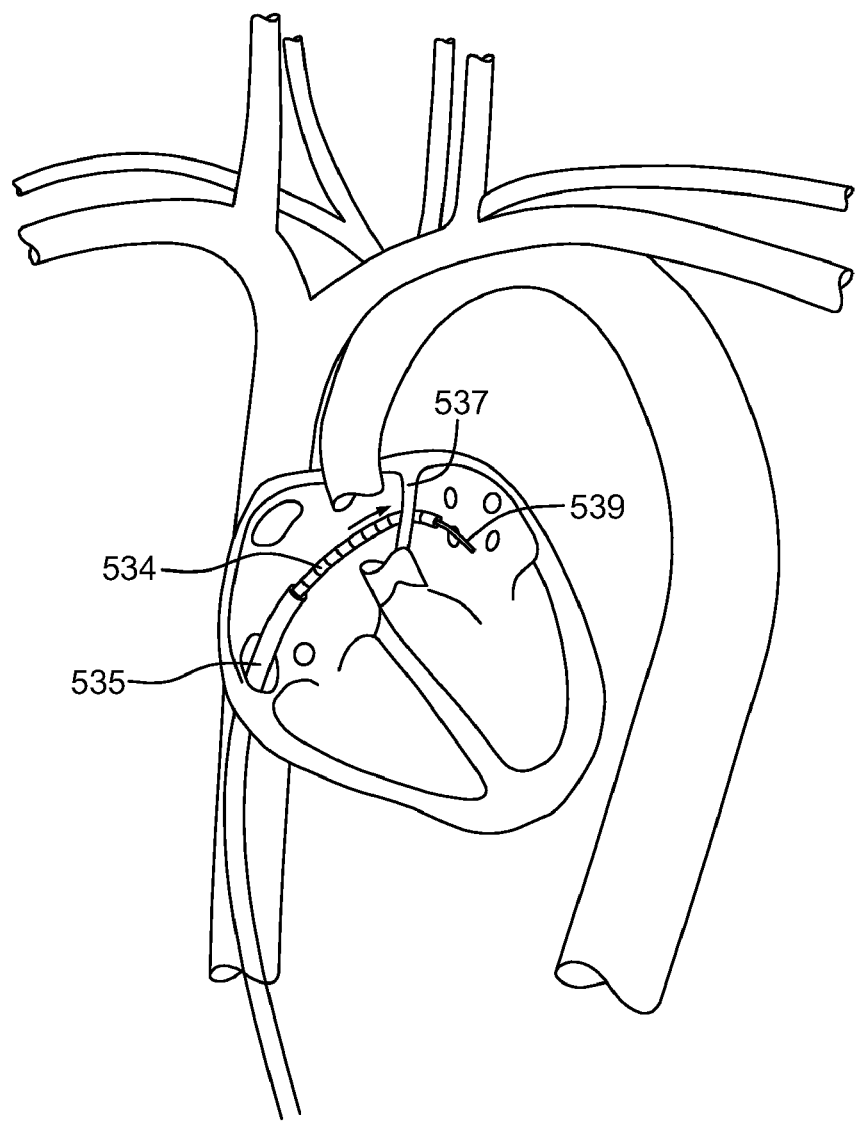

Referring to FIG. 161, a standard atrial septal approach is depicted with a robotically controlled guide catheter instrument (534) and sheath instrument (535) passing through the inferior vena cava and into the right atrium. Referring to FIG. 162, an imaging device, such as an intracardiac echo ("ICE") sonography catheter (536), is forwarded into the right atrium to provide a field of view upon the interatrial septum. The guide instrument is driven to the septum wall, as shown in FIG. 163. Referring to FIGS. 164 and 165, the septum (537) may be crossed using a conventional technique of first puncturing the fossa ovalis location with a sharpened device (538), such as a needle or wire, passed through the working lumen of the guide instrument (534), then passing a dilator (539) over the sharpened device and withdrawing the sharpened device to leave the dilator (539), over which the guide instrument (534) may be advanced, as shown in FIG. 166. It may be desirable in some embodiments to pass an instrument arrangement through the working lumen of the guide instrument comprising a needle positioned coaxially within a dilator, as is well known in conventional (i.e., non-robotic) septum crossing techniques.

Figure 167:
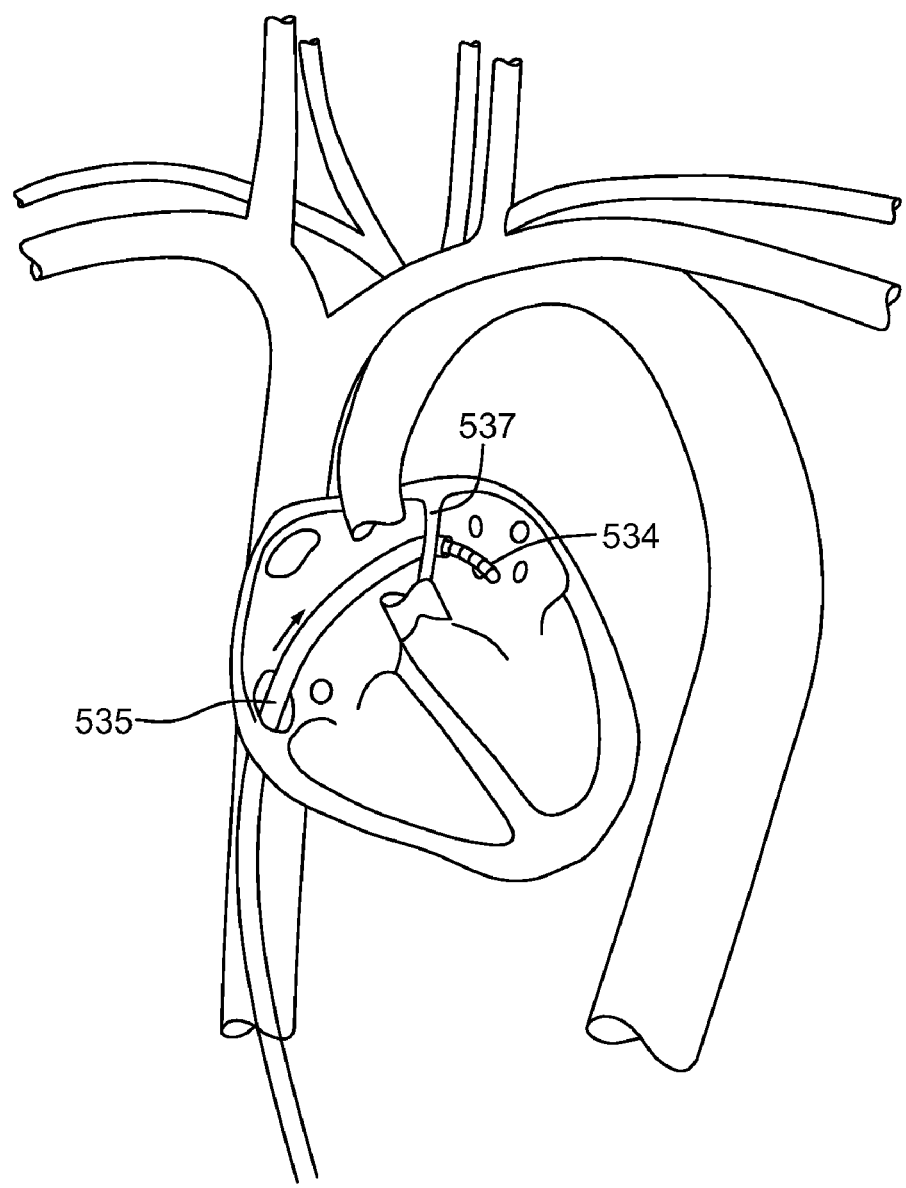
Figure 168:
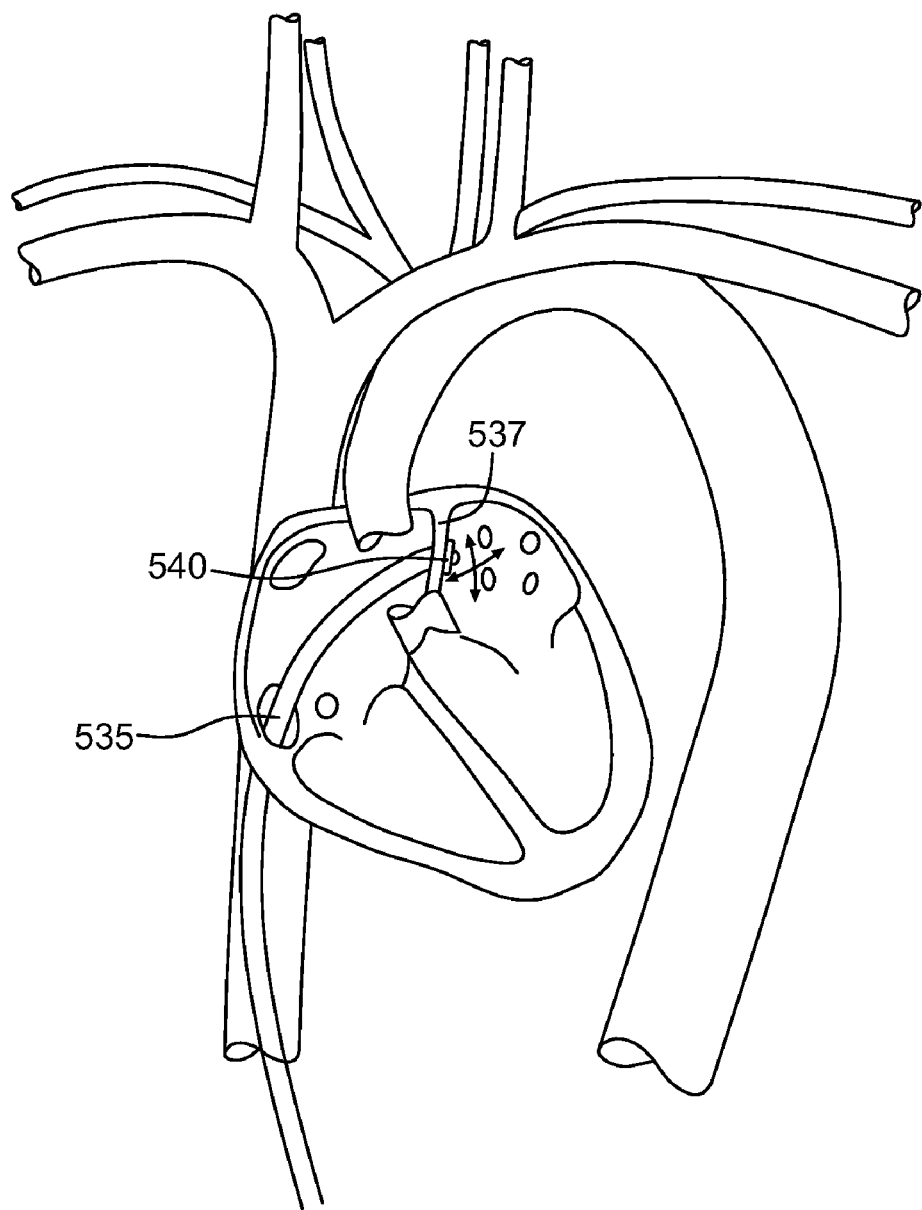
Figure 169:
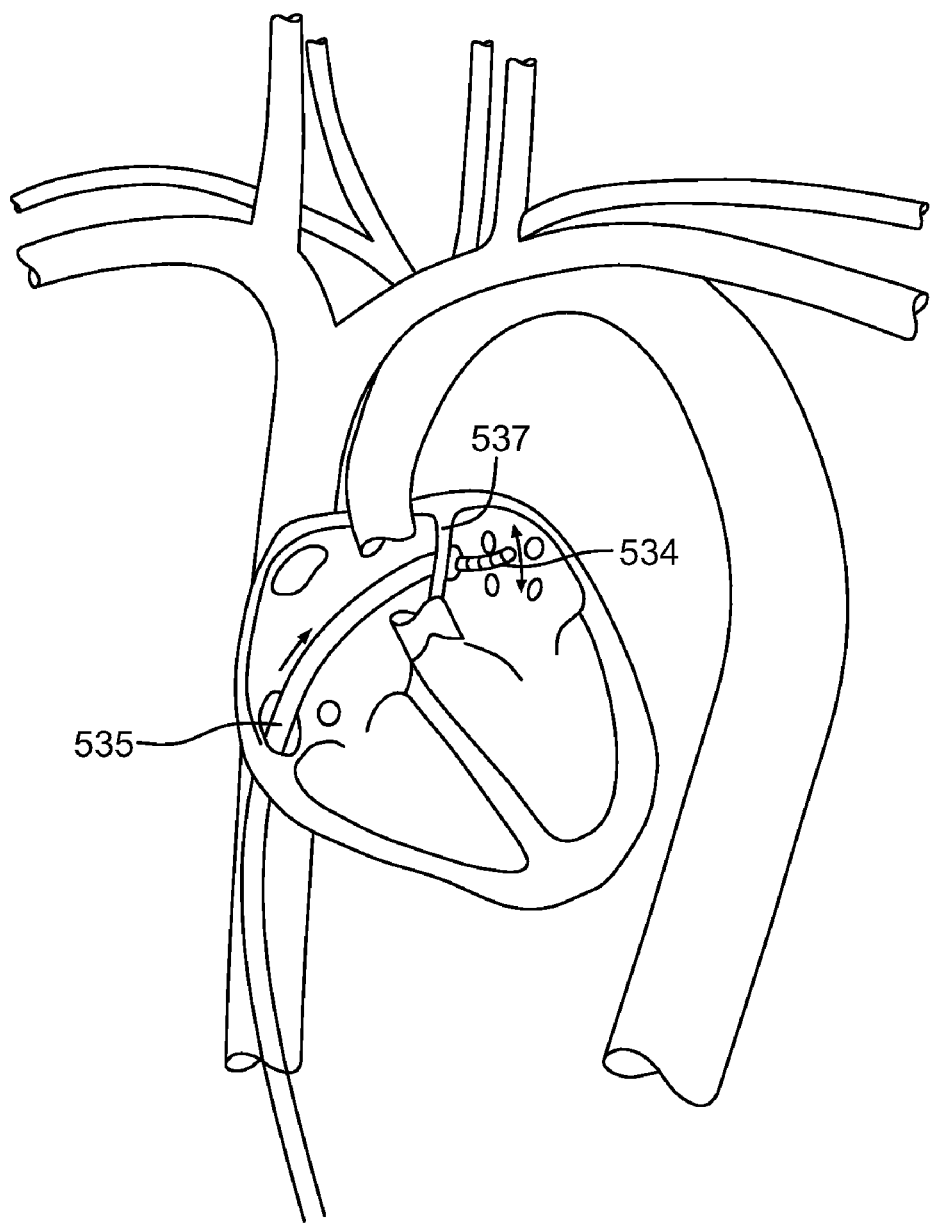

As shown in FIG. 167, subsequent to passing the guide instrument (534) across the septum (537), the guide instrument (534) may be utilized as a dilator to insert the sheath instrument (535) across the septum (537), thereby providing both instruments (534, 535) access and/or a view into the left atrium. It may be desirable to anchor the sheath instrument (535) in place just across the septum (537). For example, as shown in FIG. 168, an expanding structure such as a conventional balloon anchor (540) may be employed. As shown in FIG. 169, the guide instrument (534) may then be used to navigate inside the left atrium.

In one embodiment, a radio frequency (RF) ablation system is used with the robotic catheter system to supply energy to perform myocardial tissue ablation procedures in order block undesirable conduction pathways within the wall of the left atrium and adjoining vessels (e.g., pulmonary vein). By way of illustration, FIG. 170 depicts a system level view of such arrangement, including an operator control station (2), a computer (6), an instrument driver (16), a RF ablation energy control unit (541), a guide instrument (543) and a working instrument (547).

In one embodiment, shown in FIG. 171, a robotically controlled guide instrument (543), which may have an outer diameter of about 7 French, comprises an integrated ablation distal tip, and is passed through a sheath instrument (535). In another embodiment, shown in FIG. 172, a working instrument (547), in this instance an "off the shelf" ablation catheter such as that sold under the trade name Blazer™ by Boston Scientific Corporation, which may have an outer diameter of about 7 French, is passed through the working lumen of the guide instrument (534), which itself is passed through a sheath instrument (535). In such embodiments, the RF power may be supplied directly from the RF generator to the ablation catheter handle. Alternatively, the power supply may be coupled to the ablation catheter via a controller integrated with the robotic guide instrument in order to provide addition safety features, e.g., automatic power shut-off under defined circumstances. In such embodiments, only a small portion of the ablation catheter need be protruded beyond the distal tip of the guide instrument to expose the ablation electrodes, and the steering features which may be integrated into the "off the shelf" ablation catheter may not be needed as a result of the precision steerability provided by the robotically-controlled instrumentation through which the ablation catheter is coaxially positioned. Alternatively, a greater portion of the ablation catheter may be protruded beyond the distal tip of the guide instrument, preferably with the guide instrument held in a constant position by the system, and the manual steering functionality of the "off the shelf" ablation catheter may be utilized to place the distal portion of such device in a desired location, utilizing feedback to the operator from fluoroscopy, ultrasound, localization, or other real-time or near real-time systems. It will be appreciated by those skilled in the art that many of types of other ablation catheters or other working instruments may be passed through the working lumen of the guide instrument (534).

There are many well-known diagnostic or therapeutic distal end electrode configurations of working instruments that may used in conjunction with the guide instrument (534), such as those shown by way of non-limiting example in FIGS. 173A-D. Other tip options include non-contact means such as microwave or ultrasound energy (indicated by an "arrow" emitted from distal tip element (612) in FIG. 174A), optical laser energy (indicated by multiple "arrows" emitted from distal tip element (614) in FIG. 174B), a penetrating electrode or chemical/drug injection needle (element (616) in FIG. 174C), or mechanical grasper (element 618 in FIG. 174D).

In another embodiment, the instrument may be navigated by "direct visualization" utilizing conventional fiberscope or CCD camera devices, preferably disposed within a distally-positioned viewing balloon containing a substantially clear fluid such as saline when in a blood environment. In yet another embodiment, an infrared visualization technology, such as those available from CardioOptics Corporation, may be coupled to the instrument to provide direct visualization through a blood or similar medium without a viewing balloon or similar structure. In another embodiment wherein the instrument is navigated in a non-blood space, a viewing balloon need not be positioned to protect the camera device, and the camera lens or image intake may be positioned at the distal tip of the instrument. Whether the direct visualization device is assisted by a balloon-like visualization structure or not, the device preferably is coupled to the instrument either by insertion through the working lumen of an embodiment of the instrument, or integrated into one of the walls comprising the elongate instrument.

Conventional sensors may be disposed at and/or around the distal tip of the instrument, such as those which comprise strain gages and/or piezoelectric crystals. Also, more than one localization device may be coupled to the instrument along different positions of the instrument to allow for more complex monitoring of the position of the instrument. Such additional information may be utilized to help compensate for body movement or respiratory cycle related movement of tissues relative to a base coordinate system.

In still another embodiment of the tissue structure model acquisition modalities described above, including a contact sensor, the instrument may merely be driven around, in a planned fashion, or even at random, within a cavity to collect and store all points of contact to develop a three-dimensional model of the tissue structures. In a related embodiment, a rough model acquired utilizing a conventional imaging modality such as ultrasound or fluoroscopy may be utilized as a starting point, and then additional points added, particularly at points of interest, such as pulmonary vein and valve locations within the left atrium, utilizing a "tapping around" pattern with contact sensing to gather more points and refine the model.

While multiple embodiments and variations of the many aspects of the invention have been disclosed and described herein, such disclosure is provided for purposes of illustration only.

What is claimed:

1. A robotic instrument system, comprising:
an elongate flexible instrument that is bendable to form a curve;
a controller configured to selectively actuate one or more motors operably coupled to the instrument to thereby selectively bend the instrument; and
a haptic input device in communication with the controller and configured for generating instrument bending commands in response to a directional movement of the input device,
wherein the controller is configured to compare a desired bending of the instrument corresponding to the instrument bending commands received from the input device against one or more instrument workspace limitations and, if the desired bending of the instrument contravenes an instrument workspace limitation, transmits a bending limitation signal to the input device in response to the respective instrument bending command,
wherein the input device, upon receiving the bending limitation signal from the controller, imparts a detectable resistance to further directional movement of the input device.

2. The system of claim 1, wherein the one or more workspace limitations include mechanical characteristics of the instrument.

3. The system of claim 1, wherein the one or more workspace limitations include a range of motion of the instrument.

4. The system of claim 3, wherein the motion is bending of the instrument.

5. The system of claim 1, wherein the one or more workspace limitations include a spatial position of the instrument.

6. The system of claim 1, wherein the one or more workspace limitations include user-implemented limitations.

7. A robotic instrument system, comprising:
an elongate flexible instrument that is bendable to form a curve;
a controller configured to selectively actuate one or more motors operably coupled to the instrument to thereby selectively bend the instrument; and
a haptic input device in communication with the controller and configured for generating instrument bending commands in response to a directional movement of the input device, wherein the controller is configured to compare a desired bending of the instrument corresponding to the instrument bending commands received from the input device to a predetermined range of instrument movement and, if the desired bending of the instrument is outside of the predetermined instrument movement range, transmits a haptic limitation signal to the input device in response to the respective instrument bending command, wherein the input device, upon receiving the haptic limitation signal from the controller, imparts a detectable resistance to further directional movement of the input.

8. The system of claim 7, wherein the predetermined range of instrument motion corresponds to a flexibility of the instrument.

9. The system of claim 7, wherein the predetermined range of instrument motion defines a haptic groove.

10. The system of claim 7, wherein the predetermined range of instrument motion defines a haptic gravity well.

* * * * *

UNITED STATES PATENT AND TRADEMARK OFFICE
CERTIFICATE OF CORRECTION

PATENT NO. : 8,394,054 B2
APPLICATION NO. : 13/118309
DATED : March 12, 2013
INVENTOR(S) : Wallace et al.

It is certified that error appears in the above-identified patent and that said Letters Patent is hereby corrected as shown below:

In the Claims

At Column 43, Claim 7, line 11, "movement of the input" should read:

--movement of the input device--

Signed and Sealed this
Twenty-eighth Day of May, 2013

Teresa Stanek Rea
*Acting Director of the United States Patent and Trademark Office*